(12) United States Patent
Mori et al.

(10) Patent No.: US 11,576,972 B2
(45) Date of Patent: *Feb. 14, 2023

(54) METHOD OF FORMULATING A MULTICOMPONENT DRUG USING BASES EVALUATED BY MAHALANOBIS TAGUCHI METHOD

(71) Applicant: TSUMURA & CO., Tokyo (JP)

(72) Inventors: Yoshikazu Mori, Ibaraki (JP); Keiichi Noda, Ibaraki (JP)

(73) Assignee: Tsumura & Co., Tokyo (JP)

( * ) Notice: Subject to any disclaimer, the term of this patent is extended or adjusted under 35 U.S.C. 154(b) by 520 days.

This patent is subject to a terminal disclaimer.

(21) Appl. No.: 15/285,935

(22) Filed: Oct. 5, 2016

(65) Prior Publication Data

US 2017/0042769 A1 Feb. 16, 2017

Related U.S. Application Data

(63) Continuation-in-part of application No. 13/805,248, filed as application No. PCT/JP2012/003602 on May 31, 2012, now abandoned.

(30) Foreign Application Priority Data

Jun. 1, 2011 (JP) .............................. JP2011-123844

(51) Int. Cl.
*A61K 45/06* (2006.01)
*G01N 30/86* (2006.01)
*G01N 30/88* (2006.01)

(52) U.S. Cl.
CPC ......... *A61K 45/06* (2013.01); *G01N 30/8679* (2013.01); *G01N 2030/8886* (2013.01)

(58) Field of Classification Search
None
See application file for complete search history.

(56) References Cited

U.S. PATENT DOCUMENTS

| 5,969,228 | A | 10/1999 | Gorenstein |
| 7,660,678 | B2 | 2/2010 | Odegard et al. |
| 2003/0110000 | A1 | 6/2003 | Quimby et al. |
| 2008/0140375 | A1 | 6/2008 | Yano |
| 2008/0208485 | A1 | 8/2008 | Gorenstein et al. |
| 2009/0012723 | A1 | 1/2009 | Treado et al. |
| 2009/0149335 | A1 | 6/2009 | Mathew et al. |

FOREIGN PATENT DOCUMENTS

| CN | 1670529 A | 9/2005 |
| CN | 1965233 | 5/2007 |
| EP | 1 760 464 | 3/2007 |
| JP | 2-196959 | 8/1990 |
| JP | 10-073582 | 3/1998 |
| JP | 2002-214215 | 7/2002 |
| JP | 2007-315941 | 12/2007 |
| WO | 97/39347 | 10/1997 |
| WO | 2005/079261 | 9/2005 |

OTHER PUBLICATIONS

Pharmaceuticals Monthly, vol. 28, No. 3, pp. 67-71, (1986) (Filed in Parent U.S. Appl. No. 13/805,248).
Z.L. Cardeal, et al., "Comprehensive two dimensional gas chromotography for fingerprint pattern recognition in cachaça production", Talanta 74 (2008) pp. 793 799, Available online atwww.sciencedirect.com (Filed in Parent U.S. Appl. No. 13/805,248).
Xie, Chromatographic fingerprint analysis, Journal of Chromatography, 1112 (2006) 171-180 (Parent U.S. Appl. No. 13/806,683).

*Primary Examiner* — G Steven Vanni

(74) *Attorney, Agent, or Firm* — Norris McLaughlin, P.A.

(57) ABSTRACT

Provided are a method of and an apparatus for formulating a multicomponent drug capable of surely making a multicomponent drug meeting criteria for productization with high accuracy into a product. The method and apparatus obtain a chromatogram from an extract or a base of a multicomponent drug, evaluate whether the base meets the criteria for productization based on the obtained chromatogram with high accuracy, and subject the base determined in the high-accuracy evaluating as an accepted one meeting the criteria to dosage form processing, to produce a formulated drug having a given dosage form. The high quality evaluation is realized by performing peak assignment of a target fingerprint obtained from a chromatogram to a reference fingerprint with high accuracy.

16 Claims, 79 Drawing Sheets

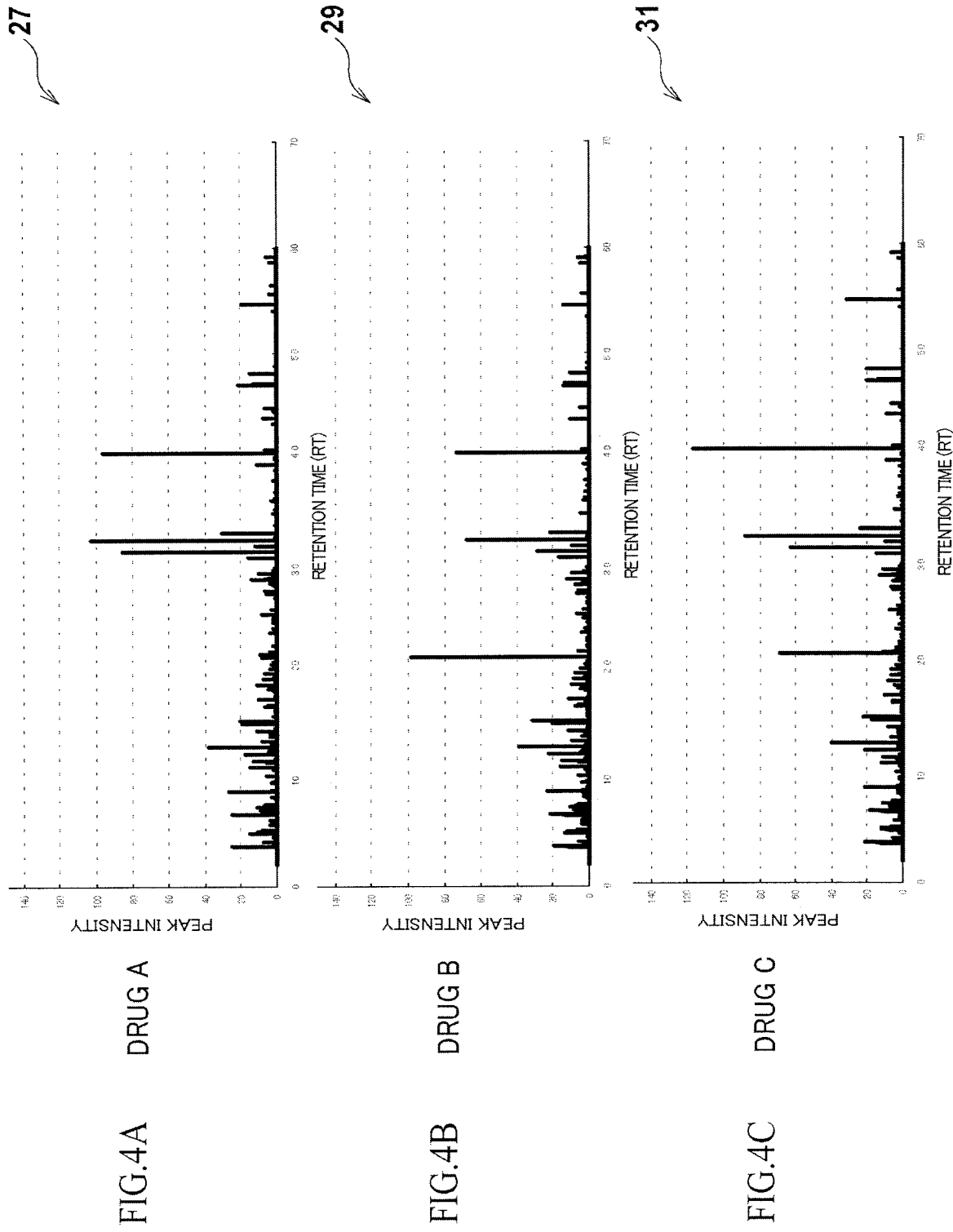

FIG.8

NUMBER OF MATCHES IN RETENTION TIME POINT APPEARANCE DISTANCE                     83

|  |  | REFERENCE FP RETENTION TIME APPEARANCE PATTERN | | | | | | | | | |
|---|---|---|---|---|---|---|---|---|---|---|---|
|  |  | 1ROW | 2ROW | 3ROW | 4ROW | 5ROW | 6ROW | 7ROW | 8ROW | 9ROW | 10ROW |
| TARGET FP RETENTION TIME APPEARANCE PATTERN | 1ROW | (7) | (7) | 7 | 6 | 6 | 5 | 4 | 4 | 3 | 2 |
|  | 2ROW | 9 | 5 | 6 | 6 | 5 | 2 | 3 | 3 | 2 | 2 |
|  | 3ROW | 3 | 8 | 5 | 4 | 5 | 5 | 4 | 2 | 2 | 2 |
|  | 4ROW | 6 | 2 | 7 | 6 | 5 | 4 | 4 | 3 | 2 | 1 |
|  | 5ROW | 3 | 4 | 5 | 6 | 5 | 4 | 3 | 3 | 2 | 1 |
|  | 6ROW | 4 | 3 | 4 | 4 | 5 | 3 | 3 | 2 | 2 | 1 |
|  | 7ROW | 2 | 4 | 2 | 2 | 1 | 4 | 3 | 2 | 2 | 2 |
|  | 8ROW | 3 | 1 | 3 | 2 | 3 | 3 | 3 | 3 | 3 | 1 |
|  | 9ROW | 2 | 2 | 2 | 1 | 1 | 2 | 2 | 2 | 2 | 2 |

FIG.9

DEGREE OF MATCHING IN RETENTION TIME APPEARANCE PATTERN                           85

|  |  | REFERENCE FP RETENTION TIME APPEARANCE PATTERN | | | | | | | | | |
|---|---|---|---|---|---|---|---|---|---|---|---|
|  |  | 1ROW | 2ROW | 3ROW | 4ROW | 5ROW | 6ROW | 7ROW | 8ROW | 9ROW | 10ROW |
| TARGET FP RETENTION TIME APPEARANCE PATTERN | 1ROW | 2.00 | 2.00 | 2.00 | 3.00 | 3.00 | 4.13 | 5.35 | 5.35 | 6.67 | 8.05 |
|  | 2ROW | (0.50) | 3.00 | 3.00 | 3.00 | 4.13 | 8.05 | 6.67 | 6.67 | 8.05 | 8.05 |
|  | 3ROW | 6.67 | 1.15 | 4.13 | 5.35 | 4.13 | 4.13 | 5.35 | 8.05 | 8.05 | 8.05 |
|  | 4ROW | 3.00 | 8.05 | 2.00 | 3.00 | 4.13 | 5.35 | 5.35 | 6.67 | 8.05 | 9.50 |
|  | 5ROW | 6.67 | 5.35 | 4.13 | 3.00 | 4.13 | 5.35 | 6.67 | 6.67 | 8.05 | 9.50 |
|  | 6ROW | 5.35 | 6.67 | 5.35 | 9.35 | 4.13 | 6.67 | 6.67 | 8.05 | 8.05 | 9.50 |
|  | 7ROW | 8.05 | 5.35 | 8.05 | 8.05 | 9.50 | 5.35 | 6.67 | 8.05 | 8.05 | 8.05 |
|  | 8ROW | 6.67 | 9.50 | 6.67 | 8.05 | 6.67 | 6.67 | 6.67 | 6.67 | 6.67 | 9.50 |
|  | 9ROW | 8.05 | 8.05 | 8.05 | 9.50 | 9.50 | 8.05 | 8.05 | 8.05 | 8.05 | 8.05 |

DEGREE OF MATCHING BETWEEN RETENTION TIME APPEARANCE PATTERNS =
(1 − (NUMBER OF MATCHES IN APPEARANCE DISTANCE/(NUMBER OF PEAKS OF TARGET FP + NUMBER OF PEAKS OF REFERENCE FP − NUMBER OF MATCHES IN APPEARANCE DISTANCE)) × (NUMBER OF PEAKS OF TARGET FP + NUMBER OF MATCHES IN APPEARANCE DISTANCE + 1)

⇩

PREPARE PEAK PATTERN WITH USE OF THREE PEAKS INCLUDING
ARBITRARY TWO OF FOUR PEAK PATTERN CONFIGURING CANDIDATE PEAKS

⇩

$_4C_2$ = 6 PATTERNS

PREPARE PEAK PATTERN WITH USE OF THREE PEAKS INCLUDING
ARBITRARY TWO OF FOUR PEAK PATTERN CONFIGURING CANDIDATE PEAKS

⇩

$_4C_2$ = 6 PATTERNS

COMPARISON OF COMPREHENSIVE PEAK PATTERNS 45 → 65 (15/36)

COMPARISON OF COMPREHENSIVE PEAK PATTERNS 45 → 65 (16/36)

COMPARISON OF COMPREHENSIVE PEAK PATTERNS 45 → 65 (25/36)

COMPARISON OF COMPREHENSIVE PEAK PATTERNS 45 → 65 (26/36)

UV_Sim(45-67) = RMSD (107 vs 111)

TARGET FP ASSIGNING PROCESS 3
(POST-PROCESS: SPECIFYING CORRESPONDING PEAKS FROM PLURAL CANDIDATE PEAKS)

PEAK FEATURE VALUE PROCESS (PREPARATION OF REFERENCE GROUP FP)

FIG.92

| DAD-Det. | 203 | 204 | 205 | 206 | 207 | ... | 296 | 297 | 298 | 299 | 300 | ← DETECTION WAVELENGTH(nm) |
|---|---|---|---|---|---|---|---|---|---|---|---|---|
| 2.002167 | 0.236511 | 0.184536 | 0.193364 | 0.132561 | 0.192642 | ... | 0.031471 | 0.034332 | -0.00715 | 0.031471 | 0.000954 | |
| 2.008833 | 0.24128 | 0.193119 | 0.205994 | 0.142574 | 0.208947 | ... | 0.026703 | 0.034332 | -0.00572 | 0.039577 | -0.00095 | |
| 2.0155 | 0.247955 | 0.199795 | 0.216007 | 0.157356 | 0.22316 | ... | 0.01812 | 0.030994 | 0.001431 | 0.048637 | -0.00238 | |
| 2.022167 | 0.258923 | 0.208378 | 0.226498 | 0.173569 | 0.239372 | ... | 0.011444 | 0.027657 | 0.009537 | 0.052929 | -0.00238 | |
| 2.028833 | 0.270367 | 0.222206 | 0.237942 | 0.189304 | 0.252724 | ... | 0.008563 | 0.023842 | 0.016609 | 0.053406 | 0.000954 | |
| 2.0355 | 0.283241 | 0.240326 | 0.249336 | 0.208655 | 0.263214 | ... | 0.010967 | 0.017643 | 0.024319 | 0.050545 | 0.007153 | SIGNAL INTENSITY |
| 2.042167 | 0.300804 | 0.257969 | 0.259076 | 0.230789 | 0.271797 | ... | 0.015259 | 0.013828 | 0.032902 | 0.044823 | 0.014782 | |
| 2.048833 | 0.323772 | 0.273705 | 0.271797 | 0.252247 | 0.281811 | ... | 0.021935 | 0.015736 | 0.03767 | 0.039577 | 0.021935 | |
| 2.0555 | 0.352383 | 0.289917 | 0.283241 | 0.272274 | 0.293732 | ... | 0.027657 | 0.024319 | 0.035286 | 0.039577 | 0.025749 | |
| 2.062167 | 0.382423 | 0.306129 | 0.298977 | 0.293255 | 0.306129 | ... | 0.030994 | 0.033855 | 0.030518 | 0.0453 | 0.026226 | |
| 2.068833 | 0.418663 | 0.323772 | 0.325203 | 0.321388 | 0.319958 | ... | 0.030041 | 0.044823 | 0.027657 | 0.052929 | 0.025272 | |
| 2.0755 | 0.460625 | 0.346661 | 0.36335 | 0.352383 | 0.339985 | ... | 0.023365 | 0.050128 | 0.025749 | 0.052929 | 0.025272 | |
| 2.082167 | 0.511169 | 0.383377 | 0.412464 | 0.387669 | 0.366088 | ... | 0.015736 | 0.069141 | 0.021458 | 0.060081 | 0.02961 | |
| 2.088833 | 0.570297 | 0.435352 | 0.46597 | 0.431538 | 0.404451 | ... | 0.01049 | 0.071526 | 0.016212 | 0.066757 | 0.030994 | |
| . | . | . | . | . | . | ... | . | . | . | . | . | |
| . | . | . | . | . | . | ... | . | . | . | . | . | |
| 59.94883 | 268.1746 | 208.0026 | 160.8496 | 125.2108 | 98.0444 | ... | 0.685215 | 0.713348 | 0.657558 | 0.6814 | 0.639915 | |
| 59.9555 | 268.3458 | 208.1509 | 160.9607 | 125.2985 | 98.11354 | ... | 0.684738 | 0.716209 | 0.657092 | 0.680447 | 0.638485 | |
| 59.96217 | 268.5189 | 208.2896 | 161.0661 | 125.3639 | 98.176 | ... | 0.683308 | 0.712395 | 0.656605 | 0.679016 | 0.638962 | |
| 59.96883 | 268.693 | 208.4146 | 161.1671 | 125.4654 | 98.23656 | ... | 0.681877 | 0.702381 | 0.658999 | 0.676632 | 0.638485 | |
| 59.9755 | 268.858 | 208.528 | 161.2616 | 125.5417 | 98.29617 | ... | 0.6814 | 0.690937 | 0.656665 | 0.674725 | 0.639439 | |
| 59.98217 | 269.0167 | 208.6338 | 161.3479 | 125.6094 | 98.35434 | ... | 0.677997 | 0.681877 | 0.671397 | 0.677586 | 0.641823 | |
| 59.98883 | 269.1703 | 208.7336 | 161.428 | 125.67 | 98.40322 | ... | 0.677586 | 0.674725 | 0.672817 | 0.681877 | 0.644684 | |
| 59.9955 | 269.3124 | 208.8246 | 161.5 | 125.7191 | 98.45686 | ... | 0.674725 | 0.67091 | 0.671864 | 0.684738 | 0.646114 | |
| ↑ | | | | | | | | | | | | |
| RETENTION TIME (MINUTE) | | | | | | | | | | | | |

| HeaderName | HeaderValue | Flags | PeakType | RetTime | Area | Height | Width | ... | AreaPercent |
|---|---|---|---|---|---|---|---|---|---|
| NumberOfRows | 119 | 2 | 0 | 3.707342119 | 149.1629486 | 24.95453835 | 0.089736186 | ... | 1.65592471 |
| NumberOfCol | 21 | 32 | 0 | 3.925331116 | 9.433002472 | 1.965691447 | 0.075986251 | ... | 0.104719986 |
| NumberOfHead | 9 | 0 | 0 | 4.191194603 | 76.68452454 | 7.853868171 | 0.139910638 | ... | 0.851309257 |
| Modified | | 0 | 0 | 4.611611161 | 13.87264156 | 1.980707884 | 0.111711942 | ... | 0.154406408 |
| DateTime | | 2 | 0 | 4.961337090 | 140.9757385 | 14.70096874 | 0.137878135 | ... | 1.565034823 |
| IntegStart | 0 | 34 | 0 | 5.159340382 | 99.85542297 | 11.33316708 | 0.128793851 | ... | 1.10853978 |
| IntegEnd | 0 | 32 | 0 | 5.294465542 | 53.13053131 | 8.221708298 | 0.09939263 | ... | 0.589825628 |
| Errors | 0 | 0 | 0 | 5.789111137 | 30.95186141 | 3.765951157 | 0.129886866 | ... | 0.3436107 |
| IntegMode | 2 | 2 | 0 | 6.094525814 | 31.32414055 | 3.210045315 | 0.147845194 | ... | 0.347743316 |
| | | 34 | 0 | 6.300107956 | 31.41418457 | 3.775012255 | 0.121085465 | ... | 0.348742935 |
| | | 34 | 0 | 6.729168415 | 337.5288696 | 25.2769146 | 0.181787893 | ... | 2.747059177 |
| | | 32 | 0 | 7.14134407 | 128.023819 | 8.647929955 | 0.198809128 | ... | 1.421249762 |
| | | | | ... | ... | ... | ... | ... | ... |
| | | 0 | 0 | 53.9373436 | 15.90642643 | 1.939949751 | 0.127659678 | ... | 0.176564365 |
| | | 0 | 0 | 54.65077972 | 184.813980 | 19.59948349 | 0.144011214 | ... | 2.051170278 |
| | | 0 | 0 | 55.67518234 | 27.47231637 | 3.244963169 | 0.132773459 | ... | 0.304908063 |
| | | 0 | 0 | 56.46019745 | 29.83968353 | 2.449590445 | 0.169354796 | ... | 0.320162246 |
| | | 0 | 0 | 58.57313156 | 27.80234528 | 3.295254707 | 0.132432669 | ... | 0.308646289 |
| | | 0 | 0 | 59.13926315 | 56.54888153 | 5.344749451 | 0.157743646 | ... | 0.627774465 |
| | | | | RETENTION TIME (MINUTE) | PEAK AREA | PEAK HEIGHT | | | |

| RETENTION TIME (MINUTES) | PEAK HEIGHT | 220 | 221 | 222 | 223 | 224 | ... | 297 | 298 | 299 | 300 |
|---|---|---|---|---|---|---|---|---|---|---|---|
| 3.737342119 | 24.95453835 | 1 | 0.946986 | 0.893759 | 0.840576 | 0.78823 | ... | 0.102586 | 0.100416 | 0.098715 | 0.096144 |
| 3.925331116 | 1.965691447 | 1 | 0.96683 | 0.933062 | 0.899785 | 0.870409 | ... | 0.148963 | 0.145536 | 0.142684 | 0.139663 |
| 4.19194603 | 7.853883171 | 1 | 0.951353 | 0.905206 | 0.861315 | 0.822083 | ... | 0.858285 | 0.854974 | 0.853741 | 0.840492 |
| 4.611811161 | 1.980707884 | 1 | 0.966231 | 0.934717 | 0.902057 | 0.875049 | ... | 0.536362 | 0.505956 | 0.476373 | 0.444965 |
| 4.961337091 | 14.70096874 | 1 | 0.955319 | 0.911156 | 0.86973 | 0.833565 | ... | 0.207648 | 0.205572 | 0.206256 | 0.203732 |
| 5.159346382 | 11.33316708 | 1 | 0.931257 | 0.872526 | 0.82505 | 0.784413 | ... | 0.307071 | 0.303897 | 0.303275 | 0.302065 |
| 5.294465542 | 8.221708298 | 1 | 0.964049 | 0.924894 | 0.884593 | 0.847809 | ... | 0.425285 | 0.425389 | 0.427005 | 0.425129 |
| 5.789111137 | 3.765951157 | 1 | 0.952489 | 0.907016 | 0.860134 | 0.816736 | ... | 0.213523 | 0.211059 | 0.209317 | 0.207167 |
| 6.094525814 | 3.210045815 | 1 | 0.962636 | 0.923002 | 0.885678 | 0.852312 | ... | 0.154766 | 0.149539 | 0.148322 | 0.146499 |
| 6.300107956 | 3.775012255 | 1 | 0.961981 | 0.924493 | 0.883414 | 0.849061 | ... | 0.161201 | 0.157036 | 0.157225 | 0.154385 |
| 6.729166415 | 25.27681461 | 1 | 0.962209 | 0.929871 | 0.898246 | 0.870401 | ... | 0.151135 | 0.147084 | 0.146431 | 0.146295 |
| 7.141344407 | 8.647929955 | 1 | 0.962426 | 0.927794 | 0.892649 | 0.86298 | ... | 0.232462 | 0.226918 | 0.229348 | 0.227739 |
| ... | ... | . | . | . | . | . | ... | . | . | . | . |
| 47.04151535 | 21.10215197 | 1 | 0.946357 | 0.898223 | 0.85577 | 0.821346 | ... | 0.010336 | 0.003716 | 0.002477 | -0.00068 |
| 47.262146 | 12.78098965 | 1 | 0.949657 | 0.903063 | 0.858554 | 0.822637 | ... | -0.00652 | -0.031092 | -0.00954 | -0.031201 |
| 48.20507431 | 14.44223309 | 1 | 0.968953 | 0.938047 | 0.912835 | 0.889156 | ... | -0.016335 | 0.011633 | 0.010432 | 0.008717 |
| 48.81657410 | 0.599506497 | 1 | 0.91256 | 0.839608 | 0.770762 | 0.707069 | ... | -0.00419 | -0.00796 | -0.00323 | -0.00631 |
| 53.93734360 | 1.939949751 | 1 | 0.913891 | 0.839232 | 0.771945 | 0.711194 | ... | 0.028755 | 0.023475 | 0.02933 | 0.024207 |
| 54.65077972 | 19.59946349 | 1 | 0.969395 | 0.940957 | 0.915986 | 0.892413 | ... | 0.031448 | 0.027065 | 0.026584 | 0.023791 |
| 55.67518234 | 3.244963169 | 1 | 0.913510 | 0.839363 | 0.77256 | 0.718174 | ... | 0.035946 | 0.032818 | 0.033752 | 0.029644 |
| 56.46019745 | 2.449590445 | 1 | 0.923736 | 0.850274 | 0.768856 | 0.736999 | ... | 0.095911 | 0.087768 | 0.085269 | 0.077855 |
| 58.57313156 | 3.295254707 | 1 | 0.921651 | 0.849726 | 0.781768 | 0.714406 | ... | 0.04279 | 0.042018 | 0.043071 | 0.041386 |
| 59.13926315 | 5.344749451 | 1 | 0.918037 | 0.841855 | 0.775269 | 0.718988 | ... | 0.051443 | 0.050853 | 0.050617 | 0.048258 |

UV SPECTRUM
(DATA NORMALIZED WITH USE OF MAXIMUM VALUE OF "1" IN UV SPECTRUM OF DETECTION WAVELENGTH OF 220 TO 300 nm)

FIG.95

DETERMINATION RESULT FILE

| | | | | | | | | REFERENCE FP | | | | | | |
|---|---|---|---|---|---|---|---|---|---|---|---|---|---|---|
| | | | | | | | | 6 | 5 | 4 | 3 | 2 | 1 | ← PEAK NUMBER |
| | | | | | | | | 5.30 | 5.14 | 4.96 | 4.19 | 3.92 | 3.73 | ← RETENTION |
| | | | | | | | | 6.32 | 11.78 | 11.70 | 5.85 | 2.06 | 24.11 | ← PEAK HEIGHT |
| TARGET FP | 7 | 5.79 | 6.02 | | 114.46 | 888888 | 888888 | 888888 | 888888 | 888888 |
| | 6 | 5.16 | 17.23 | | 27.09 | 888888 | 888888 | 888888 | 888888 | 888888 |
| | 5 | 4.91 | 12.07 | | 148.07 | 4.05 | 36.11 | 888888 | 888888 | 888888 |
| | 4 | 4.50 | 3.12 | | 888888 | 27.67 | 3.27 | 888888 | 888888 | 888888 |
| | 3 | 4.17 | 5.26 | | 888888 | 888888 | 399.00 | 96.93 | 888888 | 888888 |
| | 2 | 3.87 | 2.63 | | 888888 | 888888 | 888888 | 4.59 | 194.22 | 800.99 |
| | 1 | 3.70 | 26.53 | | 888888 | 888888 | 888888 | 178.46 | 1.07 | 83.51 |
| | | | | | 888888 | 888888 | 888888 | 706.02 | 103.15 | 0.59 |
| | PEAK NUMBER | RETENTION | PEAK HEIGHT | | | | | | | |

ASSIGNMENT CANDIDATE PEAK SCORE TABLE — 131

REFERENCE FP

| PEAK NUMBER | 6 | 5 | 4 | 3 | 2 | 1 |
|---|---|---|---|---|---|---|
| RETENTION | 5.30 | 5.14 | 4.96 | 4.19 | 3.92 | 3.73 |
| PEAK HEIGHT | 6.32 | 11.78 | 11.70 | 5.85 | 2.06 | 24.11 |
| 1ST CANDIDATE (SCORE) | 27.09 | 4.05 | 3.27 | 4.59 | 1.07 | 0.59 |
| 2ND CANDIDATE (SCORE) |  | 27.67 | 36.11 | 96.93 |  | 83.51 |
| 3RD CANDIDATE (SCORE) |  |  |  |  |  |  |

⇒ SUBSTITUTE BY PEAK NUMBER OF CORRESPONDING REFERENCE FP3

ASSIGNMENT CANDIDATE PEAK NUMBER TABLE — 133

REFERENCE FP

| PEAK NUMBER | 6 | 5 | 4 | 3 | 2 | 1 |
|---|---|---|---|---|---|---|
| RETENTION | 5.30 | 5.14 | 4.96 | 4.19 | 3.92 | 3.73 |
| PEAK HEIGHT | 6.32 | 11.78 | 11.70 | 5.85 | 2.06 | 24.11 |
| 1ST CANDIDATE (NUMBER) | 6 | 6 | 5 | 3 | 2 | 1 |
| 2ND CANDIDATE (NUMBER) |  | 5 | 6 | 4 |  | 2 |
| 3RD CANDIDATE (NUMBER) |  |  |  |  |  |  |

FIG.97

COLLATION RESULT FILE 135

| REFERENCE FP PEAK NUMBER | REFERENCE FP RETENTION TIME | REFERENCE FP PEAK DATA | TARGET FP PEAK DATA |
|---|---|---|---|
| 6 | 5.77 | 0.00 | 6.02 |
| 5 | 5.30 | 6.32 | 0.00 |
| 4 | 5.14 | 11.78 | 17.28 |
|  | 4.96 | 11.70 | 12.07 |
| 3 | 4.62 | 0.00 | 3.12 |
| 2 | 4.19 | 5.85 | 5.26 |
|  | 3.92 | 2.06 | 2.63 |
| 1 | 3.73 | 24.11 | 26.53 |

| REFERENCE FP NAME | P1 | P2 | P3 | P4 | P5 | P6 | ... | P59 | P60 | P61 | P62 | ... |
|---|---|---|---|---|---|---|---|---|---|---|---|---|
| | 3.74 | 4.19 | 4.97 | 5.15 | 5.3 | 5.79 | ... | 54.63 | 55.65 | 58.56 | 59.13 | ... |
| REFERENCE FP01 | 24.95454 | 7.653988 | 14.70097 | 11.33317 | 8.221706 | 3.765951 | ... | 19.59948 | 3.244963 | 3.295255 | 5.344749 | ... |
| REFERENCE FP02 | 24.6409 | 5.85494 | 11.60693 | 13.23757 | 6.280517 | 4.881429 | ... | 29.02091 | 4.153991 | 5.682264 | 6.406809 | ... |
| REFERENCE FP03 | 23.41309 | 6.5214 | 12.75416 | 10.8262 | 6.856468 | 6.392059 | ... | 30.35544 | 3.58835 | 4.372816 | 6.136991 | ... |
| REFERENCE FP04 | 24.18606 | 7.157524 | 12.22046 | 11.29149 | 6.495505 | 5.647078 | ... | 26.83015 | 4.332538 | 3.193285 | 5.196698 | ... |
| REFERENCE FP05 | 24.39492 | 5.397262 | 11.57015 | 12.50576 | 7.025057 | 3.999343 | ... | 24.84871 | 3.971856 | 4.557617 | 6.042276 | ... |
| REFERENCE FP06 | 23.79346 | 6.513698 | 12.60938 | 11.06297 | 6.917242 | 5.876327 | ... | 31.78834 | 3.642261 | 3.717728 | 6.79227 | ... |
| ... | | | | | | | | | | | | |
| REFERENCE FP74 | 24.34318 | 7.228315 | 12.54595 | 11.2069 | 8.476972 | 5.93889 | ... | 28.67843 | 3.249246 | 3.390216 | 4.883753 | ... |
| REFERENCE FP75 | 24.29594 | 4.890856 | 9.386555 | 12.18806 | 5.953234 | 5.845267 | ... | 31.22406 | 3.530962 | 3.596855 | 6.64429 | ... |
| REFERENCE FP76 | 23.70935 | 5.477376 | 12.64439 | 10.87211 | 8.865798 | 5.588339 | ... | 31.43591 | 4.058423 | 4.047005 | 6.010718 | ... |
| REFERENCE FP77 | 24.38124 | 6.815894 | 12.57119 | 10.90901 | 6.628439 | 5.443465 | ... | 27.19673 | 3.225539 | 2.963221 | 5.730851 | ... |
| REFERENCE FP78 | 25.64963 | 5.101483 | 9.62847 | 12.87496 | 8.267442 | 7.07402 | ... | 32.01024 | 3.428246 | 4.079995 | 6.910386 | ... |
| REFERENCE FP79 | 24.56847 | 6.399944 | 11.81665 | 11.60369 | 6.251297 | 4.853024 | ... | 30.00299 | 3.375931 | 3.21543 | 5.605225 | ... |
| REFERENCE FP80 | 25.70864 | 6.55578 | 11.56849 | 11.24369 | 7.709552 | 5.818771 | ... | 28.76077 | 3.235093 | 4.217419 | 5.674382 | ... |
| REFERENCE FP81 | 24.95631 | 6.862163 | 12.10639 | 11.19636 | 7.243775 | 5.955506 | ... | 27.85074 | 3.156492 | 2.711058 | 5.909272 | ... |
| REFERENCE FP82 | 25.13536 | 6.996024 | 12.17565 | 11.21373 | 7.206914 | 5.948516 | ... | 28.11332 | 3.297449 | 3.585945 | 5.951647 | ... |

REFERENCE GROUP FP PEAK NUMBER
REFERENCE GROUP FP RETENTION TIME (MINUTE)
PEAK HEIGHT

FIG.99

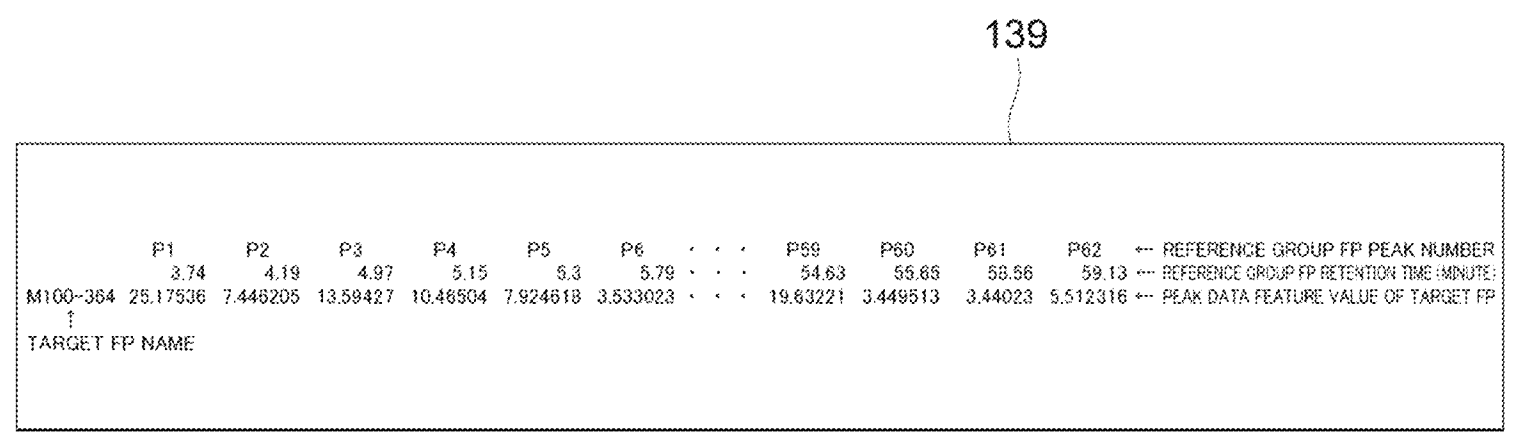

|  | P1 | P2 | P3 | P4 | P5 | P6 | ... | P59 | P60 | P61 | P62 | ← REFERENCE GROUP FP PEAK NUMBER |
|---|---|---|---|---|---|---|---|---|---|---|---|---|
|  | 3.74 | 4.19 | 4.97 | 5.15 | 5.3 | 5.79 | ... | 54.63 | 55.65 | 56.86 | 59.13 | ← REFERENCE GROUP FP RETENTION TIME:MINUTE |
| M100-364 | 25.17536 | 7.446205 | 13.59427 | 10.48504 | 7.924618 | 3.533023 | ... | 19.63221 | 3.449513 | 3.44023 | 5.512316 | ← PEAK DATA FEATURE VALUE OF TARGET FP |
| ↑ |
| TARGET FP NAME |

| UV DATA | a1 | a2 | a3 | a4 | a5 | a6 | a7 |
|---|---|---|---|---|---|---|---|
| MOVING AVERAGE <<CASE OF INTERVAL 1 (w1 = 3)>> | | | m1=(a1+a2+a3)/3 | m2=(a2+a3+a4)/3 | m3=(a3+a4+a5)/3 | m4=(a4+a5+a6)/3 | m5=(a5+a6+a7)/3 |
| MOVING INCLINATION <<CASE OF INTERVAL 2 (w2 = 3)>> | | | | | s1=(m3−m1)/3 | s1=(m4−m2)/3 | s1=(m5−m3)/3 |

METHOD OF FORMULATING A MULTICOMPONENT DRUG USING BASES EVALUATED BY MAHALANOBIS TAGUCHI METHOD

BACKGROUND OF THE INVENTION

1. Field of the Invention

The present invention relates to a method of and an apparatus for formulating a multicomponent drug such as kampo medicine.

2. Description of the Prior Art

As multicomponent materials, for example, there are natural-product-originated drugs such as kampo medicines that are drugs (hereinafter, referred to as multicomponent drugs) composed of multiple components. Quantitative and qualitative profiles in such drugs change due to a geological factor, an ecological factor, a collecting season, a collecting area, a collecting aetas, weather during the growing period and the like of raw material crude drugs.

Thus, for such multicomponent drugs and the like, predetermined criteria are regulated as qualities for securing the safety and the effectiveness thereof, and national supervising agencies, chemical organizations, manufacturers, and the like perform quality evaluations based on the criteria.

Then, a multicomponent drug meeting the criteria for productization is subjected to dosage form processing to produce granules, tablets or the like and thereafter is made into a product through packing.

In general, however, the determination criteria on the quality and the like for a multicomponent drug are set based on the content and the like of one or several distinctive components selected from components in the multicomponent drug.

For example, in 1986. Pharm Tech Japan vol. 28, No. 3, pp 67 to 71, in a case that effective components of a multicomponent drug are not identified, it selects a plurality of components that have physical properties such as a quantitative analyzability, high water-solubility, undegradability in hot water, and non-chemical reactivity with other components and uses the contents of these components acquired through chemical analysis as evaluation criteria.

In addition, it is known to apply chromatography to a multicomponent drug, obtain an ultraviolet-visible absorption spectrum for each retention time, and set evaluation criteria based on some pieces of component information included therein.

For example, according to JP 2002-214215 A, some peaks included in HPLC chromatogram data (hereinafter, referred to as a chromatogram) are selected and encoded as barcodes, thereby evaluating a multicomponent drug.

In such methods, however, evaluation targets are limited to "contents of specific components" or "peaks of specific components in chromatogram," and thus only some components contained in a multicomponent drug are set as the evaluation targets. Accordingly, since a multicomponent drug includes many components other than the components that are the evaluation targets, such methods are insufficient as a method of evaluating the multicomponent drug in terms of accuracy.

In order to accurately evaluate the quality of a multicomponent drug, it is necessary to evaluate a pattern that covers information of all peaks or almost all peaks without small peaks corresponding to several %. Accordingly, it is necessary to associate all the peaks or almost all peaks with each other between multicomponent drugs.

However, it is difficult to efficiently associate a plurality of peaks with high accuracy. This interferes with an efficient evaluation of multicomponent drugs with high accuracy.

Described more, crude drugs are natural products, and therefore, multicomponent drugs even which have the same product name may have slightly different components. Hence, even if drugs have the same quality, content ratios of components thereof may be different from each other or a component present in one drug may not be present in the other drug (hereinafter, referred to as an inter-drug error). In addition, there is also a factor that peak intensity or peak elution time in a chromatogram has no precise repeatability (hereinafter, referred to as an analysis error). Accordingly, all peaks or almost all peaks may not be associated with peaks that are originated from the same components between the multicomponent drugs (hereinafter, referred to as peak assignment), thereby interfering with an efficient evaluation with high accuracy.

If quality evaluation of a multicomponent drug can be conducted with high accuracy, it reduces the variation in multicomponent drugs to be subjected to the dosage form processing and the packing. As a result, high-quality multicomponent drugs can be made into products.

SUMMARY OF THE INVENTION

A problem to be solved is that there is a limit on an efficient evaluation of a pattern covering information of peaks with high accuracy with use of an existing evaluation technique and it is difficult to make multicomponent drugs into products with little variation.

A first aspect of the present invention provides a method of formulating a multicomponent drug capable of surely making a multicomponent drug meeting criteria for productization with high accuracy into a product. The method includes obtaining a chromatogram from a base of a multicomponent drug, evaluating whether the base meets criteria for productization based on the obtained chromatogram, and subjecting the base determined in the evaluating of the base as an accepted one meeting the criteria for productization to dosage form processing, to produce a formulated drug having a given dosage-form.

Evaluating whether the base meets the criteria includes preparing a target fingerprint composed of peaks and retention time points of the peaks detected from the chromatogram, preparing a peak pattern for an assignment target peak of the target fingerprint, the peak pattern configured by n+1 peaks that include the assignment target peak and n peripheral peaks being present on at least one of sides located in front and in the rear of the assignment target peak in a time axis direction, preparing peak patterns for respective assignment candidate peaks of a reference fingerprint, the reference fingerprint corresponding to the target fingerprint and being composed of peaks and retention time points of the peaks detected from a chromatogram of a multicomponent drug that is evaluation criteria, the assignment candidate peaks having differences in retention time relative to the assignment target peak within a set range, and each one of the peak patterns configured by n+1 peaks that includes a corresponding one of the assignment candidate peaks and n peripheral peaks being present on at least one of sides located in front and in the rear of said corresponding one of the assignment candidate peaks in the time axis direction, comparing the peak pattern for the assignment target peak and the peak patterns for the assignment candidate peaks to specify corresponding peaks between the target fingerprint and the reference fingerprint, and evaluating assigned peaks of the target fingerprint that are specified in the comparing of the peak patterns by comparison with peaks of a plurality of reference fingerprints that are evaluation criteria and finding a Mahalanobis distance using Mahalanobis-Taguchi method to determine a base having a Mahalanobis distance being equal to or less than a threshold value as the accepted one meeting the criteria for productization.

A second aspect of the present invention provides an apparatus for formulating a multicomponent drug. The apparatus includes a chromatographic device obtaining a chromatogram from a base of a multicomponent drug, an evaluating device evaluating whether the base meets criteria for productization based on the obtained chromatogram, and a dosage form processing device subjecting the base determined in the evaluating of the base as an accepted one meeting the criteria for productization device to dosage form processing, to produce a formulated drug having a given dosage form.

The evaluating device includes a fingerprint preparing part preparing a target fingerprint composed of peaks and retention time points of the peaks detected from the chromatogram of the multicomponent drug that is an evaluation target, a peak pattern preparing part preparing a peak pattern for an assignment target peak of the target fingerprint, the peak pattern configured by n+1 peaks that include the assignment target peak and n peripheral peaks being present on at least one of sides located in front and in the rear of the assignment target peak in a time axis direction and preparing peak patterns for respective assignment candidate peaks of a reference fingerprint, the reference fingerprint corresponding to the target fingerprint and being composed of peaks and retention time points of the peaks detected from a chromatogram of a multicomponent drug that is evaluation criteria, the assignment candidate peaks having differences in retention time relative to the assignment target peak within a set range, and each one of the peak patterns configured by n+1 peaks that includes a corresponding one of the assignment candidate peaks and n peripheral peaks being present on at least one of sides located in front and in the rear of said corresponding one of the assignment candidate peaks in the time axis direction, a peak assigning part comparing the peak pattern for the assignment target peak and the peak patterns for the assignment candidate peaks to specify corresponding peaks between the target fingerprint and the reference fingerprint, and an evaluating part evaluating assigned peaks of the target fingerprint that are specified in the peak assigning part by comparison with peaks of a plurality of reference fingerprints that are evaluation criteria and finding a Mahalanobis distance using Mahalanobis-Taguchi method to determine a base having a Mahalanobis distance being equal to or less than a threshold value as the accepted one meeting the criteria for productization.

According to the first aspect, peak assignment can be performed based on pattern comparison between the peak patterns. Accordingly, the peaks of the target fingerprint can be efficiently assigned to the respective peaks of the reference fingerprint with high accuracy, thereby further improving the accuracy and the efficiency of the evaluation of whether the base of the multicomponent drug meets the criteria for productization.

As a result, the first aspect of the present invention subjects the base of the multicomponent drug determined as an accepted one meeting the criteria for productization with high accuracy to the dosage form processing to make the base into a product. This reduces the variation in multicomponent drugs to be subjected to the dosage form processing and realizes the high quality of the products.

The second aspect of the present invention operates each part of the evaluating device to further improve the accuracy and the efficiency of the evaluation of whether the base of the multicomponent drug meets the criteria for productization.

As a result, the second aspect of the present invention also subjects the base of the multicomponent drug determined as an accepted one meeting the criteria for productization with high accuracy to the dosage form processing to make the base into a product. This reduces the variation in multicomponent drugs to be subjected to the dosage form processing and realizes the high quality of the products.

BRIEF DESCRIPTION OF THE DRAWINGS

FIGS. 4A to 4C are graphs illustrating FPs of respective drugs in which FIG. A is a drug A, FIG. B is a drug B, and FIG. C is a drug C according to the first embodiment;

FIG. 8 is a table illustrating the numbers of matches in a retention time appearance distance between the target FP and the reference FP according to the first embodiment;

FIG. 9 is a table illustrating the degrees of matching between the retention time appearance patterns of the target FP and the reference FP according to the first embodiment;

FIG. 92 is a table illustrating a data example of a 3D chromatogram according to the first embodiment;

FIG. 93 is a table illustrating a data example of peak information according to the first embodiment;

FIG. 94 is a table illustrating a FP data example according to the first embodiment;

FIG. 95 is a table illustrating an assignment score calculation result (determination result) file example of a target FP with respect to a reference FP according to the first embodiment;

FIG. 96 is a table illustrating a process of collating corresponding peaks between a target FP and a reference FP according to the first embodiment;

FIG. 97 is a table illustrating a collation result file example according to the first embodiment;

FIG. 98 is a table illustrating a data example of a reference group FP according to the first embodiment;

FIG. 99 is a table illustrating a target FP peak feature value file example according to the first embodiment;

FIG. 101 is a table illustrating a calculating example of moving averages and moving inclinations according to the first embodiment;

DETAILED DESCRIPTION OF EMBODIMENTS

Embodiments of the present invention accomplish the object capable of surely making a multicomponent drug highly meeting criteria for productization into a product. For this, the embodiments evaluate a multicomponent drug with high accuracy and subject the multicomponent drug to dosage form processing according to the evaluating result.

The evaluating of the multicomponent drug is realized by comparing and evaluating results as feature values that are acquired by assigning peaks of a target FP to respective peaks of a reference group FP all together with high accuracy and high efficiency.

The assigning of peaks all together with high accuracy and high efficiency is realized by comparing peak patterns that are acquired by patterning peaks of the target FP and a reference FP with use of peaks that are present at least on one of sides located in front and in the rear of the peaks to be patterned in the direction of the time axis.

The first embodiment of the present invention provides a formulating method and an formulating apparatus serving as a method of and an apparatus for formulating a multicomponent drug, the formulating method and the formulating apparatus subjecting the base of the multicomponent drug to dosage form processing to produce a formulated drug having a given dosage form.

A multicomponent drug is defined as a drug that contains a plurality of effective chemical components. Examples of the multicomponent drug include a crude drug, a combination of crude drugs, an extract thereof, and a kampo medicine, but are not limited thereto. In addition, the dosage form is not particularly limited, and, examples include a liquid medicine, an extract, a capsule, a granule, a pill, suspension emulsion, a powder, a spiritus, a tablet, an infusion decoction, a tincture, a troche, aromatic water, a fluid extract, which are specified in "general rule for preparations" of "The Japanese Pharmacopoeia", Fifteenth Edition. The embodiment exemplifies that granules of a kampo medicine as a formulated-multicomponent drug are produced from a raw material crude drug. The base of the multicomponent drug is an extract or essence extracted from the raw material crude drug in powder form, liquid form or the like. According to the embodiment, the base of the multicomponent drug is a powder extract as explained later.

Specific examples of the kampo medicine are written in Industry Standard and Voluntarily Revision of "Precautions" in 148 Prescriptions for Medical Kampo Drug Formulation and in Guide to General Kampo Prescription (1978).

Figure 1A:
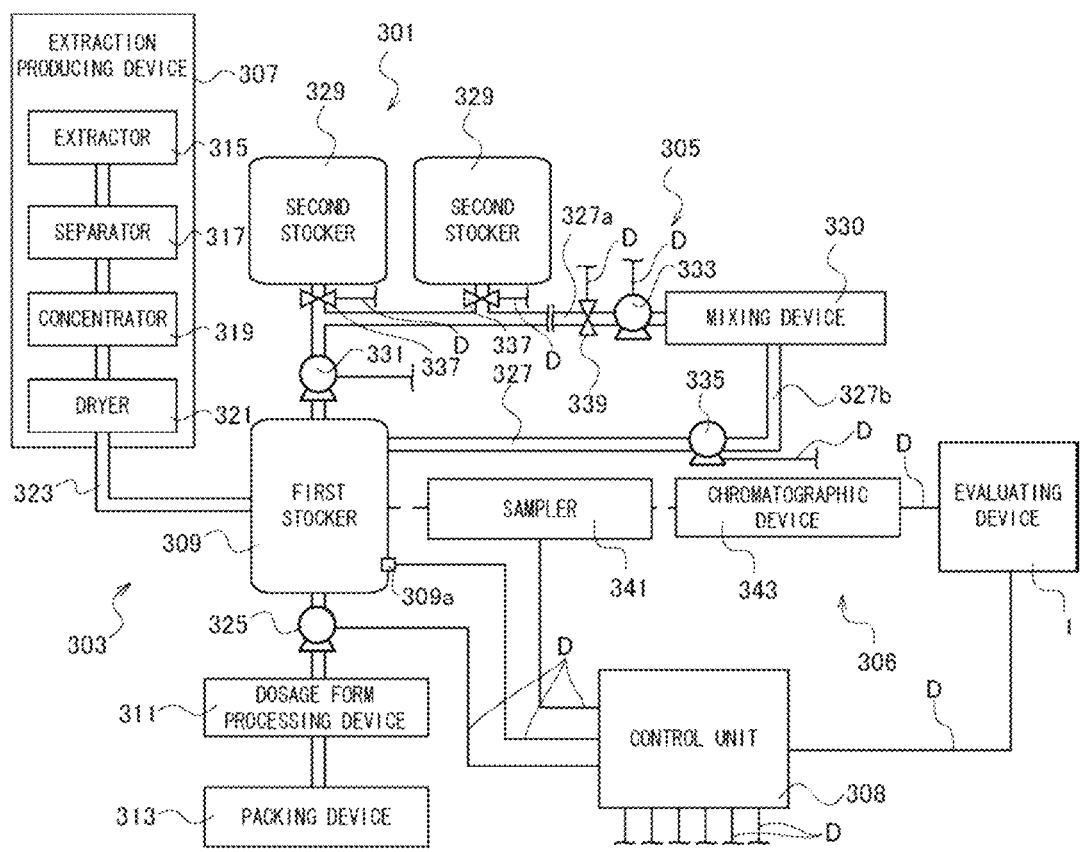
FIG. 1A is a schematic block diagram illustrating a formulating apparatus according to a first embodiment of the present invention.

FIG. 1A is a schematic block diagram illustrating the formulating apparatus 301 according to the first embodiment. The formulating apparatus 301 has a formulating line 303, a mixing line 305, and an evaluating line 306, and a control unit 308.

The formulating line 303 includes a first pipeline 323 serving as a first conveyor, an extract producing device 307 serving as a base producing device, a first stocker 309, a dosage form processing device 311, and a packing device 313. With this, the formulating line 303 is configured to extract an essence as the base of the multicomponent drug from the raw material crude drug, subject the extracted essence or extract of the multicomponent drug meeting criteria for productization to dosage form processing to produce a formulated drug and thereafter pack the formulated drug. The evaluation of whether the extract meets the criteria is conducted at the evaluating line 306 as explained later.

The first pipeline 323 is led from the extract producing device 307 to the packing device 313 through the first stocker 309 and the dosage form processing device 311, convey an extract produced by the extract producing device 307.

The extract producing device 307 is composed of an extractor 315, a separator 317, a concentrator 319 and a dryer 321 that are connected to each other through the first pipeline 323. The configuration of the extract producing device 307 is an example and therefore may exclude the dryer 321, for example. The excluded dryer may be laid downstream of the first stocker 309. The embodiment produces the extract with the extract producing device 307. The extract producing device 307 and the production of the extract, however, may be omitted.

The extractor 315 receives the raw material crude drug therein and extracts an essence as a liquid extract using a solvent. The extractor 315 is realized by, for example, a multipurpose extractor "TEX2015" manufactured by IZUMI FOOD MACHINERY Co., Ltd., a rotocel extractor manufactured by Mitsubishi Kakoki Kaisha, Ltd., a centrifugal extractor "Ultrex" manufactured by Hitachi, Ltd., or the like.

The raw material crude drug in this embodiment is cut and compounded in advance. The raw material crude drug, however, may be an uncut one. As the solvent, water, ethanol, acetic acid and the like are exemplified for hot and cold extraction. In a case of the kampo medicine according to the embodiment, it is preferred that the hot extraction is conducted at temperature of 90-100° C. using water as the solvent. The liquid extract, i.e., extraction liquid produced at the extractor 315 is conveyed to the separator 317 through the first pipeline 323.

The separator 317 removes impurities from the extraction liquid through solid-liquid separation. The separator 317 is realized by, for example, a basket type centrifugal separator "TEC-48" or decanter type centrifugal separator manufactured by TANABE WILLTEC INC., the centrifugal extractor "Ultrex" manufactured by Hitachi, Ltd., or the like. From the separator 317, the extraction liquid is conveyed to the concentrator 319 through the first pipeline 323.

The concentrator 319 concentrates or condenses the extraction liquid and is realized by, for example, flash method concentration equipment "REV-100/90" or global concentration equipment manufactured by HISAKA WORKS, LTD., a centrifugal thin film concentrator or centritherm evaporator Alfa Laval Ltd., or the like. As the concentration method for the extraction liquid, vacuum concentration is used in general. As the condition of the vacuum concentration for the kampo medicine, the degree of vacuum is set in a range of 30-760 mmHg, the evaporating temperature is set equal to or less than 100° C., preferably in a range of 30-50° C., and the like, for example. The concentrated extraction liquid, i.e., concentrated liquid is conveyed from the concentrator 319 to the dryer 321 through the first pipeline 323.

The dryer 321 dries the concentrated liquid to convert the same into powder. The dryer 321 is realized by, for example, a vacuum belt dryer (SBD) manufactured by HISAKA WORKS, LTD., a spray dryer "OC-20" manufactured by OKAWARA MFG. CO., LTD., a spray dryer for producing medicines manufactured by GEA Process Engineering Inc., or the like.

The drying method employs but is not limited to a spray drying method, a vacuum drying method or a freeze drying method depending on a kind of dryer 321. For example, the spray drying method sprays with an atomizer the concentrated liquid into a thermal current within a drying chamber maintained at high temperature of 60-300° C. so that the solvent instantly evaporates to dry the concentrated liquid. The vacuum drying method dries, under the condition in which the degree of vacuum is equal to or less than the 760 mmHg and the temperature is in a range of 5-100° C., the concentrated liquid that is the extraction liquid sufficiently subjected to the vacuum concentration. The freeze drying method freezes the concentrated liquid at the temperature of −80-0° C. and then dries the same by directly sublimating the solvent in a vacuum state being equal to or less than 1 mmHg. The powder extract due to such drying is conveyed to the first stocker 309 through the first pipeline 323.

The first stocker 309 is arranged or laid downstream of the extract producing device 307 on the first pipeline 323 to accommodate the powder extract produced at the extract producing device 307. In particular, the first stocker 309 tentatively stores the powder extract during the evaluating line 306 evaluates the powder extract.

The first stocker 309 is realized by, for example, a general tank or the like. On the downstream side of the first stocker 309, the first pipeline 323 has a blower 325. With the blower 325, the powder extract is conveyed from the first stocker 309 to the dosage form processing device 311.

The dosage form processing device 311 subjects the powder extract of the multicomponent drug to the dosage form processing to make the same into a formulated drug having a given dosage form. For example, the dosage form processing device 311 produces granules or tablets according to an intended dosage form.

According to the embodiment, the dosage form processing device 311 is configured to produce the granules and realized by, for example, a horizontal extrusion granulator "Granumaster" manufactured by OKAWARA MFG. CO., LTD., a multistage roll granulator manufactured by Kurimoto, Ltd., or the like. In the case of producing tablets, the dosage form processing device 311 may be realized by, for example, a tableting machine "AQUARIUS G" manufactured by KIKUSUI SEISAKUSHO LTD., "αX-MS type" medium-sized tableting machine manufactured by HATA TEKKOSHO CO., LTD., or the like.

The granules produced at the dosage form processing device 311 are conveyed to the packing device 313 through the first pipeline 323.

The packing device 313 subdivides and packs the granules or tablets to complete productization. The packing device 313 for the granules is realized by, for example, a powder and granule packing machine "MS101" manufactured by SANKO MACHINERY CO., LTD. or the like. In the case of the tablets, the packing device 313 is realized by, for example, a tablet four side sealing machine manufacture by ASAHI SHIKO Corporation or the like.

The mixing line 305 includes a second pipeline 327, a plurality of second stockers 329, and a mixing device 330. With this, the mixing line 305 is configured to obtain a powder extract that does not meet the criteria for productization from the first stocker 309 and store the same, mix two or more stored powder extracts and return the mixed powder extracts to the first stocker 309. In FIG. 1A, two second stockers 329 are indicated, however, the number of the second stockers 329 is not limited thereto.

The second pipeline 327 is led from and back to the first stocker 309 so as to make a loop. The second pipeline 327 includes a taking-out line 327a led out from the first stocker 309 and a return line 327b returning back to the first stocker 309.

The taking-out line 327a has a blower 331 for storing a powder extract and a blower 333 for mixing powder extracts. The return line 327b has a blower 335 for returning a powder extract.

Further, the second pipeline 327 has valves 337 and 339 laid upstream of the second stockers 329 and the mixing device 330 for storing a powder extract and mixing powder extracts, respectively.

The taking-out line 327a is configured to selectively convey a powder extract to one of the second stockers 329 according to control of the blower 331 and the valves 337. Further, the taking-out line 327a is configured to selectively take out stored powder extracts from the second stockers 329 and convey the same to the mixing device 330 according to control of the blower 333 and the valves 337 and 339. The return line 327b is configured to convey a mixed extract as a mixed base from the mixing device 330 to the first stocker 309 according to control of the blower 335.

In this specification, the powder extract means the individual powder extract produced by the extract producing device 307 and the mixed extract means a mixture of the individual powder extracts.

The second stockers 329 are laid on the second pipeline 327, in particular the taking-out line 327a to store a powder extract that does not meet the criteria for productization and is conveyed from the first stoker 309. The second stocker 329 is realized by, for example, a general tank or the like similar to the first stocker 309.

The mixing device 330 is arranged on the second pipeline 327 so that the taking-out line 327a is connected to an inlet of the mixing device 330 and the return line 327b is connected to an outlet thereof. The mixing device 330 mixes two or more stored powder extracts to produce a mixed extract. The produced mixed extract is conveyed to the first stocker 309 through the return line 327a.

The evaluating line 306 includes a sampler 341, a chromatographic device 343, and an evaluating device 1 and is configured to evaluate or examine whether a powder extract or a mixed extract in the first stocker 309 meets the criteria for productization.

The sampler 341 is arranged accessibly to the first stocker 309 and the chromatographic device 343. The sampler 341 obtains a sample of the powder extract or the mixed extract from the first stocker 309 and supplies the sample to the chromatographic device 343. According to the embodiment, the sampler 341 is realized by, for example, a powder sampler or the like that is driven by an actuator (not illustrated).

The chromatographic device 343 subjects the sample of the powder or mixed extract to high performance liquid chromatograph (HPLC) to prepare and obtain a three-dimensional chromatogram (3D chromatogram). The chromatographic device 343 is realized by a commercially-available device such as "Agilent 1100 system" manufactured by Agilent Technologies, or the like. Furthermore, the chromatography is not limited to the HPLC, and any other type of chromatography may be employed. The chromatographic device 343 is connected to the evaluating device 1 through a data line D and outputs the prepared 3D chromatogram to the evaluating device 1.

The evaluating device 1 has a function to evaluate or determine whether the powder or mixed extract meets the criteria for productization based on the input 3D chromatogram. The details of the evaluating device 1 will be explained later. The evaluating device 1 is connected to the control unit 308 through a data line D and outputs the determination or evaluating result to the control unit 308.

The control unit 308 is configured by a computer and controls each part of the formulating apparatus 301. According to the embodiment, the control unit 308 is a discrete unit separated from the evaluating device 1. The control unit 308 and the evaluating device 1, however, may be configured by a single unit.

The control unit 308 of this embodiment is connected to a sensor 309a of the first stocker 309, the sampler 341, the blowers 325, 331, 333 and 335, and the valves 337 and 339 through data lines D, respectively.

Then, the control unit 308 automatically causes the evaluating device 1 to evaluate whether the powder extract (or mixed extract) meets the criteria for productization, the dosage form processing device 311 to make the powder extract (or mixed extract) into the granules and the packing device 313 to pack the granules.

In particular, the control unit 308 determines a conveying state of the powder extract to the first stocker 309 based on a detecting signal sent from the sensor 309a of the first stocker 309. The sensor 309a is for example a load cell to detect the weight of the first stocker 309 and output the detecting signal to the control unit 308. The sensor 309a may be a flowmeter or the like.

The determination of the conveying state is performed by, for example, monitoring the rate of change of the weight of the first stocker 309. If the rate of change of the weight becomes zero, it can be determined that the conveying of the powder extract is completed. If the rate of change of the weight becomes reduced, it can be determined that the conveying of the powder extract approaches completion. The sensor may be provided to the extract producing device 307 to determine a producing state of the powder extract.

According to the conveying state of the powder extract, the control unit 308 controls the sampler 341 to feed the sample of the powder extract to the chromatographic device 343. The feeding of the sample can be performed whenever a conveyed amount of the powder extract in the first stocker 309 is sufficient to obtain the sample.

Further, the control unit 308 causes the first pipeline 323 to convey the powder extract from the first stocker 309 to the dosage form processing device 311 or one of the second stockers 329 based on the determination or evaluating result sent from the evaluating device 1.

In particular, if the evaluating device 1 determines that the powder extract meets the criteria for productization, the control unit 308 controls the first pipeline 323, in particular the blower 325 to convey the powder extract from the first stocker 309 to the dosage form processing device 311.

If the evaluating device 1 determines that the powder extract does not meet the criteria for productization, the control unit 308 controls the second pipeline 327, in particular the blower 331 and the valves 337 to convey the powder extract from the first stocker 309 to an empty one of the second stockers 329 and store the same. The determination whether the second stockers 329 are empty may be performed on the basis of detecting signals sent from sensors such as load cell provided to the respective second stockers 329.

Further, the control unit 308 controls the second pipeline 327, in particular the valves 337 and 339 and the blower 333 to convey two or more stored powder extracts in the second stockers 329 to the mixing device 330 and mix the same.

The mixing is initiated at any time during the first stocker is empty. It, however, is required that the extract producing device 307 does not start to produce the next powder extract. The determination of whether the first stocker 309 is empty can be conducted based on the detecting signal from the sensor 309a.

The selection of powder extracts to be mixed and the mixing rate is based on Mahalanobis distance (hereinafter, referred to as MD value). As explained later, the evaluation of the powder extract finds a MD value using Mahalanobis-Taguchi method (hereinafter, referred to as MT method) and determines that a powder extract meets the criteria for productization if the found MD value is equal to or less than a threshold value. According to the embodiment, the powder extracts to be mixed and the mixing rate are determined using the MD values and the determined powder extracts are mixed with the determined mixing rate to produce a mixed extract having a MD value being equal to or less than the threshold value.

After producing the mixed extract, the control unit 308 controls the second pipeline 327, in particular the blower 335 to convey the mixed extract from the mixing device 330 to the first stocker 309 and store the same. In response to the storage of the mixed extract, the control unit 308 controls the sampler 341 to feed the sample of the mixed extract to the chromatographic device 343.

As a result, the evaluating device 1 outputs the determination or evaluating result to the control unit 308. The control unit 308 conveys the mixed extract from the first stocker 309 to the dosage form processing device 311 or one of the second stockers 329 in the same way as the aforementioned powder extract.

Figure 1B:
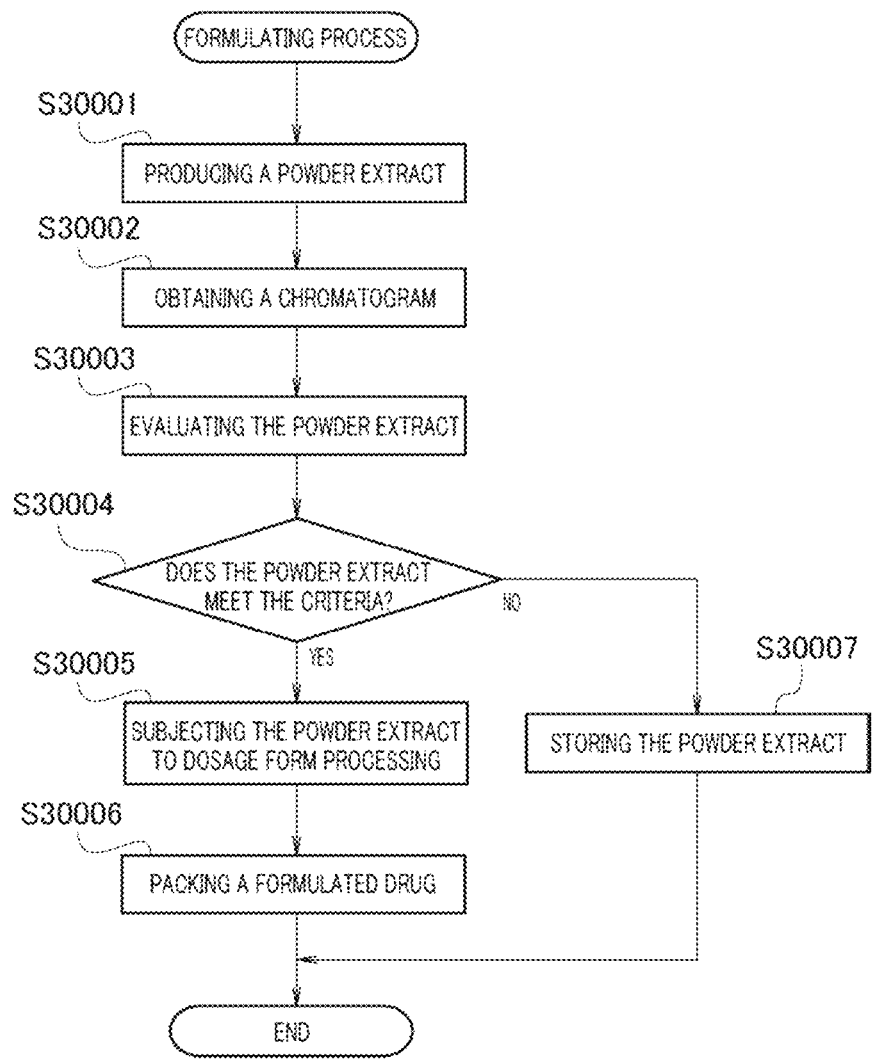
FIG. 1B is a flowchart illustrating a formulating process of a formulating method according to the first embodiment.

FIG. 1B is a flowchart illustrating a formulating process of a formulating method according to the first embodiment.

The formulating process of the formulating method of the first embodiment is started by putting the raw material crude drug into the extractor 315 of the extract producing device 307.

First, in Step S30001, a powder extract is produced. Namely, the extract producing device 307 extracts an essence as a liquid extract or an extraction liquid from the raw material crude drug at the extractor 315, subjects the extraction liquid to the solid-liquid separation at the separator 317, concentrates the extraction liquid to produce a concentrated liquid at the concentrator 319, and dries the concentrated liquid to make the same into a powder extract at the dryer 321 in sequence.

In Step S30002, a chromatogram is obtained. Namely, the powder extract produced in Step S30001 is conveyed from the extract producing device 307 to the first stocker 309 and is accommodated in the first stocker 309.

Figure 3A:
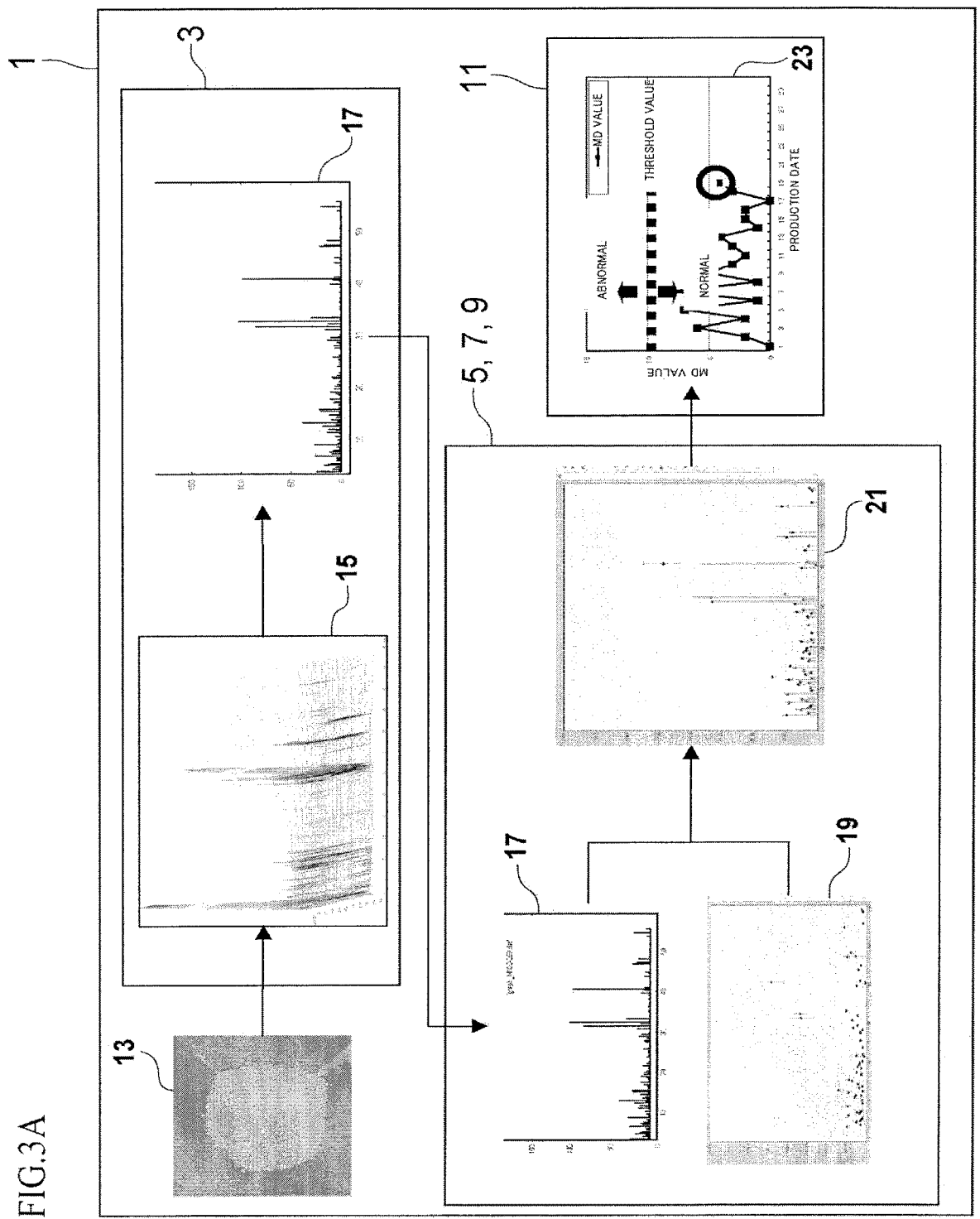
FIG. 3A is a block diagram illustrating procedures of evaluating a multicomponent drug according to the first embodiment.
Figure 3B:
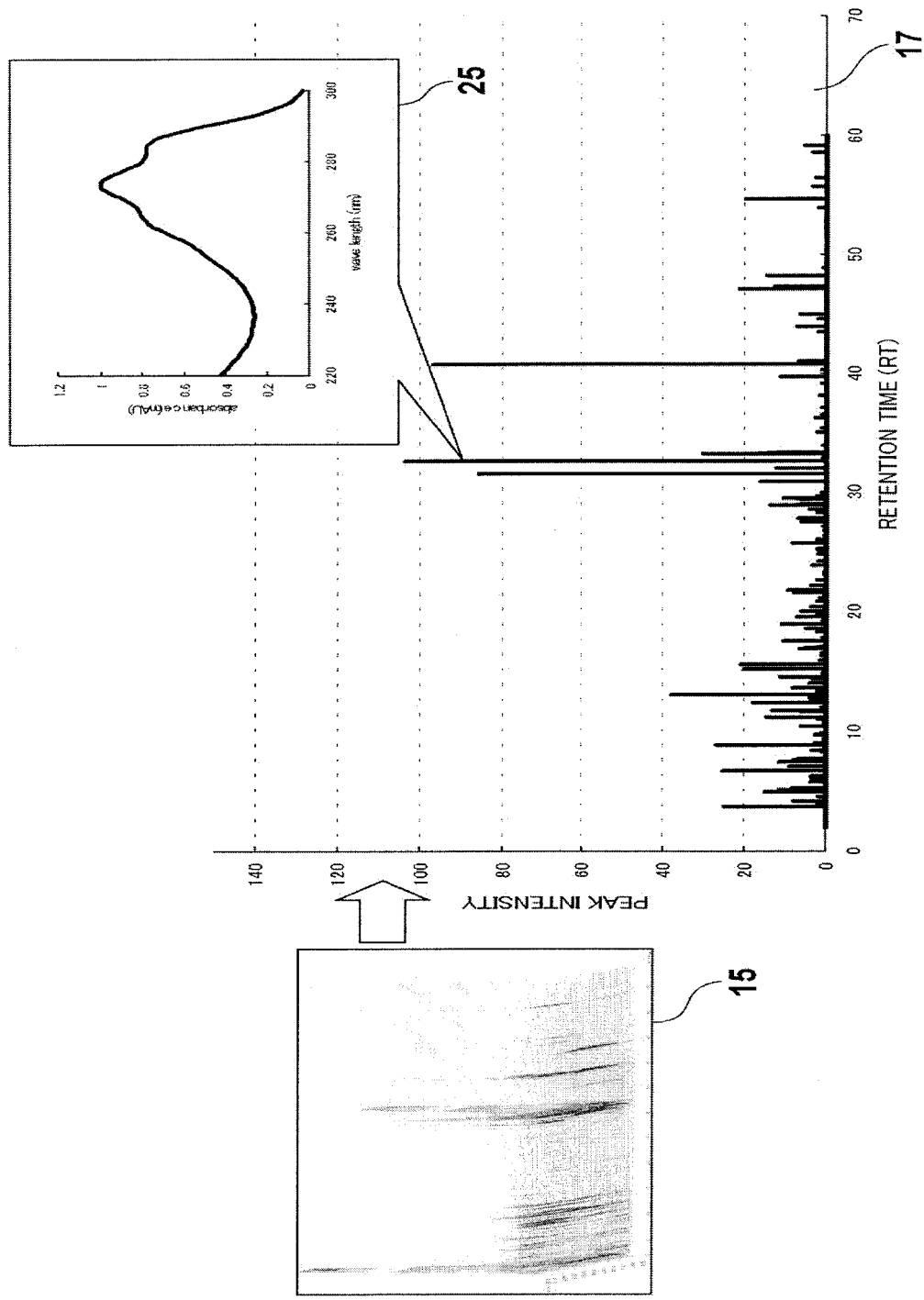
FIG. 3B is an explanatory diagram of a fingerprint (hereinafter, referred to as FP) that is prepared from a three-dimensional chromatogram data (hereinafter, referred to as a 3D chromatogram) according to the first embodiment.

At this time, the control unit 308 causes the sampler 341 to obtain a sample of the powder extract and feed the obtained sample to the chromatographic device 343 according to the conveying state of the powder extract to the first stocker 309. The chromatographic device 343 subjects the fed sample to the HPLC to prepare a 3D chromatogram (FIGS. 3A and 3B).

In Step S30003, the powder extract is evaluated. Namely, the chromatographic device 343 outputs the 3D chromatogram obtained in Step S30002 to the evaluating device 1. As explained later, the evaluating device 1 evaluates or determines whether the powder extract meets the criteria for productization based on the input 3D chromatogram.

In Step S30004, the formulating process is branched according to the evaluation of the powder extract. Namely, the evaluating device 1 outputs the determination or evaluating result of Step S30003 to the control unit 308. If the powder extract meets the criteria for productization, the control unit 308 transfers the formulating process to Step S30005. If the powder extract does not meet the criteria, the control unit 308 transfers the formulating process to Step S30007.

In Step S30005, the powder extract is subjected to the dosage form processing. Namely, the control unit 308 controls the blower 325 to convey the powder extract determined as an accepted one meeting the criteria to the dosage form processing device 311. Accordingly, the dosage form processing device 311 subjects the powder extract to the dosage form processing to produce a formulated drug, in particular granules in this embodiment.

In Step S30006, the formulated drug is packed. Namely, the granules produced in Step S30005 are subdivided and packed at the packing device 313. In this way, the productization of the powder extract is completed and the formulating process is terminated.

On the other hand, in Step S30007, the powder extract is stored. Namely, the control unit 308 controls the blower 331 and the valve 337 to convey the powder extract determined as a rejected one that does not meet the criteria to an empty one of the second stockers 329 and store that powder extract.

With this, the formulating process is terminated without producing granules for the powder extract that does not meet the criteria. At this time, the MD value of the powder extract used in the determination or evaluation of the stored powder extract is registered in a database or the like.

Figure 1C:
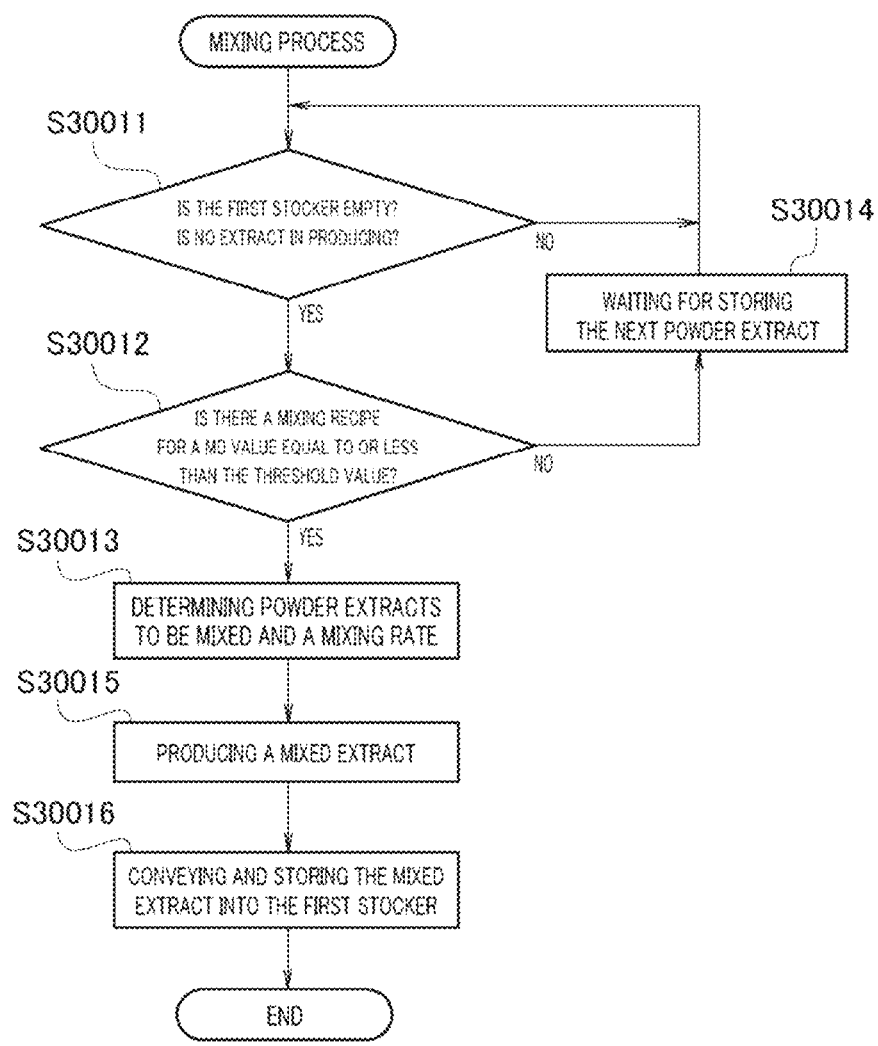
FIG. 1C is a flowchart illustrating a mixing process of the formulating method according to the first embodiment.

FIG. 1C is a flowchart illustrating a mixing process of the formulating method according to the first embodiment.

The mixing process of the formulating method of the first embodiment is started by storing two or more powder extracts in the second stokers 329.

In Step S30011, it is determined whether the first stocker 309 is empty and no extract is in producing. Namely, the control unit 308 determines whether the first stocker 309 is empty and no extract is producing based on the detecting signal of the sensor 309a. The presence or absence of an extract in producing may be more correctly determined in view of an operating signal of the extract producing device 307.

The control unit 309 transfers the mixing process to Step S30012 if the first stocker 309 is empty and no extract is in producing, and repeats Step S30011 otherwise.

In Step S30012, it is determined whether there is a mixing recipe for the stored powder extracts in the second stockers 329 capable of forming a mixed extract having a MD value being equal to or less than the threshold value.

Namely, the control unit 308, in the case where two or more powder extracts to be mixed are selected from among the stored powder extracts based on the MD values and the selected powder extracts are mixed, determines whether there is a combination and a mixing rate of two or more stored powder extracts to be mixed as a mixing recipe capable of forming a mixed extract having a MD value being equal to or less than the threshold value. The MD values for the determination may be obtained from the database or the like.

The control unit 308 transfers the mixing process to Step S30013 if there is such a mixing recipe, and to Step S30014 otherwise.

In Step S30013, a combination and a mixing rate of powder extracts to be mixed are determined. Namely, the control unit 308 determines the powder extracts to be mixed and the mixing rate based on the mixing recipe of Step S30012.

In Step S30014, it waits for storing the next powder extract. Namely, the control unit 308 cannot produce a mixed extract having a MD value being equal to or less than the threshold value from the presently stored powder extracts and waits until the next powder extract is stored.

In Step S30015, a mixed extract is produced using the determined combination and mixing rate of the powder extracts to be mixed. Namely, the control unit 308 controls the valves 337 corresponding to the second stockers 329 storing the powder extracts to be mixed, the valve 339 and the blower 333 for the mixing device 330 to convey the powder extracts to be mixed to the mixing device 330. As the control of the valves 337, 339 and the blower 333, the control unit 308 controls the open time of the valves 337 and the operating time of the blower 333 to adjust the amount of the powder extracts to be conveyed according to the mixing rate. As a result, the mixing device 330 produces the mixed extract using the combination and the mixing rate of the powder extract determined in Step S30013.

In Step S30016, the mixed extract is conveyed to and stored in the first stocker 309. Namely, the control unit 308 controls the blower 335 to convey the produced mixed extract to the first stocker 309 and accommodate the same in the first stocker 309.

In this way, the mixing process is terminated. Thereafter, the formulating method performs for the mixed extract Step S30002 and the following steps of the formulating process of FIG. 1B in sequence. Accordingly, if the mixed extract is determined as an accepted one meeting the criteria for productization, granules are produced from the mixed extract and packed. On the other hand, if the mixed extract is determined as a rejected one that does not meet the criteria for productization, the mixed extract is stored in an empty one of the second stockers 329 again. The mixed extract, however, is produced so as to meet the criteria and therefore the latter case is extremely rare. With this, in the formulating process for the mixed extract, the evaluation of whether the mixed extract meet the criteria may be omitted.

The formulating method and apparatus 301 surely make a powder extract of a multicomponent drug meeting the criteria for productization based on the high accuracy evaluation of whether the powder extract meets that criteria into a product.

Hereinafter, the high accuracy evaluation of a powder extract or a multicomponent drug will be explained in detail.

In an evaluation of a multicomponent drug, it evaluates whether or not an evaluation target drug is equivalent to a plurality of drugs that are defined as normal products. For this, first, a target FP is prepared by extracting information unique to the drug from a 3D chromatogram of the multicomponent drug as the evaluation target drug.

Next, each peak of the target FP is assigned to peak correspondence data (hereinafter, referred to as a reference group FP) of all reference FPs, which is prepared by performing a peak assigning process to all the reference FPs, whereby a peak feature value is acquired.

Next, equivalency between peaks of the reference group FP and the assigned peaks of the target FP (hereinafter, referred to as target FP assignment peaks) is evaluated by MT method. Finally, it is determined whether or not the evaluation target drug is equivalent to a normal product by comparing an acquired evaluation value (hereinafter, referred to as a MD value) with a preset determination value (an upper limit value or a threshold value of the MD value).

The 3D chromatogram is a HPLC chromatogram data (hereinafter, referred to as chromatogram) of a multicomponent drug that is a multicomponent material as an evaluation target and includes UV spectra.

The FP is fingerprint data that is configured by maximum values or area values (hereinafter, referred to as peaks) in signal strength (height) of peaks detected at a specific wavelength and by appearance time points (hereinafter, referred to as retention time points) of the peaks.

The target FP is acquired by extracting a plurality of peaks, retention time points and UV spectra thereof at a specific detection wavelength from a 3D chromatogram that is three-dimensional chromatogram data of a kampo medicine being an evaluation target.

The reference FP corresponds to the target FP and is a FP of a kampo medicine as a multicomponent drug that is a multicomponent material determined as a normal product.

Figure 2:
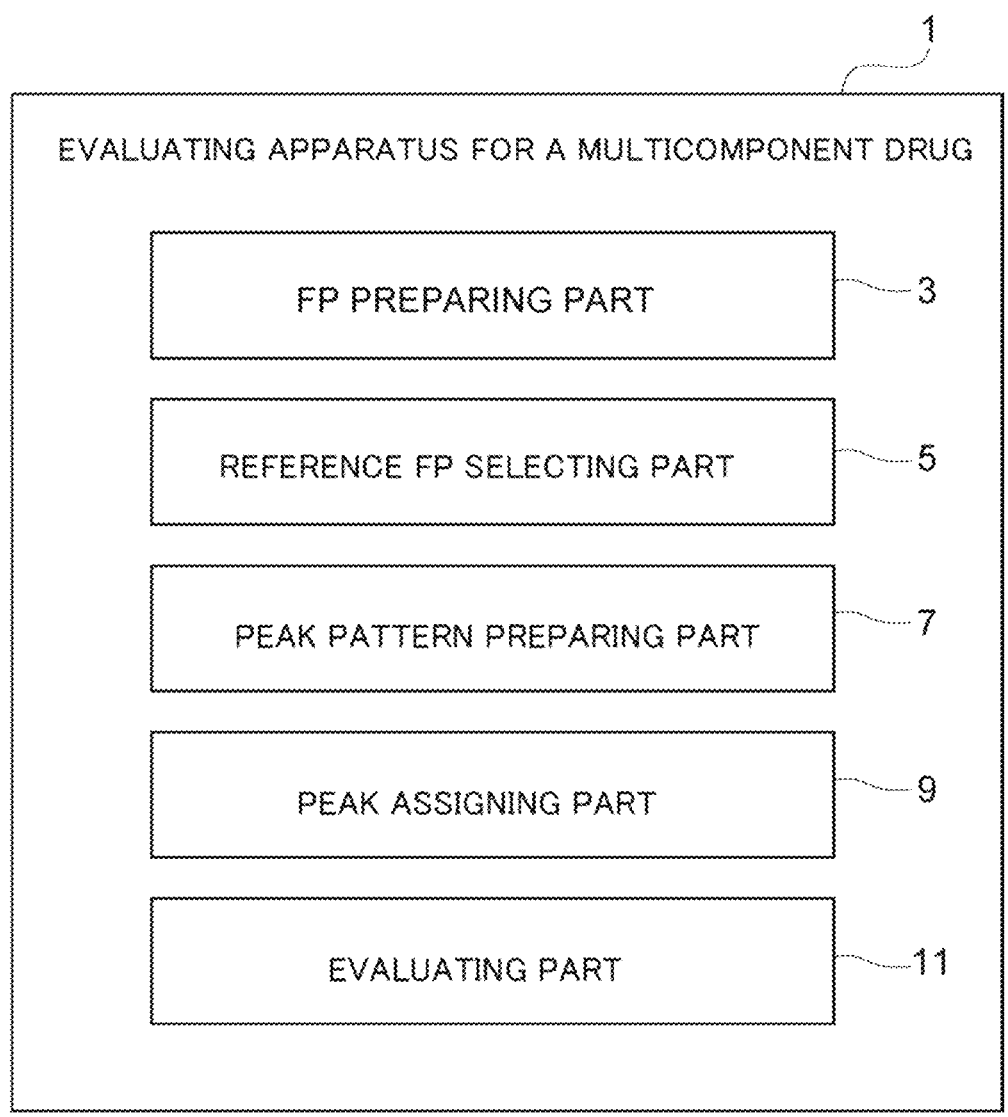
FIG. 2 is a block diagram of an evaluating apparatus for a multicomponent drug according to a first embodiment of the present invention.

FIG. 2 is a block diagram of an evaluating apparatus for a multicomponent drug, FIG. 3A is a block diagram illustrating procedures of evaluating a multicomponent drug, FIG. 3B is an explanatory diagram of a FP that is prepared from a 3D chromatogram, FIG. 4A is a FP of a drug A, FIG. 4B is a FP of a drug B, and FIG. 4C is a FP of a drug C.

As illustrated in FIGS. 2 and 3A, the evaluating device 1 for a multicomponent drug includes a FP preparing part 3, a reference FP selecting part 5, a peak pattern preparing part 7, a peak assigning part 9, and an evaluating part 11. The evaluating device 1 for a multicomponent drug is configured by a computer and, although not illustrated in the drawings, includes a CPU, a ROM, a RAM, and the like. The evaluating device 1 for a multicomponent drug can evaluate a multicomponent drug by implementing an evaluating program for a multicomponent drug as an evaluating program for a multicomponent material that is installed in the computer. However, the evaluation of the multicomponent drug may be realized by using an evaluating program recording medium for a multicomponent drug that stores the evaluating program and by reading out it with the evaluating device 1 configured by the computer for a multicomponent drug.

In this embodiment, the FP preparing part 3, the reference FP selecting part 5, the peak pattern preparing part 7, the peak assigning part 9, and the evaluating part 11 are configured by a single computer. Alternatively, the FP preparing part 3, the reference FP selecting part 5, the peak pattern preparing part 7, the peak assigning part 9, and the evaluating part 11 may be configured by respective discrete computers, or the FP preparing part 3 and the reference FP selecting part 5, the peak pattern preparing part 7 and the peak assigning part 9, and the evaluating part 11 may be configured by discrete computers.

The FP preparing part 3 gathers as a target FP peaks in which each one peak has a height that is a maximum value or an area value in signal strength and retention time points of the respective peaks detected from the 3D chromatogram. According to the embodiment, the peak height is the maximum value in signal strength. More precisely, the FP preparing part 3, for example, is a functional part that prepares and acquires a target FP 17 (hereinafter, it may be simply referred to as "FP 17") as a target pattern. The FP 17, similarly to the 3D chromatogram 15, is configured by three-dimensional information (peaks, retention time points, and UV spectra).

The FP 17, therefore, is data that directly succeed to the information unique to the drug. In spite of that, the data volume of the FP 17 is compressed at the ratio of about 1/70, and therefore, information amount to be processed is much smaller than that of the 3D chromatogram 15, thereby increasing processing speed.

The 3D chromatogram 15 is a result of applying high performance liquid chromatography (HPLC) to a kampo medicine 13 (FIG. 2) as the multicomponent drug in the chromatographic device 343 (FIG. 1A). In the 3D chromatogram 15, a movement speed of each component appears to represent as a movement distance during specific time, or an appearance in a time series from a column end is represented in a chart. In the HPLC, detector responses are plotted with respect to the time axis, and appearance time points of peaks are called retention time points.

Although the detector is not particularly limited, an absorbance detector employing an optical characteristic is used as the detector. A peak is three-dimensionally acquired as a signal strength according to a detection wavelength of ultraviolet (UV). As a detector employing an optical characteristic, a transmittance detector may be used.

The detection wavelengths are not particularly limited, and are a plurality of wavelengths selected preferably from a range of 150 nm to 900 nm, selected more preferably from a range of 200 nm to 400 nm corresponding to a UV-visible absorption range, and selected further more preferably from a range of 200 nm to 300 nm.

The 3D chromatogram 15 at least includes a number (lot number), retention time points, detection wavelengths, and peaks of a kampo medicine as data.

In the 3D chromatogram 15, as illustrated in FIGS. 3A and 3B, the x-axis represents the retention time point, the y-axis represents the detection wavelength, and the z-axis represents signal strength.

The FP 17 at least includes a number (lot number), retention time points, peaks at a specific wavelength, and UV spectra of a kampo medicine as data.

The FP 17 is two-dimensionally represented with the x-axis representing the retention time points and the y-axis representing the peaks for the specific detection wavelength as illustrated in FIGS. 3A and 3B.

Namely, the FP 17 is configured by the combination of the two-dimensional information, and therefore indicates the magnitudes (heights) and the retention time points of the peaks in two dimension and has a two-dimensional UV spectrum assigned at each one peak. However, the FP 17 is data that includes UV spectrum information for each peak that is similar to the UV spectrum 25 represented with respect to one peak as illustrated in FIG. 3. The specific detection wavelength for which the FP 17 is prepared is not particularly limited and may be selected in various manners. However, it is important for the FP 17 to include all the peaks of the 3D chromatogram in order to succeed to the information. Accordingly, in the first embodiment, the detection wavelength is set to 203 nm that includes all the peaks of the 3D chromatogram.

Meanwhile, there are cases where all the peaks are not included at a single wavelength. In such a case, a plurality of detection wavelengths are set to prepare a FP that includes all the peaks by combining the plurality of wavelengths as described later.

In the first embodiment, although the peak is set as the maximum value of the signal strength (peak height), the area value may be used as the peak. In addition, a FP may not include UV spectra, so that the FP is set as two-dimensional display information in which the x-axis represents the retention time points, and the y-axis represents the peaks for a specific wavelength. In such a case, the FP can be prepared from a 2D chromatogram as a chromatogram that includes a number (lot number) and retention time points of a kampo medicine as data.

FIG. 4A is a FP of a drug A, FIG. 4B is a FP of a drug B, and FIG. 4C is a FP of a drug C.

Figure 10:
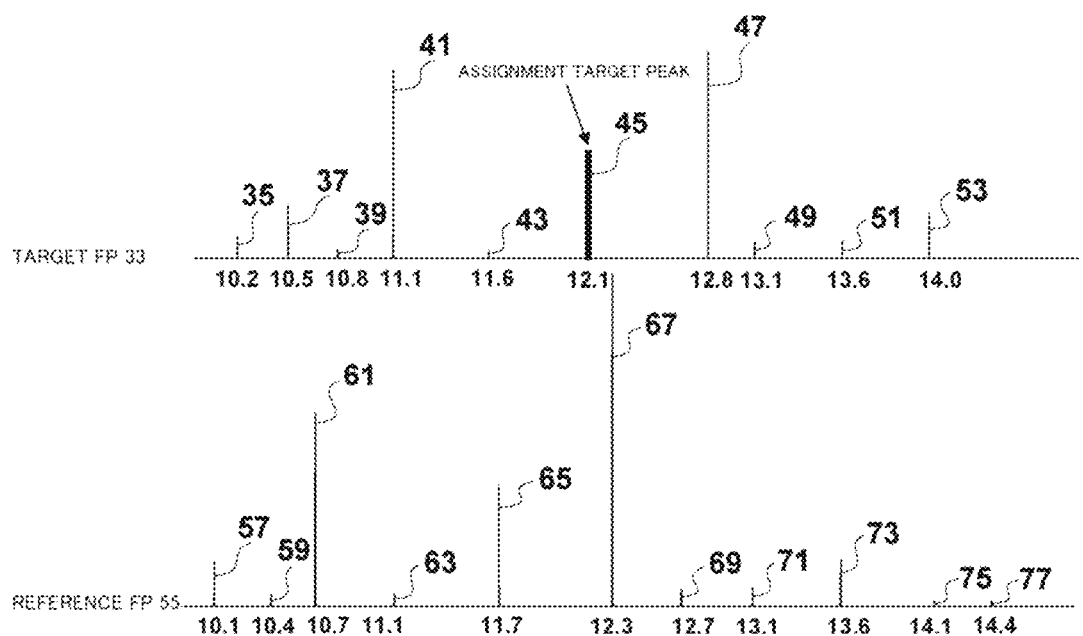
FIG. 10 is diagram illustrating an assignment target peak of the target FP according to the first embodiment.
Figure 11:
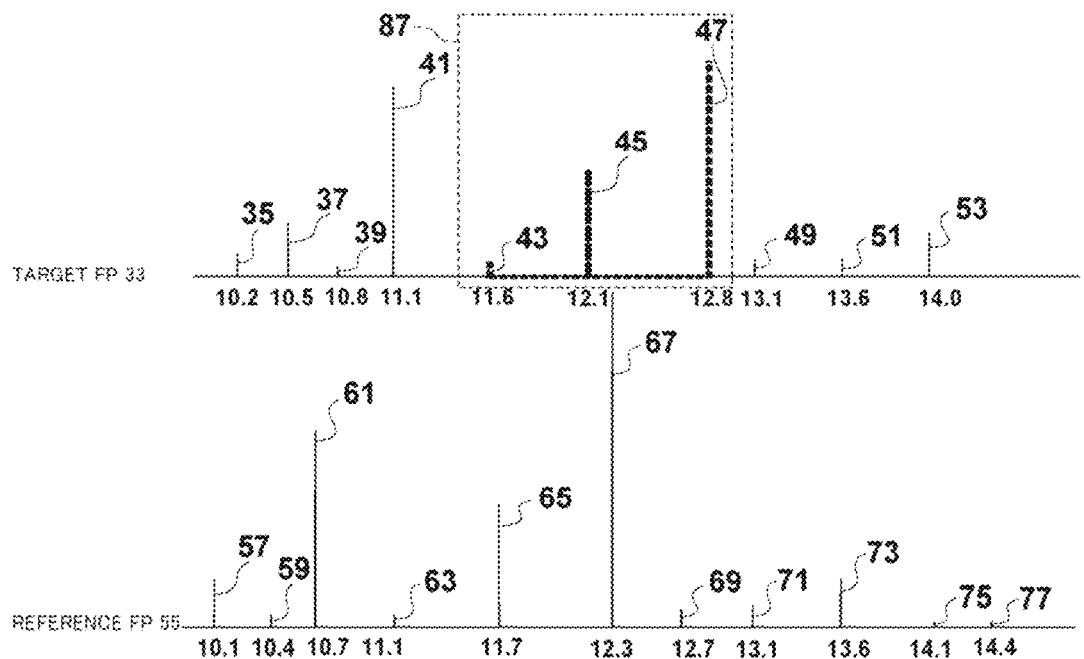
FIG. 11 is a peak pattern diagram according to three peaks including the assignment target peak
Figure 12:
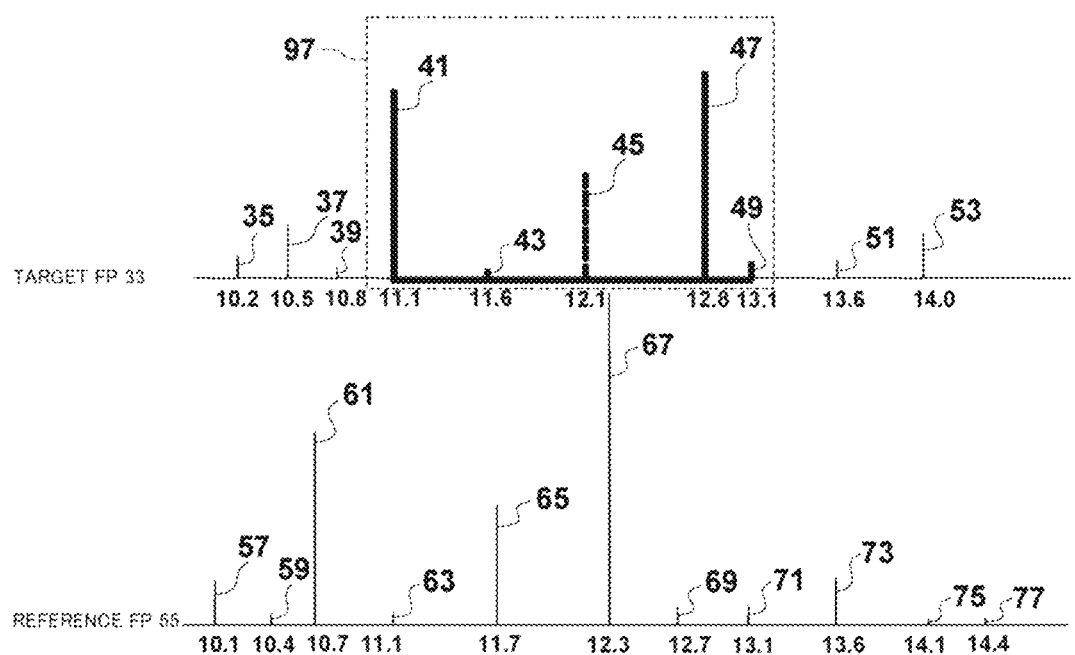
FIG. 12 is a peak pattern diagram according to five peaks including the assignment target peak according to the first embodiment.

The reference FP selecting part 5 is a functional part that selects a reference FP that is used by the peak pattern preparing part 7 from among a plurality of reference FPs. The reference FP selecting part 5 selects a FP of a multicomponent drug that is appropriate to the assignment of the peaks to the target FP from among the plurality of reference FPs. In other words, in order to perform peak assignment of each peak of the target FP with high accuracy, as illustrated in FIGS. 5 to 9, the degree of matching between retention time point appearance patterns of the peaks of the target FP and each reference FP are calculated to select a reference FP with the minimum degree of matching from among all the reference FPs. This will be described in detail later. The peak pattern preparing part 7 is a functional part that, as illustrated in FIGS. 10 to 12, prepares a peak pattern for an assignment target peak of the target FP 33 that is a target to be assigned. The peak pattern is configured by a total of n+1 peaks including the assignment target peak of the target FP 33 and n peripheral peaks that are present at least on one of sides located in front and in the rear of the assignment target peak in the direction of the time axis. Here, "n" is a natural number. This will be described in detail later.

FIG. 11 illustrates a peak pattern configured by a total of three peaks that include two peaks being present at least on one of sides located in front and in the rear in the time axis direction, and FIG. 12 illustrates a peak pattern configured by a total of five peaks that include four peaks being present at least on one of sides located in front and in the rear in the time axis direction.

In addition, the peak pattern preparing part 7 is a functional part that, as illustrated in FIGS. 13 to 22 (to be described later), prepares peak patterns for respective assignment candidate peaks of the reference FP 55. Each one of the peak patterns is configured by a total of n+1 peaks including a corresponding one of the assignment candidate peaks and n peripheral peaks that are present at least on one of sides located in front and in the rear in the time axis direction of the corresponding one of the assignment candidate peaks. The assignment candidate peaks have differences in retention time relative to the assignment target peak within a set range (allowable range). FIGS. 15 to 18 (to be described later) show peak patterns each configured by a total of three peaks including two peaks that are located at least on one of sides located in front and in the rear in the time axis direction. FIGS. 19 to 22 (to be described later) show peak patterns each configured by a total of five peaks including four peaks that are located at least on one of sides located in front and in the rear in the time axis direction.

The allowable range is not particularly limited, but is preferably in the range of 0.5 to 2 minutes with the object of the accuracy and efficiency. In the first embodiment, the allowable range is set to one minute.

In addition, the peak pattern preparing part 7 is configured to be able to flexibly respond to even a case where there is a difference between the number of the peaks of the target FP 33 and that of the reference FP 55 (in other words, there are one or more peaks that are not present on one side). For this, as illustrated in FIGS. 23 to 61 (to be described later), peak patterns are comprehensively prepared by changing peaks configuring the peak patterns (hereinafter, referred to as peak pattern configuring peaks) for both assignment target peaks and assignment candidate peaks. FIGS. 23 to 61 illustrate cases where the peak pattern is configured by a total of three peaks including two peaks that are located at least on one of sides located in front and in the rear in the time axis direction.

The peak assigning part 9 is a functional part that compares the peak patterns of the assignment target peak and the assignment candidate peaks to specify corresponding peaks between the target FP 33 and the reference FP 55. In the embodiment, the corresponding peaks are specified by calculating the degree of matching between peak patterns for assignment target peaks and assignment candidate peaks and the degree of matching between the UV spectra. It will be described specifically later.

In addition, the peak assigning part 9 is a functional part that calculates the degrees of matching for the assignment candidate peaks by integrating aforementioned two kinds of the degrees of matching to assign each peak of the target FP 33 to each peak of the reference FP 55 based on the calculated degrees of matching.

Figure 68:
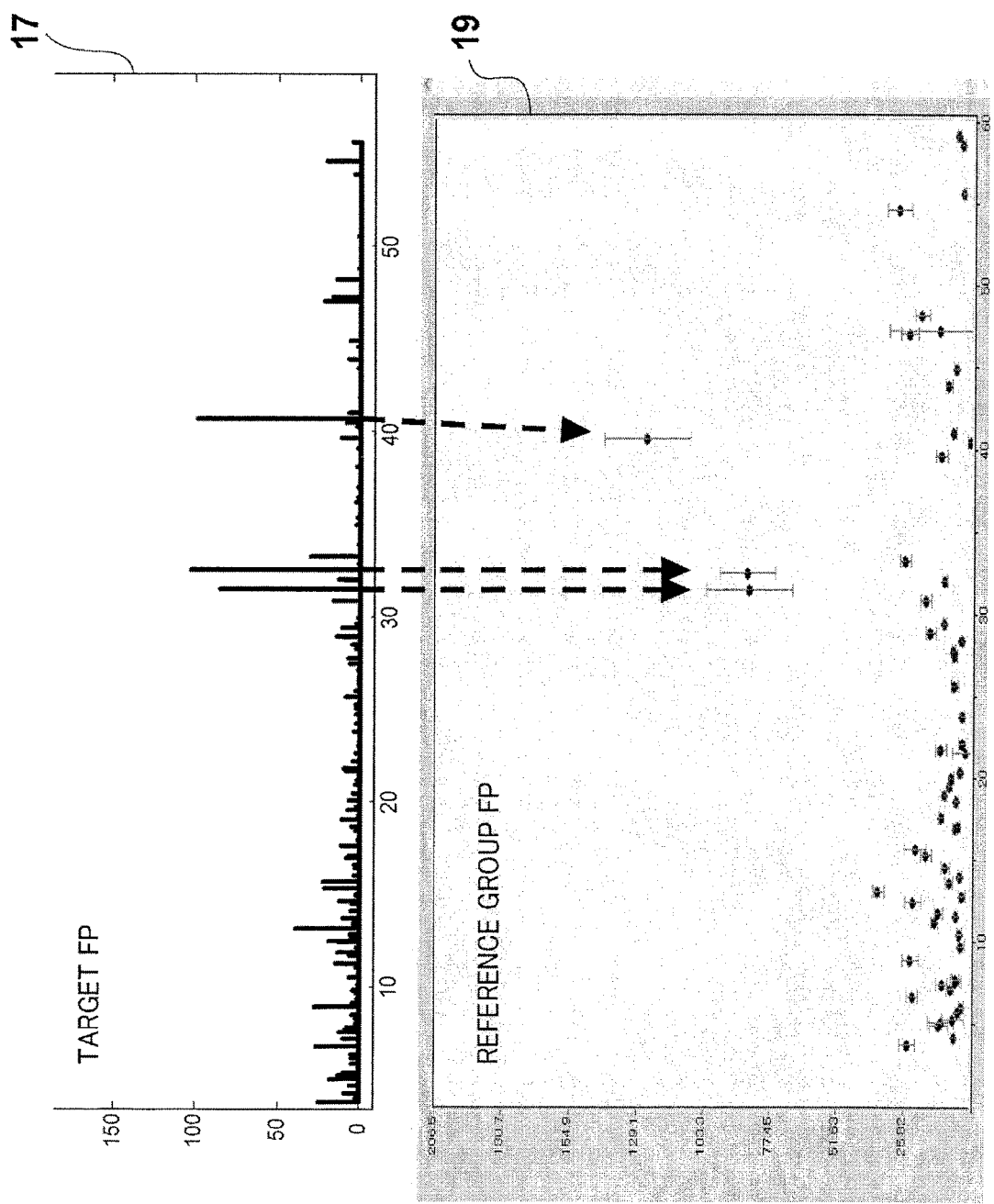
FIG. 68 is an explanatory diagram illustrating assignment of the target FP to a reference group FP according to the first embodiment.
Figure 69:
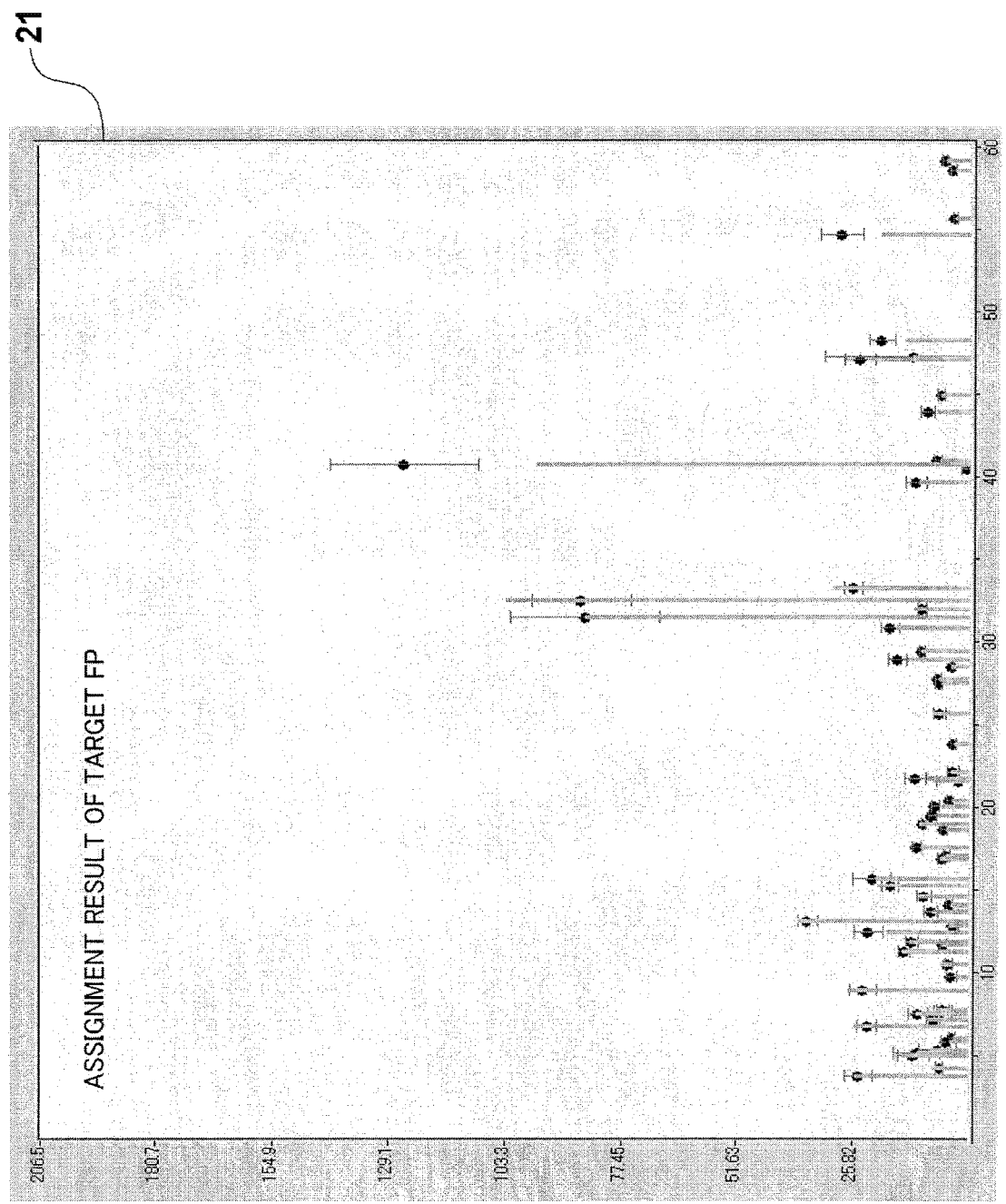
FIG. 69 is a diagram illustrating a state in which the target FP is assigned to the reference group FP according to the first embodiment.
Figure 70:
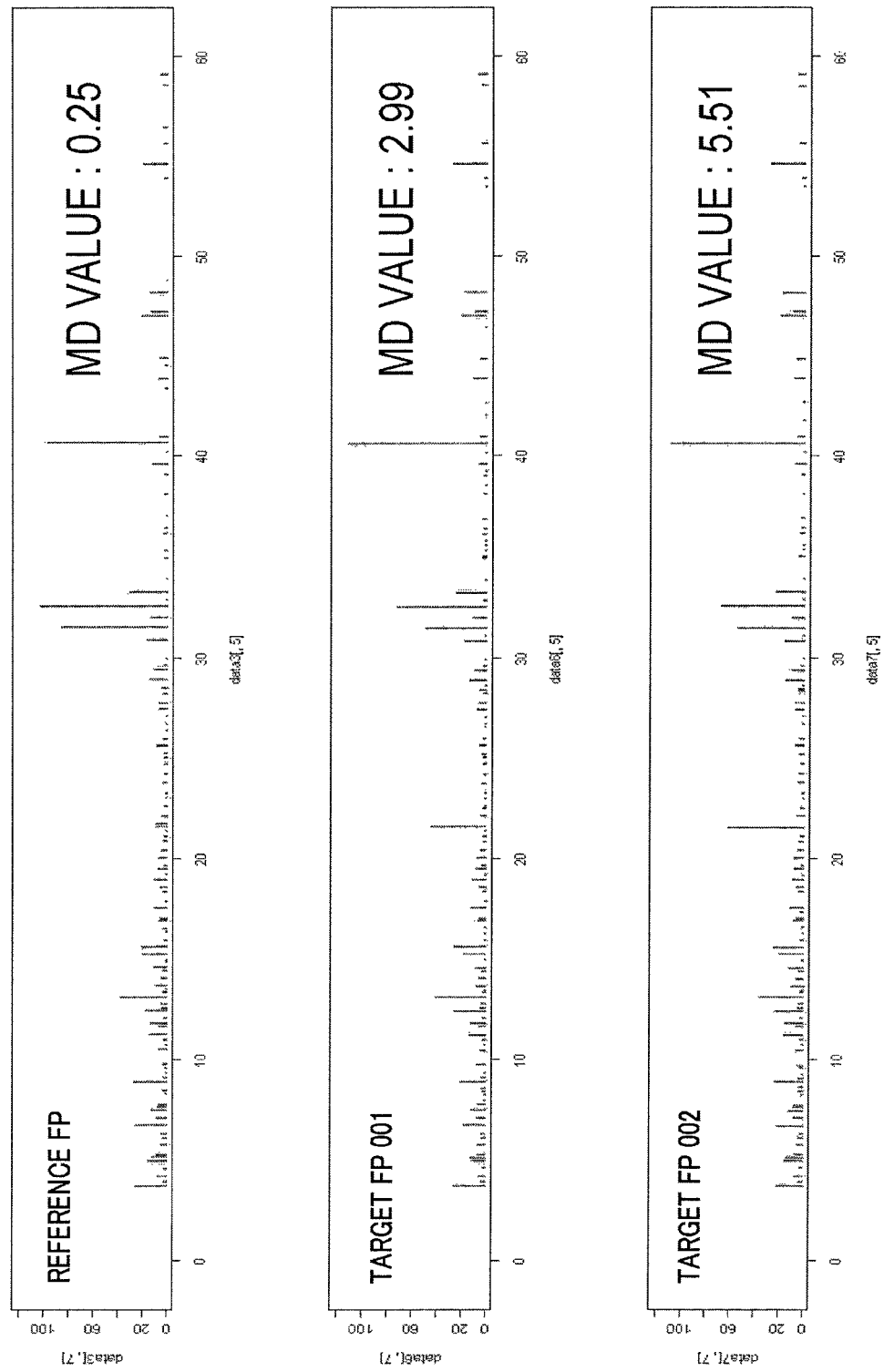
FIG. 70 is a diagram illustrating various target FPs and evaluation values (MD values) thereof according to the first embodiment.
Figure 71:
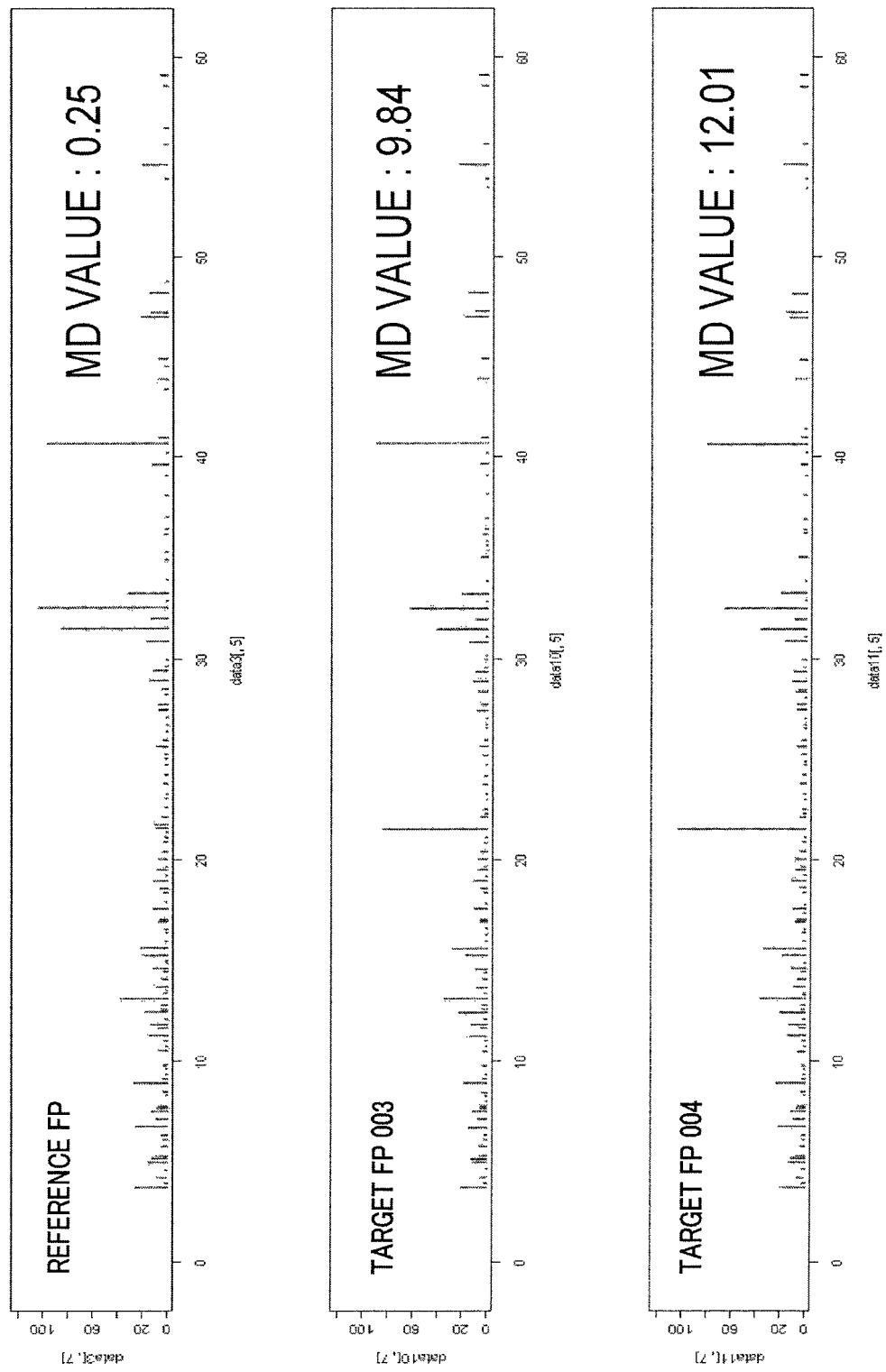
FIG. 71 is a diagram illustrating various target FPs and evaluation values (MD values) thereof according to the first embodiment.
Figure 72:
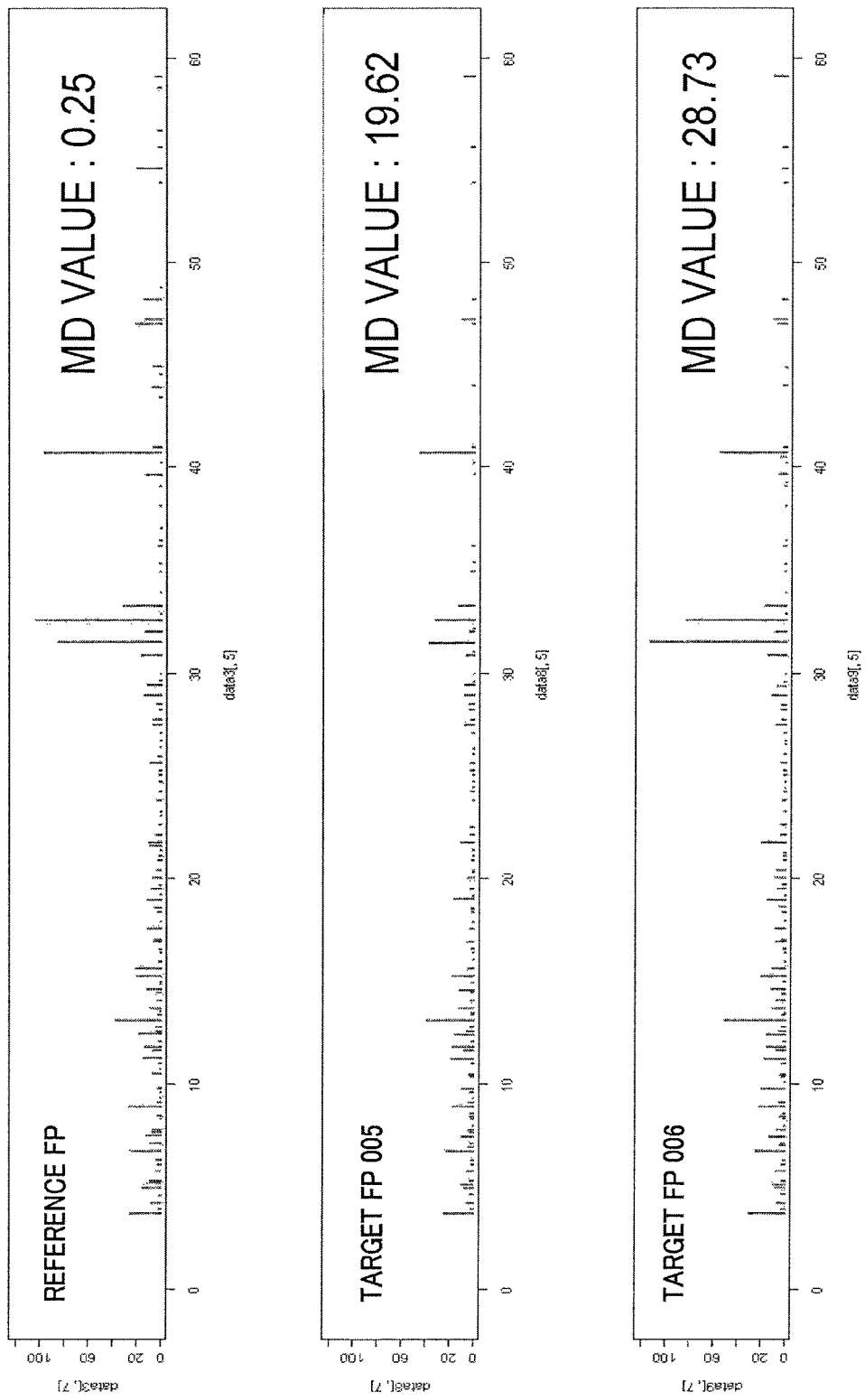
FIG. 72 is a diagram illustrating various target FPs and evaluation values (MD values) thereof according to the first embodiment.
Figure 73:
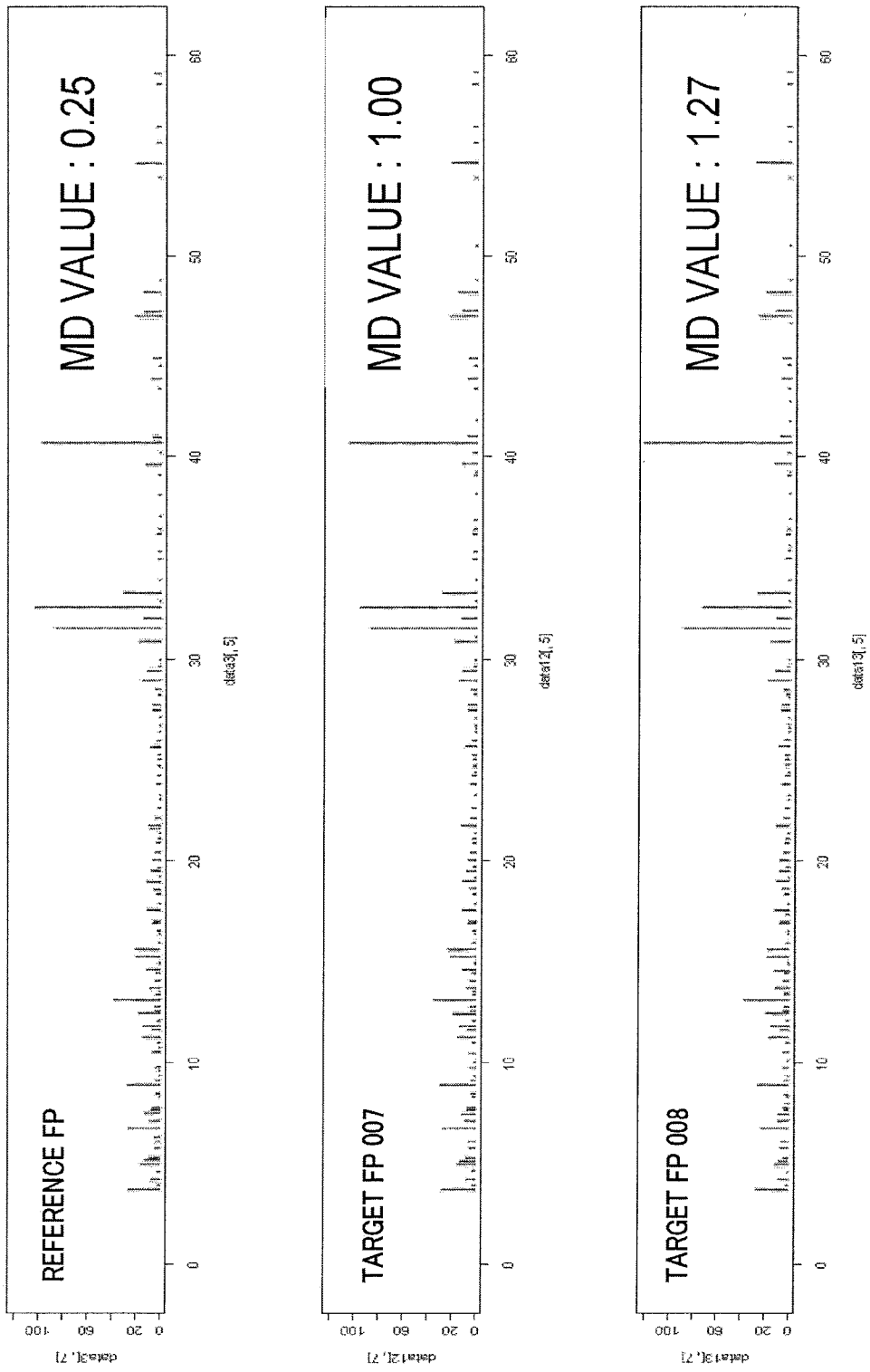
FIG. 73 is a diagram illustrating various target FPs and evaluation values (MD values) thereof according to the first embodiment.
Figure 74:
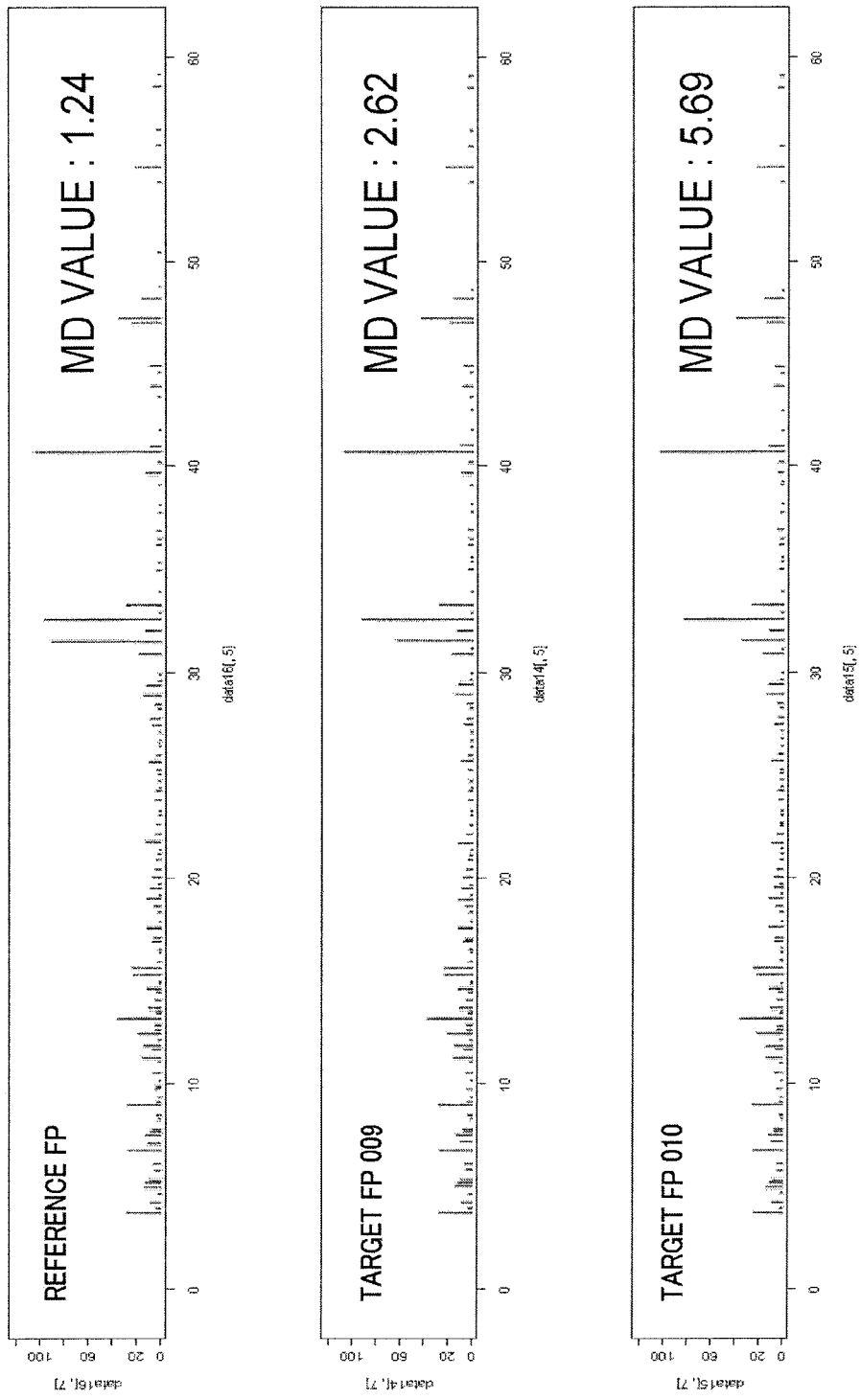
FIG. 74 is a diagram illustrating various target FPs and evaluation values (MD values) thereof according to the first embodiment.

Furthermore, the peak assigning part 9 is a functional part that finally assigns the peaks of the target FP to respective peaks of the reference group FP as illustrated in FIGS. 68 and 69 (to be described later), based on a result of the assignment between the target FP 33 and the reference FP 55.

Figure 62:
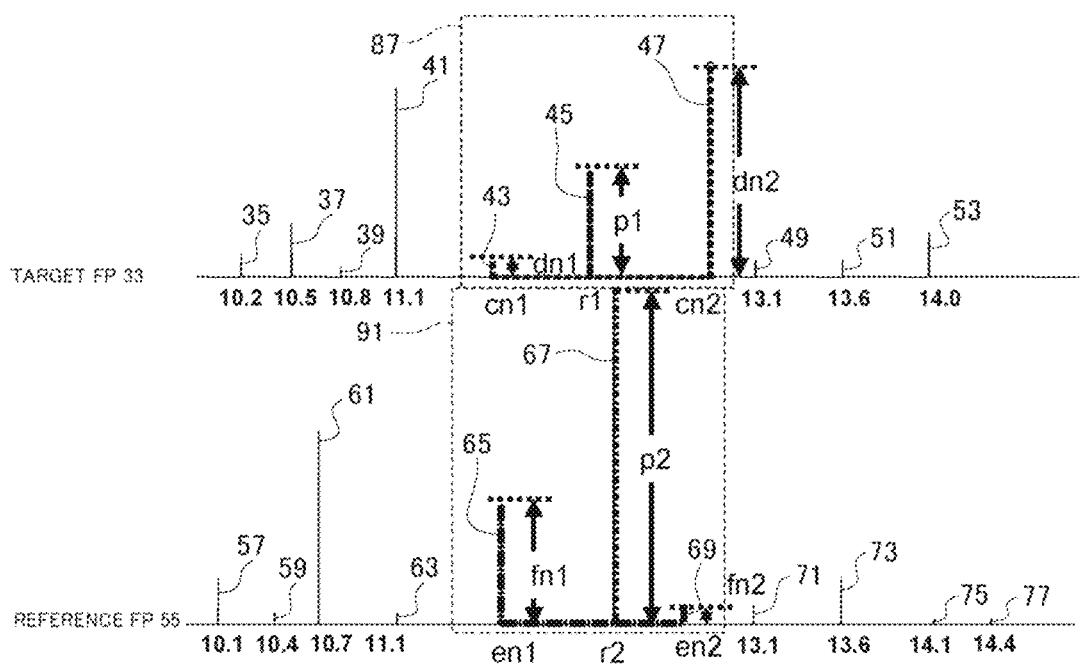
FIG. 62 is a diagram illustrating a calculating method of the degree of matching between peak patterns of the assignment target peak and an assignment candidate peak according to three peaks according to the first embodiment.
Figure 63:
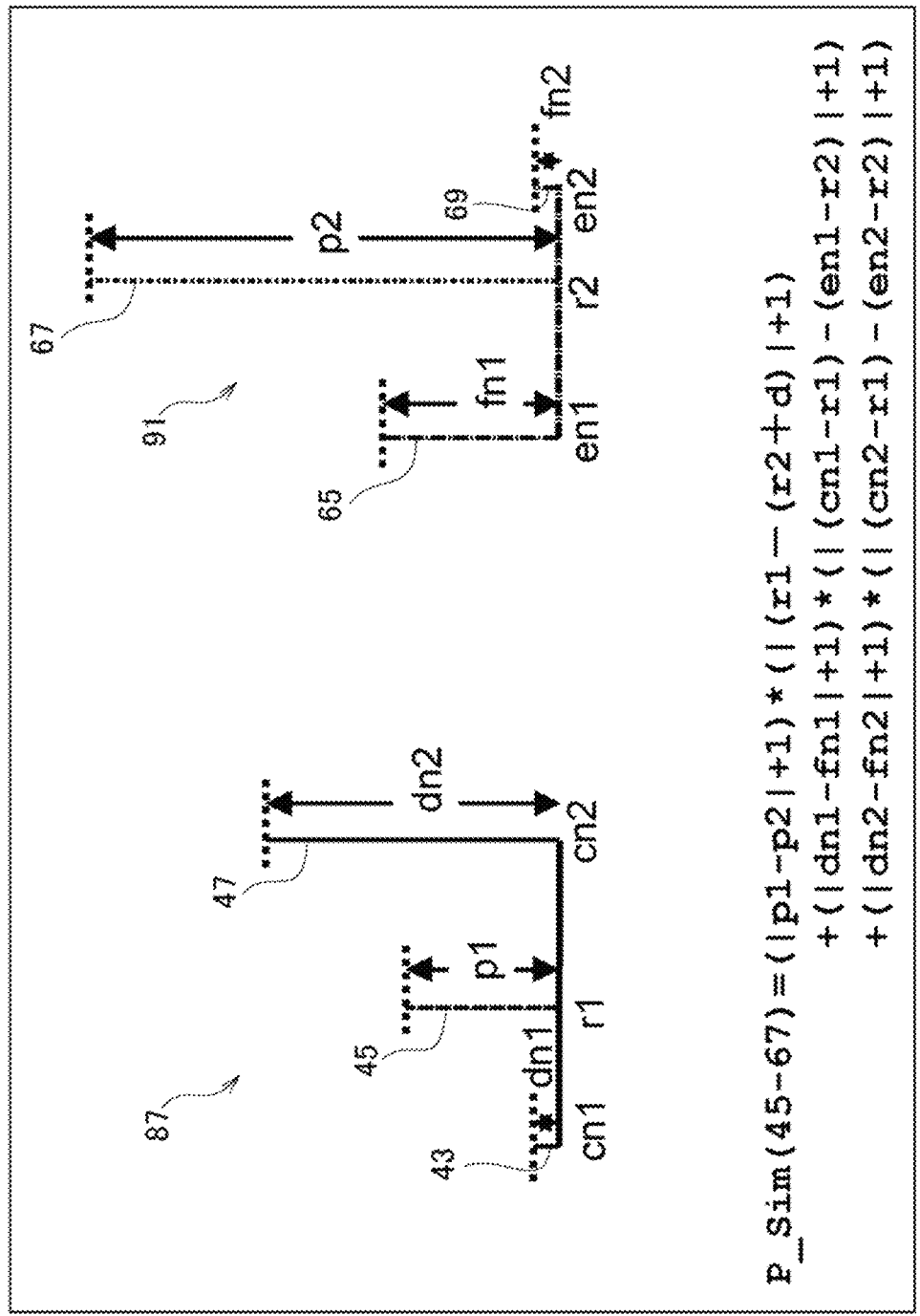
FIG. 63 is a diagram illustrating a calculating method of the degree of matching between peak patterns of the assignment target peak and the assignment candidate peak according to three peaks according to the first embodiment.
Figure 64:
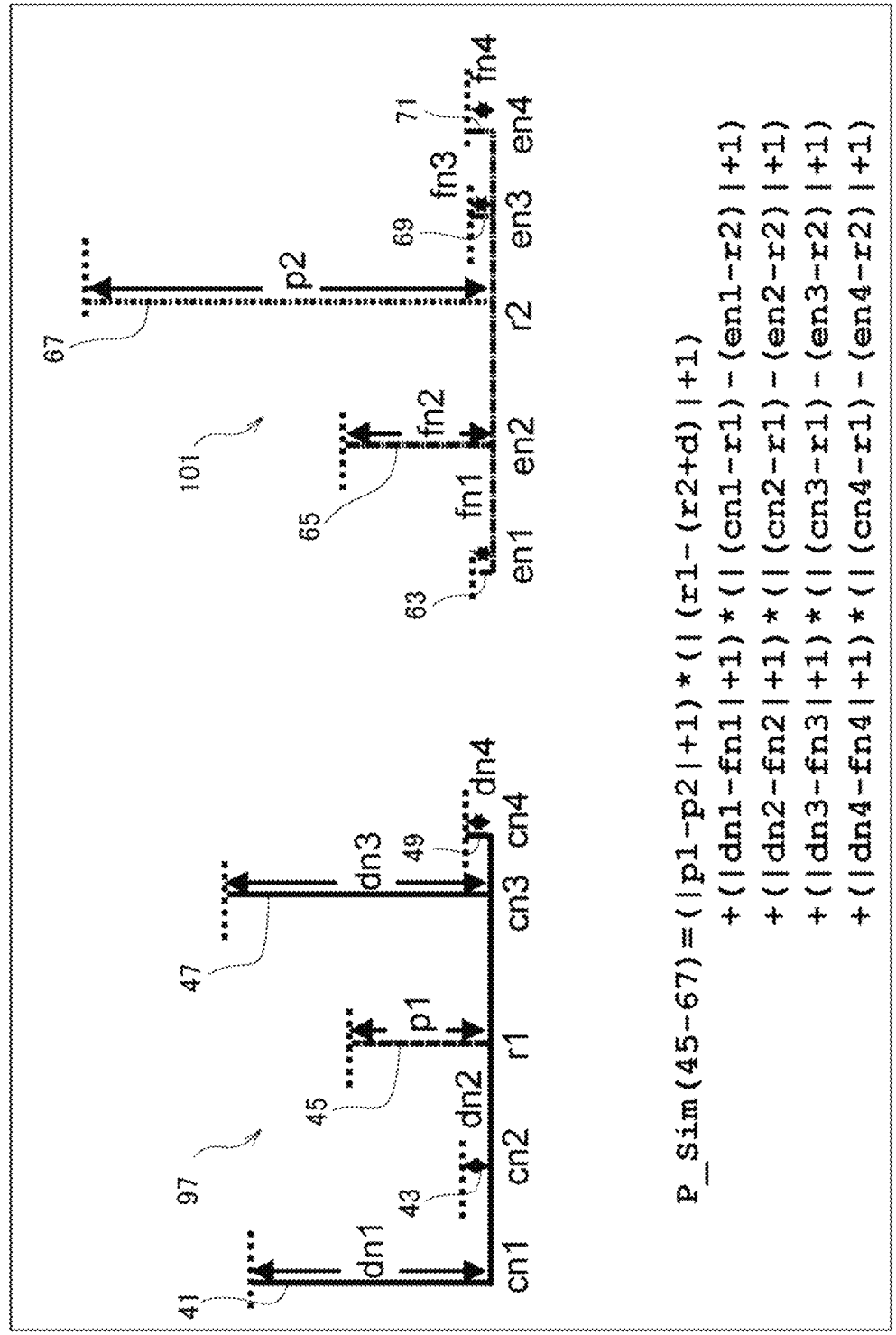
FIG. 64 is a diagram illustrating a calculating method of the degree of matching between peak patterns of the assignment target peak and the assignment candidate peak according to five peaks according to the first embodiment.
Figure 65:
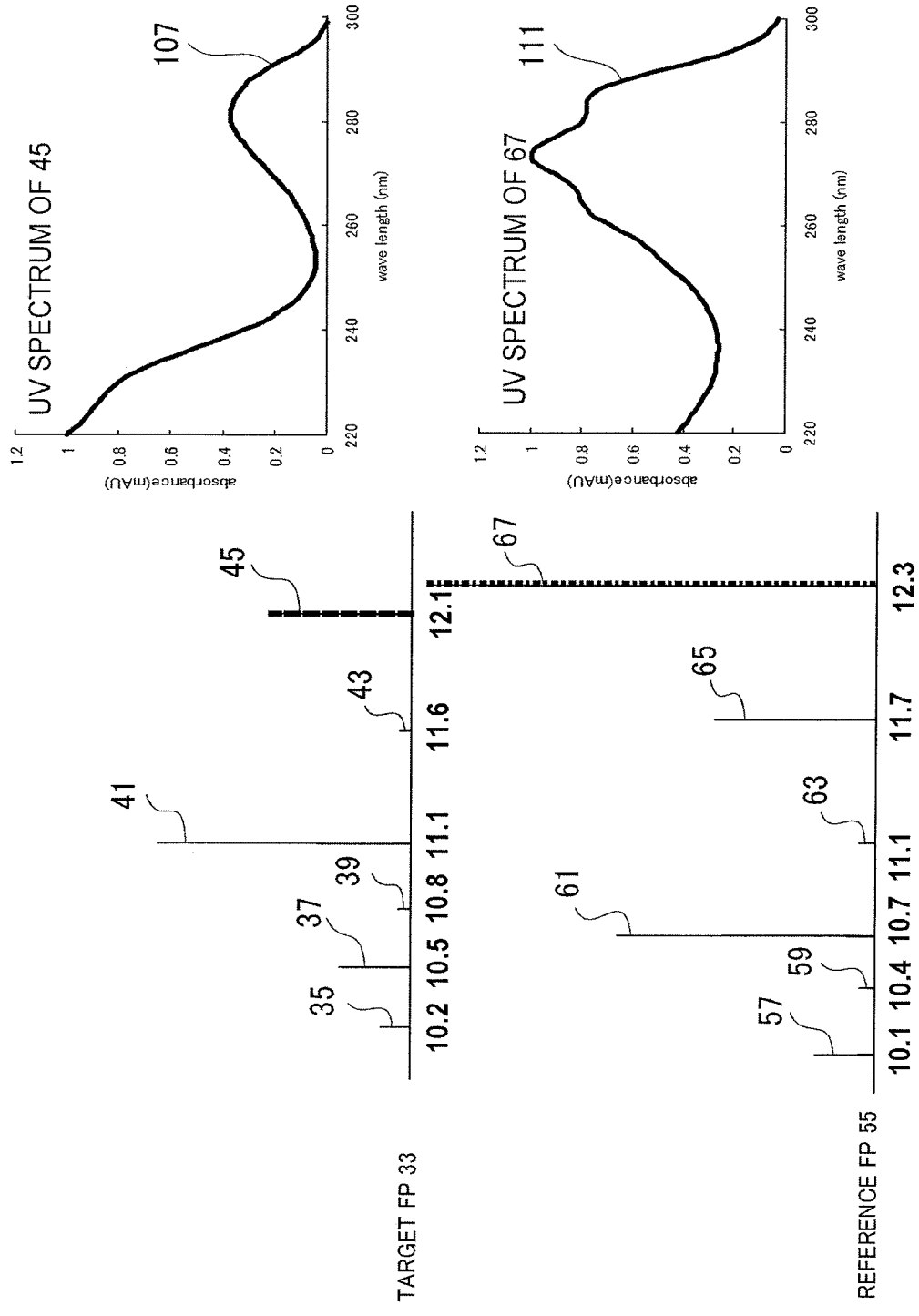
FIG. 65 is a diagram illustrating UV spectra of an assignment target peak and an assignment candidate peak according to the first embodiment.
Figure 66:
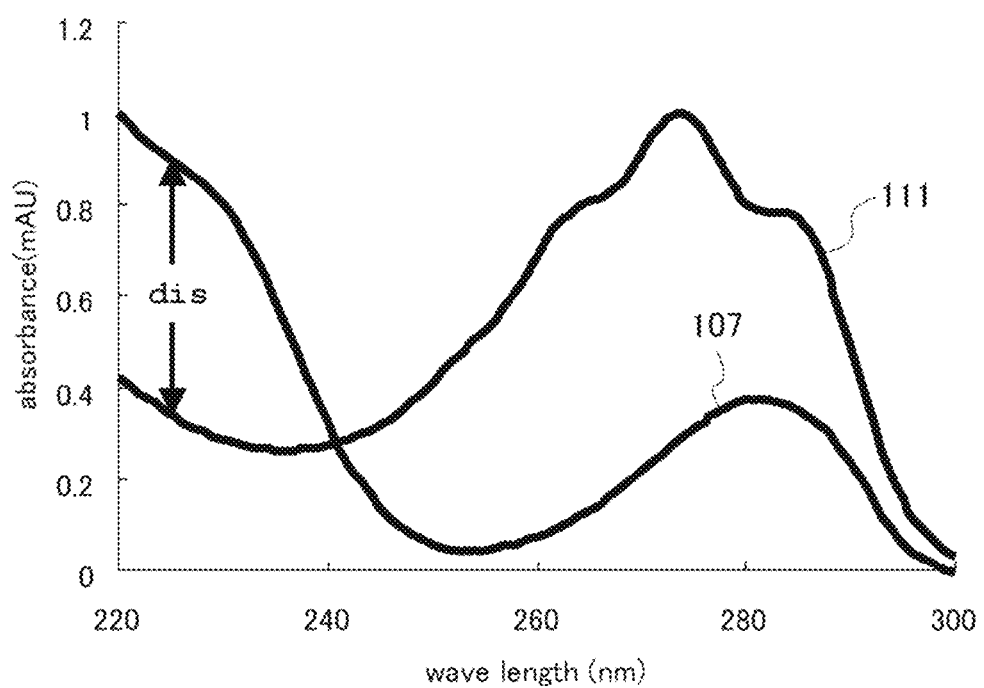
FIG. 66 is an explanatory diagram illustrating the degree of matching between the UV spectra of the assignment target peak and the assignment candidate peak according to the first embodiment.
Figure 67:
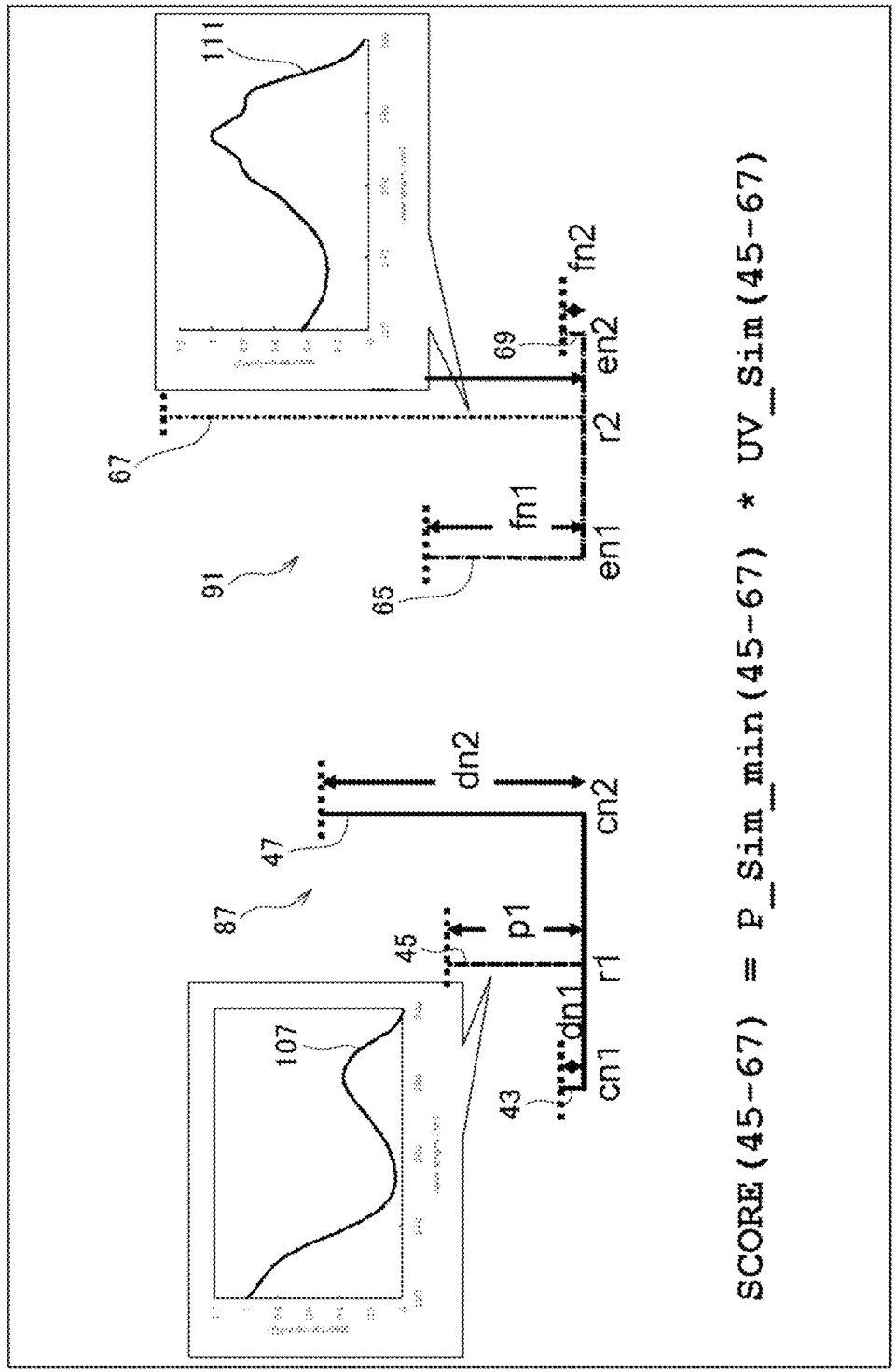
FIG. 67 is an explanatory diagram illustrating the degree of matching of the assignment candidate peak by comparison of both the peak patterns and the UV spectra together according to the first embodiment.

The peak assigning part 9 calculates the degree of matching between peak patterns based on differences between corresponding peaks and retention time points of the peak patterns of the assignment target peak and the assignment candidate peak as illustrated in FIGS. 62 to 64 (to be described later). The degree of matching between the UV spectra is calculated based on a difference between the absorbance of the UV spectrum 107 of an assignment target peak 45 and the absorbance of the UV spectrum 111 of a assignment candidate peak 67 for each wavelength as illustrated in FIGS. 65 and 66 (to be described later). Further, as illustrated in FIG. 67 (to be described later), the degree of matching of the assignment candidate peak 67 is calculated by multiplying these two kinds of the degrees of matching together.

The evaluating part 11 is a functional part that evaluates the peaks of the target FP 33 that are specified and assigned by the peak assigning part 9 by comparison with the peaks of the plurality of reference FPs, to determine whether a powder extract of a multicomponent drug as an evaluation target meets the criteria for productization. In the embodiment, the evaluating part 11 is a functional part that evaluates the equivalency between the target FP assignment peaks 21 and the reference group FP 19 with MT method.

MT method represents a calculation technique that is generally known in quality engineering. For example, MT method is described in pp 136 to 138, "Mathematics for Quality Engineering" published by Japanese Standards Association (2000); in pp 454 to 456 of Quality Engineering of Application Course "Technical Developments in Chemistry, Pharmacy and Biology" published by Japanese Standards Association (1999); in pp 78 to 84 of Quality Engineering 11(5) (2003); and in "Introduction to MT System" (2008).

In addition, MT method program software that is commercially available in the market can be used. As such commercially-available MT method program software, there are "ATMTS" provided by Angle Try Associates, "TM-ANOVA" provided by Japanese Standards Association, an "MT method for Windows" provided by OHKEN Co., Ltd, and the like.

The evaluating part 11 assigns a variable axis according to MT method to one of the lot number and the retention time point of a kampo medicine or the UV detection wavelength of the target FP 17 and sets the peaks as feature values according to MT method.

Although the assignment of the variable axis is not particularly limited, it is preferable that the retention time point is assigned to a so-called category axis according to MT method, the number of a multicomponent-based drug is assigned to a so-called number row axis, and the peak is assigned to a so-called feature value according to MT method.

Here, the category axis and the number row axis are defined as below. According to MT method, an average value $m_j$ and a standard deviation $\sigma_j$ are acquired for a data set $X_{ij}$, a correlation coefficient "r" between "i" and "j" is acquired from a value $x_{ij} = (X_{ij} - m_j)/\sigma_j$ that is the standardized $X_{ij}$, and accordingly, a unit space or a Mahalanobis distance is acquired. At this time, the category axis and the number row axis are defined such that "the average value $m_j$ and the standard deviation $\sigma_j$ are acquired for each value of the category axis by changing the value of the number row axis."

Based on the data and the feature values to which the axes are assigned, a reference point and an unit quantity (it may be abbreviated as a "unit space") are acquired using MT method. Here, the reference point, the unit quantity, and the unit space are defined in accordance with the description of MT method presented in the above-described literatures.

According to MT method, an MD value is acquired as a value that represents the degree of a difference between a drug to be evaluated and the unit space. Here, the MD value is defined in the same way as the description of MT method presented in the literatures, and the MD value is acquired with the method described in the literatures.

By using the MD value acquired in this manner, the drug to be evaluated can be evaluated by determining the degree of a difference from a plurality of drugs defined as normal products.

For example, by performing the assignment process for each target FP illustrated in FIGS. 70 to 74 as above, a MD value (MD value: 0.25, 2.99, or the like) can be acquired in accordance with MT method.

When this MD value is evaluated with respect to an MD value of a normal product, MD values are similarly acquired for a plurality of drugs defined as normal products. A threshold value is set from the MD values of these normal products, the MD value of the evaluation target drug is plotted as an evaluation result 23 of the evaluating part 11 illustrated in FIG. 3A to determine whether a normal product or an abnormal product. In the evaluation result 23 of the evaluating part 11 illustrated in FIG. 3A, for example, an MD value of 10 or less is determined as a normal product.

Figure 5:
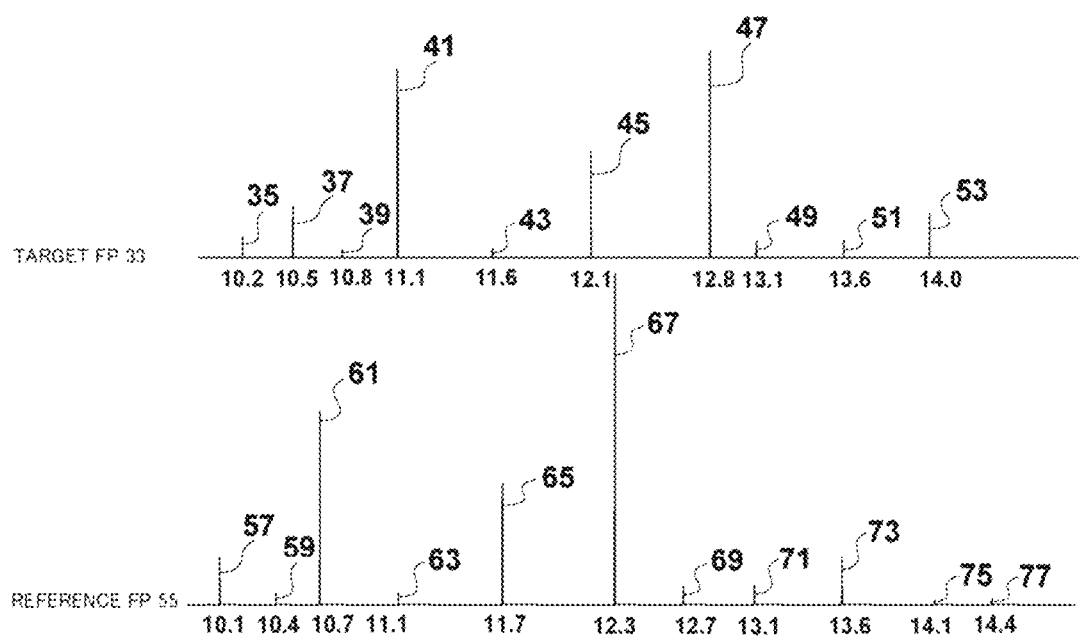
FIG. 5 is a diagram illustrating retention time points of a target FP and a reference FP according to the first embodiment.

FIGS. 5 to 67 illustrate an operating principle of the reference FP selecting part 5, the peak pattern preparing part 7, the peak assigning part 9, and the evaluating part 11.

Figure 6:
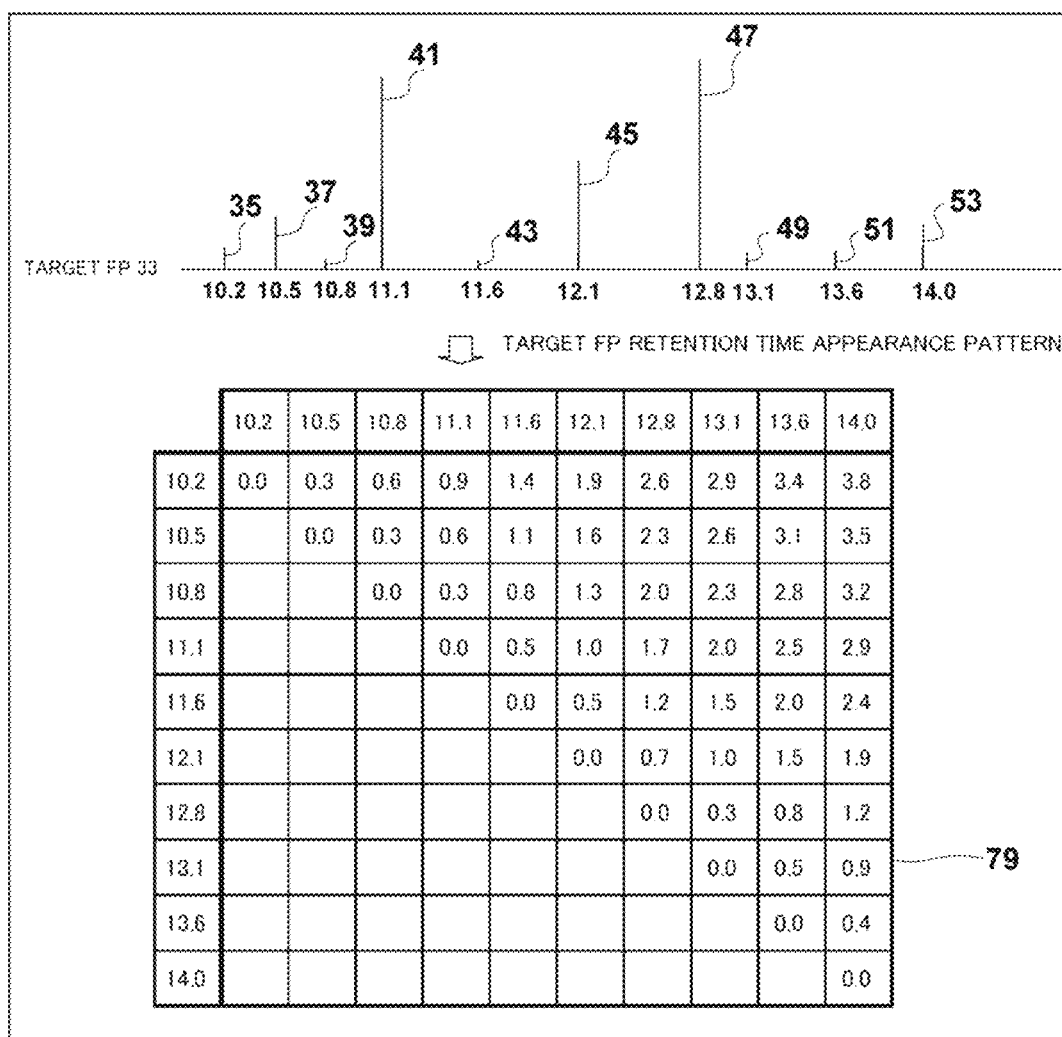
FIG. 6 is a diagram illustrating a retention time appearance pattern of the target FP according to the first embodiment.
Figure 7:
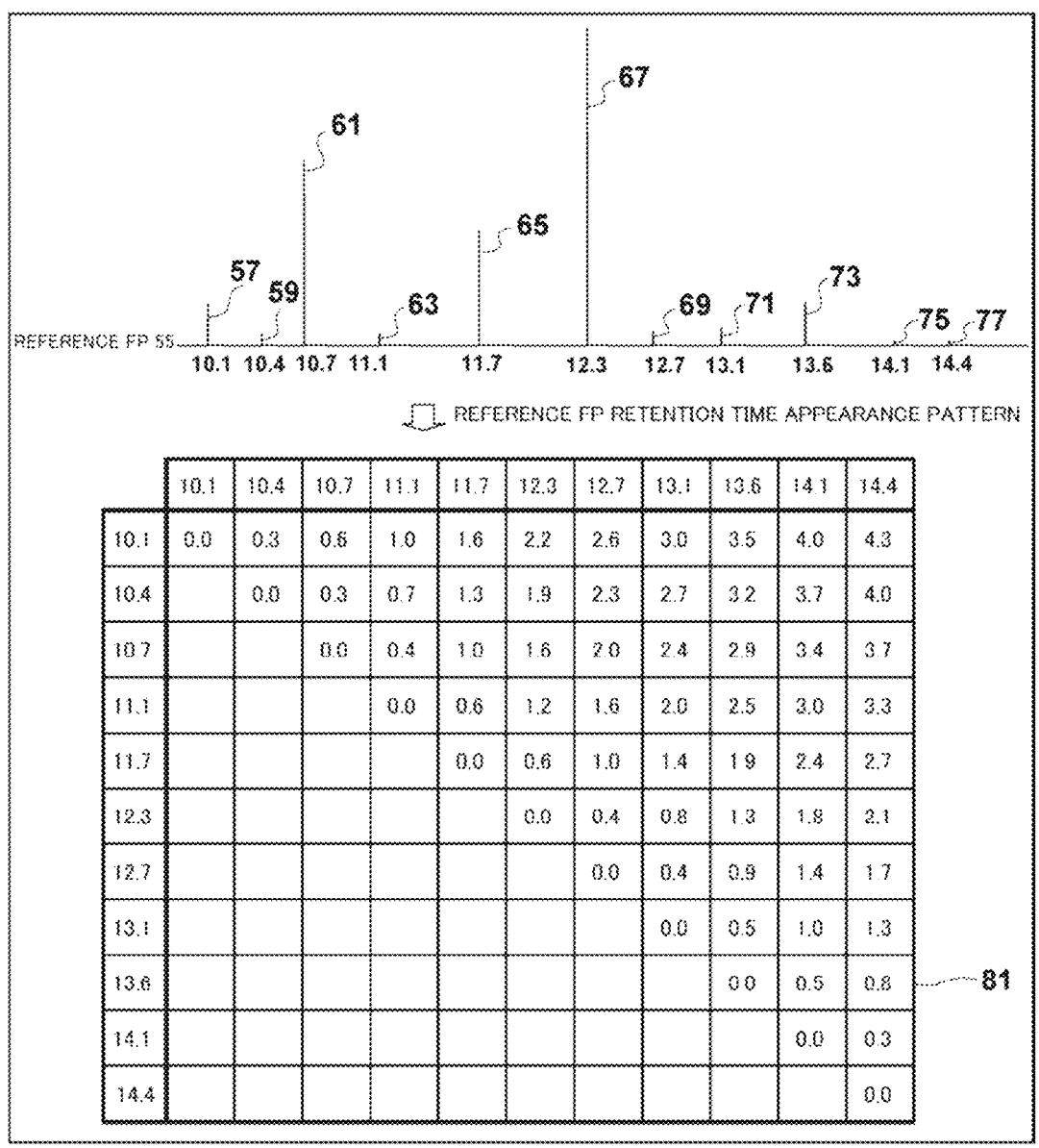
FIG. 7 is a diagram illustrating a retention time appearance pattern of the reference FP according to the first embodiment.

FIGS. 5 to 9 are diagrams each illustrating the degree of matching between the retention time appearance patterns of the target FP and the reference FP according to the reference FP selecting part 5. FIG. 5 is a diagram illustrating the retention time points of the target FP and the reference FP, FIG. 6 is a diagram illustrating the retention time appearance pattern of the target FP, and FIG. 7 is a diagram illustrating the retention time appearance pattern of the reference FP. FIG. 8 is a diagram illustrating the number of matches in the retention time appearance distance between the target FP and the reference FP, and FIG. 9 is a diagram illustrating the degrees of matching between the retention time appearance patterns of the target FP and the reference FP.

FIG. 5 shows the retention time points of the target FP 33 and the reference FP 55. FIGS. 6 and 7 show the retention time appearance patterns in which all of inter-retention time point distances calculated based on the retention time points of the target FP 33 and the reference FP 55 are arranged in a table form. FIG. 8 shows the numbers of matches between the retention time appearance distances calculated based on the appearance patterns and arranged in a table form. FIG. 9 shows the degrees of matching between the retention time appearance patterns calculated based on the number of matches and arranged in a table form. FIGS. 10 to 12 are diagrams explaining a peak pattern that is prepared with use of an assignment target peak and peripheral peaks thereof by the peak pattern preparing part 7. FIG. 10 is a diagram that shows the assignment target peak of the target FP, FIG. 11 is diagram that shows a peak pattern prepared with use of three peaks including two peripheral peaks, and FIG. 12 is a diagram that shows a peak pattern prepared with use of five peaks including four peripheral peaks.

Figure 13:
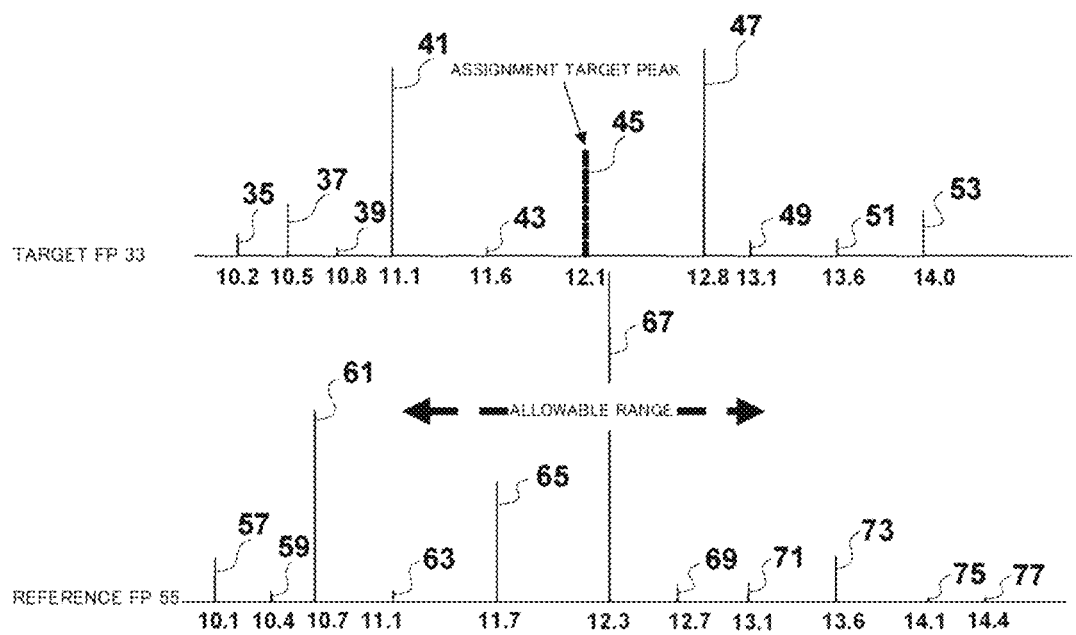
FIG. 13 is a diagram illustrating an allowable range for the assignment target peak according to the first embodiment.
Figure 14:
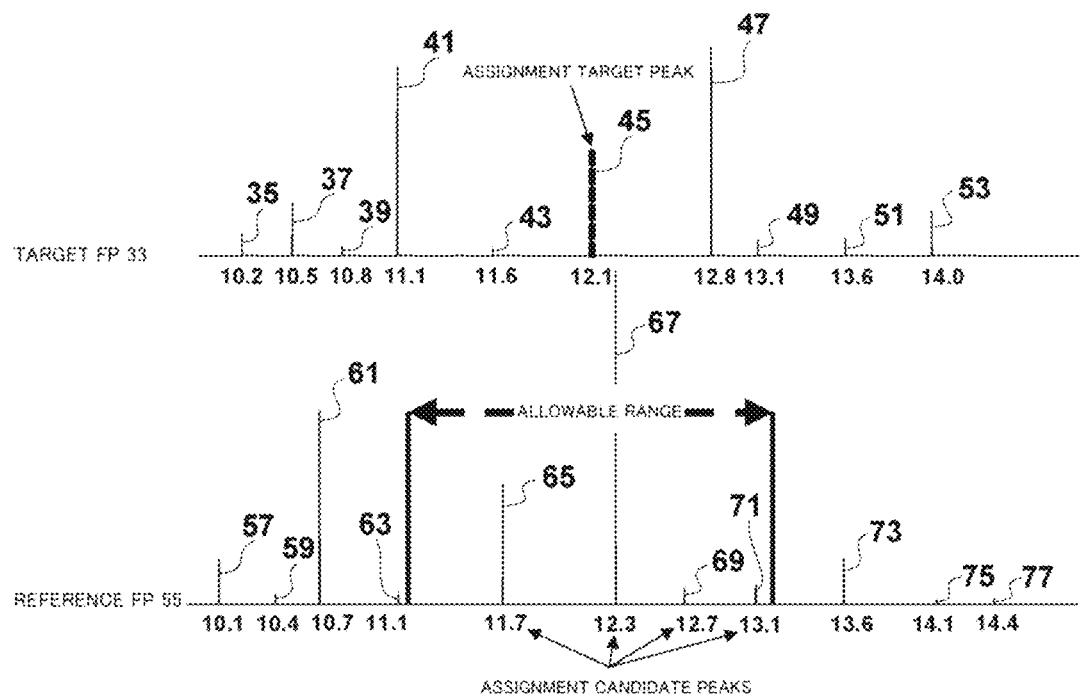
FIG. 14 is a diagram illustrating assignment candidate peaks of the reference FP for the assignment target peak according to the first embodiment.

FIGS. 13 and 14 explain a relation between the assignment target peak and assignment candidate peaks according to the peak pattern preparing part 7, FIG. 13 is a diagram illustrating an allowable range of the assignment target peak, and FIG. 14 is a diagram illustrating assignment candidate peaks of the reference FP for the assignment target peak.

Figure 15:
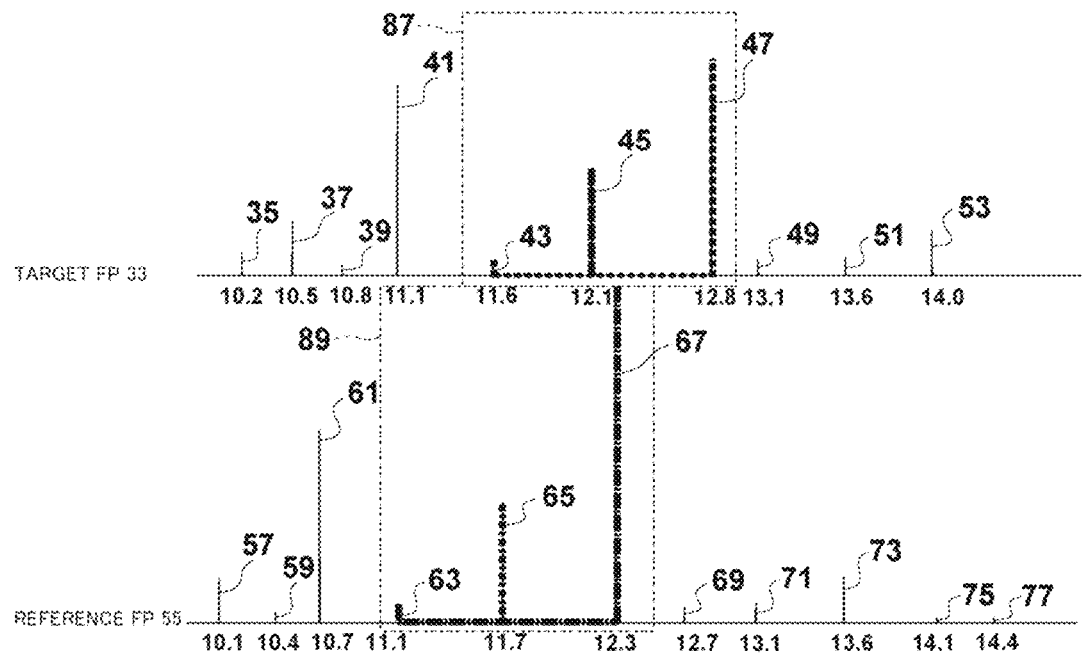
FIG. 15 is a peak pattern diagram according to three peaks of assignment candidate peaks for the assignment target peak according to the first embodiment.
Figure 16:
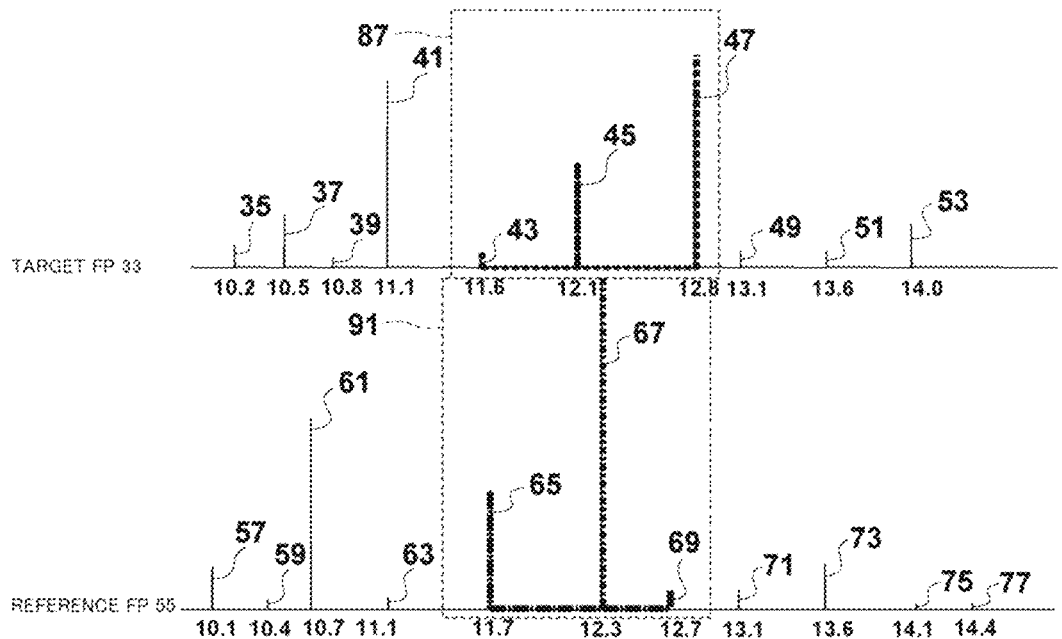
FIG. 16 is a peak pattern diagram according to three peaks of another assignment candidate peaks for the assignment target peak according to the first embodiment.
Figure 17:
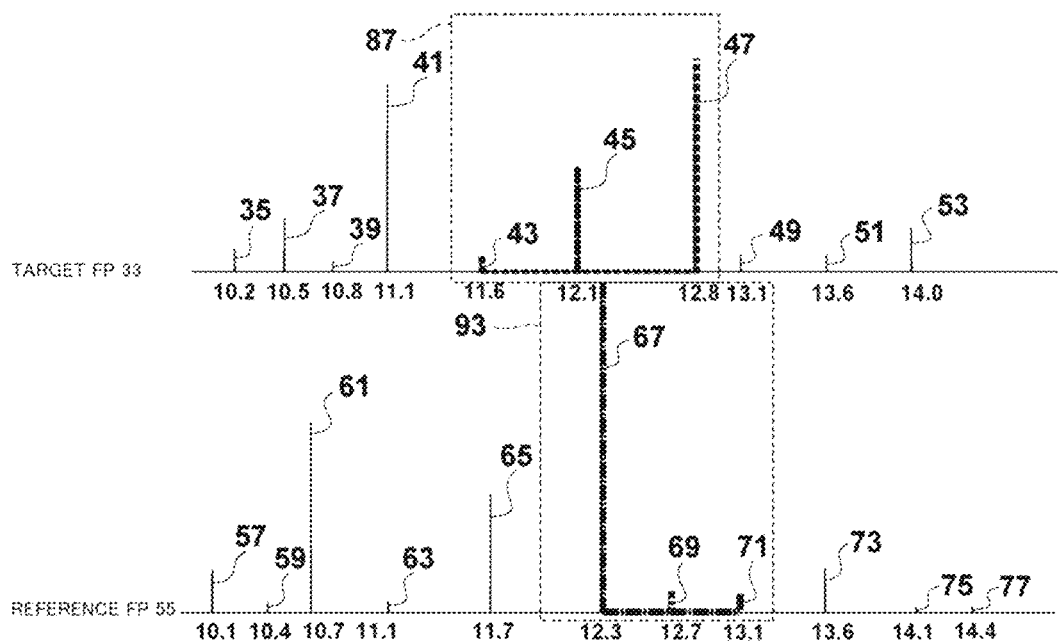
FIG. 17 is a peak pattern diagram according to three peaks of another assignment candidate peaks for the assignment target peak according to the first embodiment.
Figure 18:
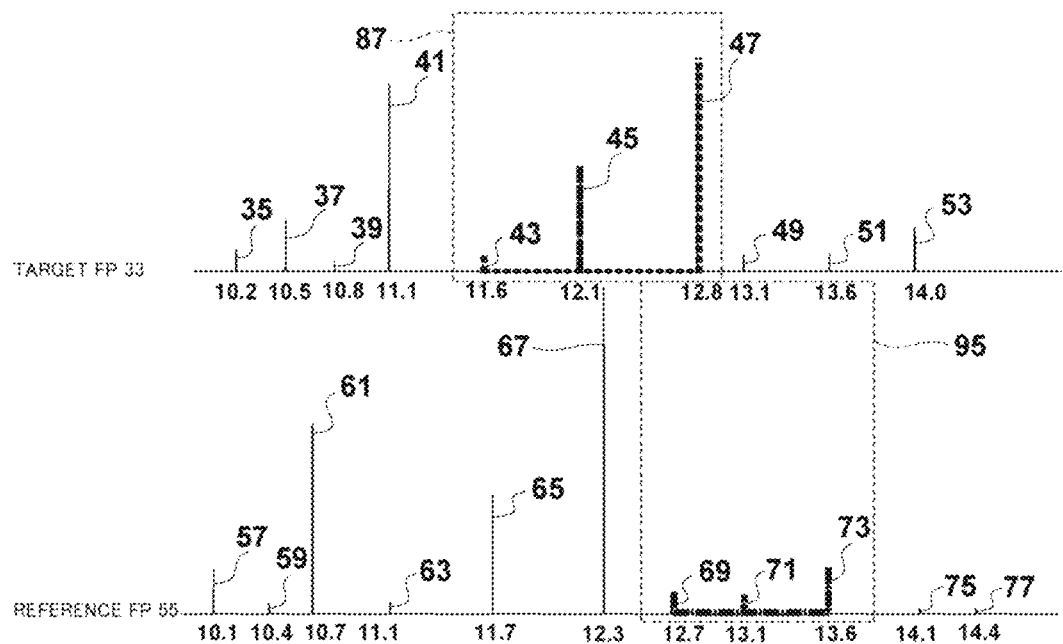
FIG. 18 is a peak pattern diagram according to three peaks of another assignment candidate peaks for the assignment target peak according to the first embodiment.

FIGS. 15 to 18 are peak pattern examples of the assignment target peak and assignment candidate peak that are prepared by three peaks according to the peak pattern preparing part 7. FIG. 15 is a peak pattern diagram according to three peaks of the assignment target peak and assignment candidate peaks, FIG. 16 is a peak pattern diagram according to three peaks of another assignment candidate peaks for the assignment target peak, FIG. 17 is a peak pattern diagram according to three peaks of another assignment candidate peaks for the assignment target peak, and FIG. 18 is a peak pattern diagram according to three peaks of another assignment candidate peaks for the assignment target peak.

FIGS. 19 to 22 are peak pattern diagrams of an assignment target peak and assignment candidate peak that are prepared with use of five peaks according to the peak pattern preparing part 7.

FIGS. 23 to 61 are diagrams explaining the principle of comprehensive comparison in which peak patterns of the assignment target peak and assignment candidate peak according to the peak pattern preparing part 7 are comprehensively prepared and compared with each other.

FIGS. 62 and 63 are diagrams explaining a calculating method of the degree of matching between peak patterns prepared with use of three peaks according to the peak assigning part 9.

FIG. 64 is a diagram explaining a calculating method of the degree of matching between peak patterns prepared with use of five peaks according to the peak assigning part 9.

FIG. 65 is a diagram illustrating UV spectra 107 and 111 of the assignment target peak 45 and the assignment candidate peak 67 according to the peak assigning part 9.

FIG. 66 is a diagram explaining the degree of matching between the UV spectrum 107 of the assignment target peak 45 and the UV spectrum 111 of the assignment candidate peak 67 according to the peak assigning part 9.

FIG. 67 is a diagram explaining the degree of matching of the assignment candidate peak that is calculated based on the degree of matching between peak patterns of the assignment target peak 45 and the assignment candidate peak 67 and the degree of matching between UV spectra according to the peak assigning part 9.

FIG. 68 is a diagram explaining the assignment of each peak of the target FP 17 to the reference group FP 19 according to the peak assigning part 9.

FIG. 69 is a diagram explaining a target FP peak feature value 21 that represents a state in which each peak of the target FP 17 is assigned to the reference group FP 19 according to the peak assigning part 9.

FIGS. 70 to 74 are diagrams illustrating various target FPs and evaluation values (MD values) thereof according to the evaluating part 11.

The function of the above-described reference FP selecting part 5 will be further described with reference to FIGS. 5 to 9.

FIG. 5 is the diagram illustrating the retention time points of the target FP and the reference FP, FIG. 6 is the diagram illustrating the retention time appearance pattern of the target FP, and FIG. 7 is the diagram illustrating the retention time appearance pattern of the reference FP. FIG. 8 is the diagram illustrating the number of matches in the retention time appearance distance between the target FP and the reference FP, and FIG. 9 is the diagram illustrating the degrees of matching between the retention time appearance patterns of the target FP and the reference FP.

FIG. 5 shows the retention time points of the target FP 33 and the reference FP 55. FIGS. 6 and 7 show the retention time appearance patterns in which all of inter-retention time point distances calculated based on the retention time points of the target FP 33 and the reference FP 55 are arranged in a table form. FIG. 8 shows the numbers of matches between the retention time appearance distances calculated based on the appearance patterns and arranged in a table form. FIG. 9 shows the degrees of matching between the retention time appearance patterns calculated based on the number of matches and arranged in a table form.

In the peak assigning process for the target FP 33, the peaks of the target FP 33 are assigned to a reference FP whose FP pattern is closest to the target FP 33 as much as possible. Selecting this reference FP that is closest to the target FP 33 from among a plurality of reference FPs is an important point for performing assignment with high accuracy.

Thus, as a method of evaluating similarity to a FP pattern of the target FP 33 in an objective and simplified manner, the similarity of the FP pattern is evaluated based on the degree of matching between the retention time appearance patterns.

For example, in a case where the retention time points of the target FP 33 and the reference FP 55 are as illustrated in FIG. 5, retention time appearance patterns of the target FP 33 and the reference FP 55 are formed as illustrated in FIGS. 6 and 7. In FIGS. 6 and 7, for the target FP 33 and the reference FP 55 illustrated on the upper side, as tables illustrated on the lower side, patterns are prepared in the form of tables in which the value of each cell is configured by an inter-retention time point distance.

In FIG. 6, the retention time points of peaks (35, 37, 39, 41, 43, 45, 47, 49, 51, and 53) of the target FP 33 are (10.2), (10.5), (10.8), (11.1), (11.6), (12.1), (12.8), (13.1), (13.6), and (14.0).

Accordingly, an inter-retention time point distance between the peaks 35 and 37 is (10.5)–(10.2)=(0.3). Similarly, a distance between the peaks 35 and 39 is (0.6), a distance between the peaks 37 and 39 is (0.3), etc. The followings are similarly acquired and a target FP appearance pattern 79 is formed into a table on the lower side of FIG. 6.

In FIG. 7, the retention time points of the peaks (57, 59, 61, 63, 65, 67, 69, 71, 73, 75, and 77) of the reference FP 55 are (10.1), (10.4), (10.7), (11.1), (11.7), (12.3), (12.7), (13.1), (13.6), (14.1), and (14.4).

Accordingly, in the same way, inter-retention time point distances form a reference FP appearance pattern 81 into a table on the lower side of FIG. 7.

The individual peaks patterned as illustrated in FIGS. 6 and 7 are compared in a round-robin system so as to acquire the number of matches. For example, the value of each cell of the target FP appearance pattern represented in the table illustrated on the lower side of FIG. 6 is compared with the value of each cell of the reference FP appearance pattern represented in the table on the lower side of FIG. 7, thereby acquiring the number 83 of matches as illustrated in FIG. 8.

Namely, all the inter-retention time point distances of the retention time appearance patterns of the target FP 33 and the reference FP 55 are sequentially compared with each other in units of rows in a round-robin system, thereby calculating the number of the distances that match within a set range.

For example, comparing the first rows of the target and reference FP retention time appearance patterns 79 and 81 in FIGS. 6 and 7, the number of matches is seven. This number of matches of seven is written into the first row of the target and reference FP retention time appearance pattern illustrated in FIG. 8. For the other rows in FIGS. 6 and 7, similarly, the first to ninth rows of the target FP retention time appearance pattern is compared with the first to tenth rows of the reference FP retention time appearance pattern in a round-robin system, thereby acquiring the numbers of matches, respectively.

The results are represented in FIG. 8. In FIG. 8, a leftmost circled number of 7 is a result of the comparison between the first rows of the target and reference FP retention time appearance patterns, and a number of 7 represented next thereto is a result of the comparison between the first row of the target FP retention time appearance pattern and the second row of the reference FP retention time appearance pattern. The set range is preferably in the rage of 0.05 to 0.2 minutes, but is not limited thereto. In the first embodiment, the set range is 0.1 minutes.

When the degree of matching between retention time appearance patterns is RP, a degree ($RP_{fg}$) of matching between a retention time appearance pattern of the f-th row of the target FP 33 and a retention time appearance pattern of the g-th row of the reference FP 55 is calculated using Tanimoto coefficient as:

$$RP_{fg} = \{1-(m/(a+b-m))\} \times (a-m+1).$$

In the equation, "a" is the number of peaks of the target FP 33 (the number of target FP peaks), "b" is the number of peaks of the reference FP 55 (the number of reference FP peaks), and "m" is the number of matches in an appearance distance (see FIG. 8). The degree (RP) of matching between retention time appearance patterns is calculated by the above-described equation based on the number 83 of matches in FIG. 8 (see the degree 85 of matching in FIG. 9).

A minimum value (RP_min) of these RPs is set as the degree of matching between the retention time appearance patterns of the target FP 33 and the reference FP 55. In the case of FIG. 9, (0.50) is the degree of matching of the target FP 33 with respect to the reference FP.

The degrees of matching are calculated for all the reference FPs, and a reference FP having the smallest degree of matching is selected, and the peaks of the target FP are assigned to the reference FP.

The reference FP selecting part 5 may pattern the target FP 33 and the reference FP 55 at peak heights ratios.

The peaks patterned with use of the peak height ratios are compared in a round-robin system, to calculate the number of matches in the height ratio within a set range. By performing the calculation, similarly to the case of FIG. 8, the number of matches can be acquired.

In addition, in the case where the peaks are patterned at the peak height ratios, there is a case where a plurality of similar values are present in one row, and thus these values are required not to be counted a plurality of times.

The degree of matching can be acquired by setting the Tanimoto coefficient as "the number of matches in height ratio/(the number of target FP peaks+the number of reference FP peaks−the number of matches in the height ratio)" and approaching (1−Tanimoto coefficient) to zero.

In addition, (1−Tanimoto coefficient) is weighted by (the number of target FP peaks−the number of matches in height ratio+1) to be "(1−Tanimoto coefficient)×(the number of target FP peaks−the number of matches the an appearance distance or the height ratio+1", whereby a reference FP that matches more peaks (35, 37, . . . ) of the target FP 33 in accordance with the weighting can be selected.

The functions of the peak pattern preparing part 7 and the peak assigning part 9 will be described further with reference to FIGS. 10 to 69.

When the assignment target peak 45 is assigned to one of peaks of the reference FP 55, it works out to that the peak should be assigned to which one of the peaks as illustrated in FIG. 10. If this peak assignment is carried out based on only information of the peak retention time points or UV spectra, sufficient accuracy cannot be acquired by the peak assignment based on the single kind of information. This is because all the three kinds of information include errors due to the inter-drug error and the analysis error.

In addition, as illustrated in FIGS. 13 and 14, in a case of setting an allowable range of a deviation between the retention time points of each peak of the assignment target peak 45 and the reference FP 55 and performing peak assignment based on two kinds of information including presence of peaks of the reference FP 55 within the allowable range and UV spectrum information, an assignment destination is determined by synthesizing all the information to improve accuracy compared to the peak assignment according to the single kind of information.

However, even in a case where the peak assignment is performed based on the three kinds of information, UV spectra with similar components are the almost same as the characteristics. Accordingly, if a plurality similar components are included in the assignment candidate peaks, the assignment is consequently performed based on only peak information, whereby sufficient accuracy cannot be acquired. Hence, in order to perform peak assignment with high accuracy, more information is necessary to be added to the three kinds of information.

Then, peak patterns including information of peripheral peaks as illustrated in FIGS. 11 and 12 are prepared, and the peak assignment is performed based on the comparison of the peak patterns.

If the peak pattern includes the peripheral peaks, the peripheral information is added to the prior three kinds of information. Accordingly, the peak assignment can be performed based on four kinds of information, whereby higher assignment accuracy can be acquired.

As a result, massive peaks can be efficiently assigned all together through one assignment process with high accuracy.

In addition, by configuring data used for the peak assignment as the four kinds of information including the peripheral information, there is no need of restriction conditions (definition of peaks and the like) to be set in a conventional peak assignment process.

In the case illustrated in FIG. 11, a peak pattern 87 that includes peaks 43 and 47 being present on both sides in the time axis direction is prepared for the assignment target peak 45.

In the case illustrated in FIG. 12, a peak pattern 97 including peaks 41, 43, 47, and 49 that are present on both sides in the time axis direction is prepared for the assignment target peak 45.

In the cases of FIGS. 13 and 14, an allowable range of the deviation between the retention time points of each peak of the assignment target peak 45 and the reference FP 55 is set, and peaks of the reference FP 55 that are present within the allowable range are set as candidate peaks (hereinafter, referred to as assignment candidate peaks) that correspond to the assignment target peak 45.

In the case of FIG. 15, as a peak pattern to be compared with the peak pattern 87 for the assignment target peak 45, a peak pattern 89 that includes peaks 63 and 67 being present on both sides located in front and in the rear in the time axis direction is prepared for an assignment candidate peak 65.

In the cases of FIGS. 16 to 18, as a peak pattern to be compared with the peak pattern 87 for the assignment target peak 45, peak patterns 91, 93, and 95 that include peaks that are present on both sides located in front and in the rear in the time axis direction are prepared for another assignment candidate peaks 67, 69, and 71, respectively.

In order to compare peak patterns with higher accuracy, it is important to prepare a peak pattern in which the numbers of peripheral peaks are increased for both the target FP and the reference FP as illustrated in FIGS. 19 to 22.

For example, by comparing peak patterns having a total of five peaks that includes four peripheral peaks, higher assignment accuracy is acquired.

Figure 19:
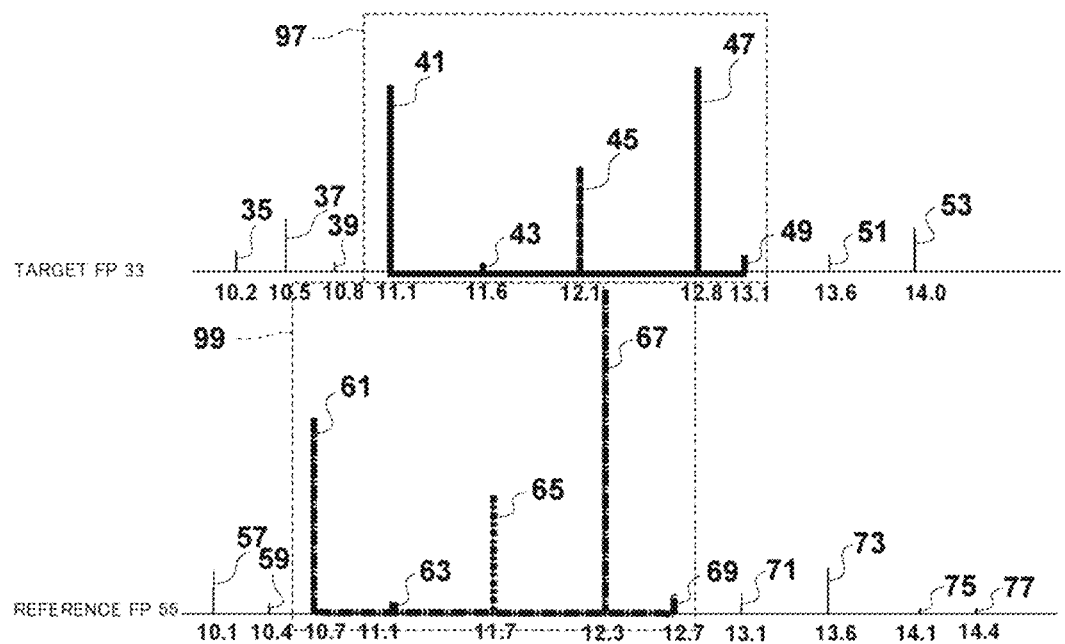
FIG. 19 is a peak pattern diagram according to five peaks of assignment candidate peaks for the assignment target peak according to the first embodiment.

In the case of FIG. 19, as a peak pattern to be compared with the peak pattern 97 for the assignment target peak 45, a peak pattern 99 that includes peaks 61, 63, 67, and 69 being present on both sides located in front and in the rear in the time axis direction are prepared for the assignment candidate peak 65.

Figure 20:
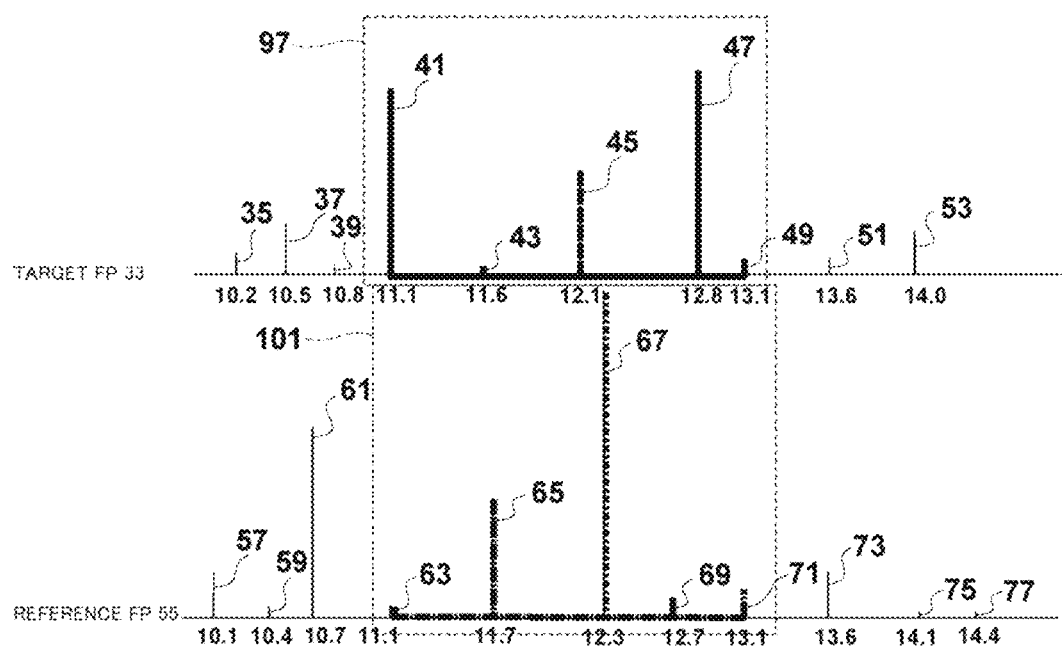
FIG. 20 is a peak pattern diagram according to five peaks of another assignment candidate peaks for the assignment target peak according to the first embodiment.
Figure 21:
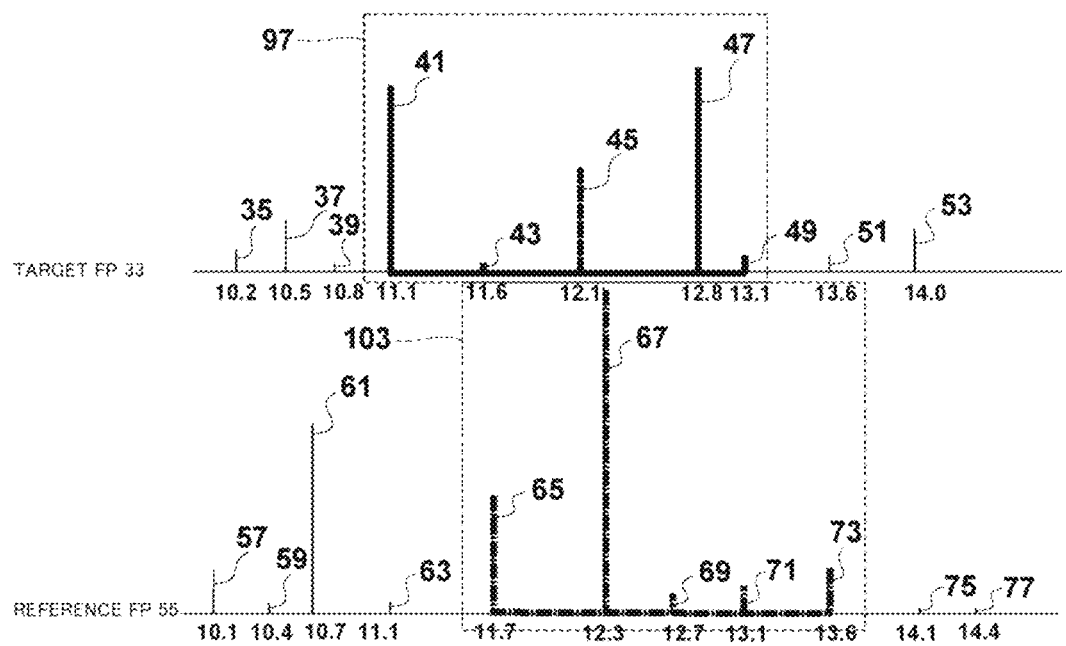
FIG. 21 is a peak pattern diagram according to five peaks of another assignment candidate peaks for the assignment target peak according to the first embodiment.
Figure 22:
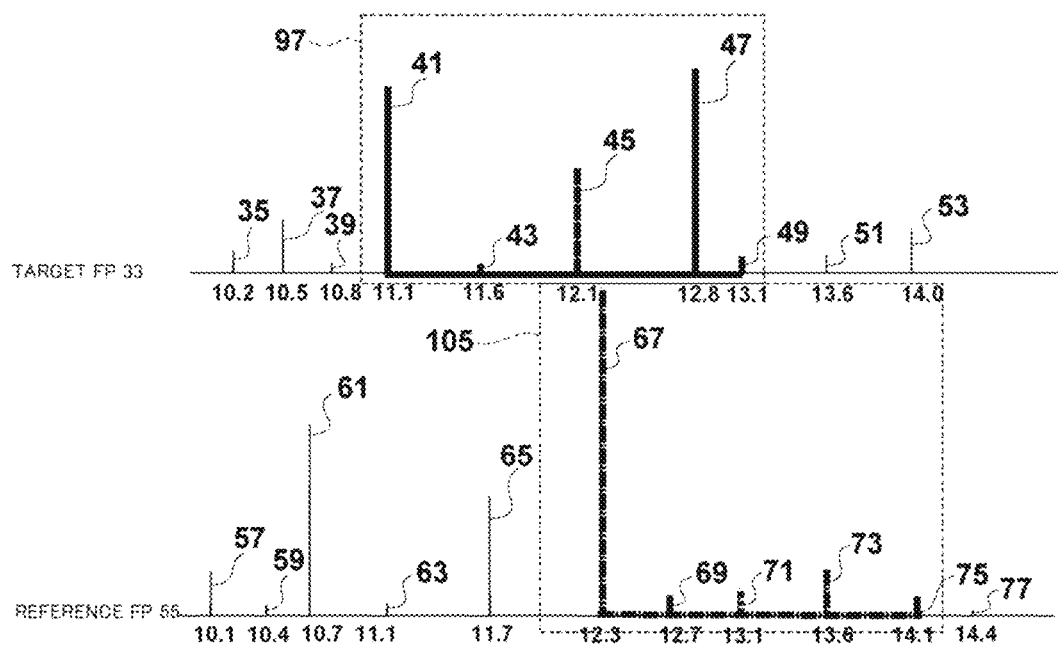
FIG. 22 is a peak pattern diagram according to five peaks of another assignment candidate peaks for the assignment target peak according to the first embodiment.

In the cases of FIGS. 20 to 22, as a peak pattern to be compared with a peak pattern 97 for the assignment target peak 45, peak patterns 101, 103, and 105 that include peaks being present on both sides located in front and in the rear in the time axis direction are prepared as peak patterns for another assignment candidate peaks 67, 69, and 71, respectively.

Figure 24:
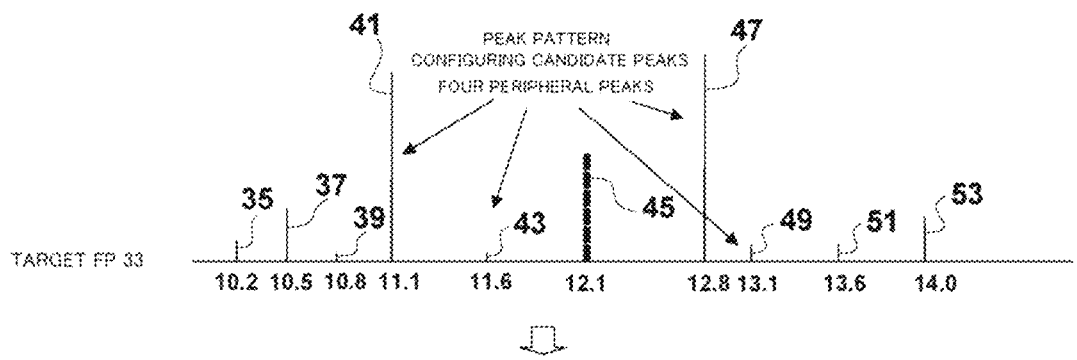
FIG. 24 is a diagram illustrating the number of all the peak patterns for the assignment target peak in a case that four peak pattern configuring candidate peaks are set according to the first embodiment.
Figure 25:
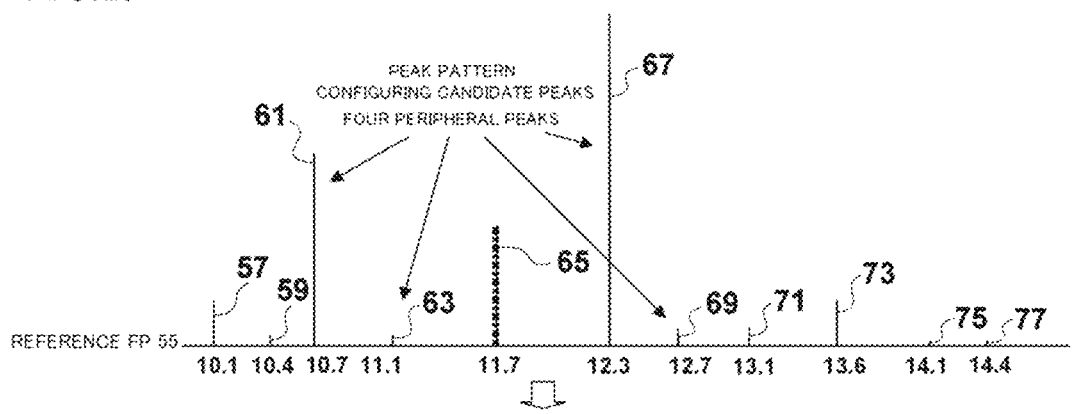
FIG. 25 is a diagram illustrating the number of all the peak patterns for an assignment candidate peak in a case that four peak pattern configuring candidate peaks are set according to the first embodiment.
Figure 26:
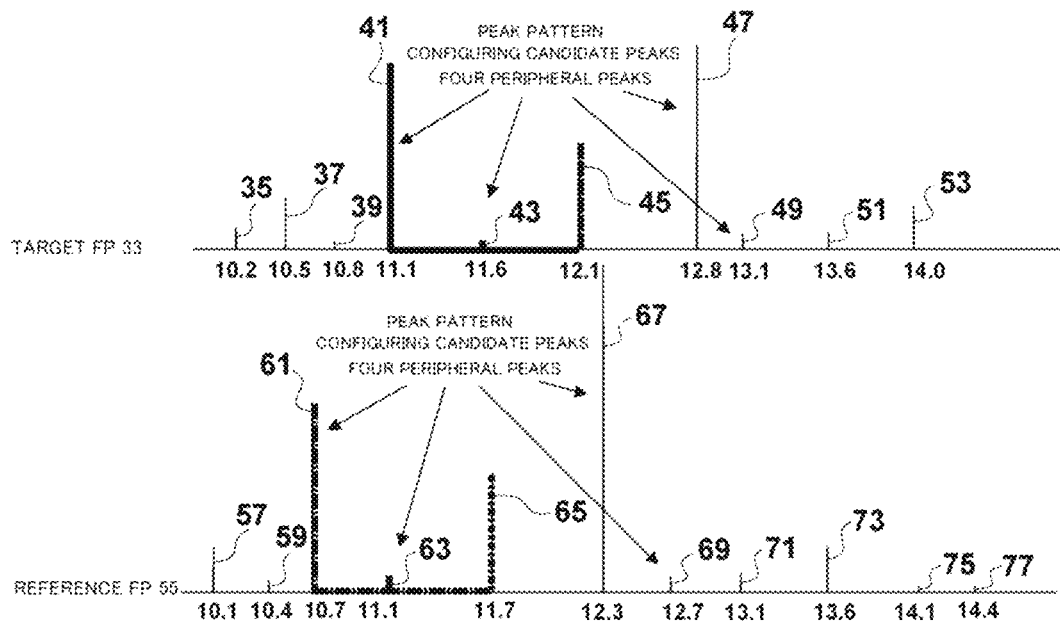
FIG. 26 is an explanatory diagram illustrating comprehensive comparison of peak patterns for the assignment target peak with respect to peak patterns for an assignment candidate peak according to the first embodiment.
Figure 27:
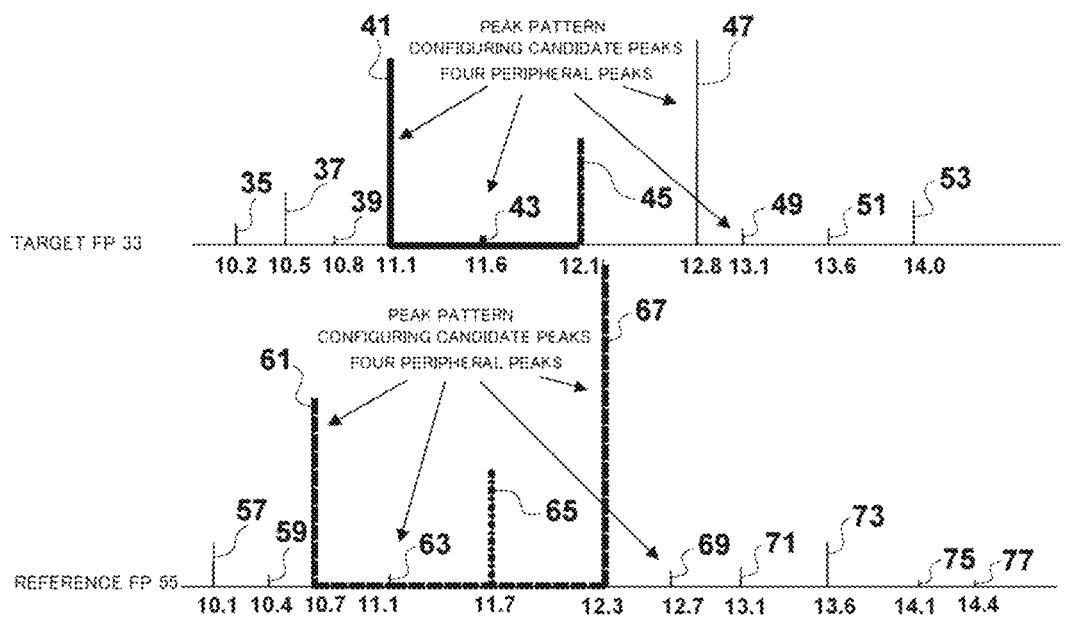
FIG. 27 is an explanatory diagram illustrating comprehensive comparison of peak patterns for the assignment target peak with respect to peak patterns for the assignment candidate peak according to the first embodiment.
Figure 28:
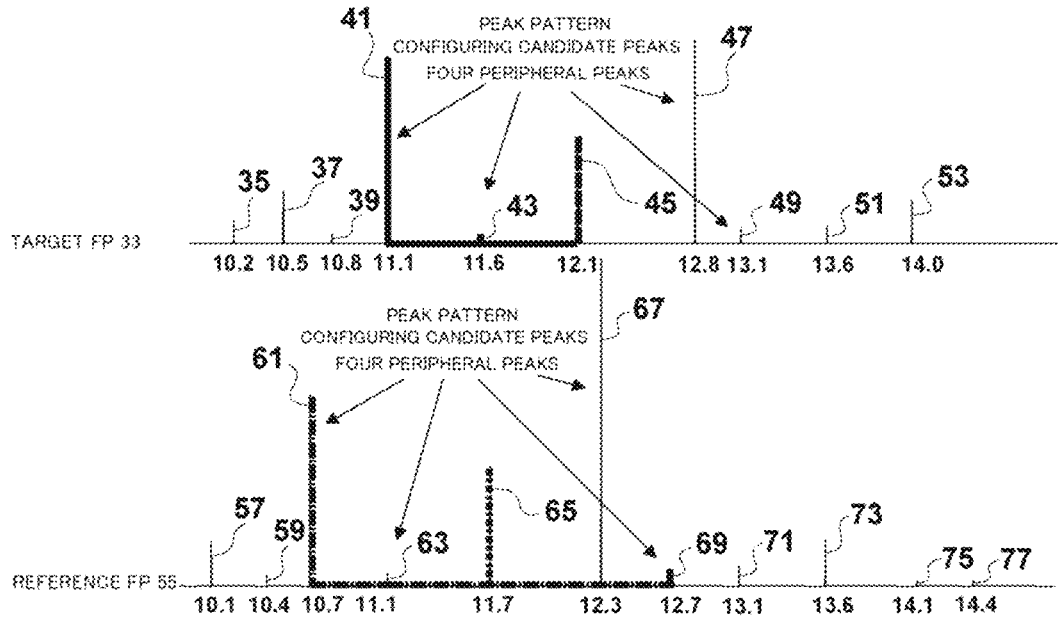
FIG. 28 is an explanatory diagram illustrating comprehensive comparison of peak patterns for the assignment target peak with respect to peak patterns for the assignment candidate peak according to the first embodiment.
Figure 29:
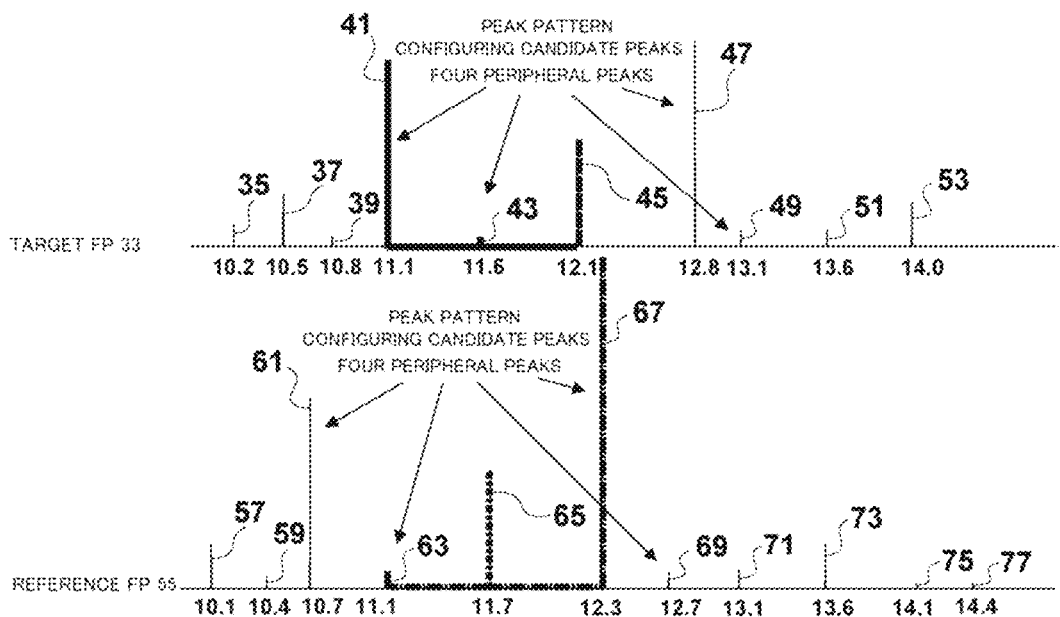
FIG. 29 is an explanatory diagram illustrating comprehensive comparison of peak patterns for the assignment target peak with respect to peak patterns for the assignment candidate peak according to the first embodiment.
Figure 30:
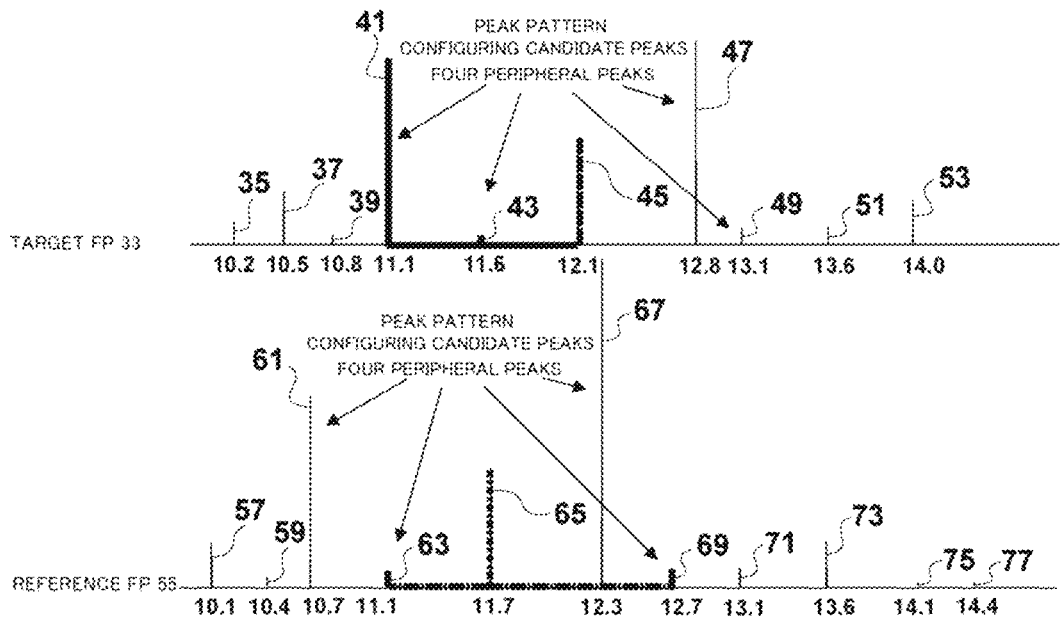
FIG. 30 is an explanatory diagram illustrating comprehensive comparison of peak patterns for the assignment target peak with respect to peak patterns for the assignment candidate peak according to the first embodiment.
Figure 31:
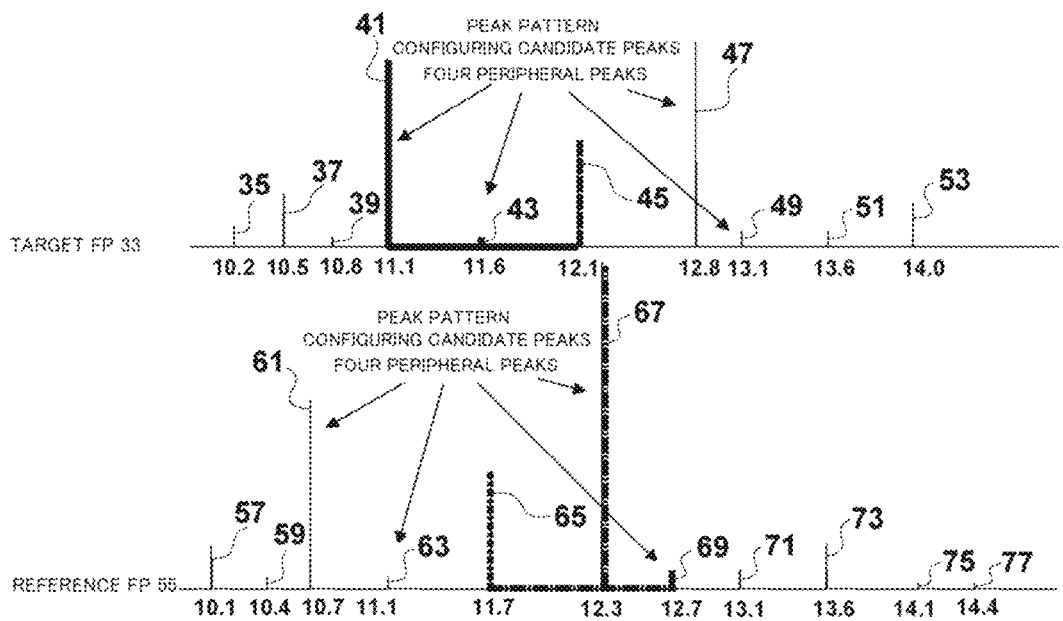
FIG. 31 is an explanatory diagram illustrating comprehensive comparison of peak patterns for the assignment target peak with respect to peak patterns for the assignment candidate peak according to the first embodiment.
Figure 32:
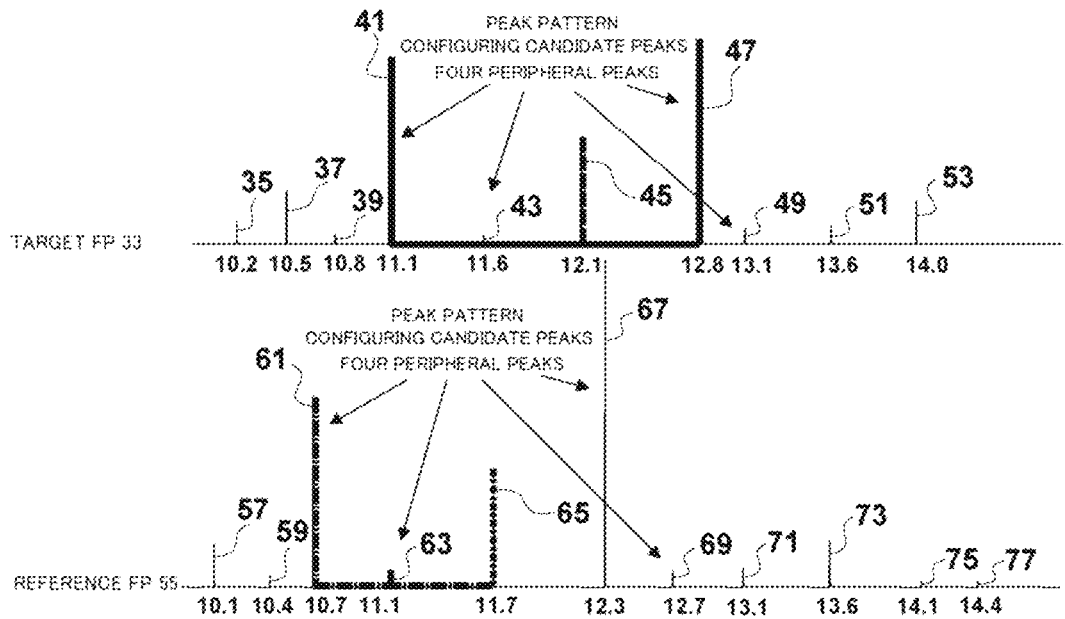
FIG. 32 is an explanatory diagram illustrating comprehensive comparison of peak patterns for the assignment target peak with respect to peak patterns for the assignment candidate peak according to the first embodiment.
Figure 33:
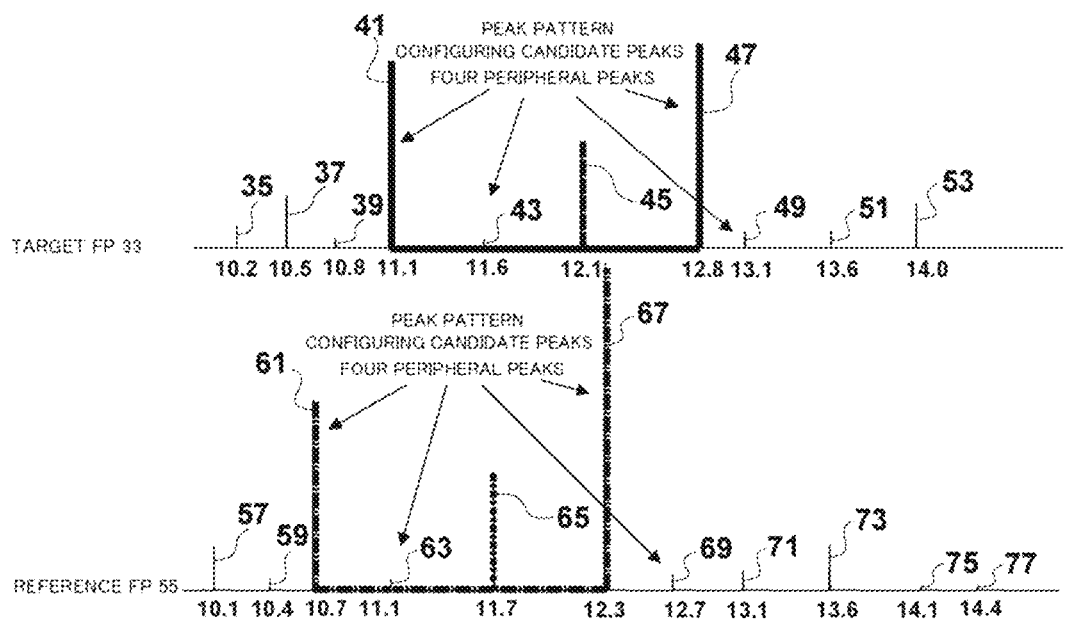
FIG. 33 is an explanatory diagram illustrating comprehensive comparison of peak patterns for the assignment target peak with respect to peak patterns for the assignment candidate peak according to the first embodiment.
Figure 34:
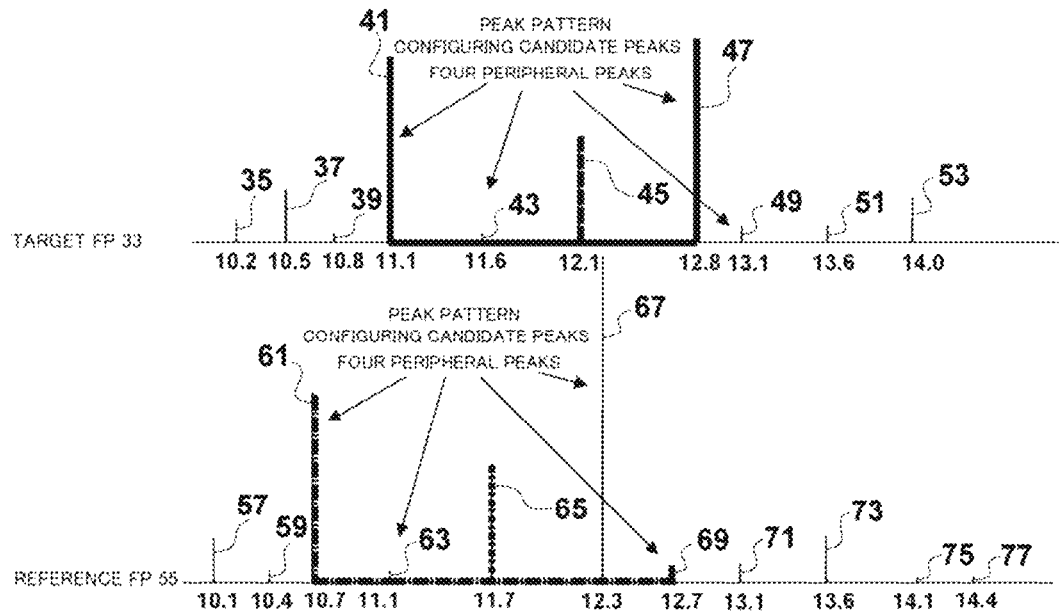
FIG. 34 is an explanatory diagram illustrating comprehensive comparison of peak patterns for the assignment target peak with respect to peak patterns for the assignment candidate peak according to the first embodiment.
Figure 35:
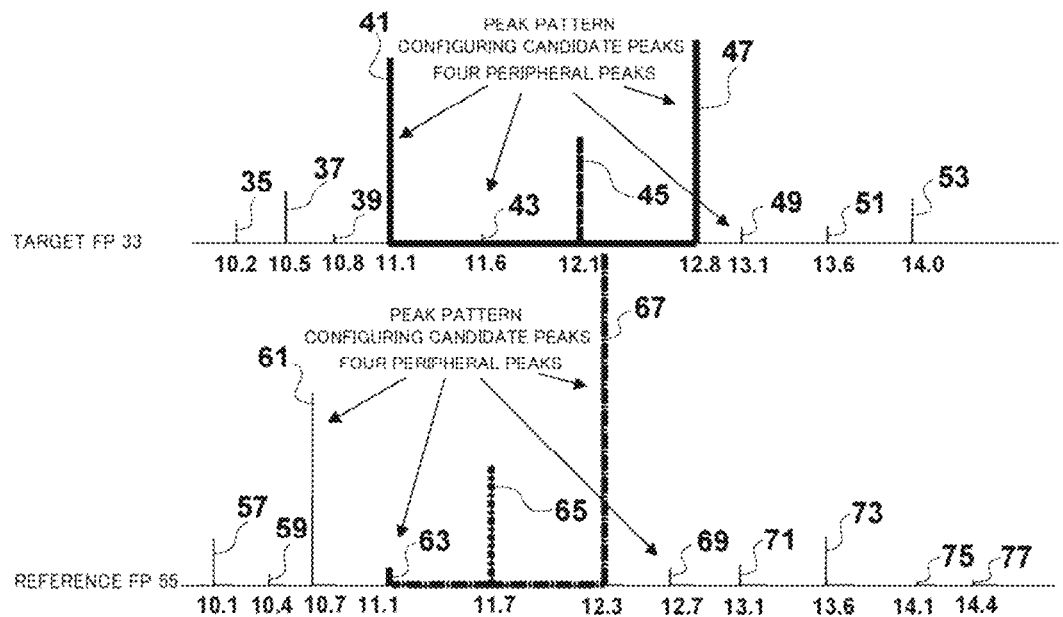
FIG. 35 is an explanatory diagram illustrating comprehensive comparison of peak patterns for the assignment target peak with respect to peak patterns for the assignment candidate peak according to the first embodiment.
Figure 36:
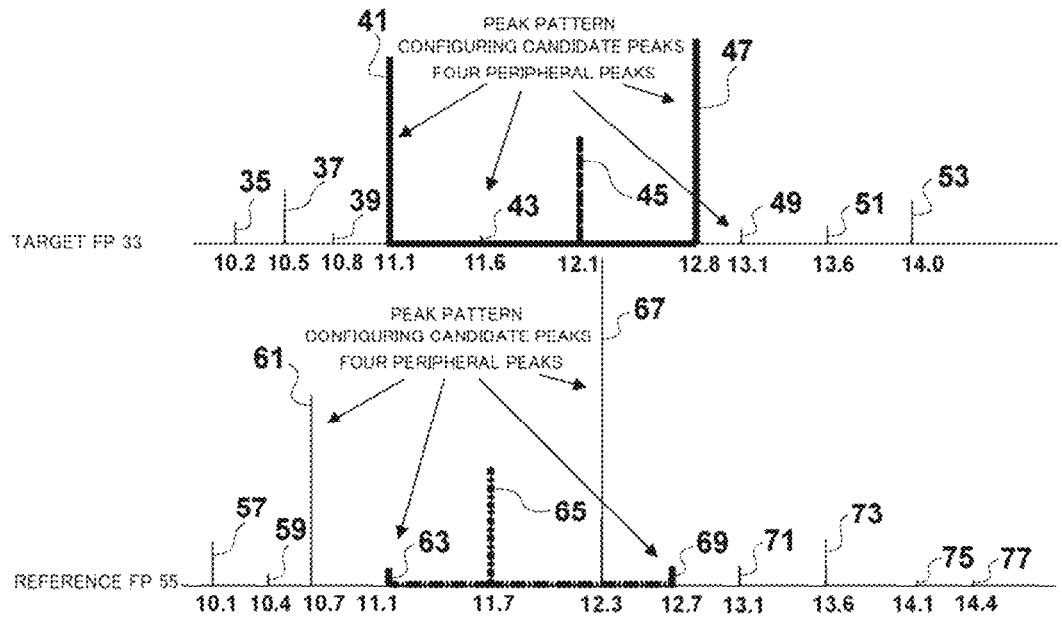
FIG. 36 is an explanatory diagram illustrating comprehensive comparison of peak patterns for the assignment target peak with respect to peak patterns for the assignment candidate peak according to the first embodiment.
Figure 37:
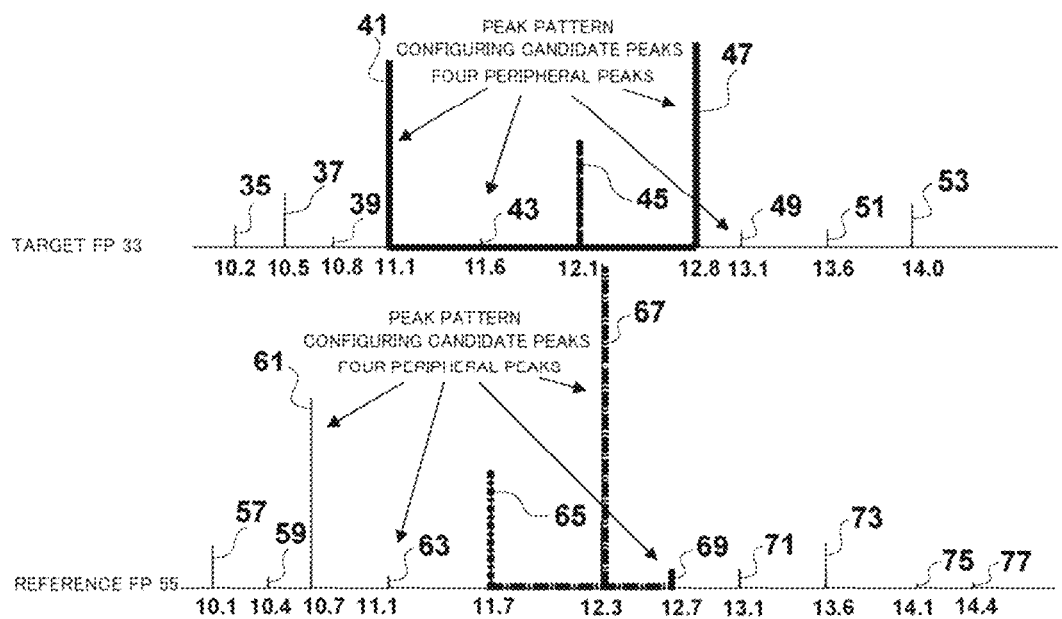
FIG. 37 is an explanatory diagram illustrating comprehensive comparison of peak patterns for the assignment target peak with respect to peak patterns for the assignment candidate peak according to the first embodiment.
Figure 38:
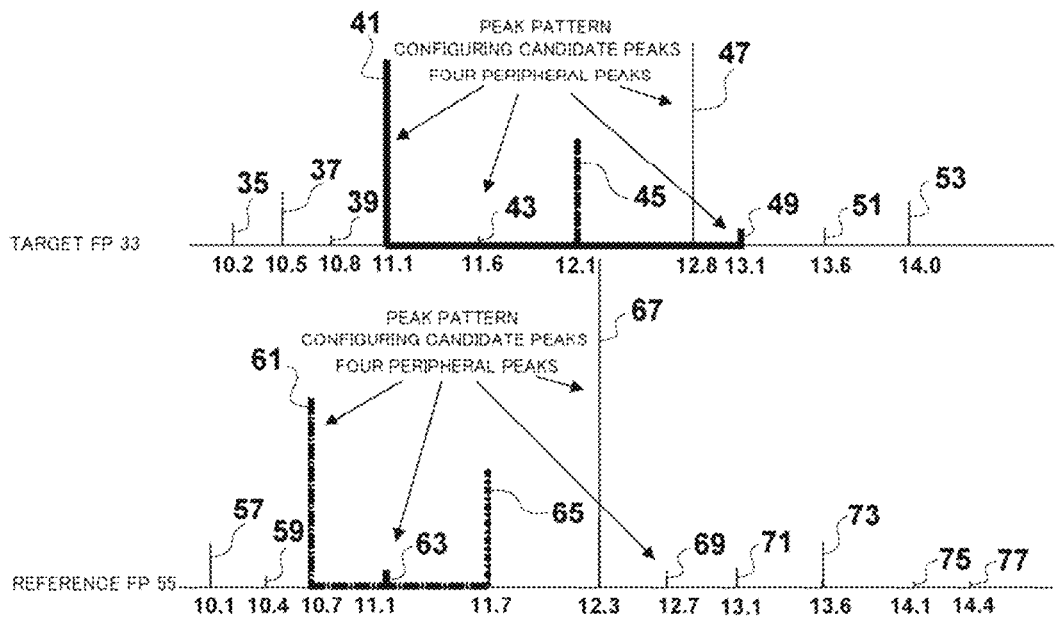
FIG. 38 is an explanatory diagram illustrating comprehensive comparison of peak patterns for the assignment target peak with respect to peak patterns for the assignment candidate peak according to the first embodiment.
Figure 39:
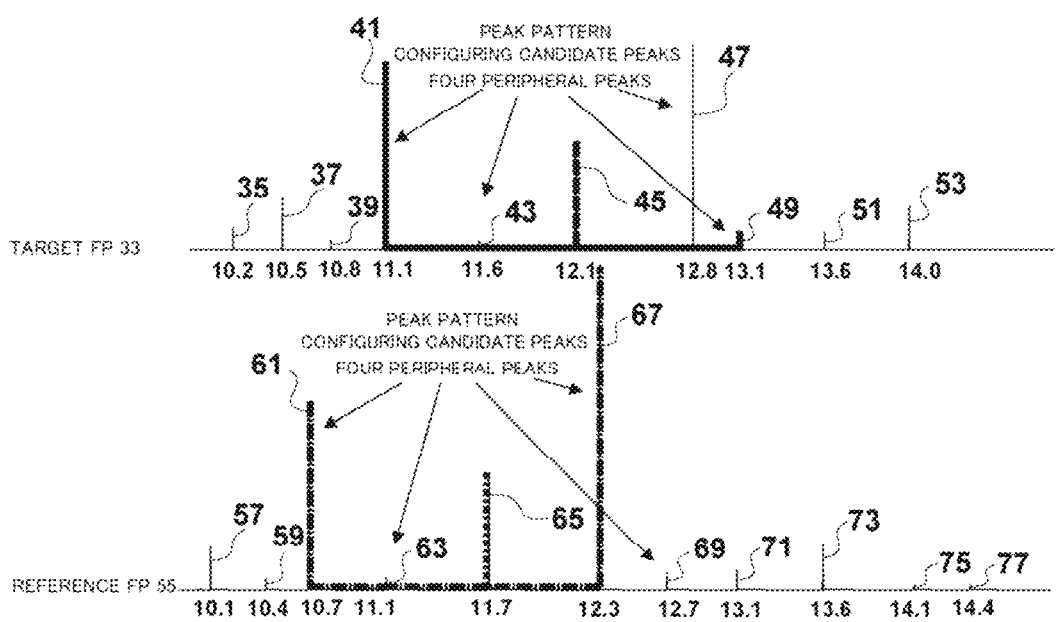
FIG. 39 is an explanatory diagram illustrating comprehensive comparison of peak patterns for the assignment target peak with respect to peak patterns for the assignment candidate peak according to the first embodiment.
Figure 40:
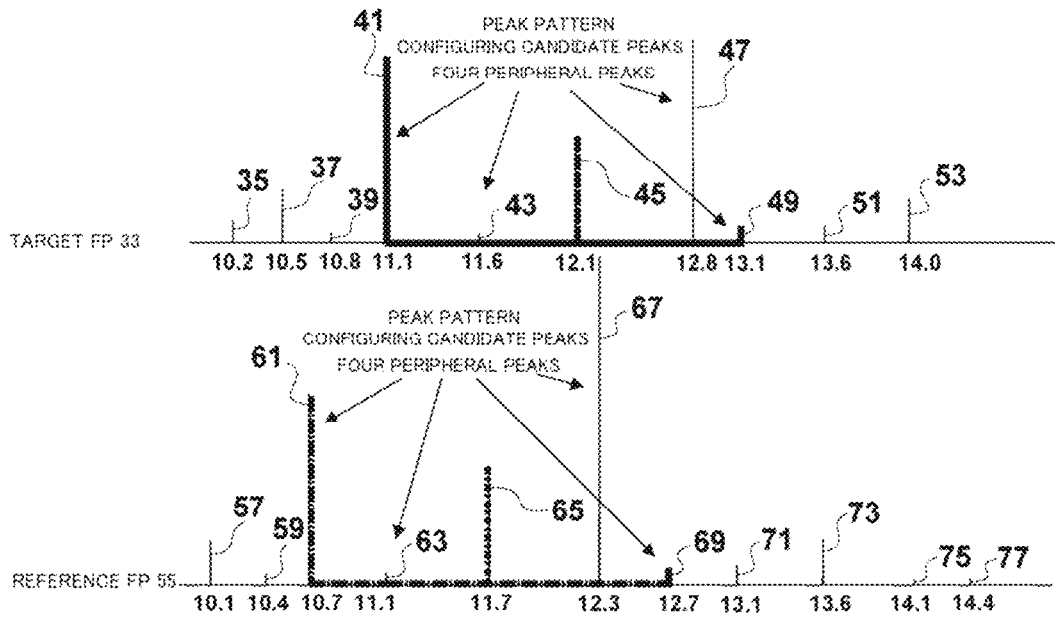
FIG. 40 is an explanatory diagram illustrating comprehensive comparison of peak patterns for the assignment target peak with respect to peak patterns for the assignment candidate peak according to the first embodiment.
Figure 41:
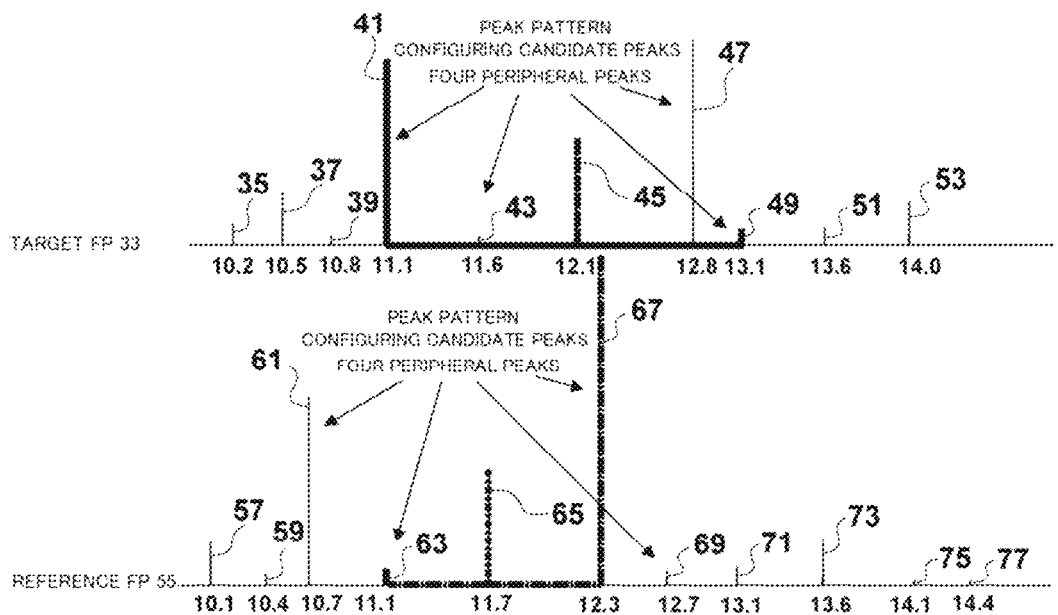
FIG. 41 is an explanatory diagram illustrating comprehensive comparison of peak patterns for the assignment target peak with respect to peak patterns for the assignment candidate peak according to the first embodiment.
Figure 42:
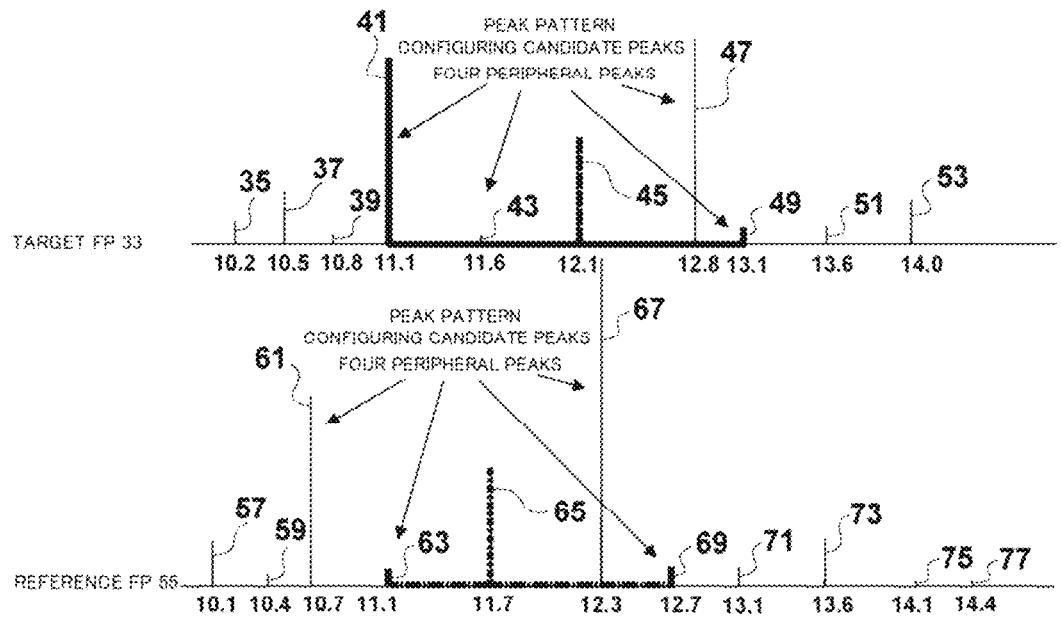
FIG. 42 is an explanatory diagram illustrating comprehensive comparison of peak patterns for the assignment target peak with respect to peak patterns for the assignment candidate peak according to the first embodiment.
Figure 43:
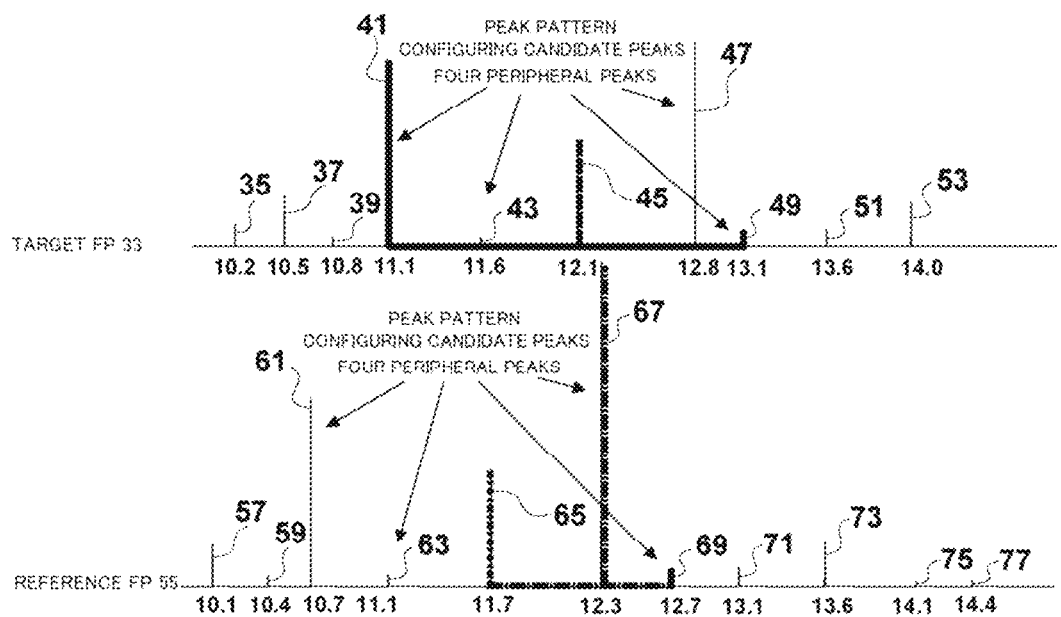
FIG. 43 is an explanatory diagram illustrating comprehensive comparison of peak patterns for the assignment target peak with respect to peak patterns for the assignment candidate peak according to the first embodiment.
Figure 44:
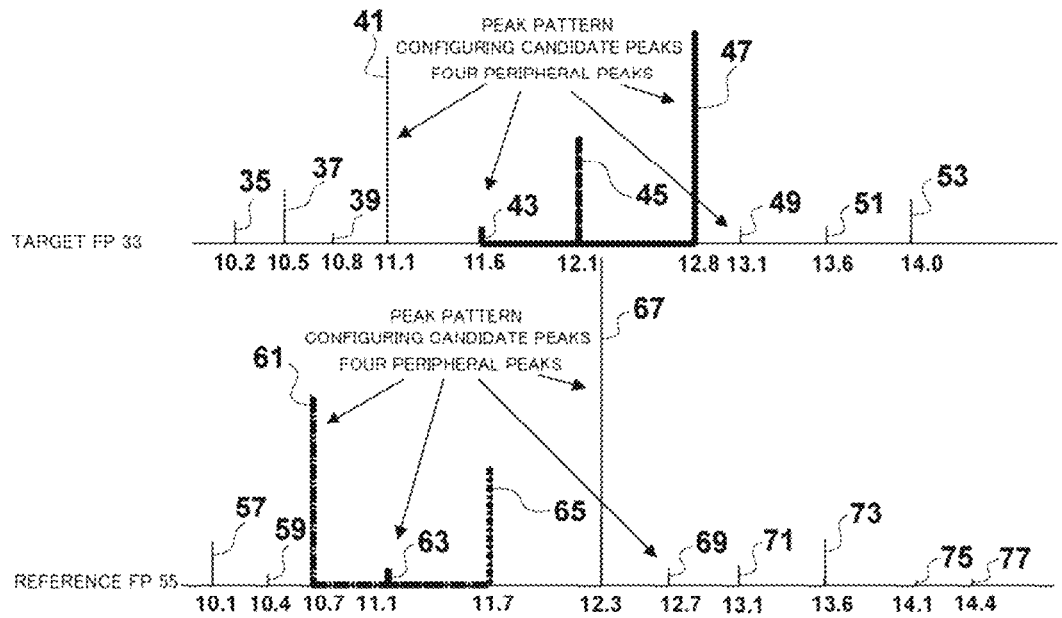
FIG. 44 is an explanatory diagram illustrating comprehensive comparison of peak patterns for the assignment target peak with respect to peak patterns for the assignment candidate peak according to the first embodiment.
Figure 45:
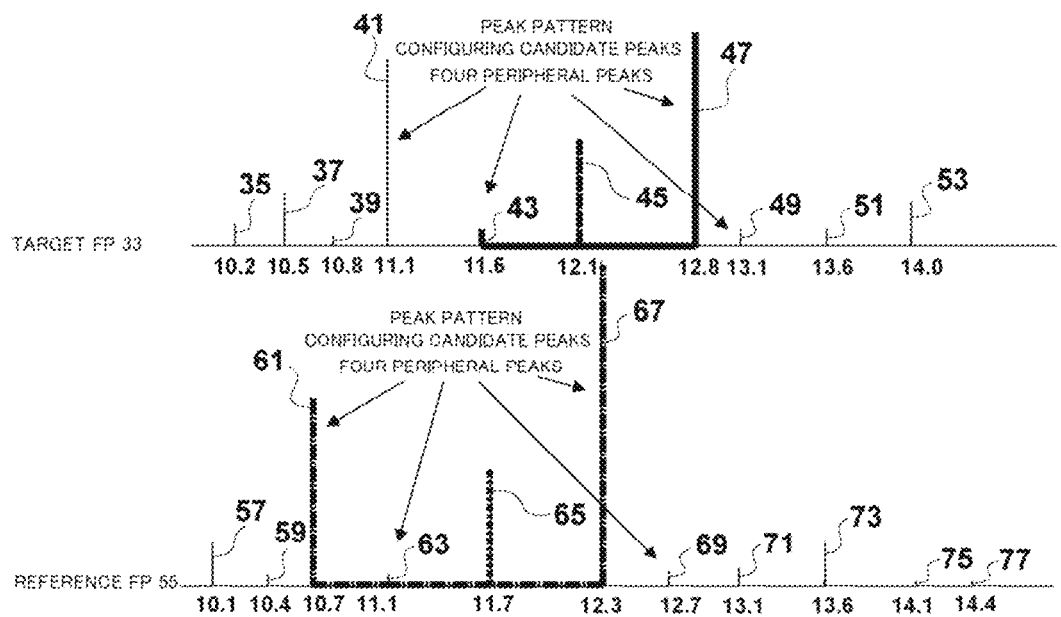
FIG. 45 is an explanatory diagram illustrating comprehensive comparison of peak patterns for the assignment target peak with respect to peak patterns for the assignment candidate peak according to the first embodiment.
Figure 46:
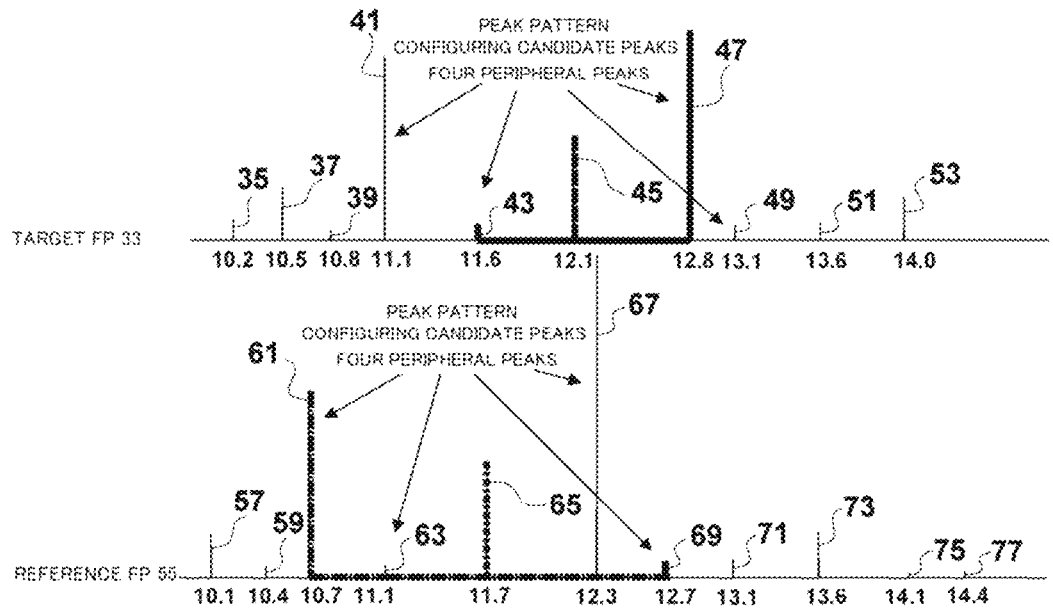
FIG. 46 is an explanatory diagram illustrating comprehensive comparison of peak patterns for the assignment target peak with respect to peak patterns for the assignment candidate peak according to the first embodiment.
Figure 47:
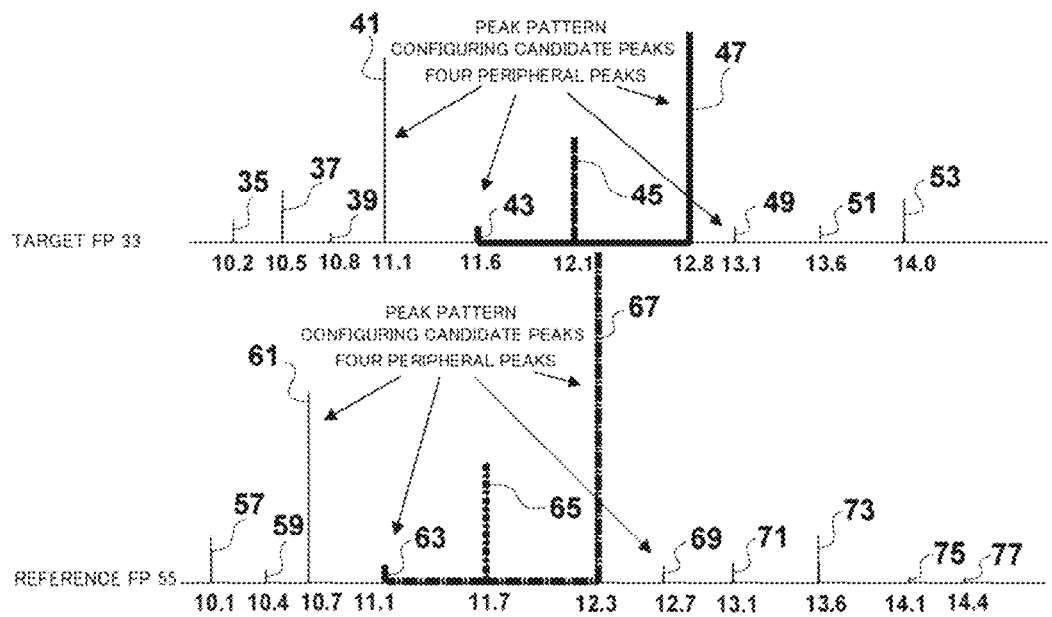
FIG. 47 is an explanatory diagram illustrating comprehensive comparison of peak patterns for the assignment target peak with respect to peak patterns for the assignment candidate peak according to the first embodiment.
Figure 48:
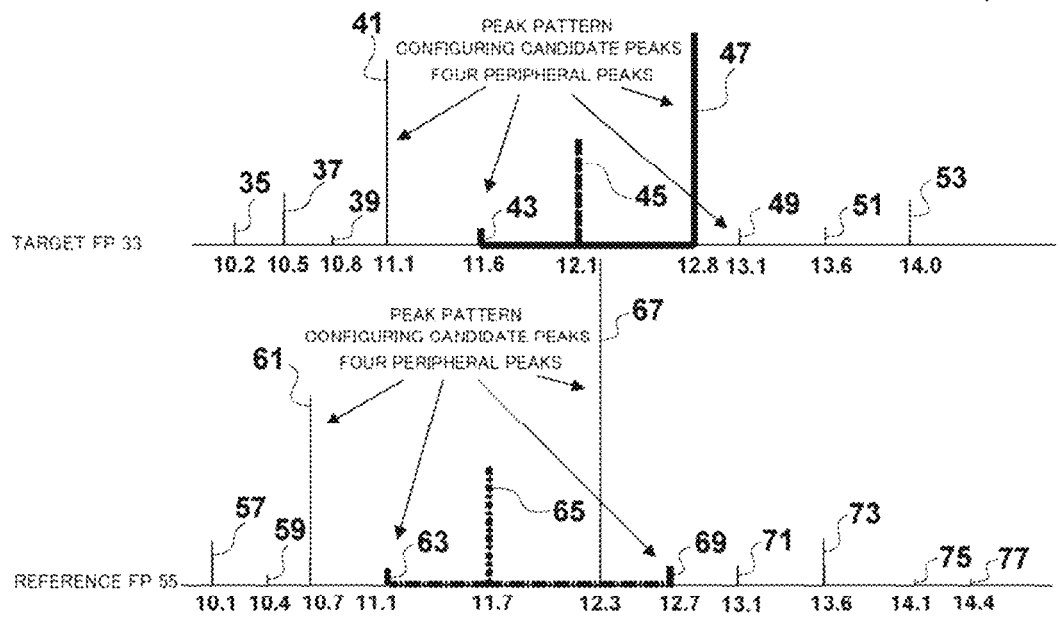
FIG. 48 is an explanatory diagram illustrating comprehensive comparison of peak patterns for the assignment target peak with respect to peak patterns for the assignment candidate peak according to the first embodiment.
Figure 49:
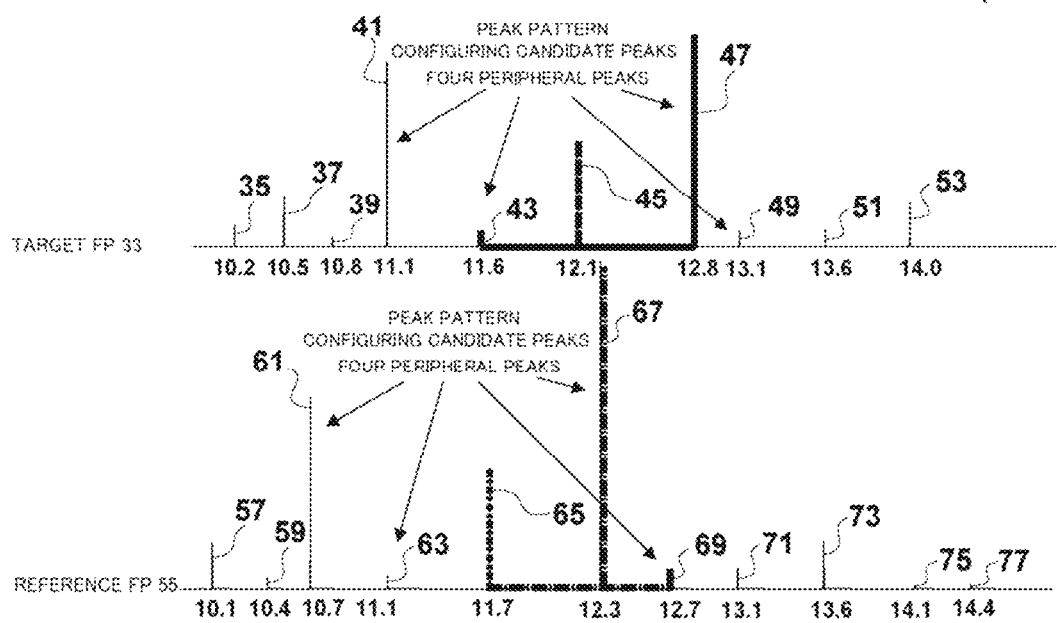
FIG. 49 is an explanatory diagram illustrating comprehensive comparison of peak patterns for the assignment target peak with respect to peak patterns for the assignment candidate peak according to the first embodiment.
Figure 50:
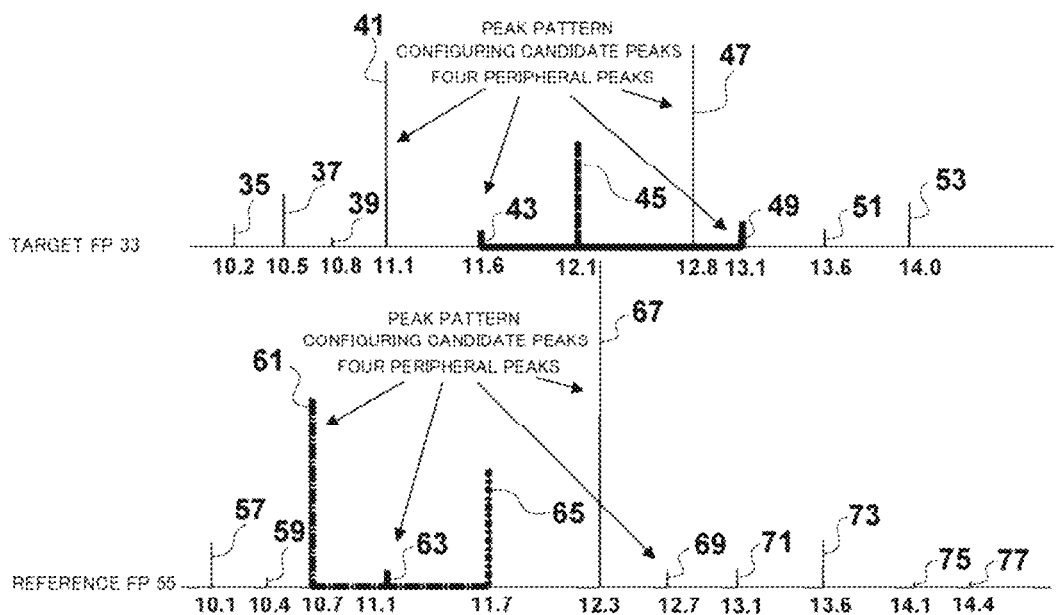
FIG. 50 is an explanatory diagram illustrating comprehensive comparison of peak patterns for the assignment target peak with respect to peak patterns for the assignment candidate peak according to the first embodiment.
Figure 51:
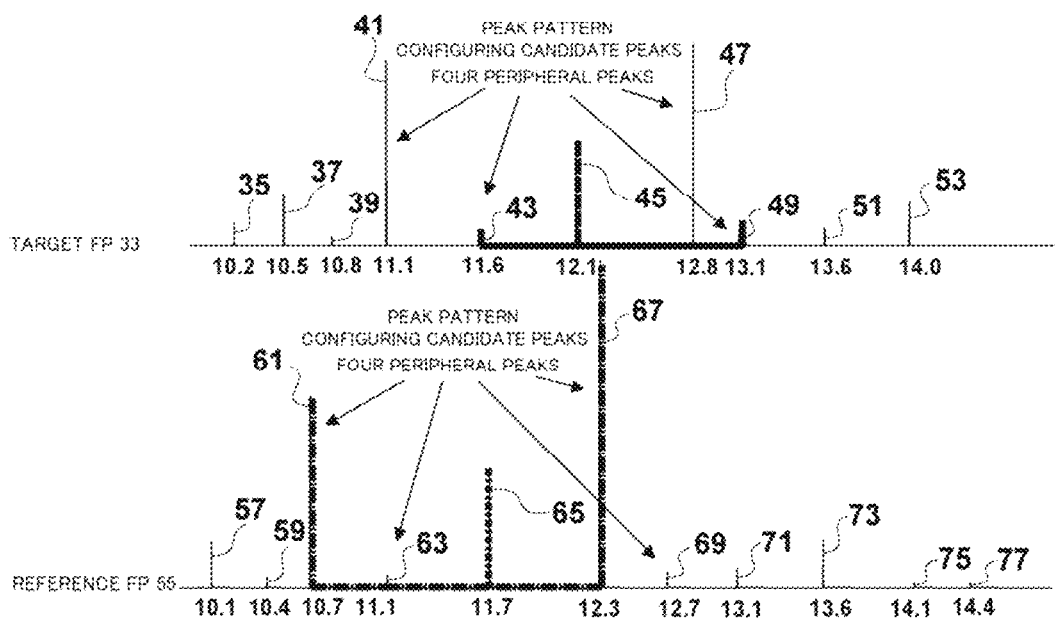
FIG. 51 is an explanatory diagram illustrating comprehensive comparison of peak patterns for the assignment target peak with respect to peak patterns for the assignment candidate peak according to the first embodiment.
Figure 52:
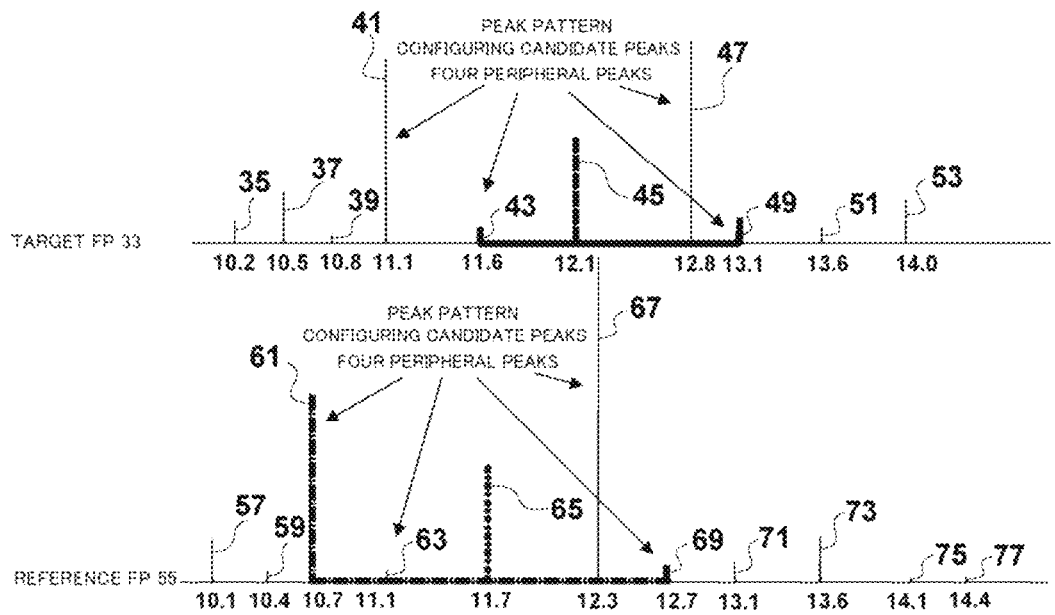
FIG. 52 is an explanatory diagram illustrating comprehensive comparison of peak patterns for the assignment target peak with respect to peak patterns for the assignment candidate peak according to the first embodiment.
Figure 53:
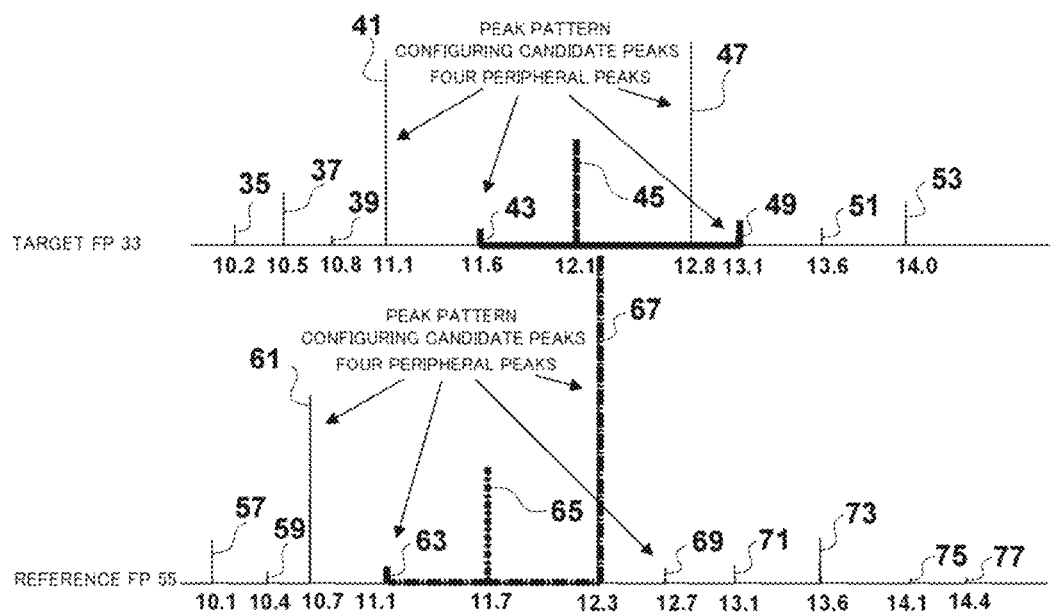
FIG. 53 is an explanatory diagram illustrating comprehensive comparison of peak patterns for the assignment target peak with respect to peak patterns for the assignment candidate peak according to the first embodiment.
Figure 54:
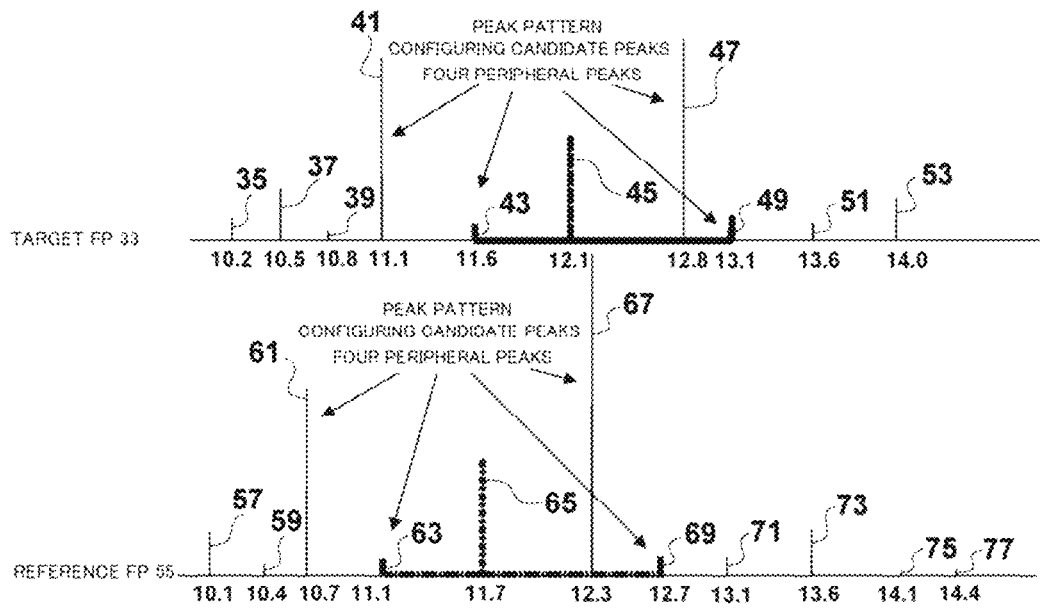
FIG. 54 is an explanatory diagram illustrating comprehensive comparison of peak patterns for the assignment target peak with respect to peak patterns for the assignment candidate peak according to the first embodiment.
Figure 55:
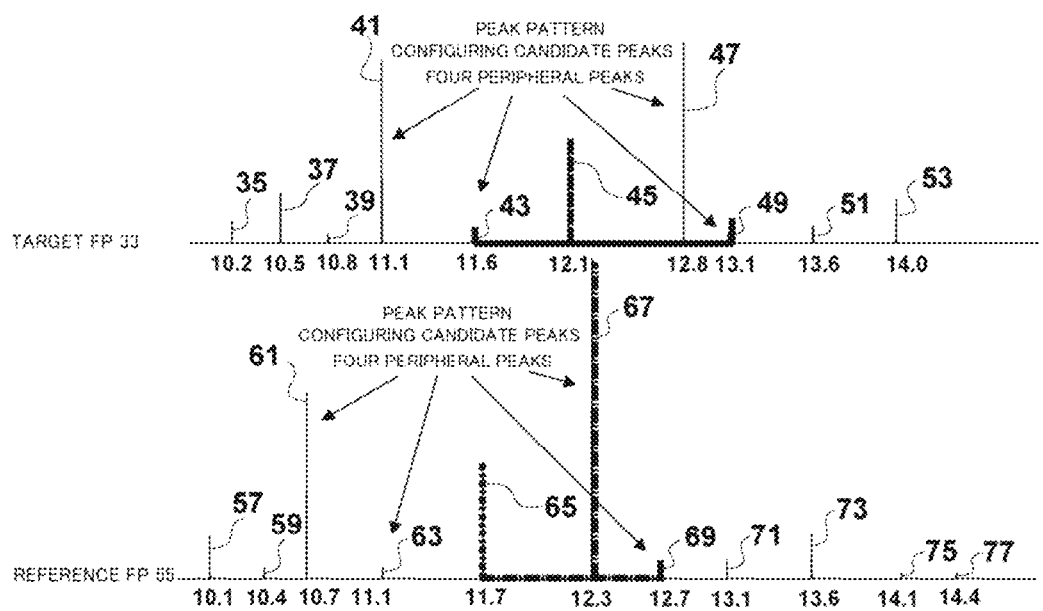
FIG. 55 is an explanatory diagram illustrating comprehensive comparison of peak patterns for the assignment target peak with respect to peak patterns for the assignment candidate peak according to the first embodiment.
Figure 56:
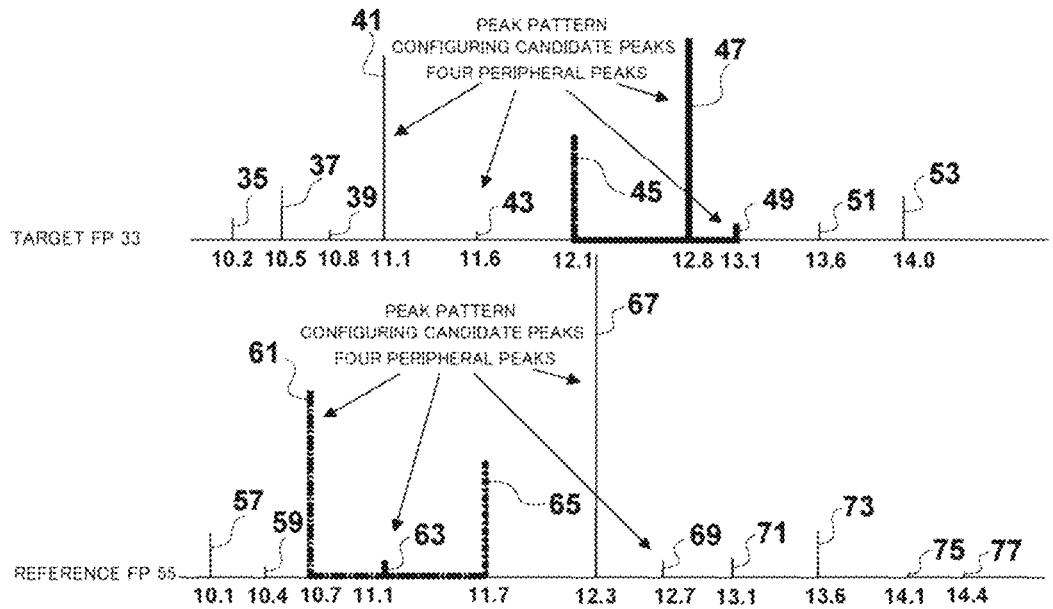
FIG. 56 is an explanatory diagram illustrating comprehensive comparison of peak patterns for the assignment target peak with respect to peak patterns for the assignment candidate peak according to the first embodiment.
Figure 57:
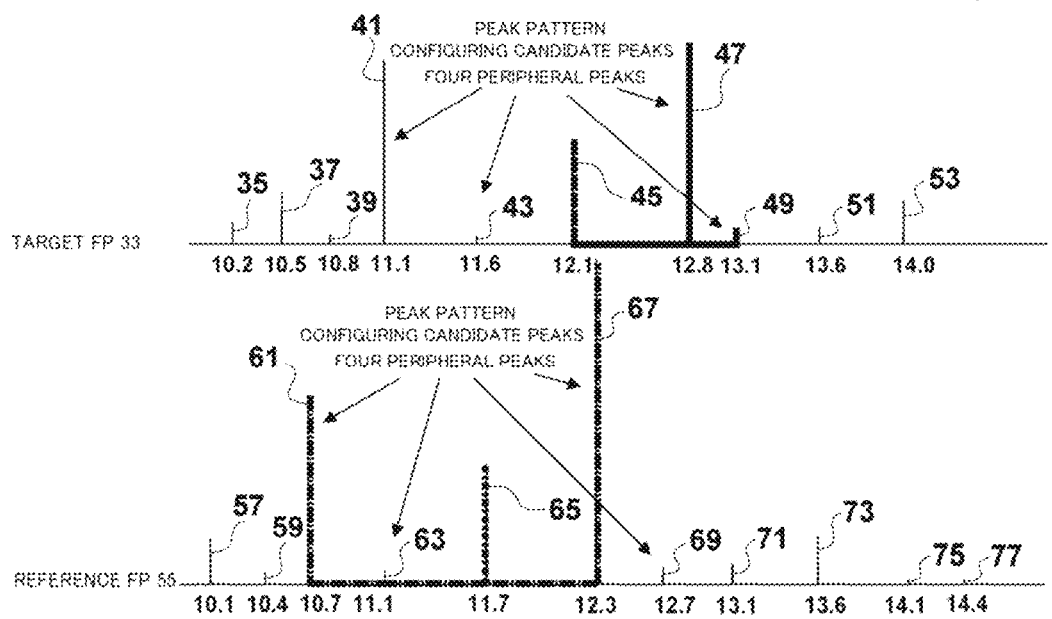
FIG. 57 is an explanatory diagram illustrating comprehensive comparison of peak patterns for the assignment target peak with respect to peak patterns for the assignment candidate peak according to the first embodiment.
Figure 58:
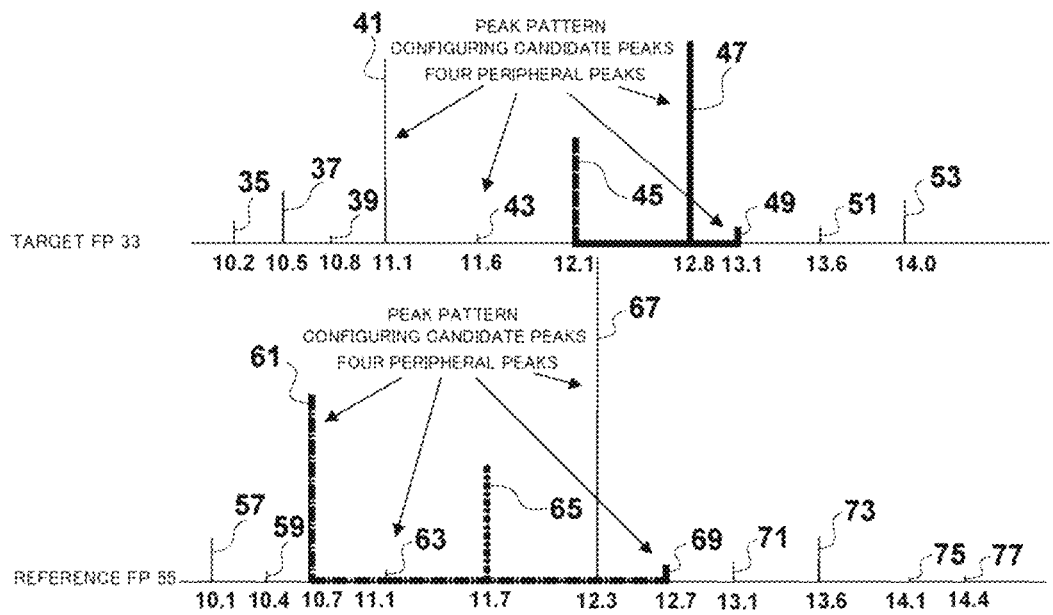
FIG. 58 is an explanatory diagram illustrating comprehensive comparison of peak patterns for the assignment target peak with respect to peak patterns for the assignment candidate peak according to the first embodiment.
Figure 59:
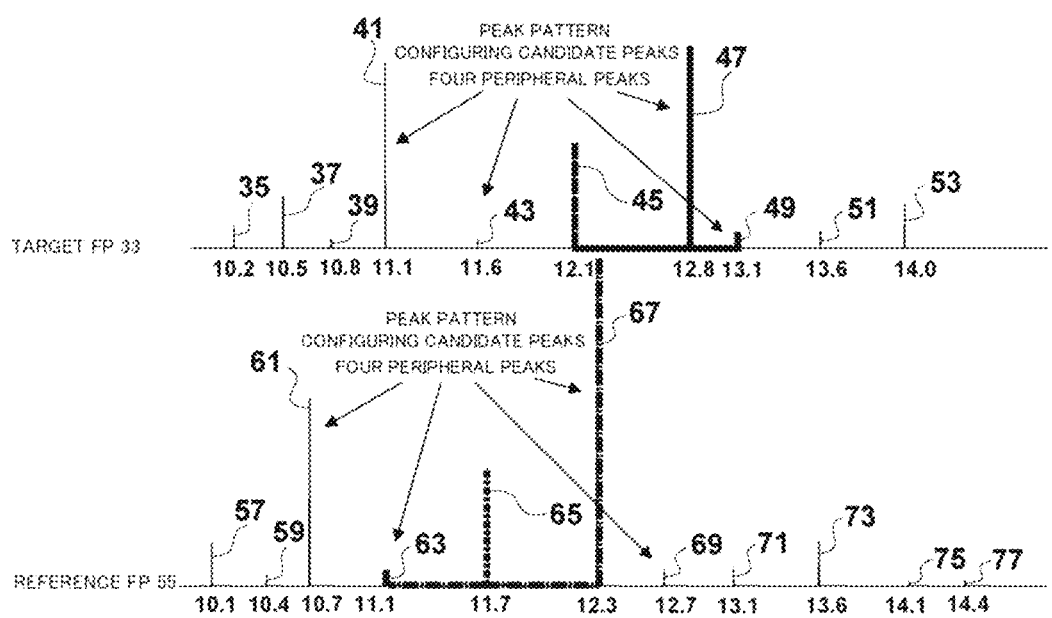
FIG. 59 is an explanatory diagram illustrating comprehensive comparison of peak patterns for the assignment target peak with respect to peak patterns for the assignment candidate peak according to the first embodiment.
Figure 60:
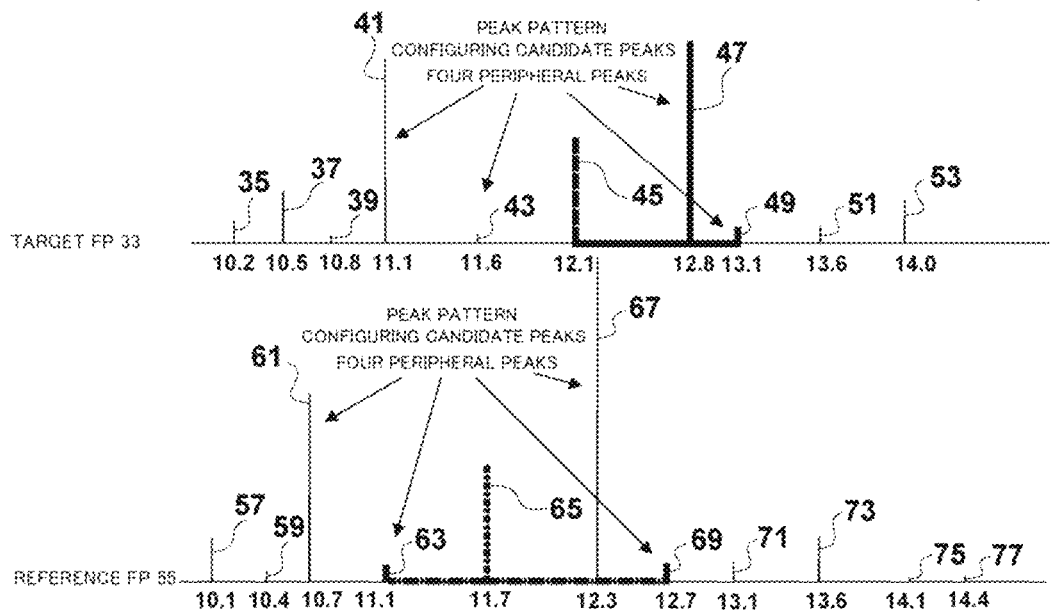
FIG. 60 is an explanatory diagram illustrating comprehensive comparison of peak patterns for the assignment target peak with respect to peak patterns for the assignment candidate peak according to the first embodiment.
Figure 61:
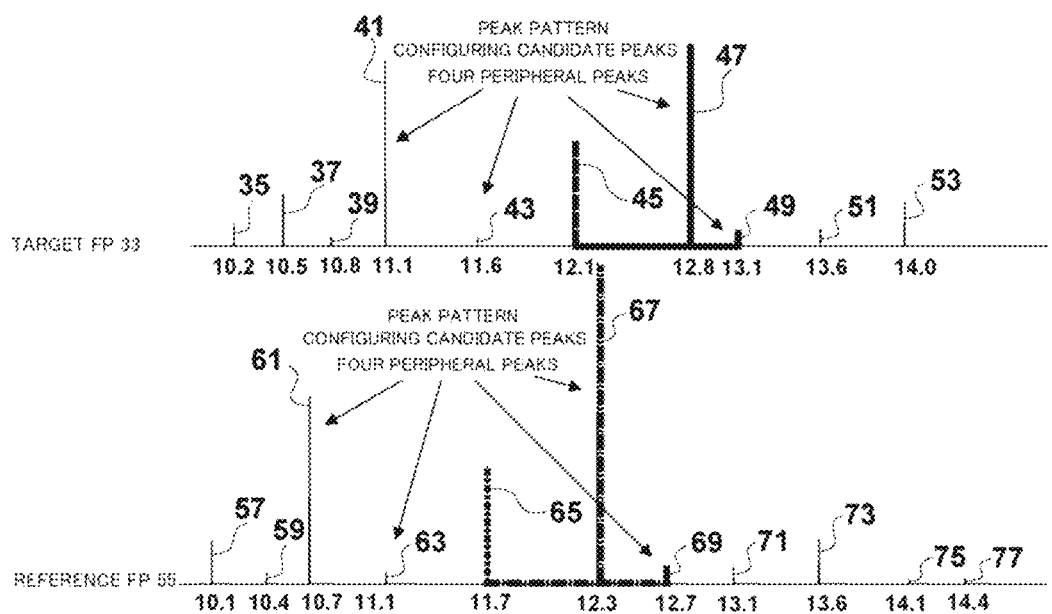
FIG. 61 is an explanatory diagram illustrating comprehensive comparison of peak patterns for the assignment target peak with respect to peak patterns for the assignment candidate peak according to the first embodiment.

In addition, in order to perform the assignment according to the peak patterns with higher accuracy, it is necessary to respond to a case in which there is a difference between the number of peaks of the target FP and the number of peaks of the reference FP (in other words, there is a peak that is not present on one side). For this, it is important to prepare peak patterns in which peak pattern configuring peaks are comprehensively changed for both the assignment target peak and the assignment candidate peak, as illustrated in FIGS. 23 to 25.

More specifically, peaks being candidates for the peak pattern configuring peak (hereinafter, peak pattern configuring candidate peaks) are set from among peripheral peaks of the assignment target peak of the target FP in advance. Peak patterns are prepared by setting the peak pattern configuring candidate peaks as the peak pattern configuring peak in turns. Also for the assignment candidate peaks of the reference FP, similarly, peak pattern configuring candidate peaks are set to prepare peak patterns are by setting the peak pattern configuring candidate peaks as the peak pattern configuring peak in turn.

Figure 23:
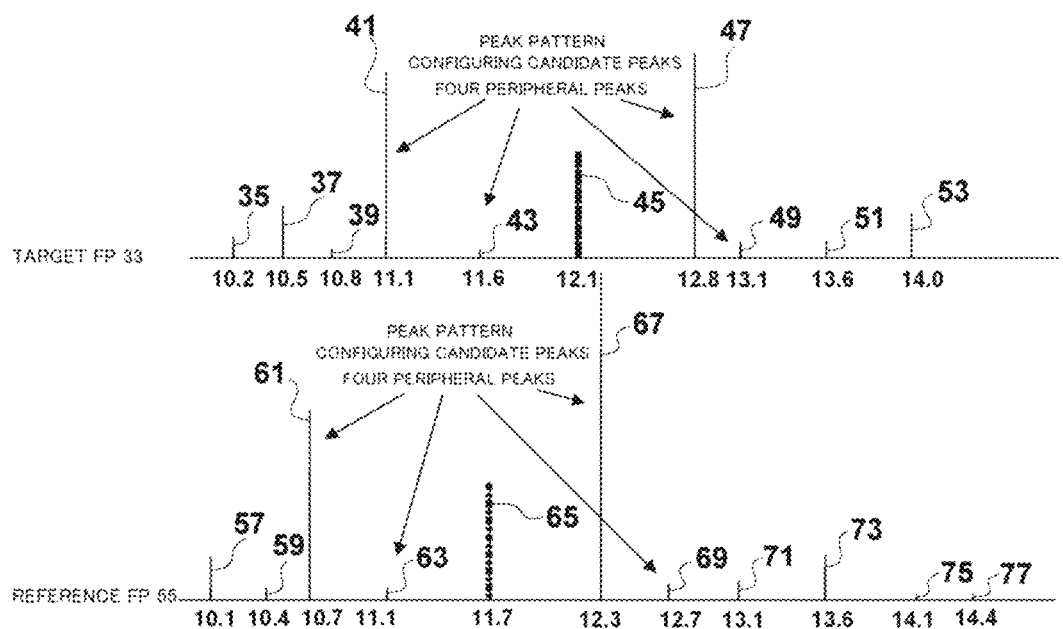
FIG. 23 is a diagram illustrating peak pattern configuring candidate peaks for the assignment target peak and an assignment candidate peak according to the first embodiment.

For example, as illustrated in FIG. 23, four peaks (41, 43, 47, and 49) located on the periphery in the time axis direction are set as the peak pattern configuring candidate peaks for the assignment target peak 45, and four peaks (61, 63, 67, and 69) located on the periphery in the time axis direction are set as the peak pattern configuring candidate peaks for the assignment candidate peak 65, and the peak pattern configuring peaks are set to arbitrary two peaks. In this case, peak patterns of $4C2$ (=6) patterns are prepared for each of the assignment target peak 45 and the assignment candidate peak 65 as illustrated in FIGS. 24 and 25.

In addition, in a case where ten peak pattern configuring candidate peaks are set, arbitrary two peak pattern configuring peaks are set, and peak patterns of $10C2$ (=45) patterns are prepared for each one of the assignment target peak and the assignment candidate peak. In a case where arbitrary four peaks are set as the peak pattern configuring peaks, peak patterns of $10C4$ (=210) patterns are prepared for each one of the assignment target peak and the assignment candidate peak.

The function of the peak assigning part 9 will be described further with reference to FIGS. 26 to 67.

The peak assigning part 9 calculates the degree of matching between peak patterns (hereinafter, referred to as P_Sim) based on differences in corresponding peaks and retention time points over all the peak patterns for the assignment target peak and the assignment candidate peaks prepared by the peak pattern preparing part 7. The peak assigning part 9 sets the minimum value of the P_Sim (hereinafter, referred to as P_Sim_min) as the degree of matching between peak patterns for the assignment target peak and the assignment candidate peak.

For example, as illustrated in FIGS. 26 to 61, for each one of the assignment target peak 45 and the assignment candidate peak 65, four peripheral peaks located in front and in the rear in the time axis direction are set as the peak pattern configuring candidate peaks, and two arbitrary peaks are set as the peak pattern configuring peaks. According to this setting, peak patterns of $4C2$ (=6) patterns are prepared for each one of the assignment target peak and the assignment candidate peak. Accordingly, the P_Sims of the assignment target peak 45 and the assignment candidate peak 65 are calculated as 6 patterns×6 patterns (=36), and the P_Sim_min that is the minimum value of the P_Sims is set as the degree of matching between the assignment target peak 45 and the assignment candidate peak 65.

Incidentally, in a case where ten peak pattern configuring candidate peaks located in front and in the rear in the time axis direction are set and the peak pattern configuring peaks are set as two arbitrary peaks for each one of the assignment target peak 45 and the assignment candidate peak 65, peak patterns of $4C2$ (=45) patterns are prepared for each one of the assignment target peak and the assignment candidate peak. Accordingly, the P_Sims of the assignment target peak 45 and the assignment candidate peak 65 are calculated as 45 patterns×45 patterns (=2025), and the P_Sim_min that is the minimum value of the P_Sims is set as the degree of matching between the assignment target peak 45 and the assignment candidate peak 65. In addition, in a case where the peak pattern configuring peaks are set as four arbitrary peaks, peak patterns of $10C4$ (=210) patterns are prepared for each one of the assignment target peak and the assignment candidate peak. Accordingly, the P_Sims of the assignment target peak 45 and the assignment candidate peak 65 are calculated as 210 patterns×210 patterns (=44100), and the P_Sim_min that is the minimum value of the P_Sims is set as the degree of matching between the assignment target peak 45 and the assignment candidate peak 65.

The P_Sim is similarly calculated for all the assignment candidate peaks for the assignment target peak 45.

A calculating method of the degree of matching between peak patterns for comparing peak patterns each configured by three peaks will be described with reference to FIGS. 62 and 63. In this case, the peak pattern 87 of the assignment target peak 45 and the peak pattern 91 of the assignment candidate peak 67 will be described as an example.

In the peak pattern 87 of the assignment target peak 45, peak data and a retention time point of the assignment target peak 45 are assumed to be p1 and r1, peak data and a retention time point of a peak pattern configuring peak 43 are assumed to be dn1 and cn1, and peak data and a retention time point of a peak pattern configuring peak 47 are assumed to be dn2 and cn2.

In the peak pattern 91 of the assignment candidate peak 67, peak data and a retention time point of the assignment candidate peak 67 are assumed to be p2 and r2, peak data and a retention time point of a peak pattern configuring peak 65 are assumed to be fn1 and en1, and peak data and a retention time point of a peak pattern configuring peak 69 are assumed to be fn2 and en2.

When the degree of matching between peak patterns is P_Sim, the degree of matching between peak patterns (P_Sim(45-67)), each configured by three peaks, of the assignment target peak 45 and the assignment candidate peak 67 is calculated as:

$$P\_Sim(45-67) = (|p1-p2|+1) \times (|(r1-(r2+d)|+1) + $$
$$(|dn1-fn1|+1) \times (|(cn1-r1)-(en1-r2)|+1) + $$
$$(|dn2-fn2|+1) \times (|(cn2-r1)-(en2-r2)|+1).$$

Here, d represented in the equation is a value used for correcting the deviation of the retention time point.

The calculating method of the degree of matching between peak patterns used for comparing the peak patterns each configured by five peaks will be described with reference to FIG. 64. In this case, the peak pattern 97 of the assignment target peak 45 and the peak pattern 101 of the assignment candidate peak 67 will be described as an example.

In the peak pattern 97 of the assignment target peak 45, peak data and a retention time point of the assignment target peak 45 are assumed to be p1 and r1, and peak data and retention time points of peak pattern configuring peaks 41, 43, 47, and 49 are assumed to be dn1 and cn1, dn2 and cn2, dn3 and cn3, and dn4 and cn4.

In the peak pattern 101 of the assignment candidate peak 67, peak data and a retention time point of the assignment candidate peak 67 are assumed to be p2 and r2, and peak data and retention time points of peak pattern configuring peaks 63, 65, 69, and 71 are assumed to be fn1 and en1, fn2 and en2, fn3 and en3, and fn4 and en4.

The degree of matching between peak patterns (P_Sim (45-67)) each configured by five peaks, of the assignment target peak 45 and the assignment candidate peak 67 is calculated as:

$$P\_Sim(45-67) = (|p1-p2|+1) \times (|(r1-(r2+d)|+1) + $$
$$(|dn1-fn1|+1) \times (|(cn1-r1)-(en1-r2)|+1) + $$
$$(|dn2-fn2|+1) \times (|(cn2-r1)-(en2-r2)|+1) + $$
$$(|dn3-fn3|+1) \times (|(cn3-r1)-(en3-r2)|+1) + $$
$$(|dn4-fn4|+1) \times (|(cn4-r1)-(en4-r2)|+1).$$

Here, d represented in the equation is a value used for correcting the deviation of the retention time point.

The peak assigning part 9 calculates the degree of matching between the UV spectra of the assignment target peak and the assignment candidate peak as illustrated in FIGS. 65 and 66.

FIG. 65 is the diagram illustrating UV spectra (107 and 111) of the assignment target peak 45 and the assignment candidate peak 67, and, as illustrated in FIG. 66, the degree of matching between these two UV spectra (UV_Sim(45-67)) is calculated as:

UV_Sim(45-67)=RMSD(107 vs 111).

The RMSD is defined as a mean square deviation and is defined as the square root of arithmetic average of a value that is a square of a distance between two corresponding points (dis). In other words, RMSD is calculated as $\sqrt{\{\Sigma dis^2/n\}}$.

"n" is the number of "dis."

Here, the waveform of the UV spectrum has a maximum wavelength and a minimum wavelength, and the degree of matching also can be calculated by comparing either the maximum wavelengths or the minimum wavelengths. However, compounds having no absorbance property or compounds having similar absorbance properties, they may quite differs from each other in the waveforms as a whole while having the same maximum and minimum wavelengths. Accordingly, there is a risk that the degree of matching between the waveforms may not be calculated by comparing either the maximum wavelengths or the minimum wavelengths.

In contrast to this, in a case where the RMSD is used in accordance with the waveforms of the UV spectra, the whole waveforms are compared with each other. Therefore, the degree of matching between the waveforms of the UV spectra can be calculated with accuracy, whereby even compounds having no absorbance property or compounds having similar absorbance properties can be identified with accuracy.

The degree of matching between the UV spectra is calculated similarly for all the assignment candidate peaks of the assignment target peak 45.

In addition, the peak assigning part 9 calculates the degree of matching of the assignment candidate peak that is acquired by integrating the above-described two degrees of matching as illustrated in FIG. 67.

As illustrated in FIG. 67, the degree (SCORE(45-67)) of matching of the assignment candidate peak is calculated by multiplying the degree of matching between the peak patterns by the degree of matching between the UV spectra. It is assumed that a score representing the degree of matching between peak patterns 45 and 67 is P_Sim_min(45-67), and a score representing the degree of matching between the corresponding UV spectra 107 and 111 is UV_Sim(45-67). At this time, the degree SCORE(45-67) of matching of the assignment candidate peaks is calculated as:

SCORE(45-67)=P_Sim_min(45-67)×UV_Sim(45-67).

The degree of matching of assignment candidate peak is similarly calculated for all the assignment candidate peaks for the assignment target peak 45.

Then, the SCOREs of all the assignment candidate peaks are compared to determine an assignment candidate peak having a lowest SCORE as an assignment peak of the assignment target peak 45.

Since the peak assigning part 9 determines the peaks to which the assignment target peaks should be assigned by integrating two viewpoints, it can realize peak assignment with accuracy.

In addition, the peak assigning part 9 assigns each peak of the target FP 17 to the reference group FP 19 based on the result of the assignment of the target FP to the reference FP as illustrated in FIG. 68.

Each peak of the target FP 17 is assigned to the reference FP configuring the reference group FP through the above-described assignment process. Base on the result of the assignment, finally, the peaks are assigned to the reference group FP 19.

In addition, the reference group FP 19 is prepared by performing an assignment process like the above for the plurality of reference FPs determined as normal products, and each peak is represented by an average value (black point) of assigned peaks±standard deviation (vertical line).

FIG. 69 shows the result of assigning the target FP 17 to the reference group FP 19, and this result is the final result of the process of assigning the target FP 17.

From this result, the MD value (MD values: 0.25, 2.99, and the like) can be acquired by MT method (see FIGS. 70 to 74) as described above.

Figure 75:
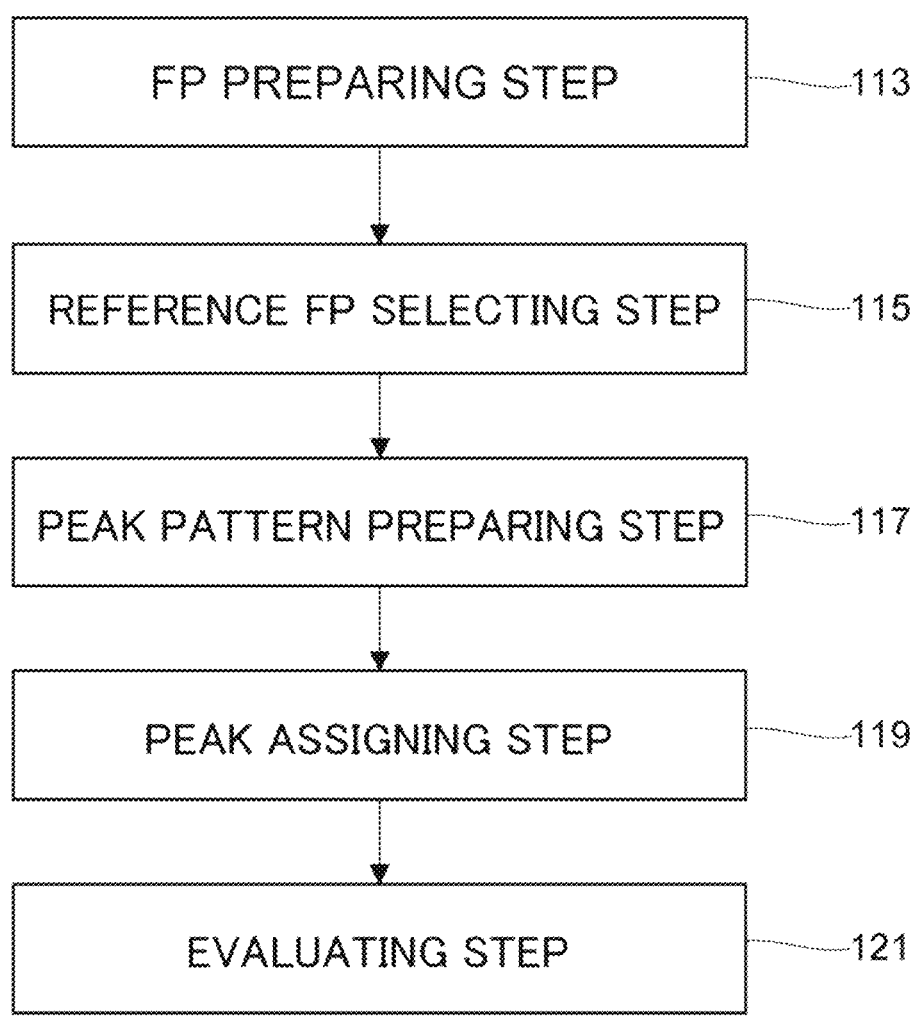
FIG. 75 is a process chart illustrating an evaluating method of a multicomponent drug according to the first embodiment.

FIG. 75 is a process chart illustrating an evaluating method of a multicomponent drug according to the first embodiment of the present invention.

As illustrated in FIG. 75, the evaluating method of a multicomponent drug includes: a FP preparing process 113 as a pattern acquiring process; a reference FP selecting process 115; a peak pattern preparing step 117; a peak assigning step 119; and an evaluating step 121. The FP preparing process 113, the reference FP selecting process 115, the peak pattern preparing step 117, the peak assigning step 119, and the evaluating step 121 are performed by using the above-described evaluating device 1 for a multicomponent drug in this embodiment, the FP preparing process 113 can be performed by using the function of the FP preparing part 3, and, similarly, the reference FP selecting process 115, the peak pattern preparing step 117, the peak assigning step 119, the evaluating step 121 can be performed by using the functions of the reference FP selecting part 5, the peak pattern specifying unit 7, the peak assigning part 9, and the evaluating part 11.

FIGS. 76 to 91 are flowcharts according to the evaluating program for a multicomponent drug, FIG. 92 is a table representing a data example of 3D chromatogram, FIG. 93 is a table illustrating a peak information data example, FIG. 94 is a table illustrating a FP data example, FIG. 95 is a table illustrating a determination result file example prepared in Step S3, FIG. 96 is a table illustrating a two intermediate file example (an assignment candidate peak score table and an assignment candidate peak number table) that are prepared in the process of specifying corresponding peaks between the target FP and the reference FP, FIG. 97 is a table illustrating a collation result file example that is a result of specifying corresponding peaks between the target FP and the reference FP, FIG. 98 is a table illustrating a reference group FP data example, and FIG. 99 is a table illustrating a peak feature value file example of the target FP that is data of the target FP assigning peak.

Figure 76:
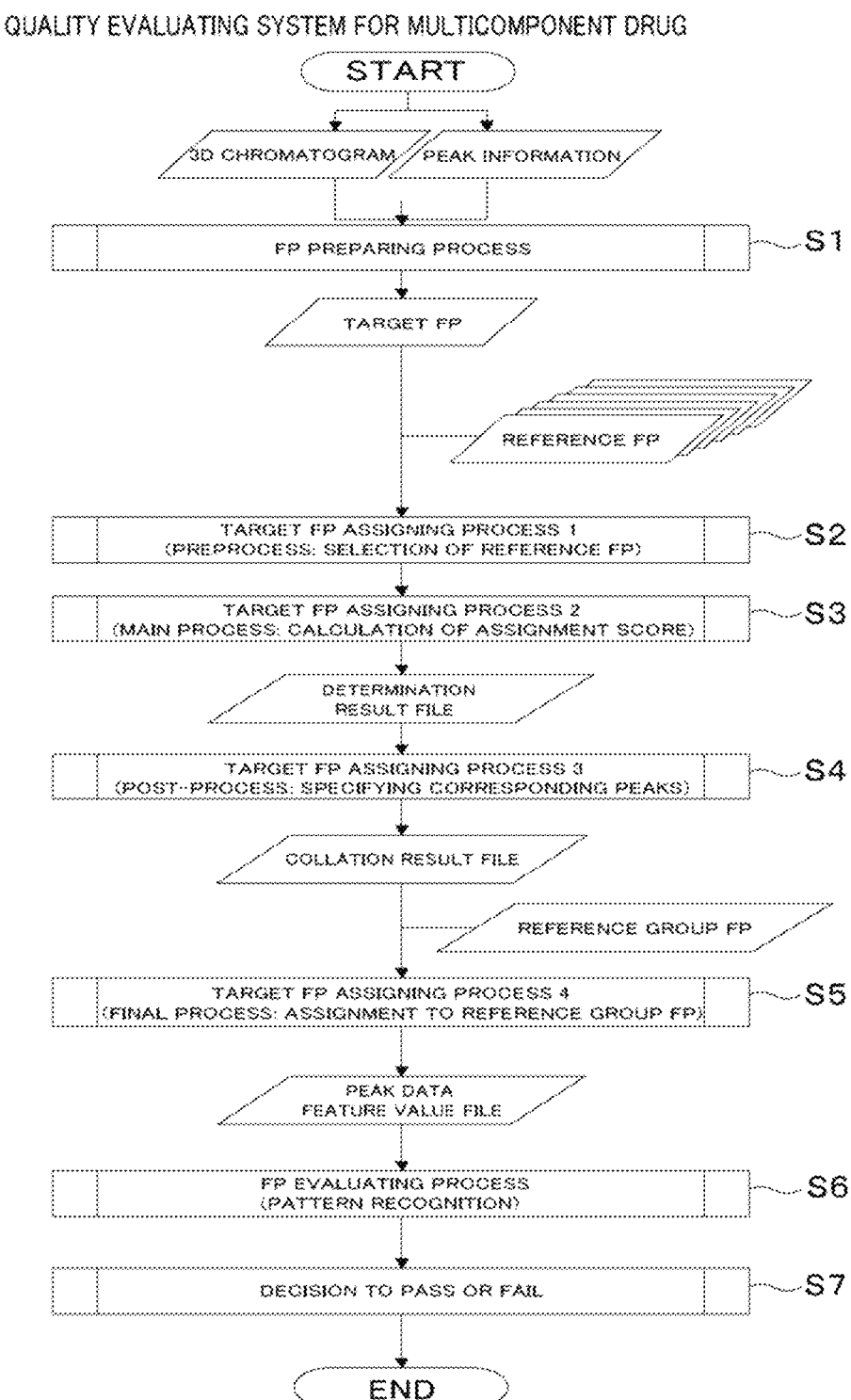
FIG. 76 is an evaluating flowchart for a multicomponent drug according to the first embodiment.

FIG. 76 is a flowchart illustrating steps of the whole process performed for evaluating an evaluation target drug. It is started in accordance with system activation to realize the FP preparing function of the FP preparing part 3, the reference FP selecting function of the reference FP selecting part 5, the peak pattern preparing function of the peak pattern preparing part 7, the peak assigning function of the peak assigning part 9, and the evaluating function of the evaluating part 11 in the computer.

The FP preparing function is realized in Step S1, the reference FP selecting function is realized in Step S2, the peak pattern preparing function is realized in Step S3, the peak assigning function is realized in Steps S3 to S5, and the evaluating function is realized in Steps S6 and S7.

In Step S1, the "FP preparing process" is performed with a 3D chromatogram and peak information at a specific detection wavelength as input data.

The 3D chromatogram is data that is acquired by analyzing an evaluation target drug through HPLC and it is configured as three-dimensional information including a retention time points, detection wavelengths, and peaks (signal strength) as represented as a data example 123 of the 3D chromatogram in FIG. 92. The peak information is data that is acquired by processing chromatogram data at a specific wavelength, which is acquired through the same HPLC analysis, with a HPLC data analyzing tool (for example, "ChemStation" or the like). As represented as the peak information data example 125 in FIG. 93, the peak information is data configured by the maximum values and area values of all peaks detected as peaks and retention time points at those time point.

In Step S1, the FP preparing part 3 (FIG. 2) of the computer functions to prepare the target FP 17 (FIG. 3A) based on the 3D chromatogram and the peak information and output the data as a file. The target FP 17, like the FP data example 127 in FIG. 94, is data configured by retention time points, peak heights, and UV spectra for respective peak heights.

In Step S2, the "target FP assigning process 1" is performed with input of the target FP and all the reference FPs output in Step S1.

In Step S2, the reference FP selecting part 5 of the computer functions to calculate the degree of matching between retention time appearance patterns of all the reference FPs with respect to the target FP 17, to select a reference FP that is appropriate to the assignment of the target FP 17.

The reference FPs are FPs prepared by the same process as that of Step S1 based on the 3D chromatogram and peak information of drugs determined as normal products. In addition, the normal product is defined as a drug of which the safety and the effectiveness are checked and a plurality of drugs with different product lots correspond thereto. The reference FP is data configured similarly to the FP data example 127 in FIG. 94.

In Step S3, the "target FP assigning process 2" is performed according to the target FP 17 and the reference FP selected in Step S2 as input.

In Step S3, the peak pattern preparing part 7 (FIG. 2) and the peak assigning part 9 (FIG. 2) of the computer functions. Through the functions thereof, peak patterns are comprehensively prepared for all the peaks of the target FP 17 and the reference FP selected in Step S2 as illustrated in FIGS. 23 to 61, to calculate the degree of matching between the peak patterns (P_Sim illustrated in FIG. 63 or 64). In addition, the degree of matching between the UV spectra (UV_Sim illustrated in FIG. 66) of the target FP and the reference FP is calculated. Furthermore, the degree of matching of the assignment candidate peak (SCORE illustrated in FIG. 67) is calculated based on these two kinds of the degrees of matching, and the calculation result is output in the form of a file (determination result file).

In Step S4, the "target FP assigning process 3" is performed according to the determination result file output in Step S3 as an input.

In Step S4, the peak assigning part 7 of the computer functions to, between the target FP 17 and the reference FP, specify peaks of the reference FP that correspond to the respective peaks of the target FP based on the degree (SCORE) of matching of the assignment candidate peaks and outputs the result in the form of a file (collation result file).

In Step S5, the "target FP assigning process 4" is performed according to the collation result file output in Step S4 and the reference group FP as inputs.

The reference group FP is peak correspondence data over all the reference FPs prepared from the all reference FPs in the same process as that of Steps S2 to S4.

In Step S5, the peak assigning part 7 of the computer functions to assign the peaks of the target FP 17 to the respective peaks of the reference group FP based on the collation result file of the target FP 17 as illustrated in FIGS. 68 and 69, and outputs the result to in the form of a file (peak data feature value file).

In Step S6, the "FP evaluating process" is performed according to the peak data feature value file output in Step S5 and the reference group FP as inputs.

In Step S6, the evaluating part 11 of the computer functions to evaluate the equivalency between the peak data feature value data output in Step S5 and the reference group FP by MT method, and outputs the evaluation result as an MD value (FIGS. 70 to 74).

In Step S7, the "determination of a success or not" is performed according to the MD value output in Step S6 as input.

In Step S7, the evaluating part 11 of the computer functions to compare the MD value output in Step S6 with a threshold value (the upper limit of the MD value) set in advance so as to make a decision to pass or fail, i.e., whether the powder extract of the multicomponent drug meets the criteria for productization (Graph 23 illustrated in FIG. 3A).

Figure 77:
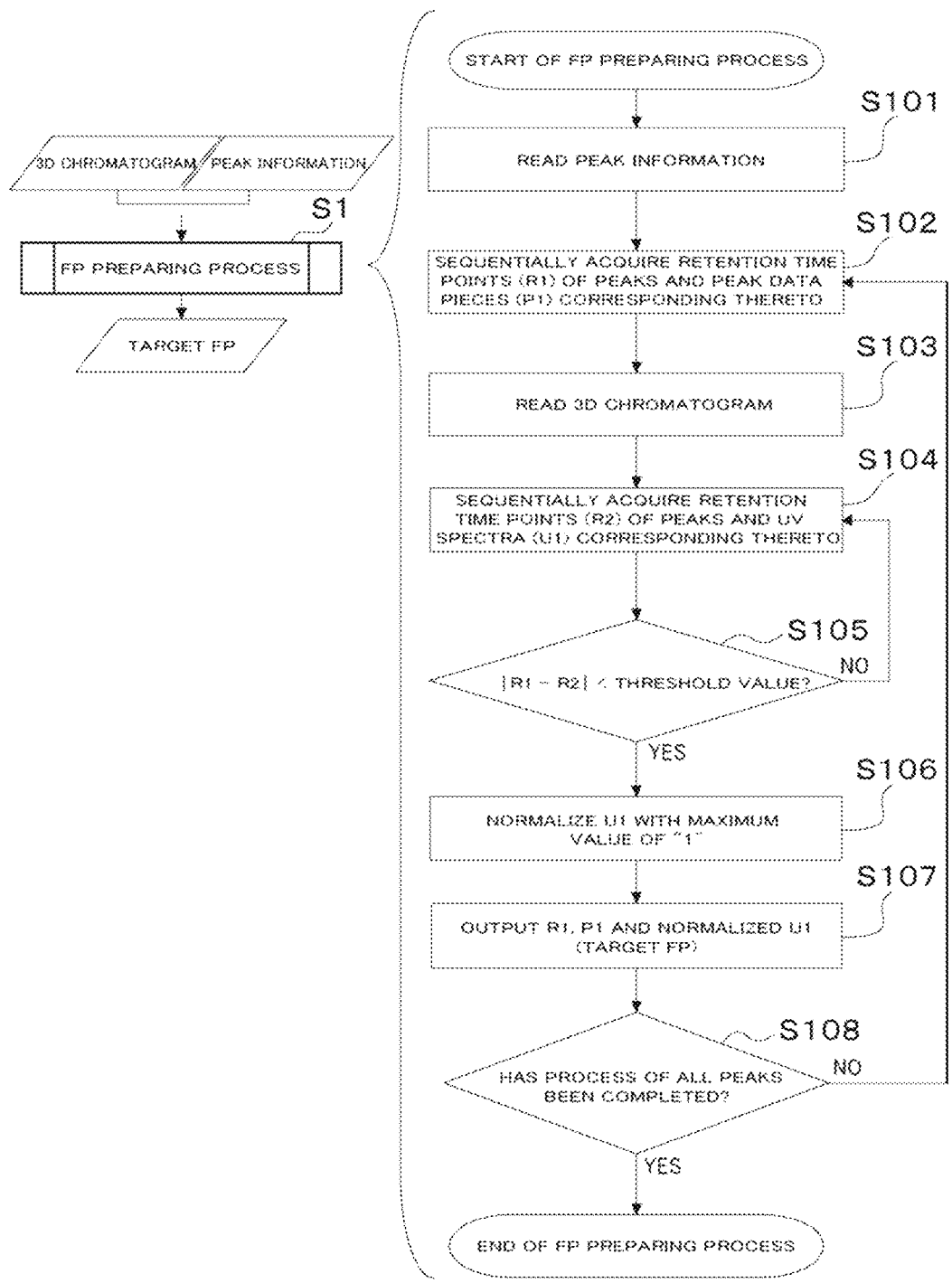
FIG. 77 is a data processing flowchart of a FP preparing function according to a single wavelength according to the first embodiment.

FIG. 77 is a flowchart in a case where single-wavelength peak information of the "FP preparing process" in Step S1 illustrated in FIG. 76 is used.

FIG. 77 shows details of the step of preparing the evaluation target FP for a single wavelength, for example, 203 nm. In this process, based on the 3D chromatogram and the peak information at the detection wavelength being 203 nm, a FP is prepared to comprise a retention time point, a peak and a UV spectrum of each peak detected at the detection wavelength of 203 nm.

In Step S101, a process of "reading peak information" is performed. In this process, peak information is read out as the first one of two kinds of data that are necessary for preparing a FP, and it proceeds to Step S102.

In Step S102, a process of "sequentially acquiring a retention time point (R1) of a peak and peak data (P1) corresponding thereto" is performed. In this process, retention time points (R1) and peak data (P1) of the peaks are sequentially acquired from the peak information one by one, and it proceeds to Step S103.

In Step S103, a process of "reading a 3D chromatogram" is performed. In this process, a 3D chromatogram is read as the second one of the two kinds of data necessary for preparing the FP, and it proceeds to Step S104.

In Step S104, a process of "sequentially acquiring a retention time point (R2) of a peak and a UV spectrum (U1) corresponding thereto" is performed. In this process, retention time points (R2) and UV spectra (U1) are acquired from the 3D chromatogram at each period that is a half of a sampling rate at the time of analyzing the HPLC, and it proceeds to Step S105.

In Step S105, a determining process "|R1−R2|≤Threshold Value?" is performed. In this process, it is determined whether or not the retention time points R1 and R2 read in Steps S102 and S104 correspond to each other within a threshold value range. If corresponding (YES), it is determined that two retention time points are the same and the UV spectrum of the peak at the retention time point R1 is U1. Then, it proceeds to Step S106. If not corresponding (NO), it is determined that the two retention time points are not the same and the UV spectrum of the peak at the retention time point of R1 is not the UV spectrum U1. Then, it proceeds to Step S104 so as to perform comparison with the next data of the 3D chromatogram. The threshold value used in this determination process is the "sampling rate" of the 3D chromatogram. In Step S105, it is determined that the UV spectrum extracted from the 3D chromatogram and having the smallest difference in retention time relative to a peak of the FP corresponds to that peak of the FP according to the setting of the threshold value and the like.

In Step S106, a process of "normalizing the UV spectrum U1 with the maximum value of "1"" is performed. In this process, the UV spectrum U1 determined as the UV spectrum of the retention time point R1 in Step S105 is normalized with the maximum value of "1," and it proceeds to Step S107.

In Step S107, a process of "outputting R1 and P1 as well as the normalized U1 (target FP)" is performed. In this process, the R1 and P1 acquired from the peak information and the U1 normalized in S106 are output to the target FP, and it proceeds to Step S108.

In Step S108, a determining process "Has the process for all the peaks been completed?" is performed. In this process, it is determined whether or not all the peaks included in the peak information have been processed. If the process has not been completed for all the peaks (NO), it proceeds to Step S102 in order to process one or more peaks that have not been processed. The process of Steps S102 to S108 is repeated until the process of all the peaks is completed. If the process of all the peaks has been completed (YES), the FP preparing process is finished.

Figure 78:
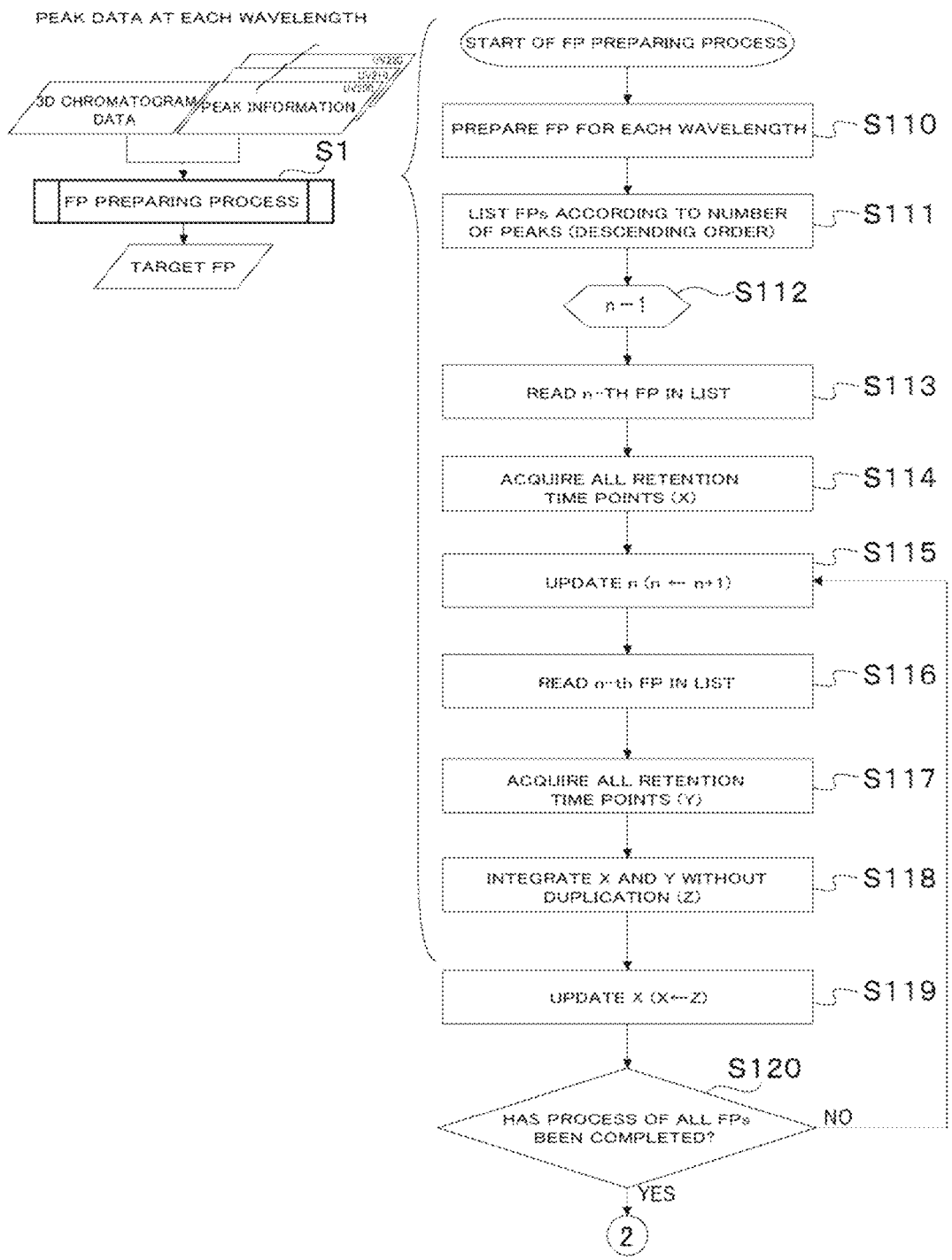
FIG. 78 is a data processing flowchart of a FP preparing function according to a plurality of wavelengths according to the first embodiment.
Figure 79:
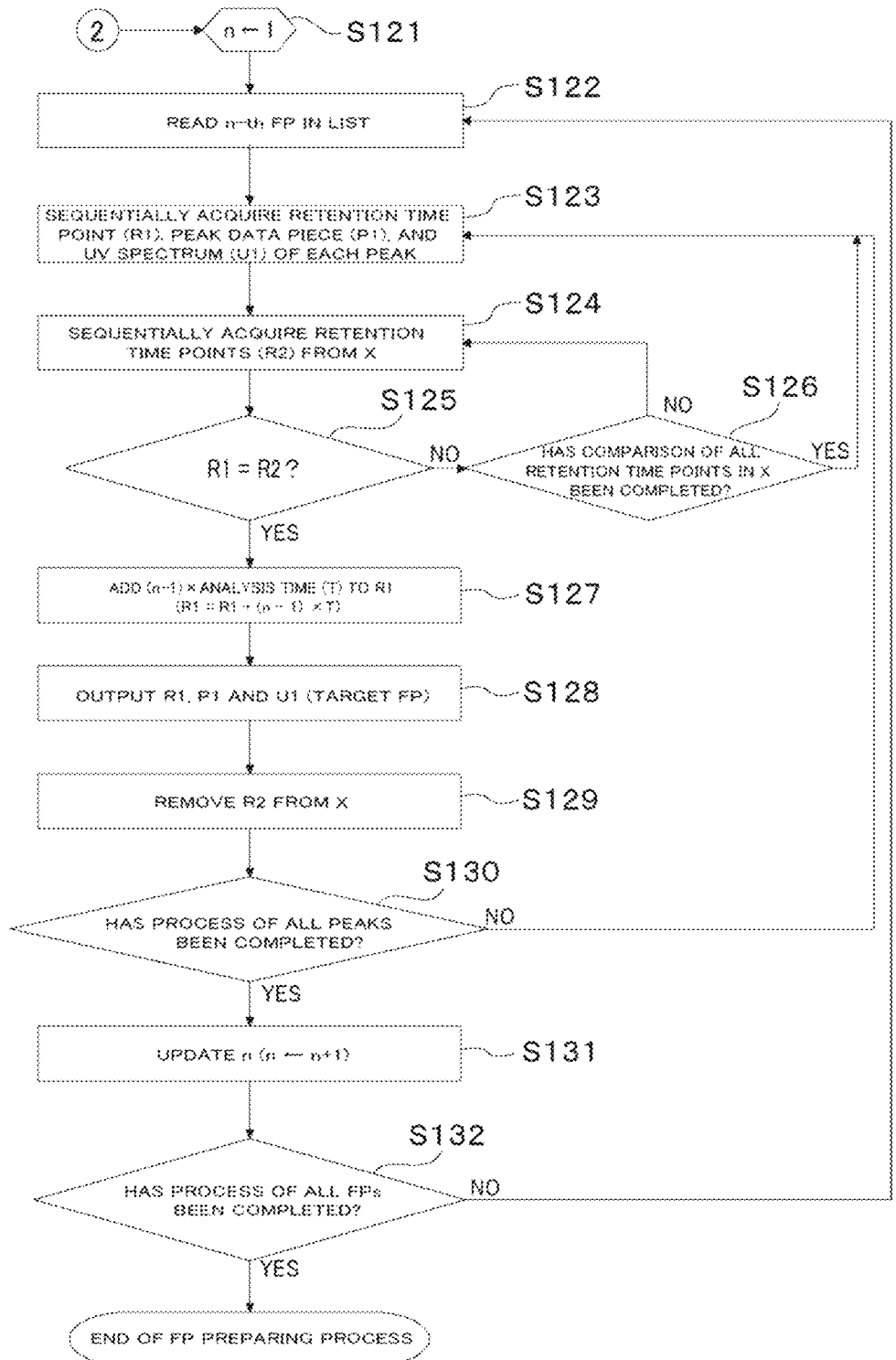
FIG. 79 is a data processing flowchart of the FP preparing function according to the plurality of wavelengths according to the first embodiment.

FIGS. 78 and 79 are flowcharts of a case where peak information at a plurality of wavelengths are used instead of the peak information at the single wavelength in the "FP preparing process" of Step S1 illustrated in FIG. 76. For example, this is a case where a plurality of (n) wavelengths are selected in the direction of the detection wavelength axis including 203 nm to prepare a FP.

This FP preparing process is for preparing a FP that covers all the peaks of the 3D chromatogram with use of peak information of a plurality of wavelengths in a case where all the peaks detected in the 3D chromatogram cannot be covered at the single wavelength as illustrated in FIG. 77.

In addition, FIGS. 78 and 79 illustrate details of the step in which n FPs are prepared at respective wavelengths by performing the above-described FP preparing process by means of only a single wavelength, and, based on the FPs, a FP according to the plurality of wavelengths is prepared.

In Step S110, a process of "preparing a FP for each wavelength" is performed. In this process, the above-described FP preparing process using only the single wavelength is performed for each wavelength so as to prepare n FPs, and it proceeds to Step S111.

In Step S111, a process of "listing the FPs according to the number of peaks (descending order)" is performed. In this process, the n FPs are listed in the descending order of the number of peaks, and it proceeds to Step S112.

In Step S112, as initialization of a counter for sequentially processing n FPs, one is substituted into n (n←1), and it proceeds to Step S113.

In Step S113, a process of "reading the n-th FP in the list" is performed. In this process, the n-th FP in the list is read, and it proceeds to Step S114.

In Step S114, a process of "acquiring all the retention time points (X)" is performed. In this process, all the retention time point information of the FPs read in S113 is acquired, and it proceeds to Step S115.

In Step S115, a process of "updating n (n←n+1)" is performed. In this process, "n+1" is substituted into "n" as the update of "n" in order to transfer the process to the next FP, and it proceeds to Step S116.

In Step S116, a process of "reading the n-th FP in the list" is performed. In this process, the n-th FP in the list is read, and it proceeds to Step S117.

In Step S117, a process of "acquiring all the retention time points (Y)" is performed. In this process, the retention time point information of all the FPs read in S116 is acquired, and it proceeds to Step S118.

In Step S118, a process of "integrating X and Y without duplication (Z)" is performed. In this process, the retention time point information X acquired in S114 and retention time point information Y acquired in Step S117 are integrated without duplication, thereafter, the integrated information is stored in Z, and it proceeds to Step S119.

In Step S119, a process of "updating X (X←Z)" is performed. In this process, as the update of X, Z stored in Step S118 is substituted for X, and it proceeds to Step S120.

In Step S120, a determining process "Have all the FPs been processed?" is performed. In this process, it is determined whether or not all the n FPs prepared in Step S110 have been processed. If processed (YES), it proceeds to Step S121. If there are one or more FPs that have not been processed (NO), it proceeds to Step S115 in order to perform the process of Steps S115 to S120 for the FPs that have not been processed. Until the process of all the FPs are completed, the process of Steps S115 to S120 is repeated.

In Step S121, as the initialization of the counter for sequentially processing n FPs, "1" is substituted into "n" (n←1), and it proceeds to Step S122.

In Step S122, a process of "reading the n-th FP in the list" is performed. In this process, the n-th FP in the list is read, and it proceeds to Step S123.

In Step S123, a process of "sequentially acquiring a retention time point (R1), peak data (P1), and a UV spectrum (U1) of each peak" is performed. In this process, retention time points (R1), peak data pieces (P1), and UV spectra (U1) of peaks are sequentially acquired from the FP read in Step S122 one by one, and it proceeds to Step S124.

In Step S124, a process of "sequentially acquiring retention time points (R2) from X" is performed. In this process, retention time points (R2) are sequentially acquired from X in which the retention time points of all the FPs are stored without duplication one by one, and it proceeds to Step S125.

In Step S125, a determining process "R1=R2?" is performed. In this process, it is determined whether or not R1 acquired in Step S123 and R2 acquired in Step S124 are the same. If being the same (YES), it proceeds to Step S127. If not being the same (NO), it proceeds to Step S126.

In Step S126, a determining process "Has the comparison of all the retention time points of X been completed?" is performed. In this process, it is determined whether or not the comparison of R1 acquired in S123 with all the retention time points of X has been completed. If completed (YES), it is determined that the peak at the retention time point of R1 has been processed and it proceeds to Step S123 in order to transfer the process to the next peak. If not completed (NO), it proceeds to Step S124 in order to transfer the process to the next retention time point of X.

In Step S127, a process of "adding (n−1)×analysis time (T) to R1 (R1←R1+(n−1)×T)" is performed. In this process, for each retention time point that is present in the first FP, which has the highest number of peaks, in the list, the retention time point is unchanged. For the retention time of a peak that is not present in the 1st FP in the list but is present in the 2nd FP, an analysis time (T) is added to R1. For the retention time of a peak that is not present in the 1st to (n−1)-th FP in the list but is present in the n-th FP, (n−1)×T is added to R1. Then, it proceeds to Step S128.

In Step S128, a process of "outputting R1, P1, and U1 (target FP)" is performed. In this process, R1 processed in Step S127, P1 and U1 acquired in Step S123 are output to the target FP, and it proceeds to Step S129.

In Step S129, a process of "removing R2 from X" is performed. In this process, since the process at the retention time points R1 (=R2) have been completed in Steps S127 and S128, the retention time points (R2) that have been processed are removed from X, and it proceeds to S130.

In Step S130, a determining process "Have all peak processes been completed?" is performed. In this process, it is determined whether or not the process has been completed for all the peaks of the n-th FP in the list. If completed (YES), the FP preparing process for the n-th FP in the list is finished to proceed to Step S131. If not completed (NO), it proceeds to Step S123 in order to process any peak that has not been completed. Until the process of all the peaks is finished, the process of Steps S123 to S130 is repeated.

In Step S131, a process of "updating n (n←n+1)" is performed. In this process, in order to transfer the process to the next FP, "n+1" is substituted into "n" as the update of "n" to proceed to Step S132.

In Step S132, a determining process "Have all FP processes been completed?" is performed. In this process, it is determined whether or not all the n FPs prepared in Step S110 have been processed. If processed (YES), the FP preparing process is finished. If there are one or more FPs that have not been processed (NO), it proceeds to Step S122 in order to perform the process of Steps S122 to S132 for the FPs that have not been processed. Until the process of all the FPs is completed, the process of Steps S122 to S132 is repeated.

Figure 80:
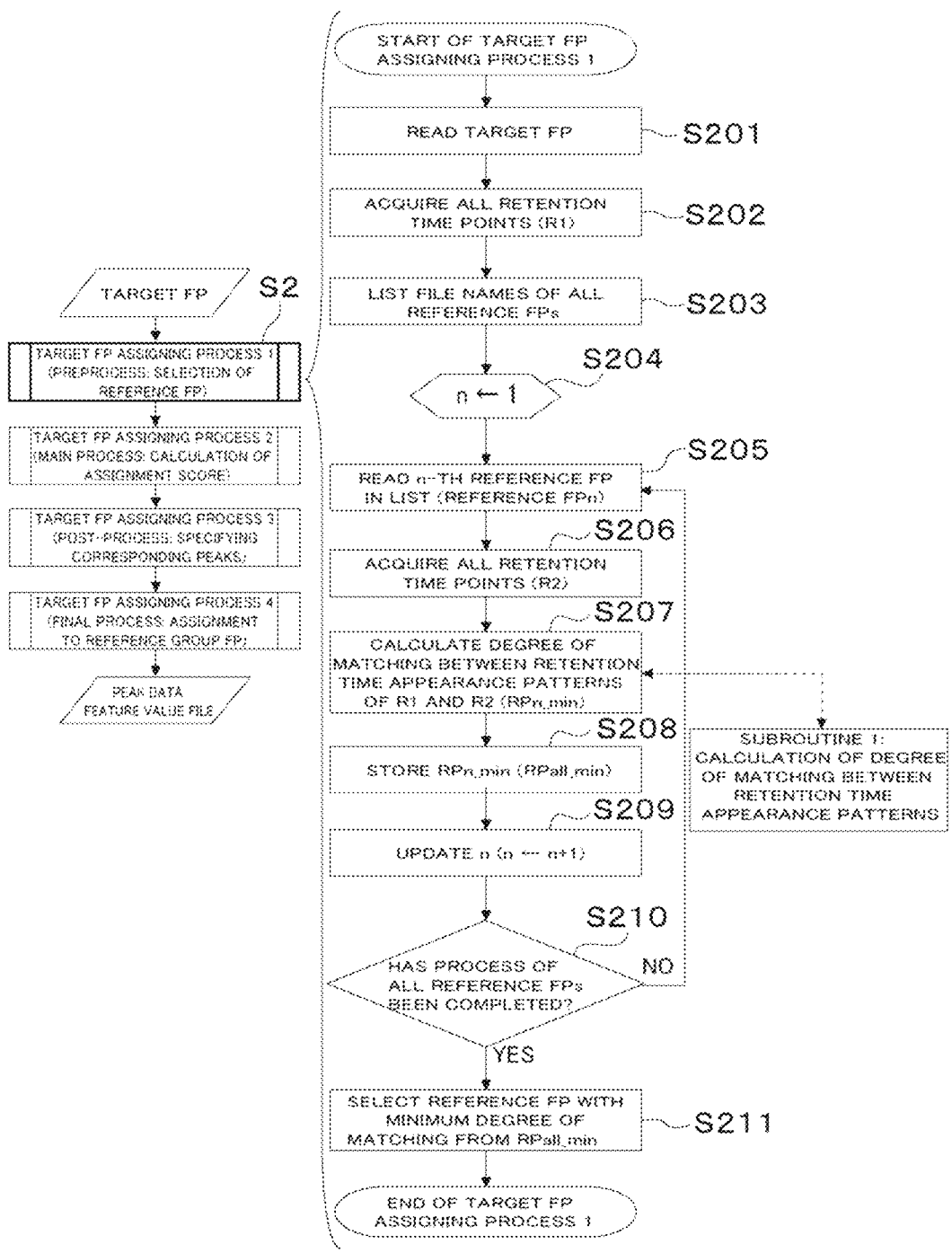
FIG. 80 is a data processing flowchart of a peak assigning process 1 (selection of a reference FP) according to the first embodiment.

FIG. 80 is a flowchart illustrating details of the "target FP assigning process 1" of Step S2 in FIG. 76. This process is a preprocess of the assigning process and selects a reference FP that is appropriate to the assignment of the target FP 17 from among a plurality of reference FPs regarded as normal products.

In Step S201, a process of "reading a target FP" is performed. In this process, the FP that is an assignment target is read, and it proceeds to Step S202.

In Step S202, a process of "acquiring all the retention time points (R1)" is performed. In this process, all the retention time point information of the target FP that is read in S201 is acquired, and it proceeds to Step S203.

In Step S203, a process of "listing file names of all the reference FPs" is performed. In this process, file names of all the reference FPs are listed in advance in order to sequentially process all the reference FPs later, and it proceeds to Step S204.

In Step S204, "1" is substituted into "n" (n←1) as an initial value of the counter used for sequentially processing all the reference FPs, and it proceeds to Step S205.

In Step S205, a process of "reading the n-th reference FP (reference $FP_n$) in the list" is performed. In this process, the n-th FP of the file name list of all the reference FPs listed in Step S203 is read, and it proceeds to Step S206.

In Step S206, a process of "acquiring all the retention time points (R2)" is performed. In this process, all of the retention time point information of the reference FP that are read in S205 are acquired, and it proceeds to Step S207.

In Step S207, a process of "calculating the degree of matching between retention time appearance patterns of R1 and R2 ($RP_n$_min)" is performed. In this process, $RP_n$_min is calculated based on the retention time point of the target FP that is acquired in Step S202 and the retention time point of the reference FP that is acquired in Step S206, and it proceeds to Step S208. A detailed calculation flow of $RP_n$_min will be described with reference to "Subroutine 1" of FIG. 85 separately.

In Step S208, a process of "storing $RP_n$_min ($RP_{all}$_min)" is performed. In this process, $RP_n$_min calculated in Step S207 is stored in $RP_{all}$_min, and it proceeds to Step S209.

In Step S209, a process of "updating n (n←n+1)" is performed. In this process, in order to transfer the process to the next FP, "n+1" is substituted for n as the update of n, and it proceeds to Step S210.

In Step S210, a determining process "Have all reference FP processes been completed?" is performed. In this process, it is determined whether or not all the reference FPs have been processed. If processed (YES), it proceeds to Step S211. If there are one or more reference FPs that have not been processed (NO), it proceeds to Step S205 in order to perform the process of Steps S205 to S210 for the FPs that have not been processed. Until the process of all the reference FPs are completed, the process of Steps S205 to S210 is repeated.

In Step S211, a process of "selecting a reference FP demonstrating the minimum degree of matching from $RP_{all}$_min" is performed. In this process, RP1_min to RPn_min calculated for all the reference FPs are compared with each other to select a reference FP demonstrating the minimum degree of matching with respect to the retention time appearance pattern of the target FP, and the target FP assigning process 1 is finished.

Figure 81:
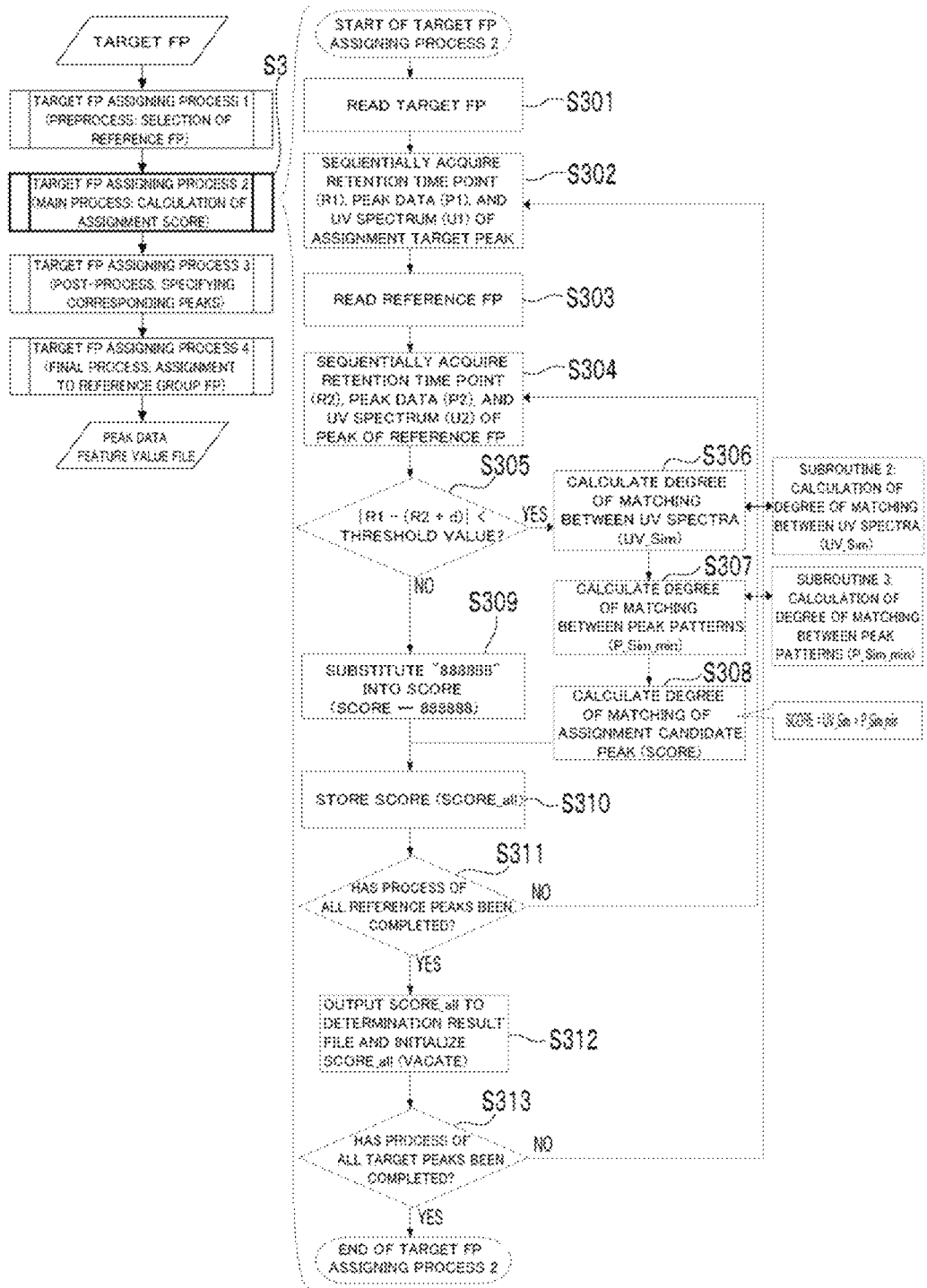
FIG. 81 is a data processing flowchart of a peak assigning process 2 (calculation of an assignment score) according to the first embodiment.

FIG. 81 is a flowchart illustrating details of the "target FP assigning process 2" of Step S3 in FIG. 76. This process is a main process of the assigning process and calculates the degree (SCORE) of matching for each assignment candidate peak based on the degrees of matching between the peak patterns and the UV spectra of the target FP 17 and the reference FP selected in Step S2.

In Step S301, a process of "reading a target FP" is performed. In this process, the FP that is an assignment target is read, and it proceeds to Step S302.

In Step S302, a process of "sequentially acquiring a retention time point (R1), peak data (P1), and a UV spectrum (U1) of an assignment target peak" is performed. In this process, the peaks of the target FP read in Step S301 are sequentially set as the assignment target peak to acquire R1, P1, and U1, and it proceeds to Step S303.

In Step S303, a process of "reading the reference FP" is performed. In this process, the reference FP that is selected in the "Target FP Assigning Process 1" in FIG. 80 is read, and it proceeds to Step S304.

In Step S304, a process of "sequentially acquiring a retention time point (R2), peak data (P2), and a UV spectrum (U2) of a peak of the reference FP" is performed. In this process, R2, P2, and U2 are acquired from the reference FP read in Step S303 for each peak, and it proceeds to Step S305.

In Step S305, a determining process "|R1−(R2+d)|<Threshold Value?" is performed. In this process, it is determined whether or not R1 and R2 read in Steps S302 and S304 correspond to each other within the threshold value range. If corresponding (YES), it is determined that the peak of which the retention time point is R2 is an assignment candidate peak of the peak of which the retention time point is R1. Then, in order to calculate the degree of matching for the assignment candidate peak (SCORE), it proceeds to Step S306. If not corresponding (NO), since the peak of which the retention time point is R2 and the peak of which the retention time point is R1 have a great difference in the retention time, it is determined that the peak cannot be set as the assignment candidate peak, and it proceeds to Step S309. In addition, "d" used in this determination process is a value for correcting the retention time points of the peaks of the target FP and the reference FP, and the initial value is set to zero. A difference between retention time points of peaks is acquired whenever being assigned during the progress of the process to update "d" with the value. In addition, the threshold value is an allowable range of the retention time points used for determining whether to be set as an assignment candidate peak.

In Step S306, a process of "calculating the degree of matching between UV spectra (UV_Sim)" is performed. In this process, UV_Sim is calculated based on U1 of the assignment target peak acquired in Step S302 and U2 of the assignment candidate peak acquired in S304, and it proceeds to Step S307. In addition, a detailed calculation flow of UV_Sim will be described with reference to "Subroutine 2" in FIG. 86 separately.

In Step S307, a process of "calculating the degree of matching between peak patterns (P_Sim_min)" is performed. In this process, from R1 and P1 of the assignment target peak acquired in Step S302 and R2 and P2 of the assignment candidate peak acquired in Step S304, peak patterns are comprehensively prepared for these peaks. In addition, P_Sim_min of these peak patterns is calculated, and it proceeds to Step S308. A detailed calculation flow of P_Sim_min will be described with reference to "Subroutine 3" in FIG. 87 separately.

In Step S308, a process of "calculating the degree of matching for the assignment candidate peak (SCORE)" is performed. In this process, from UV_Sim calculated in Step S306 and P_Sim_min calculated in Step S307, SCORE of the assignment target peak and the assignment candidate peak is calculated as:

$$\text{SCORE} = \text{UV\_Sim} \times P\_\text{Sim\_min}.$$

It proceeds to Step S310.

In Step S309, a process of "substituting "888888" into SCORE (SCORE←888888)" is performed. In this process, SCORE of a peak of an assignment target peak that does not correspond to an assignment candidate peak is set to "888888", and it proceeds to Step S310.

In Step S310, a process of "storing SCORE (SCORE_all)" is performed. In this process, SCORE acquired in Step S308 or S309 is stored in the SCORE_all, and it proceeds to Step S311.

In Step S311, a determining process "Has the process of all reference peaks been completed?" is performed. In this process, it is determined whether or not all the peaks of the reference FP have been processed. If processed (YES), it proceeds to Step S312. If there are one or more peaks that have not been processed (NO), it proceeds to Step S304 in order to perform the process of S304 to S311 for the unprocessed peaks. Until the process of all the peaks is completed, the process of Steps S304 to S311 is repeated.

In Step S312, a process of "outputting the SCORE_all to a determination result file to initialize (vacate) the SCORE_all" is performed. In this process, the SCORE_all is output to the determination result file, and thereafter, the SCORE_all is initialized (vacated), and it proceeds to Step S313.

In Step S313, a determining process "Has the process of all target peaks been completed?" is performed. In this process, it is determined whether all the peaks of the target FP have been processed. If processed (YES), the target FP assigning process 2 is finished. If there are one or more peaks that have not been processed (NO), it proceeds to Step S302 in order to perform the process of Steps S302 to S313 for the unprocessed peaks. Until the process of all the peaks is completed, the process of S302 to S313 is repeated.

FIG. 95 illustrates an output determination result file example 129.

Figure 82:
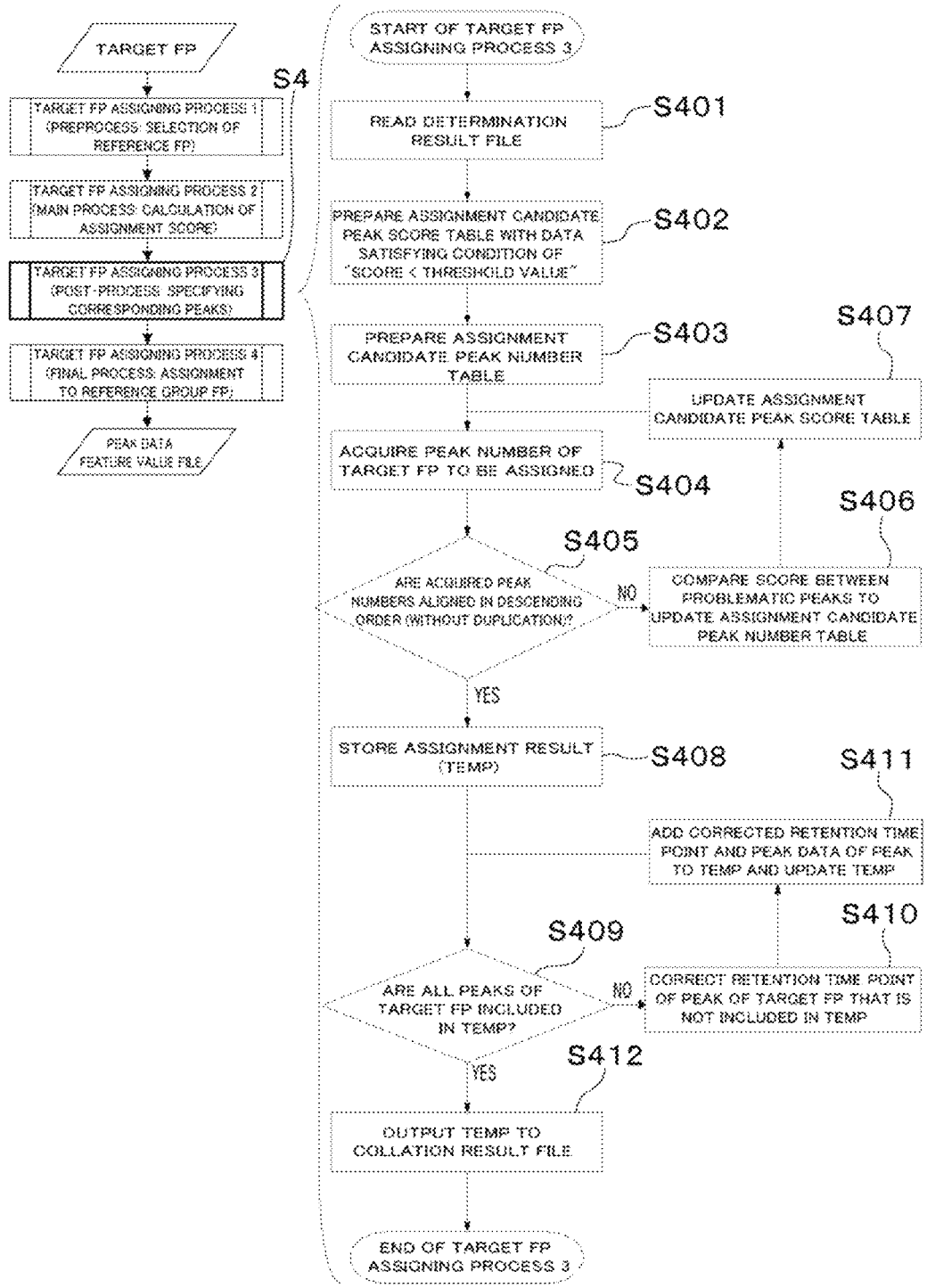
FIG. 82 is a data processing flowchart of a peak assigning process 3 (specifying a corresponding peak) according to the first embodiment.

FIG. 82 is a flowchart illustrating the "target FP assigning process 3" of Step S4 in FIG. 76. This process is a post-process of the assignment and specifies the peak of the reference FP corresponding to each peak of the target FP based on the degree of matching of the assignment candidate peak (SCORE) calculated as described above.

In Step S401, a process of "reading the determination result file" is performed. In this process, the determination result file prepared by the "target FP assigning process 2" in FIG. 81 is read, and it proceeds to Step S402.

In Step S402, a process of "preparing an assignment candidate peak score table with data satisfying the condition of "SCORE<Threshold value"" is performed. In this process, an assignment candidate score table 131 is prepared in FIG. 96 (upper diagram) based on the SCORE of the determination result file, and it proceeds to Step S403. This assignment candidate peak score table is a table in which only SCOREs less than the threshold value in the SCORE calculated for the all peaks of the target FP are aligned in an ascending order for each peak of the reference FP. The smaller the value of the SCORE is, the higher the possibility for a peak to be assigned is. In addition, the threshold value is an upper limit value for the SCOREs to determine whether to set as an assignment candidate.

In Step S403, a process of "preparing an assignment candidate peak number table" is performed. In this process, an assignment candidate peak number table 133 illustrated in FIG. 96 (lower diagram) is prepared based on the assignment candidate peak score table, and it proceeds to Step S404. This assignment candidate peak number table is a table that is acquired by substituting each score included in the assignment candidate peak score table into a peak number of the target FP corresponding to the score. Accordingly, this table is a table that sequentially aligns the peak numbers of the target FP to be associated for each peak of the reference FP.

In Step S404, a process of "acquiring the peak numbers of the target FP to be assigned" is performed. In this process, a peak number of the target FP that is located at the highest position is acquired for each peak of the reference FP from the assignment candidate peak number table prepared in Step S403, and it proceeds to Step S405.

In Step S405, a determining process "Are the acquired peak numbers aligned in a descending order (without duplication)?" is performed. In this process, it is determined whether or not the peak numbers of the target FP acquired in Step S404 are aligned in the descending order without duplication. If aligned (YES), it is determined that the peaks of the target FP corresponding to respective peaks of the reference FP can be settled, and it proceeds to Step S408. If not aligned (NO), in order to reconsider one or more problematic peaks of the target FP to be assigned to peaks of the reference FP, it proceeds to Step S406.

In Step S406, a process of "comparing SCOREs of problematic peaks to update the assignment candidate peak number table" is performed. In this process, SCOREs corresponding to the peak numbers of the target FP that have the problem are compared with use of the assignment candidate score table, and the assignment candidate peak number table is updated in which a peak number having a larger SCORE is substituted into a peak number located in the second, and it proceeds to Step S407.

In Step S407, a process of "updating the assignment candidate peak store table" is performed. In this process, in accordance with the updated content of the assignment candidate peak number table in Step S406, the assignment candidate peak score table is updated, and it proceeds to Step S404. Until there is no problem in the peak numbers of the target FP (there is no duplication, or the peak numbers are aligned in the descending order), the process of Steps S404 to S407 is repeated.

In Step S408, a process of "storing an assignment result (TEMP)" is performed. In this process, the peak numbers of all the peaks, the retention time points and the peaks of the reference FP and peak data of the target FP that is specified as the peaks corresponding to these peak of the reference FP are stored in TEMP, and it proceeds to Step S409.

In Step S409, a determining process "Are all the peaks of the target FP included in TEMP?" is performed. In this process, it is determined whether the peak data of all the peaks of the target FP is included in TEMP stored in Step S408. If all included (YES), it is determined that the process for all the peaks of the target FP has been completed, and it proceeds to Step S412. If there is any excluded peak (NO), in order to add peak data of the excluded peak, it proceeds to Step S410. In Step S410, a process of "correcting the retention time point of the peak of the target FP that is not included in TEMP" is performed. In this process, the retention time point of the peak of the target FP (the peak of the target FP that is needed to be corrected) that is excluded from TEMP is corrected as a correction value=k1+(k2−k1)*(t0−t1)/(t2−t1), wherein:

k1: it is a retention time point of a peak having a shorter retention time point of two reference FP-side peaks that are assigned in the vicinity of a peak of a target FP for which correction is necessary;

k2: it is a retention time point of a peak having a larger retention time point of two reference FP-side peaks that are assigned in the vicinity of the peak of the target FP for which correction is necessary;

t0: it is a retention time point of the peak of the target FP for which correction is necessary;

t1: it is a retention time point of a peak having a shorter retention time point of two target FP-side peaks that are assigned in the vicinity of the peak of the target FP for which correction is necessary; and t2: it is a retention time point of a peak having a longer retention time point of two target FP-side peaks that are assigned in the vicinity of the peak of the target FP for which correction is necessary, and it proceeds to Step S411.

In Step S411, a process of "adding the corrected retention time point and the peak data thereof to TEMP, and updating TEMP" is performed. In this process, the retention time point of the peak of the target FP corrected in S410 and not included in TEMP is compared with the retention time points of the reference FP in TEMP, to add the corrected retention time point and peak data of the peak of the target FP that is not included in TEMP to a valid position in TEMP and update TEMP, and it proceeds to Step S409. Until all the peaks of the target FP are added, the process of Steps S409 to S411 is repeated.

In Step S412, a process of "outputting TEMP to a collation result file" is performed. In this process, TEMP that specifies the correspondence relation between all the peaks of the reference FP and the all the peaks of the target FP is output as a collation result file, and the target FP assigning process 3 ends.

FIG. 97 illustrates a collation result file example 135 output as described above.

Figure 83:
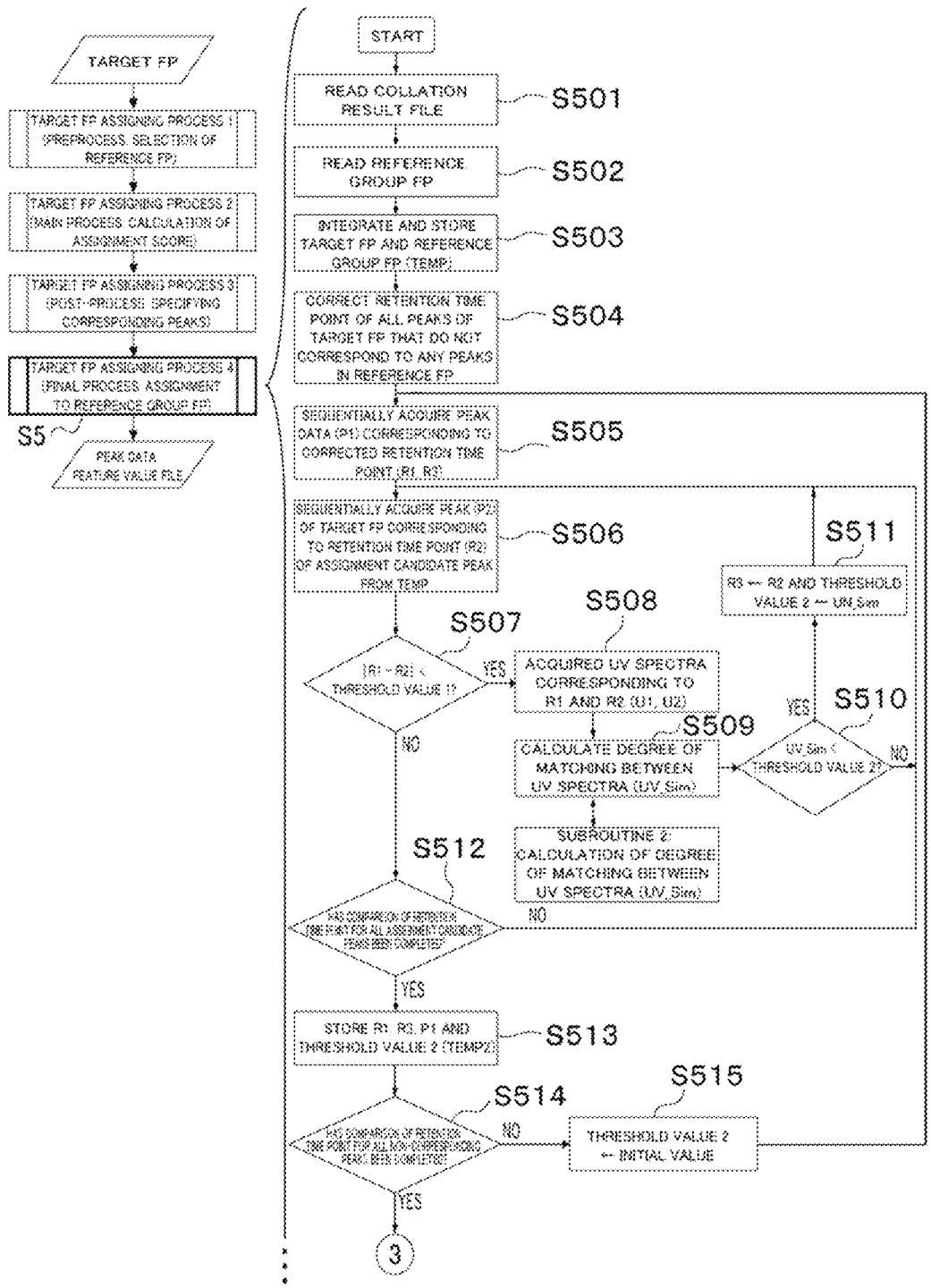
FIG. 83 is a data processing flowchart of a peak assigning process 4 (assignment to a reference group FP) according to the first embodiment.
Figure 84:
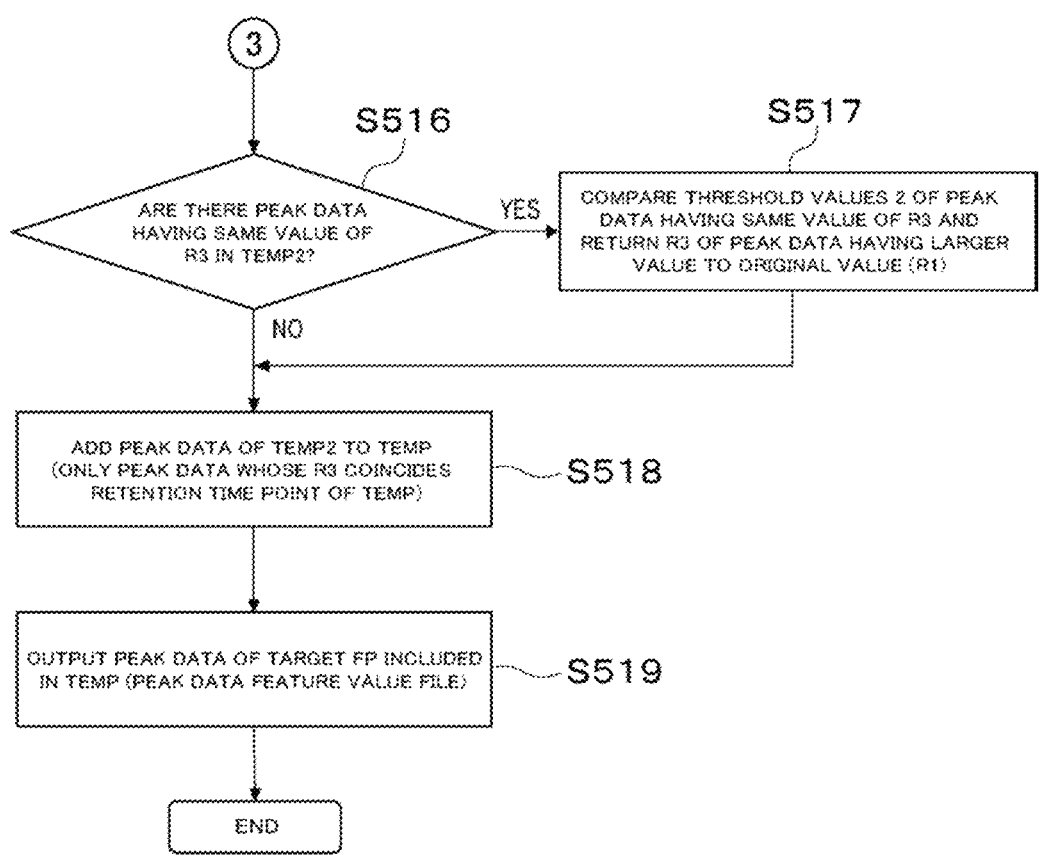
FIG. 84 is a data processing flowchart of the peak assigning process 4 (assignment to the reference group FP) according to the first embodiment.

FIGS. 83 and 84 are flowcharts illustrating details of the "target FP assigning process 4" of Step S5 in FIG. 76. This process is a final process of the assignment and assigns the peaks of the target FP to the respective peaks of the reference group FP based on the collation result file prepared in Step S4 of FIG. 76. In addition, the reference group FP is a FP that specifies the correspondence relation among all the reference FPs as described above. The reference group FP is data configured by reference group FP peak numbers, reference group retention time points and peak heights similar to the example of the reference group FP data 137 in FIG. 98. As the reference group FP 19 illustrated in FIG. 3A, each peak can be denoted by an average value (black point)±standard deviation (vertical line).

In Step S501, a process of "reading the collation result file" is performed. In this process, the collation result file output in Step S412 illustrated in FIG. 82 is read, and it proceeds to Step S502.

In Step S502, a process of "reading the reference group FP" is performed. In this process, the reference group FP that is a final assignment opponent of each peak of the target FP is read, and it proceeds to Step S503.

In Step S503, a process of "integrating and storing the target FP and the reference group FP (TEMP)" is performed. In this process, two files are integrated based on the peak data of the reference FP that is commonly present in the collation result file and the reference group FP to store the result as TEMP, and it proceeds to Step S504.

In Step S504, a process of "correcting the retention time point of the peak of the target FP that does not correspond to any peaks in the reference FP" is performed. In this process, the retention time points of all the peaks of the target FP that do not correspond to any peaks in the reference FP in the collation result file are corrected to the retention time points of TEMP stored in Step S503, and it proceeds to Step S505. In addition, the correction for the retention time point is performed by the same method as that of Step S410 of the "Target FP Assigning Process 3".

In Step S505, a process of "sequentially acquiring the peak data (P1) corresponding to the corrected retention time point (R1 and R3)" is performed. In this process, peak data pieces of peaks corresponding to retention time points corrected in Step S504 as R1 and R3 are sequentially acquired as P1, and it proceeds to Step S506.

In Step S506, a process of "sequentially acquiring peak data (P2) of the target FP corresponding to retention time point (R2) of assignment candidate peak from TEMP" is performed. In this process, peak data pieces are sequentially acquired as P2 corresponding to retention time points R2 at which no peak of the target FP are assigned from TEMP stored in Step S503, and it proceeds to Step S507.

In Step S507, a determining process "|R1−R2|<threshold value 1?" is performed. In this process, it is determined whether or not a difference between the retention time points R1 and R2 acquired in Steps S505 and S506 is less than the threshold value 1. If a difference is less than the threshold value (YES), it is determined that there is a possibility that the retention time point of the target FP with the retention time point R1 corresponding to the retention time point of the reference FP with the retention time point R2, and it proceeds to Step S508. If a difference between the retention time points R1 and R2 is the threshold value 1 or more (NO), it is determined that there is no possibility of the correspondence, and it proceeds to Step S512.

In Step S508, a process of "acquiring UV spectra (U1, U2) corresponding to the retention time points R1 and R2" is performed. In this process, the UV spectra corresponding to the peaks of the retention time points of R1 and R2 that are determined to have the possibility of the correspondence in Step S507 are acquired from respective FPs, and it proceeds to Step S509.

In Step S509, a process of "calculating the degree of matching between the UV spectra (UV_Sim)" is performed. In this process, the UV_Sim is calculated using the same method as that of Step S306 of the "Target FP Assigning Process 2" of Step S3 based on the UV spectra U1 and U2 acquired in Step S508, and it proceeds to Step S510. In addition, a detailed calculation flow of the UV_Sim will be additionally described with reference to Subroutine 2 illustrated in FIG. 86 separately.

In Step S510, a determining process "UV_Sim<threshold value 2?" is performed. In this process, it is determined whether the UV_Sim calculated in Step S509 is less than the threshold value 2. If it is less than the threshold value 2 (YES), it is determined that the peak of the UV spectrum U1 corresponds to the peak of U2, and it proceeds to Step S511. If the UV_Sim is the threshold value 2 or more (NO), it is determined that there is no correspondence, and it proceeds to Step S507.

In Step S511, a process of "R3←R2, and threshold value 2←UV_Sim" is performed. In this process, the retention time point R3 (that is, R1) determined to have the correspondence in Step S510 is updated with R2 that is the retention time point of the corresponding opponent, and thereafter, the threshold value 2 is updated with the value of UV_Sim, and it proceeds to Step S507.

In Step S512, a determining process "Have the retention time points of all the assignment candidate peaks been compared?" is performed. In this process, it is determined whether comparisons of R1 with the retention time points of all the assignment candidate peaks have been completed. If completed (YES), it proceeds to Step S513. If not completed (NO), it proceeds to Step S507.

In Step S513, a process of "storing R1, R3 and P1 as well as the threshold value 2 (TEMP2)" is performed. In this process, the retention time point (R1) determined to have the correspondence in Step S510 and the peak (P1) corresponding to R3 updated to the retention time point (R2) of the corresponding opponent are stored as well as the threshold value 2 at this time (TEMP2), and it proceeds to Step S507.

In Step S514, a determining process "Have the retention time points of all non-corresponding peaks been compared?" is performed. In this process, it is determined whether or not comparisons with the retention time points of the assignment candidate peaks have been completed in the retention time points of all non-corresponding peaks. If completed (YES), it is determined that the assignment process of all the non-corresponding peaks has been completed, and it proceeds to Step S516. If not completed (NO), it is determined that one or more non-corresponding peaks that have not been processed remain, and it proceeds to Step S515.

In Step S515, a process of "threshold value 2←initial value" is performed. In this process, the threshold value 2 that is updated to UV_Sim in Step S511 is returned to the initial value, and it proceeds to Step S505.

In Step S516, a determining process "Are there peaks having the same value of R3 present in TEMP2?" is performed. In this process, it is determined whether or not a plurality of non-corresponding peaks are assigned to the same peak in TEMP. If there are non-corresponding peaks assigned to the same peak (YES), it proceeds to Step S517. If such non-corresponding peak is not present (NO), it proceeds to Step S518.

In Step S517, a process of "comparing the threshold values 2 of the peaks having the same values of R3 and returning R3 of the peak having a larger threshold value to its original value (R1)" is performed. In this process, the threshold values 2 of the peaks having the same value of R3 in TEMP2 are compared with each other, to return the value of R3 of the peak having a larger threshold value to its original value (in other words, R1), and it proceeds to Step S518.

In Step S518, a process of "adding a peak of TEMP2 to TEMP (only a peak of whose R3 coincides with the retention time point of TEMP)" is performed. In this process, every peak of which R3 coincides with the retention time point of TEMP is added to TEMP, and it proceeds to Step S519. Every peak of which R3 does not coincide with the retention time point of TEMP is not added, because there is no peak to be an assignment opponent in the reference group FP.

In Step S519, a process of "outputting the peaks of the target FP included in TEMP (peak feature value file)" is performed. In this process, the peak data of the target FP assigned to the reference group FP 137 is output as a peak data feature value file, to finish the target FP assigning process 4.

FIG. 99 shows an example of the peak data feature value file 139 output as described above.

Figure 85:
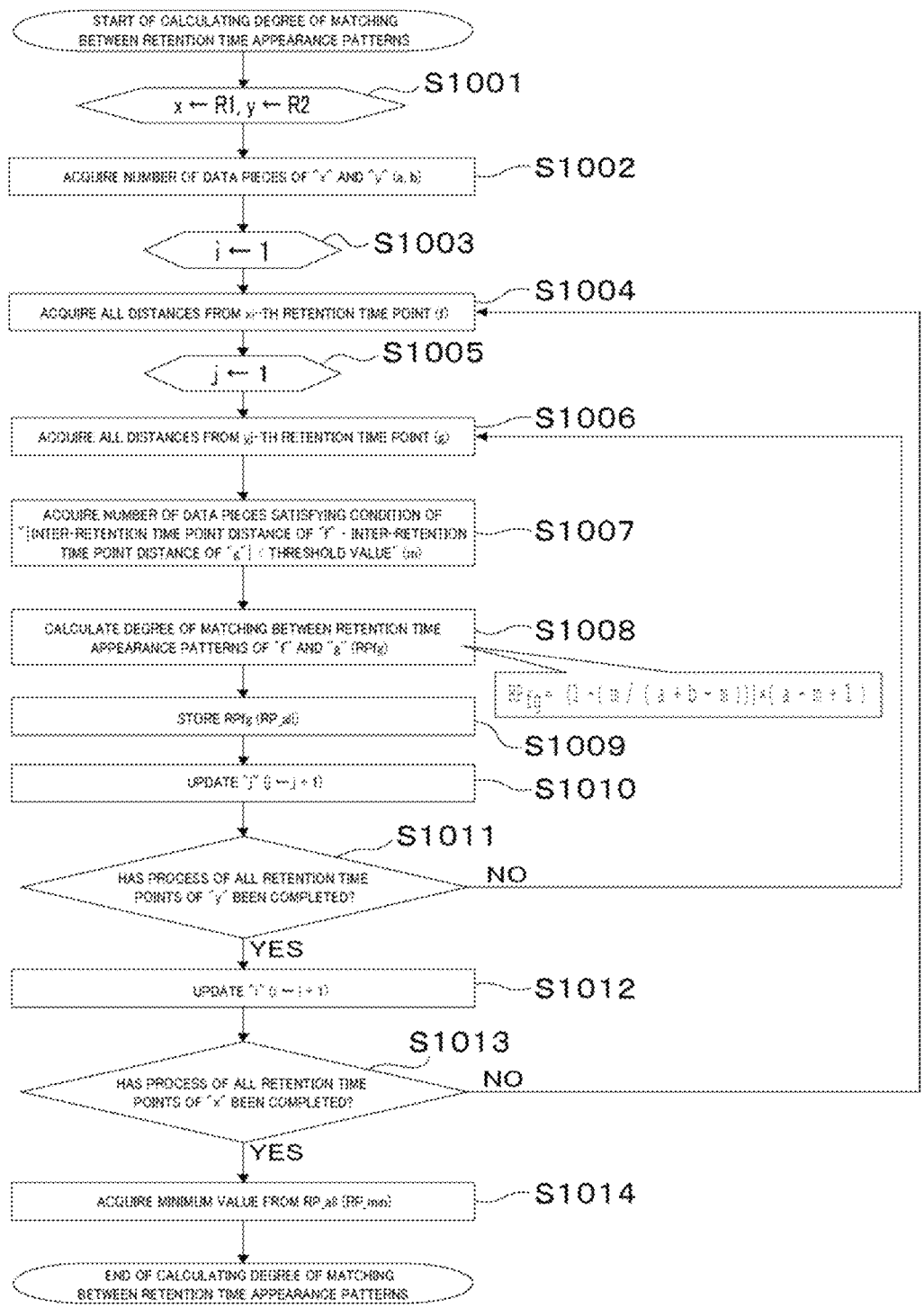
FIG. 85 is a flowchart of a process of calculating the degree of matching between retention time appearance patterns in the peak assigning process 1 (selection of the reference FP) according to the first embodiment.

FIG. 85 is a flowchart that illustrates details of the "Subroutine 1" of the "reference FP selecting process" of FIG. 80. This process calculates the degree of matching between retention time appearance patterns of FPs (for example, a target FP and a reference FP).

In Step S1001, a process of "x←R1 and y←R2" is performed. In this process, R1 and R2 acquired in Steps S202 and S206 of FIG. 80 are respectively substituted into "x" and "y", and it proceeds to Step S1002.

In Step S1002, a process of "acquiring the numbers of data "x" and "y" (a, b)" is performed. In this process, the numbers of data "x" and "y" are acquired as "a" and "b," respectively, and it proceeds to Step S1003.

In Step S1003, as an initial value of a counter used for sequentially invoking the retention time points of "x", "1" is substituted into "i" (i←1), and it proceeds to Step S1004.

In Step S1004, a process of "acquiring all distances from the xi-th retention time point (f)" is performed. In this process, all distances, from the xi-th retention time point, of retention time points after the xi-th retention time point are acquired as "f", and it proceeds to Step S1005.

In Step S1005, as an initial value of a counter for sequentially invoking the retention time points of "y", "1" is substituted into "j" (j←1), and it proceeds to Step S1006.

In Step S1006, a process of "acquiring all distances from the yj-th retention time point (g)" is performed. In this process, all distances, from the yj-th retention time point, of retention time points after the yj-th retention time point are acquired as "g", and it proceeds to Step S1007.

In Step S1007, a process of "acquiring the number of data pieces satisfying a condition of "|inter-retention time point distance of "f"–inter-retention time point distance of "g"|<threshold value" (m)" is performed. In this process, inter-retention time point distances "f" and "g" acquired in Steps S1004 and S1006 are compared with each other in a round robin manner, the number of data pieces satisfying the condition of "|inter-retention time point distance of "f"–inter retention time point distance of "g"|<threshold value" is acquired as "m", and it proceeds to Step S1008.

In Step S1008, a process of "calculating the degree of matching between the retention time appearance patterns of "f" and "g" ($RP_{fg}$)" is performed. In this process, $RP_{fg}$ is calculated based on "a" and "b" acquired in Step S1002 and "m" acquired in Step S1007 as:

$$RP_{fg}=(1-(m/(a+b-m)))\times(a-m+1).$$

It proceeds to Step S1009.

In Step S1009, a process of "storing $RP_{fg}$ (RP_all)" is performed. In this process, the degree of matching calculated in Step S1008 is stored in RP_all, and it proceeds to Step S1010.

In Step S1010, a process of "updating j (j←j+1)" is performed. In this process, in order to perform the process of "y" at the next retention time point, "j+1" is substituted into "j" as the update of "j", and it proceeds to Step S1011.

In Step S1011, a determining process "Has the process been completed at all the retention time points of "y"?" is performed. In this process, it is determined whether or not the process of all the retention time points of "y" has been completed. If completed (YES), it is determined that the process of all the retention time points has been completed, to proceed to Step S1012. If not completed (NO), it is determined that one or more retention time points that have not been processed remain in "y", to proceed to Step S1006. In other words, the process of Steps S1006 to S1011 is repeated until all the retention time points of "y" are processed.

In Step S1012, a process of "updating "i" (i←i+1)" is performed. In this process, as the update of "i" for bringing the process of "x" to the next retention time point, "i+1" is substituted into "i", and it proceeds to Step S1013.

In Step S1013, a determining process "Has the process been completed at all the retention time points of "x"?" is performed. In this process, it is determined whether or not the process of all the retention time points of "x" has been completed. If completed (YES), it is determined that the process of all the retention time points of "x" has been completed, to proceed to Step S1014. If not completed (NO), it is determined that one ore more retention time points that have not been processed remain in "x", to proceed to Step S1004. In other words, the process of Steps S1004 to S1013 is repeated until all the retention time points of "x" are processed.

In Step S1014, a process of "acquiring a minimum value from RP_all (RP_min)" is performed. In this process, the minimum value in RP_all in which RPs for all the combinations of the retention time appearance patterns of the target FP and the reference FP are stored is acquired as RP_min, and RP_min is input to Step S207 of FIG. 80 to finish the process of calculating the degree of matching between the retention time appearance patterns.

Figure 86:
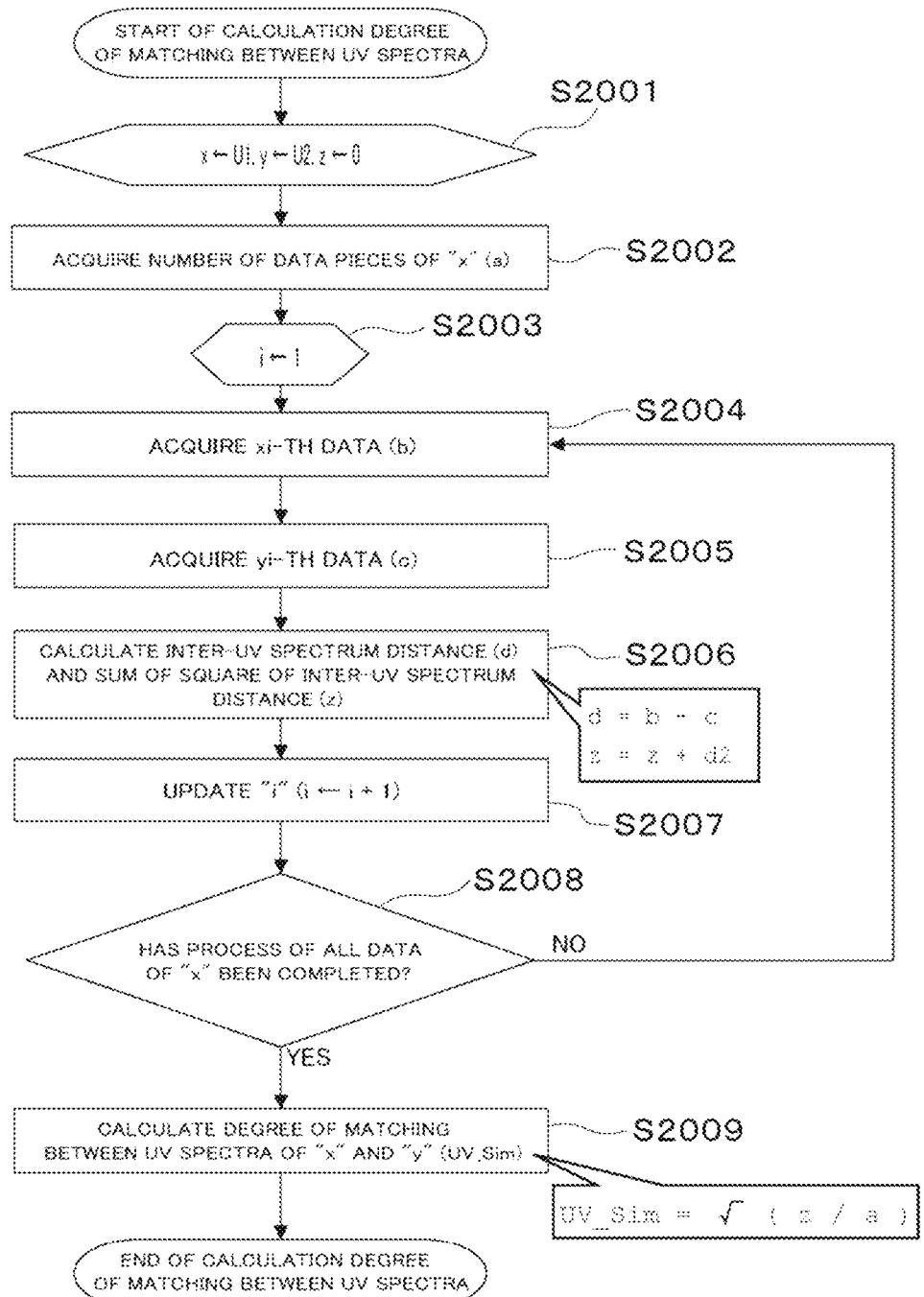
FIG. 86 is a flowchart of a process of calculating the degree of matching between UV spectra in the peak assigning process 2 (calculation of an assignment score) according to the first embodiment.

FIG. 86 is a flowchart that illustrates the "Subroutine 2" of the "target FP assigning process 2" of FIG. 81 in detail. In this process, the degree of matching between the UV spectra is calculated.

In Step S2001, a process of "x←U1, y←U2, z←0" is performed. In this process, the UV spectra U1 and U2 acquired in Steps S302 and S304 of FIG. 81 are respectively substituted into "x" and "y", and furthermore, "0" is substituted as an initial value of the sum (z) of squares of a distance of the UV spectra, and it proceeds to Step S2002.

In Step S2002, a process of "acquiring the number of data pieces of "x" (a)" is performed. In this process, the number of data pieces of "x" is acquired as "a", and it proceeds to Step S2003.

In Step S2003, a process of "i←1" is performed. In this process, "1" is substituted into "i" as an initial value used for sequentially invoking absorbance at each detection wavelength configuring the UV spectra U1 and U2 from "x" and "y", and it proceeds to Step S2004.

In Step S2004, a process of "acquiring the xi-th data (b)" is performed. In this process, the i-th absorbance data of "x" into which the UV spectrum "U1" is substituted is acquired as "b", and it proceeds to Step S2005.

In Step S2005, a process of "acquiring yi-th data (c)" is performed. In this process, the i-th absorbance data of "y" into which UV spectrum U2 is substituted is acquired as "c", and it proceeds to Step S2006.

In Step S2006, a process of "calculating an inter-UV spectra distance (d) and a sum (z) of squares of the inter-UV spectra distance" is performed. In this process, the inter-UV spectra distance "d" and the sum "z" of squares of the inter-UV spectra distance are calculated as:

$$d=b-c; \text{ and}$$

$$z=z+d^2.$$

It proceeds to Step S2007.

In Step S2007, a process of "updating i (i←i+1)" is performed. In this process, as the update of "i," "i+1" is substituted into "i," to proceed to Step S2008.

In Step S2008, a determining process "Have the process of all data of "x" been completed?" is performed. In this process, it is determined whether the process of all data of "x" and "y" have been completed. If completed (YES), it is determined that the process of all data of "x" and "y" have been completed, to proceed to Step S2009. If not completed (NO), it is determined that there are one or more data pieces of "x" and "y" that have not been processed, to proceed to Step S2004. In other words, the process of Steps S2004 to S2008 is repeated until all the absorbance data of "x" and "y" is processed.

In Step S2009, a process of "calculating the degree of matching between the UV spectra of "x" and "y" (UV_Sim)" is performed. In this process, UV_Sim is calculated based on the sum "z" of squares of the inter-UV spectra distance and the number "a" of data of "x" as follows:

$$UV\_Sim=\sqrt{(z/a)}.$$

UV_Sim is input to Step S306 of FIG. 81, to finish the process of calculating the degree of matching between UV spectra.

Figure 87:
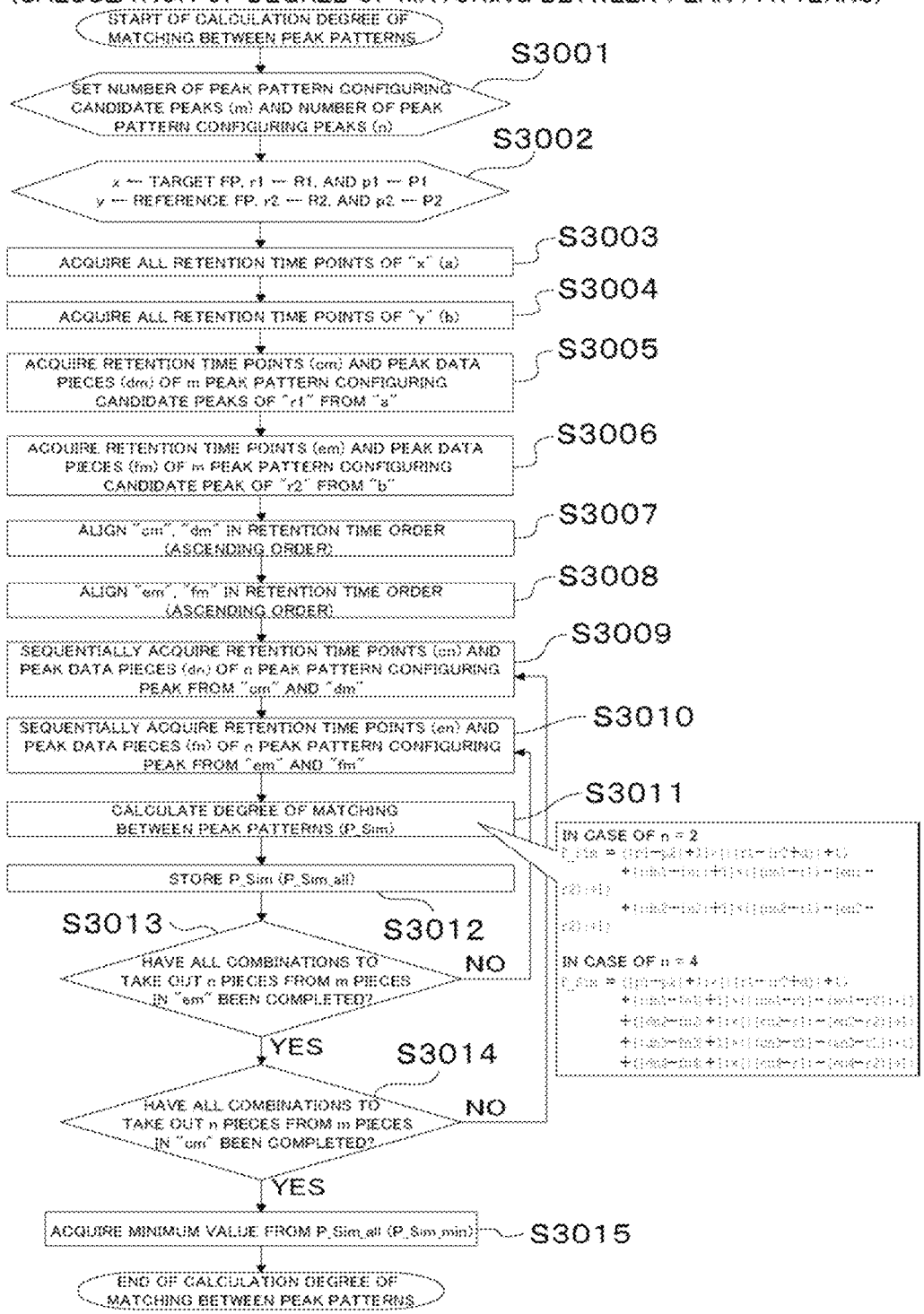
FIG. 87 is a flowchart of a process of calculating the degree of matching between peak patterns in the peak assigning process 2 (calculation of an assignment score) according to the first embodiment.

FIG. 87 is a flowchart of that illustrates details of the "Subroutine 3" of the "target FP assigning process 2" of FIG. 81. In this process, the degrees of matching between peak patterns are calculated.

In Step S3001, a process of "setting the number (m) of peak pattern configuring candidates and the number (n) of peak pattern configuring peaks" is performed. In this process, as setting for comprehensively preparing peak patterns, the number (m) of peak pattern configuring candidates and the number (n) of peak pattern configuring peaks are set, and it proceeds to Step S3002.

In Step S3002, a process of "x←target FP name, r1←R1, p1←P1, y←reference FP name, r2←R2, and p2←P2" is performed. In this process, the file names of the target FP and the reference FP that are necessary for the process, and the retention time points and the peak data acquired in Steps S302 and S304 of FIG. 81 are substituted into "x," "r1," and "p1," and "y," "r2," and "p2," and it proceeds to Step S3003.

In Step S3003, a process of "acquiring all retention time points of "x" (a)" is performed. In this process, a file (target FP) having a name substituted into "x" in Step S3002 is read, all the retention time points of the file are acquired as "a", and it proceeds to Step S3004.

In Step S3004, a process of "acquiring all retention time points of "y" (b)" is performed. In this process, a file (reference FP) having a name substituted into "y" in Step S3002 is read, all the retention time points of the file are acquired as "b", and it proceeds to Step S3005.

In Step S3005, a process of "acquiring retention time points (cm) and peak data (dm) of m peak pattern configuring candidate peaks of "r1" from "a"" is performed. In this process, retention time points of m peak pattern configuring candidate peaks of "r1" that are the retention time points of the assignment target peaks are acquired as "cm" and the peak data thereof as "dm" from "a", and it proceeds to Step S3006. Here, m peak pattern configuring candidate peaks are m peaks with retention time points close to "r1."

In Step S3006, a process of "acquiring retention time points (em) and peak date (fm) of m peak pattern configuring candidate peaks of "r2" from "b"" is performed. In this process, retention time points of m peak pattern configuring candidate peaks of "r2" that are the retention time points of the assignment target peaks are acquired as "em" and the peak data thereof as "fm" from "b", and it proceeds to Step S3007. Here, m peak pattern configuring candidate peaks are m peaks with retention time points close to "r2".

In Step S3007, a process of "aligning "cm" and "dm" in the retention time order (ascending order)" is performed. In this process, "cm" and "dm" acquired in Step S3005 are rearranged so as to be in the ascending order of the retention time, and it proceeds to Step S3008.

In Step S3008, a process of "aligning "em" and "fm" in the retention time order (ascending order)" is performed. In this process, "em" and "fm" acquired in Step S3006 are rearranged so as to be in the ascending order of the retention time, and it proceeds to Step S3009.

In Step S3009, a process of "sequentially acquiring retention time points (cn) and peak data (dn) of n peak pattern configuring peaks from "cm" and "dm"" is performed. In this process, retention time points are sequentially acquired as "cn" and the peak data thereof as "dn" from "cm" and "dm" of m peak pattern configuring candidate peaks, and it proceeds to Step S3010.

In Step S3010, a process of "sequentially acquiring retention time points (en) and peak data (fn) of n peak pattern configuring peaks from "em" and "fm"" is performed. In this process, retention time points of n peak pattern configuring peaks are sequentially acquired as "en" and the peak data thereof as "fn" from "em" and "fm" of m peak pattern configuring candidate peak, and it proceeds to Step S3011.

In Step S3011, a process of "calculating the degree of matching between peak patterns (P_Sim)" is performed. In this process, the degree (P_Sim) of matching between peak patterns is calculated based on "r1" and "p1" of the assignment target peaks, "cn" and "dn" of n peak pattern configuring peaks, "r2" and "p2" of the assignment candidate peaks, and "en" and "fn" of n peak pattern configuring peaks, which have been acquired until now as:

$$P\_Sim = (|p1 - p2| + 1) \times (|(r1 - (r2 + d)| + 1) +$$
$$(|dn1 - fn1| + 1) \times (|(cn1 - r1) - (en1 - r2)| + 1) +$$
$$(|dn2 - fn2| + 1) \times (|(cn2 - r1) - (en2 - r2)| + 1) +$$
$$(|dn3 - fn3| + 1) \times (|(cn3 - r1) - (en3 - r2)| + 1) +$$
$$(|dn4 - fn4| + 1) \times (|(cn4 - r1) - (en4 - r2)| + 1)$$

in the case of n=4 as an example as represented in FIG. 64, and it proceeds to Step S3012.

In Step S3012, a process of "storing P_Sim (P_Sim all)" is performed. In this process, P_Sim calculated in Step S3011 is sequentially stored in P_Sim-all, and it proceeds to Step S3013.

In Step S3013, a determining process "Have all the combinations to take out n pieces from m pieces included in "em" been completed?" is performed. In this process, it is determined whether or not the process has been completed for all the combinations to take out n peak pattern configuration peaks out from m peak pattern configuring candidate peaks. If completed (YES), it is determined that the preparation of comprehensive peak patterns and the calculation of the degrees of matching for the patterns have been completed for the assignment candidate peaks, to proceed to Step S3014. If not completed (NO), it is determined that one or more combinations to take out n pieces out from m pieces have not been completed, to proceed to Step S3010. In other words, the process of Steps S3010 to S3013 is repeated until the process is completed for all the combinations to take out n pieces out from m pieces.

In Step S3014, a process of determining "Have all the combinations to take out m pieces from n pieces included in "cm" been completed?" is performed. In this process, it is determined whether or not the process has been completed for all the combinations to take out n peak pattern configuring peaks from m peak pattern configuring candidate peaks of the assignment target peak. If completed (YES), it is determined that the preparation of comprehensive peak patterns and the calculation of the degrees of matching for the patterns have been completed for the assignment candidate peak, to proceed to Step S3015. If not completed (NO), it is determined that one or more combinations to take out n pieces from m pieces has not been completed, to proceed to Step S3009. In other words, the process of Steps S3009 to S3014 is repeated until the process is completed for all the combinations to take out n pieces out from m pieces.

In Step S3015, a process of "acquiring a minimum value from P_Sim all (P_Sim_min)" is performed. In this process, the minimum value of the P_Sim-all stored in S3012 is acquired as P_Sim_min, and the P_Sim_min is input to Step S307 of FIG. 81 to finish the process of calculating the degree of matching between peak patterns.

The reference FP feature value file is prepared for comparing the target FP feature value data with the reference FP feature value data as illustrated in FIGS. 88 to 91.

Figure 88:
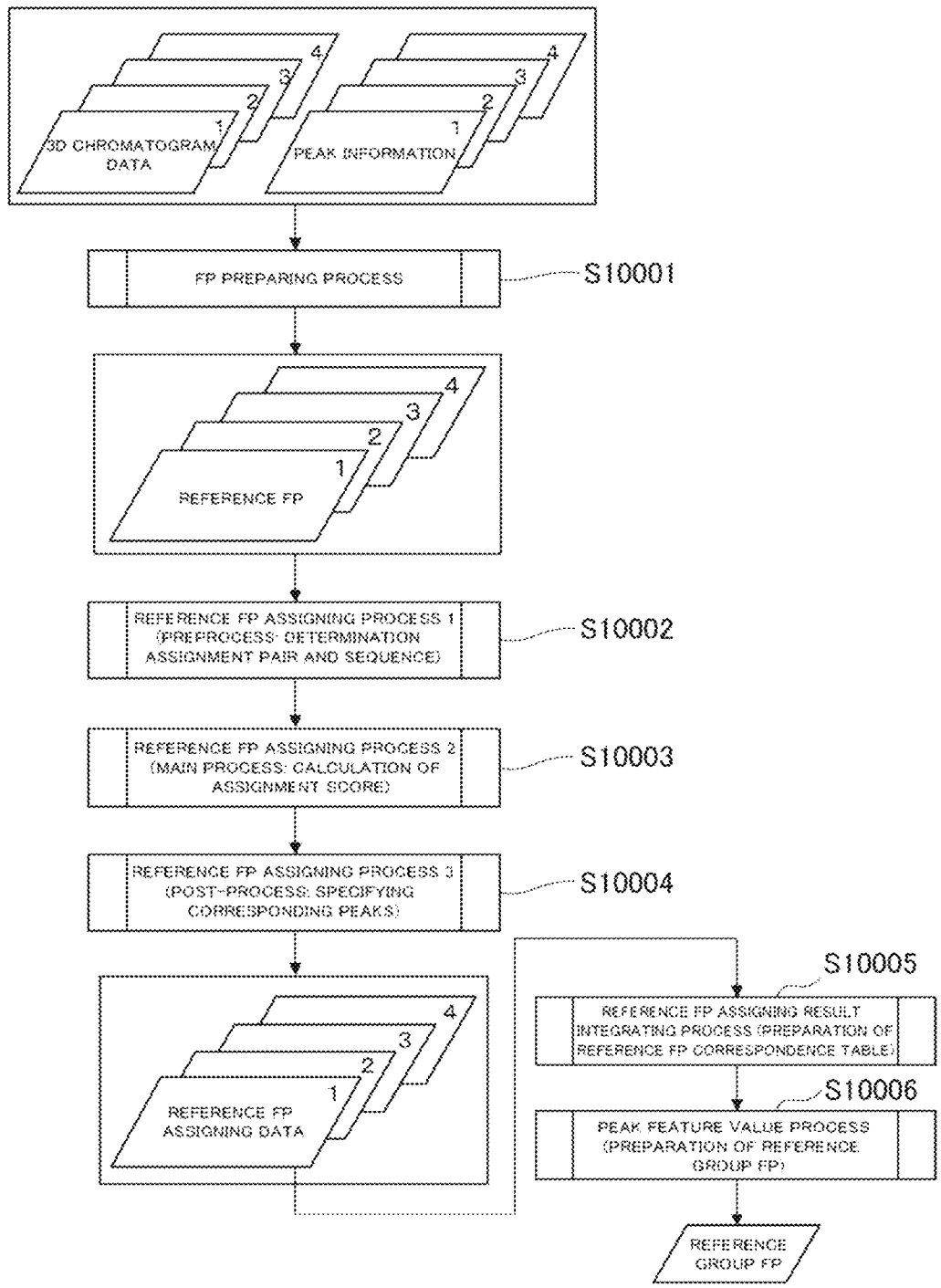
FIG. 88 is a flowchart for preparing a reference FP feature value file according to the first embodiment.

FIG. 88 is a flowchart that is used for preparing a reference FP feature value file. It realizes a FP preparing function of a reference FP preparing part, a reference FP peak assigning function of a reference FP peak assigning part, a reference FP assigning result integrating function of a reference FP assigning result integrating part, and a reference FP peak feature value preparing function of a reference FP peak feature value preparing unit in a computer.

The reference FP preparing function is realized in Step S10001. The reference FP peak assigning function is realized in Steps S10002, S10003, and S10004. The reference FP assigning result integrating function is realized in Step S10005. The reference FP peak feature value preparing function is realized in Step S10006.

Steps S10001 to S10004 correspond to Steps S1 to S4 relating to the preparation of the target FP feature value integrating file illustrated in FIG. 76.

In Step S10001, the "FP preparing process" is performed according to a 3D chromatogram and peak information at a specific detection wavelength as inputs.

Both the 3D chromatograph and the peak data are provided for each one of a plurality of evaluation reference drug (reference kampo medicine) that are evaluation criteria.

In Step S10001, the reference FP preparing part of the computer functions and a reference FP is prepared similarly to the target FP 17 (FIG. 3A) based on the 3D chromatogram and the peak information, and data of the reference FP is output as a file.

In Step S10002, the "reference FP assigning process 1" is performed according to all reference FPs output in Step S10001 as inputs.

In Step S10002, the reference FP peak assigning part of the computer functions, and, for all the reference FPs, a combination is selected from among the all reference FPs in order to calculate assignment scores for the selected combination in the selected order, and it proceeds to Step S10003.

In Step S10003, the "reference FP assigning process 2" is performed according to the selected combination of the reference FPs as an input.

In Step S10003, for all the peaks of the combination of the reference FPs that is selected in Step S2, peak patterns are comprehensively prepared as illustrated in FIGS. 23 to 61. Then, the degrees of matching between the peak patterns (P_Sim illustrated in FIG. 63 or 64) are calculated. In addition, the degrees of matching between UV spectra (UV_Sim illustrated in FIG. 66) of the peaks of the selected combination of the reference FPs are calculated. Furthermore, the degrees of matching of the assignment candidate peaks (SCORE illustrated in FIG. 67) are calculated based on these two degrees of matching. The calculation result is output as a determination result file (see the determination result file example 129 illustrated in FIG. 95).

In Step S10004, the "reference FP assigning process 3" is performed according to the determination result file output in Step S10003 as input.

In Step S10004, between the reference FPs in the selected combinations, peaks of the reference FPs in the selected combinations, which correspond to each other are specified based on the degree of matching between the assignment candidate peaks (SCORE). The result is output as the reference FP assigning data for each reference FP.

In Step S10005, the "reference FP assigning result integrating process" is performed according to all the reference FP assigning data output in Step S10004 is received as input.

In Step S10005, the reference FP assigning result integrating part of the computer functions to prepare a reference FP correspondence table by integrating all the FP assigning data with reference to the peak correspondence relation of the individual reference FP specified by the reference FP peak assigning part, and it proceeds to Step S10006.

In Step S10006, the reference FP peak feature value preparing part of the computer functions to prepare a peak feature value (reference group FP) according to the all reference FPs based on the reference FP correspondence table that is prepared by the reference FP assigning result integrating part. In the process at the reference FP peak feature value preparing part, statistic values (a maximum value, a minimum value, a medium value, an average value, and the like) are calculated for each peak (column) in the reference FP correspondence table, to select the peak (column) based on the calculated information. The selected peak (column) is output as the reference group FP (see the reference group FP example 137 illustrated in FIG. 98).

Figure 89:
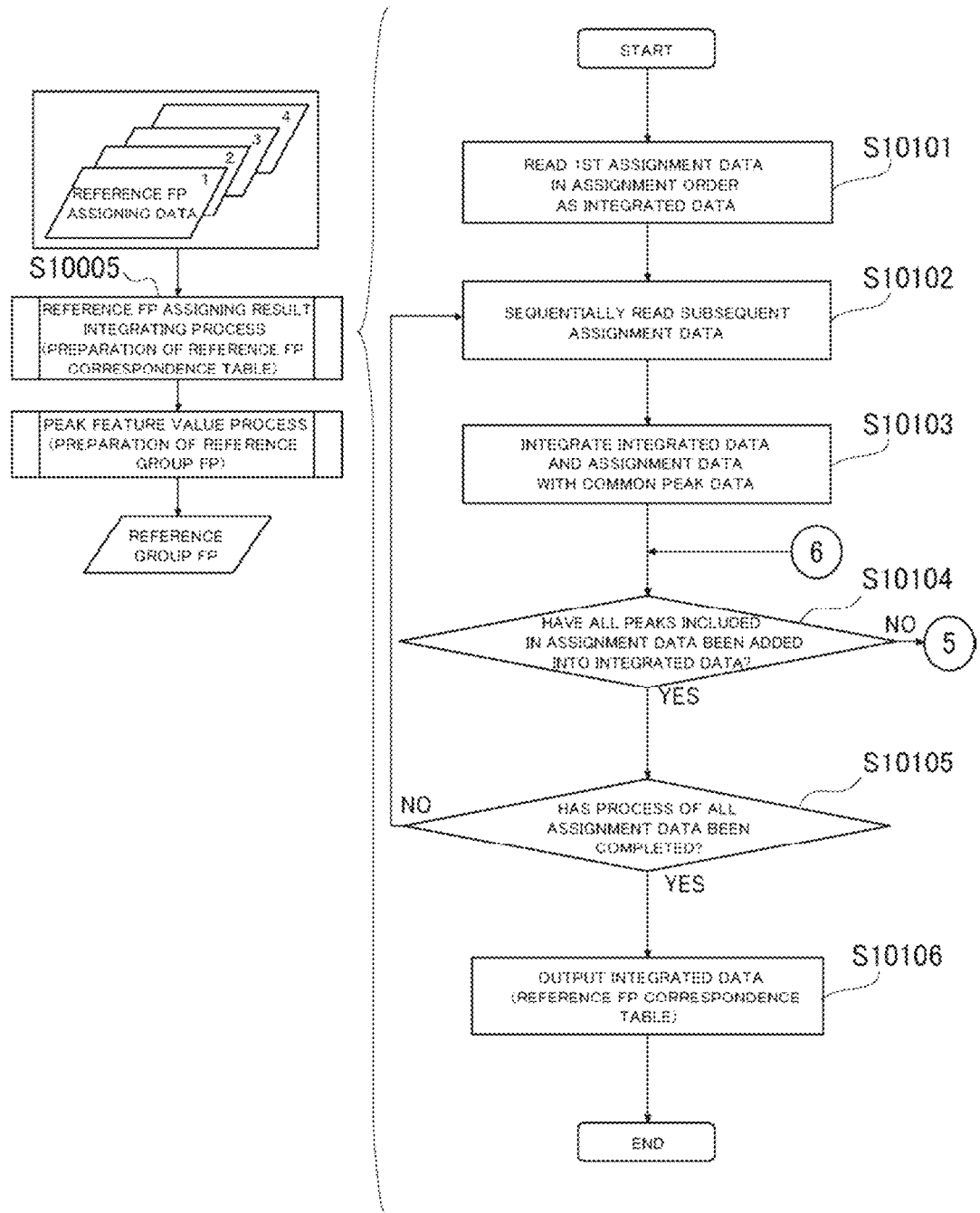
FIG. 89 is a flowchart illustrating details of a "process of integrating reference FP assigning results (preparation of a FP correspondence table)" according to the first embodiment.
Figure 90:
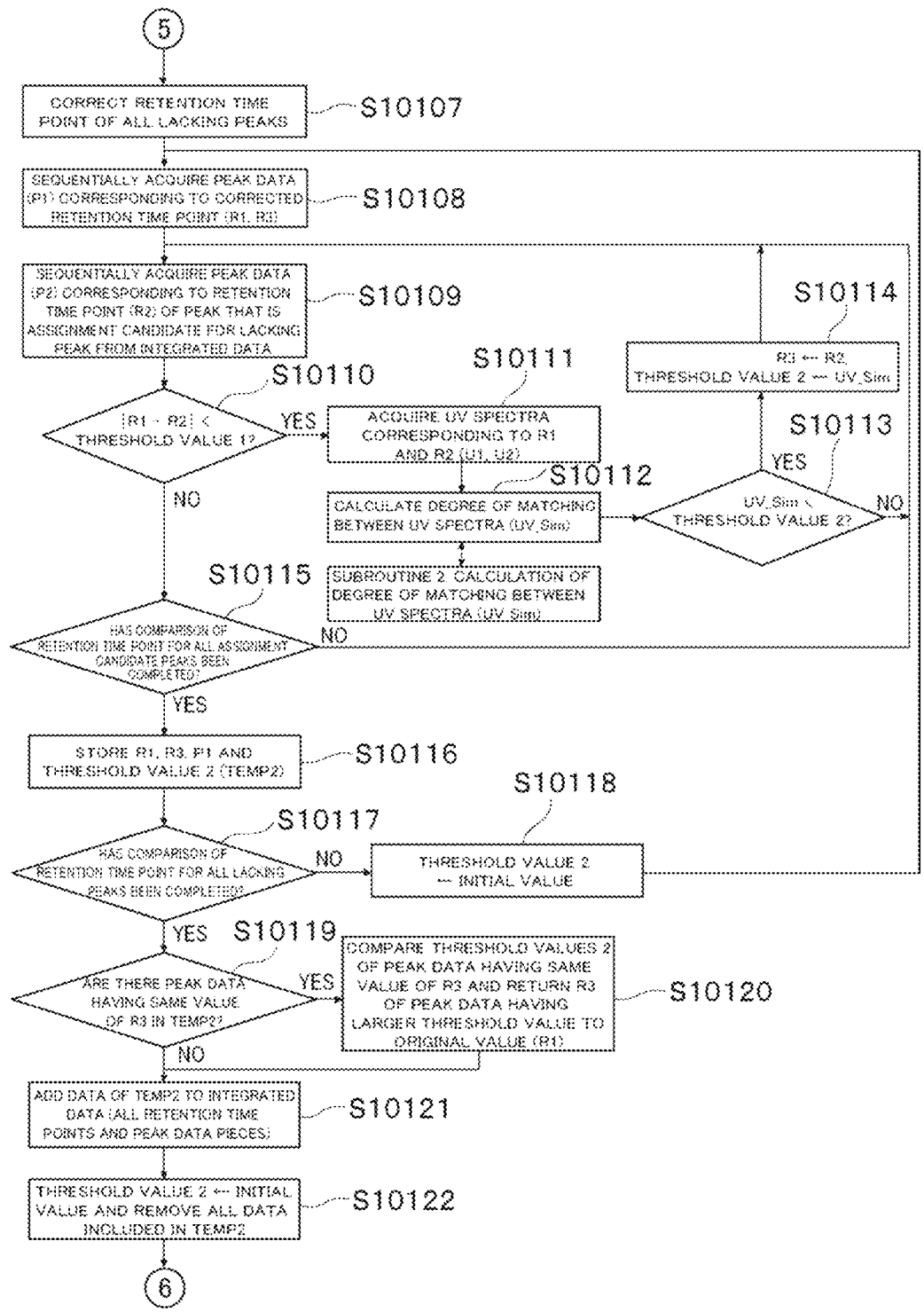
FIG. 90 is a flowchart illustrating details of the "process of integrating reference FP assigning results (preparation of a FP correspondence table)" according to the first embodiment.

FIGS. 89 and 90 are flowcharts that illustrate details of the "reference FP assigning result integrating process illustrated in Step S10005 (preparation of a reference FP correspondence table)."

In Step S10101, a process of "reading the 1st assignment data in the assignment order as integrated data" is performed. In this process, the reference FP assigning data, in which the assignment process is performed first to specify the correspondence relation of peaks in Step S10004, is read as the integrated data. Then, it proceeds to Step S10102.

In Step S10102, a process of "sequentially reading subsequent assignment data" is performed. In this process, at first the reference FP assigning data, in which the assignment process is secondarily performed to specify the correspondence relation of peaks in Step S10004, is read as integrated data. Then, it proceeds to Step S10103.

In Step S10103, a process of "integrating the integrated data and the assignment data with common peak data" is performed. In this process, the two files are integrated based on the peak data of the reference FP commonly-existing in the integrated data and the assignment data, the integrated data is updated as a result thereof, and it proceeds to Step S10104.

In Step S10104, a determining process "Have all the peaks included in the assignment data been added to the integrated data?" is performed. In this process, it is determined whether or not all the peaks in the assignment data have been added to the integrated data. If added (YES), it proceeds to Step S10105. If there is one or more peaks (lacking peaks) that have not been added (NO), in order to add the lacking peaks to the integrated data, it proceeds to Step S10107. In addition, in the process (S10107 to S10120) of adding the lacking peaks to the integrated data, the same process as that of Steps S504 to S517 in S5 (target FP assigning process 4) is performed.

In Step S10121, a process of "adding data of TEMP2 to the integrated data (all the retention time points and peaks)" is performed. In this process, all the retention time points (R3) and the peaks (P1) in TEMP2 are added to corresponding positions in the integrated data, and it proceeds to Step S10122.

In Step S10122, a process of "threshold value 2←initial value, and deleting all the data in TEMP2" is performed. In this process, the threshold value 2 updated to UV_Sim is returned to the original value, all the data are deleted from TEMP2 storing data such as retention time points and peaks of all the lacking peaks and the like, and it is returned to Step S10104.

In Step S10105 to which it proceeds from Step S10104, a determining process "Has the process of all the assignment data been completed?" is performed. In this process, it is determined whether or not the process of all reference data has been completed. If completed (YES), in order to output a reference FP correspondence table that is an integration result of all the assignment data, it proceeds to Step S10106. If not completed (NO), it is returned to Step S10102 to sequentially process the remaining assignment data.

In Step S10106, a process of "outputting the integrated data (reference FP correspondence table)" is performed. In this process, the result integrating all the assignment data is output as the reference FP correspondence table, to finish the process of preparing the reference FP correspondence table.

Figure 91:
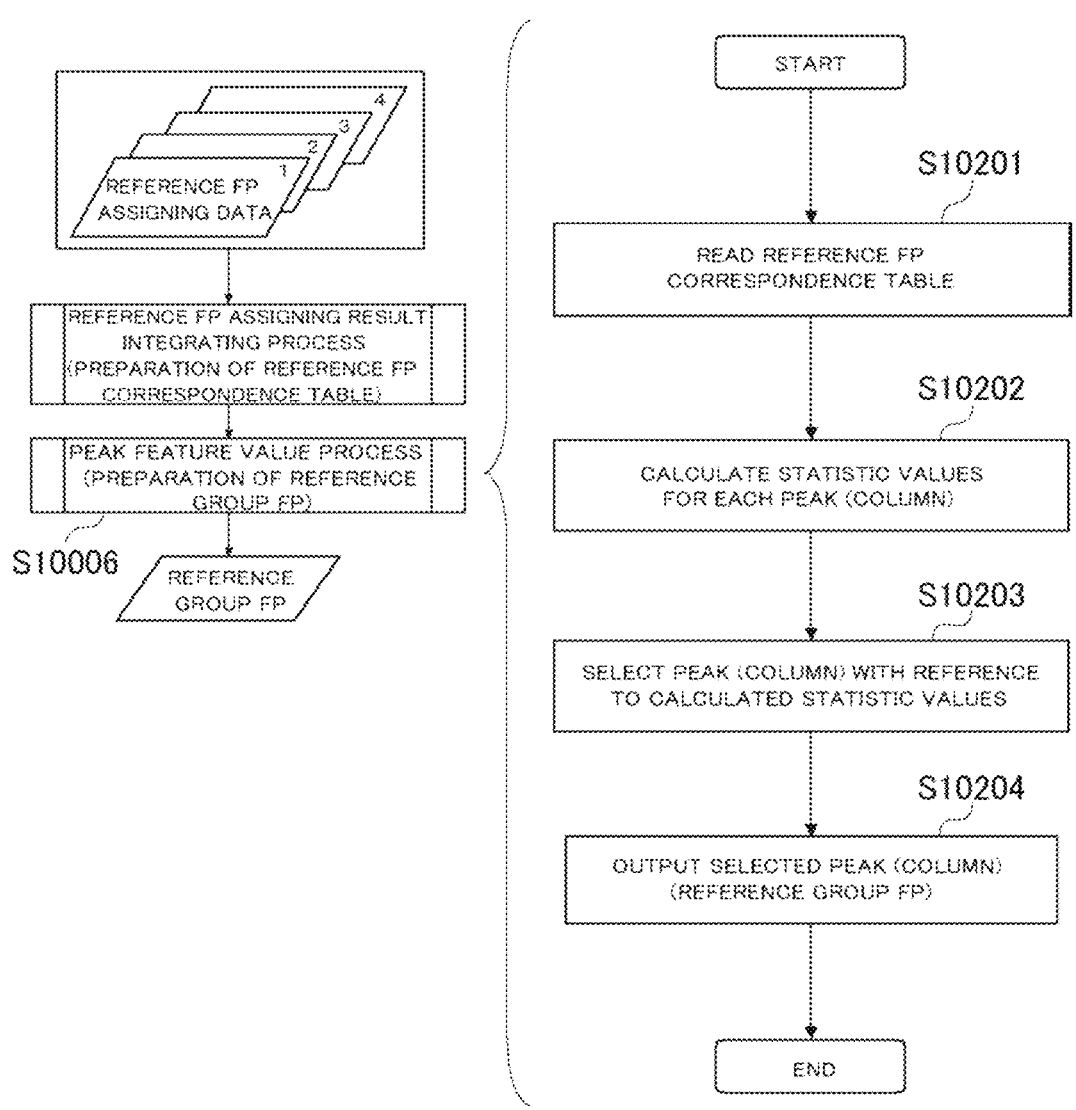
FIG. 91 is a flowchart illustrating details of a "peak-feature value converting process (preparation of a reference group FP)" in detail according to the first embodiment.

FIG. 91 is a flowchart that illustrates details of the "peak feature value process (preparation of a reference group FP)" of Step S10006 in FIG. 88.

In Step S10201, a process of "reading the reference FP correspondence table" is performed. In this process, the reference FP correspondence table prepared in Step S10005 is read to proceed to Step S10202.

In Step S10202, a process of "calculating statistic values for each peak (column)" is performed. In this process, the statistic values (a maximum value, a minimum value, a medium value, an average value, a variance, a standard deviation, an existence number, and an existence ratio) are calculated for each peak (column) of the reference FP correspondence table. Then, it proceeds to Step S10203.

In Step S10203, a process of "selecting a peak (column) with reference to the calculated statistic values" is performed. In this process, a peak is selected with reference to the statistic values calculated in Step S10102, to proceeds to Step S10204.

In Step S10204, a process of "outputting the selected peak (column) (reference group FP)" is performed. In this process, the selecting result of the peak (column) according to the statistic amounts is output as the reference group FP to finish the process of preparing the reference group FP.

FIG. 98 illustrates a reference FP correspondence table example 137 output as described above.

In the first embodiment of the present invention, the formulating method includes the FP preparing step 113 preparing target FP 17 that comprises peaks, retention time points and UV spectra of the peaks detected from the 3D chromatogram 15 of the multicomponent drug that is the evaluation target at a specific wavelength, for example, 203 nm; the reference FP selecting step 115 selecting a reference FP that is appropriate to peak assignment of the target FP 17 from among a plurality of reference FPs; a peak pattern preparing step 117 preparing peak patterns for the assignment target peak of the target FP and the assignment candidate peaks of the selected reference FP having differences in retention time within the allowable range relative to the assignment target peak, each peak pattern configured by, for example, three peaks including a corresponding one of the assignment target peak and the assignment candidate peaks and two peaks that are present at least on one of sides located in front and in the rear in a time axis direction for the corresponding one of the assignment target and assignment candidate peaks; the peak assigning step 119 comparing the assignment target and assignment candidate peaks in peak pattern and UV spectrum of to specify corresponding peaks between the target FP and the selected reference FP; and the evaluating step 121 evaluating the assigned peaks of the target FP by comparison with the peaks of the plurality of reference FPs using MT method to find a MD value and determine a powder extract of a multicomponent drug having a MD value being equal to or less than a threshold value as the accepted one meeting the criteria for productization.

By processing the 3D chromatogram 15 of the multicomponent drug that is an evaluation target through these five steps (113, 115, 117, 119, and 121), it can improve the accuracy and the efficiency of the quality evaluation of whether a powder extract of a multicomponent drug as the evaluation target drug meets the criteria for productization.

Accordingly, the embodiment surely subjects a powder extract of a multicomponent drug determined as an accepted one meeting the criteria for productization with high accuracy to the dosage form processing to make the powder extract into a product. This reduces the variation in multi-component drugs to be subjected to the dosage form processing and realizes the high quality of the products.

The target FP 17 prepared by the FP preparing step 113, similarly to the 3D chromatogram 15, is configured as three dimensional information (peaks, retention time points, and UV spectra). Accordingly, the target FP 17 is data directly succeeding to the information unique to the drug. In spite of that, the data volume is compressed at the ratio of about 1/70, compared to the 3D chromatogram 15, the amount of information to be processed can be greatly reduced to increase the processing speed.

The FP preparing step 113 prepares a FP by composing a plurality of FPs at different detection wavelengths. Accordingly, for even a multicomponent drug acquired by combining components all of which cannot be detected using one wavelength, a quality evaluation including all the components can be performed by composing FPs having a plurality of detection wavelengths.

The FP preparing step 113 prepares a FP that includes all the peaks detected in the 3D chromatogram. Accordingly, the FP preparing step is suited for an evaluation of the quality of a kampo medicine that is a multicomponent drug.

The reference FP selecting step 115 compares retention time appearance patterns of FPs with each other, to select a reference FP having a high degree of matching between patterns as a reference FP that is appropriate to the assignment. Accordingly, in the peak assigning step 119, the assignment process can be performed between FPs having similar patterns, whereby assignment can be performed with high accuracy.

The peak pattern preparing step 117 comprehensively prepares peak patterns with use of a plurality of peripheral peaks for each of the assignment target peak and the assignment candidate peak. Accordingly, even if there is a difference between the whole patterns of the target FP and the reference FP more or less, assignment can be performed through the peak assigning step 119 with high accuracy.

In the peak assigning step 119, in addition to the degree of matching between peak patterns prepared by the peak pattern preparing step 117, the degree of matching between UV spectra of the assignment target peak and the assignment candidate peak is used for specifying the peak to be assigned. Accordingly, assignment can be performed with high accuracy.

The peak assigning step 119 assigns all the peaks of the target FP to the peaks of the reference FP all together. Accordingly, the assignment process can be performed with high efficiency.

The evaluating step 121 collects a FP that is composed by multiple components as multi-dimensional data as a MD value in one dimension by MT method, to easily compare and evaluate a plurality of evaluation target lots. Accordingly, it is suited for evaluating a multicomponent based drug that is composed of multiple components.

Further, the formulating method of this embodiment mixes the powder extract of the multicomponent drug determined as a rejected one that does not meet the criteria for productization with one or more other powder extracts that do not meet the criteria for productization to form a mixed extract without subjecting the evaluated powder extract to the dosage form processing, evaluates whether the mixed extract meets the criteria for productization, and subjects the mixed extract determined as an accepted one meeting the criteria for productization to the dosage form processing.

Thus, even the powder extract that does not meet the criteria for productization is made into a product by mixing with the other powder extracts.

The producing of a mixed extract uses MD values to determine a mixing rate of powder extracts to be mixed and mixes the powder extracts with the determined mixing rate to form the mixed extract having a MD value that is equal to or less than the threshold value.

Accordingly, the formulating method surely produces the mixed extract having the MD value being equal to or less than the threshold value, i.e., meeting the criteria for productization and therefore improves the accuracy and the efficiency of the productization of the mixed extract of the multicomponent drug.

The formulating apparatus 301 for a multicomponent drug according to this embodiment of the present invention operates the units 3, 5, 7, 9 and 11 to improve the accuracy and the efficiency of the evaluation of whether the powder extract of the multicomponent drug meets the criteria for productization.

As a result, the formulating apparatus 301 of this embodiment subjects a powder extract of a multicomponent drug determined as an accepted one meeting the criteria for productization with high accuracy to the dosage form processing to make the powder extract into a product.

According to the embodiment, the formulating apparatus 301 includes the extract producing device 307 extracting an essence from a raw material crude drug to produce a powder extract of a multicomponent drug, the first pipeline 323 led from the extract producing device 307 to the dosage form processing device 311, the first stocker 309 arranged on the first pipeline 323 to accommodate the produced powder extract, the sampler 341 obtaining a sample from the powder extract accommodated in the first stocker 309 and feeding the obtained sample to the chromatographic device 343, and the control unit 308 controlling the sampler 341 to feed the sample to the chromatographic device 343 and then controlling the first pipeline 323 to convey the powder extract from the first stocker 309 to the dosage form processing device 311 in response to a determination made at the evaluating device 1 that the powder extract meets the criteria for productization.

The formulating apparatus 301 of this embodiment automatically conducts the formulating process in which the powder extract is produced from the raw material crude drug and the powder extract meeting the criteria for productization is subjected to the dosage form processing. Further, the pipeline 323 is extended from the dosage form processing device 311 to the packing device 313 and automatically conducts also the packing of the formulated drug subsequent to the dosage form processing.

The formulating apparatus 301 includes the second pipeline 327 led from and back to the first stocker 309, and the second stockers 329 arranged on the second pipeline 327 for accommodating powder extracts that do not meet the criteria for productization. The control unit 308 controls the second pipeline 327 to convey that powder extract from the first stocker 309 to an empty one of the second stokers 329 in response to a determination made at the evaluating device 1 that the powder extract does not meet the criteria for productization.

Accordingly, the formulating apparatus 301 automatically stores the produced powder extract without the dosage form processing if that powder extract does not meet the criteria for productization.

The formulating apparatus 301 includes the mixing device 330 arranged on the second pipeline 327. The control unit 308 controls the second pipeline 327 to convey two or more powder extracts accommodated in the second stockers 329 to the mixing device 330 at which the conveyed extracts are mixed to form the mixed extract and to convey the mixed extract from the mixing device 330 to the first stocker 309 at which the mixed extract is accommodated and then controls the sampler 341 to feed the sample of the mixed extract to the chromatographic device 343.

Accordingly, the formulating apparatus 301 automatically conducts the evaluation of whether the produced mixed extract meets the criteria for productization and automatically subjects the mixed extract to the dosage form processing or store the mixed extract according to the evaluation.

In addition, the formulating apparatus 301 realizes the formulating method to obtain the same effects as the formulating method.

In the case of FIGS. 63, 64, and 87, the calculation of the degree of matching between peak patterns (P_Sim) is performed based on a difference between peak heights of comparison targets in the above-described embodiment in which the FPs are prepared with use of peak heights.

In the formulating method and apparatus for a multicomponent drug, there may be a case where a peak represents a maximum value of a signal strength (height) as described above or a case where a peak represents an area value (peak area) of a signal strength in a form of a height.

In other words, even in the case where the FP is prepared with use of peak areas, the area values are represented in a form of heights to prepare the FP. Accordingly, the FP has the same representation as that of the case where the FP is prepared with use of the peak heights as in the above-described embodiment. Therefore, similar to the case where the FP is prepared with use of the peak heights, the FP can be evaluated by the process of the above-described embodiment.

However, in the case where the FP is prepared with use of the peak areas, differences between the peak values of comparison targets are larger. Accordingly, it is appropriate that the calculation is made based on a ratio so as to make the handling thereof easy.

Hereinafter, the degree of matching between peak patterns (P_Sim) that is calculated based on the ratios will be represented for exemplary cases where n=2 and n=4.

In the case where n=2, the calculation is represented as follows:

$$P\_Sim = (p1/p2^{\#1}) \times$$
$$(|(r1-(r2+d)|+1) + (dn1/fn1^{\#1}) \times (|(cn1-r1)-(en1-r2)|+1) +$$
$$(dn2/fn2^{\#1}) \times (|(cn2-r1)-(en2-r2)|+1).$$

In a case where n=4, the calculation is represented as follows:

$$P\_Sim = (p1/p2^{\#1}) \times$$
$$(|(r1-(r2+d)|+1) + (dn1/fn1^{\#1}) \times (|(cn1-r1)-(en1-r2)|+1) +$$
$$(dn2/fn2^{\#1}) \times (|(cn2-r1)-(en2-r2)|+1) +$$
$$(dn3/fn3^{\#1}) \times (|(cn3-r1)-(en3-r2)|+1) +$$
$$(dn4/fn4^{\#1}) \times (|(cn4-r1)-(en4-r2)|+1).$$

Here, $^{\#1}$ represents a ratio (larger value/smaller value) of two comparison target values.

In addition, also in the case where the FP is prepared by means of the peak heights, the degree of matching between peak patterns (P_Sim) can be calculated based on a ratio, and, also in the case where the FP is prepared by means of the peak areas, similarly to the case of a difference between the peak heights, the degree of matching between peak patterns (P_Sim) can be acquired based on a difference between peak area values.

Figure 100:
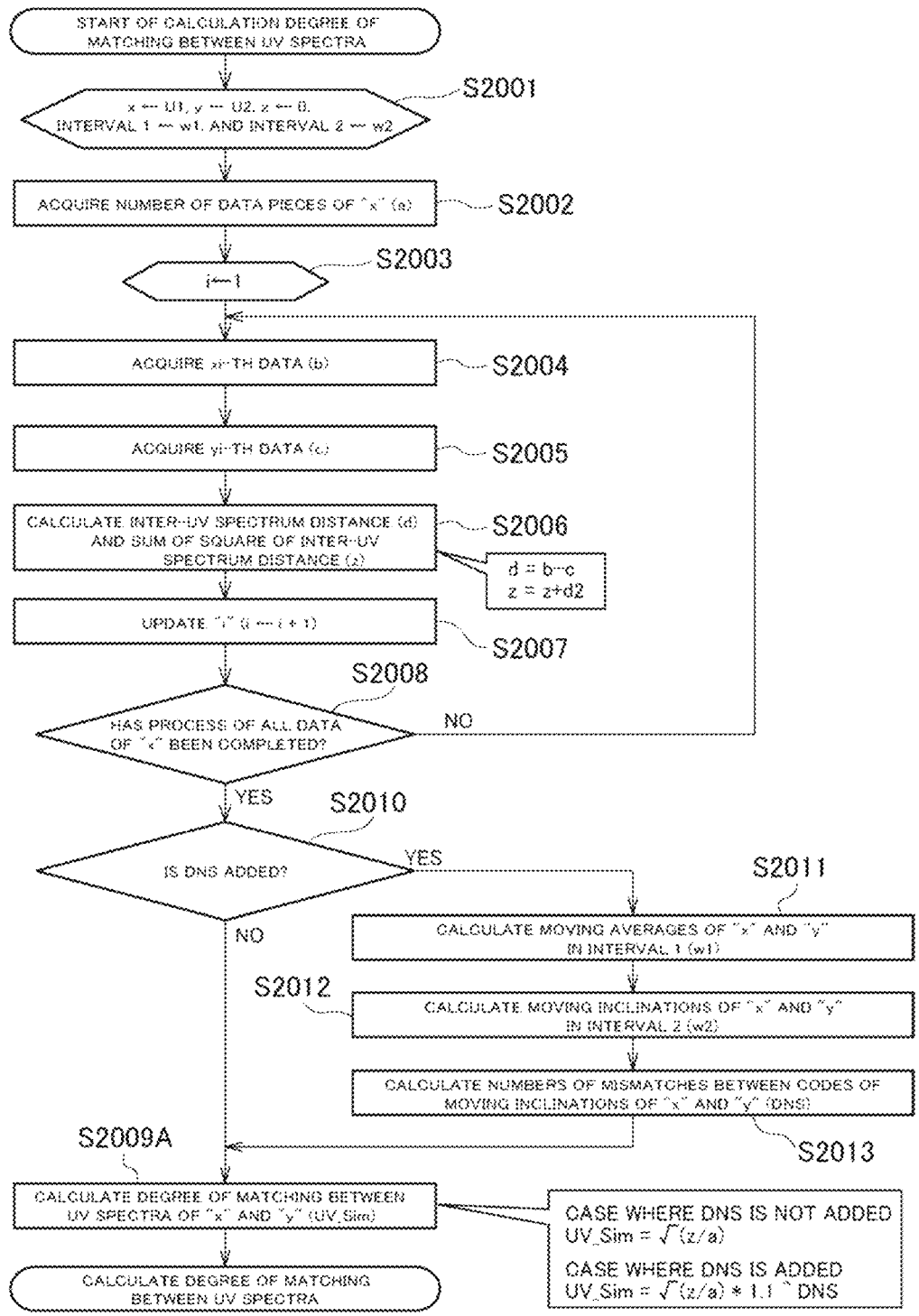
FIG. 100 is a flowchart illustrating details of a modified example of Subroutine 2 that is applied instead of the process illustrated in FIG. 86 according to the first embodiment.

FIG. 100 is a modified example of the "Subroutine 2" that is applied instead of that illustrated in FIG. 86 and is a flowchart illustrating details of the modified example of Subroutine 2 in the "target FP assigning process 2" illustrated in FIG. 81. The degree of matching between UV spectra is calculated by the process according to this modified example.

In the modified example of this Subroutine 2, a process of adding inclination information in moving average of a UV pattern (DNS) to the RMSD of Subroutine 2 in FIG. 86 can be performed. The DNS is represented in an equation to be described later and is defined as the number of mismatches of inclination codes (+/−) when the moving inclinations of the moving average values in the UV pattern are compared between two patterns. In other words, the DNS is a value that represents an evaluation of the matching state of the positions of the maximum and minimum values of the UV patterns.

By adding the DNS information to the RMSD, the degree of matching between waveforms of UV spectra can be calculated more accurately.

In Subroutine 2 according to the modified example of FIG. 100, Steps S2001 to S2008 are almost the same as those of Subroutine 2 in FIG. 86. However, in Step S2001, initial setting of "Interval 1←w1 and Interval 2←w2" is additionally performed, to be used for calculating the moving average and the moving inclination to be described later.

In Subroutine 2 of this modified example, Steps S2010 to S2013 are added so as to add the DNS, so that it enables Step S2009A to calculate the degree of matching to which the DNS is added.

In Step S2010, a determining process of "Is the DNS added?" is performed. If the DNS is determined to be added (YES), it proceeds to Step S2011. If the DNS is determined not to be added (NO), it proceeds to Step S2009A. The determination whether the DNS is added or not is based on, for example, an initial setting. For example, if the FP is prepared by means of peak areas, the DNS is set to be added; and if the FP is prepared by means of peak heights, the DNS is set to be not added.

However, also in the case of the above-described embodiment in which the FP is prepared by means of peak heights, the degree of matching between UV patterns can be calculated through a process to which the DNS is added; and also in the case where the FP is prepared by means of peak areas, the degree of matching between UV patterns can be calculated through the process of the above-described embodiment to which the DNS is not added.

In Step S2011, a process of "calculating the moving averages of "x" and "y" in interval 1 (w1)" is performed, to find the moving averages for interval 1 (w1). Interval 1 (w1) is an interval relating to the wavelength of the UV data. In a case where w1=3 in the initial setting of Step S2001, interval 1 (3) is set and the average of the UV intensities of three wavelengths is acquired. More specifically, description will be made later with reference to a table represented in FIG. 101.

In Step S2012, the process of "calculating the moving inclinations of "x" and "y" in interval 2 (w2)" is performed to acquire the moving inclinations in interval 2 (w2). Interval 2 (w2) is an interval relating to the moving average acquired in Step S2011. If w2=3 in the initial setting performed in Step S2001, interval 2 (3) is set to acquire inclinations of (±) over the three moving averages based on the moving averages calculated in Step S2011. More specifically, description will be made later with reference to a table illustrated in FIG. 101.

In Step S2013, a process of "calculating the number of mismatches between the codes of the moving inclinations of "x" and "y" (DNS)" is performed, to calculate the number of matches in the inclinations of (±) based on the moving inclinations calculated in Step S2012. The moving inclination of (+) represents rising to the right in FIG. 66, and the moving inclination of (−) represents falling to the right.

When proceeding from Step S2013 to Step S2009A, the degree of matching to which the DNS is added is calculated in the process of Step S2009A.

In Step S2009A, a process of "calculating the degree of matching between UV spectra of "x" and "y" (UV_Sim)" is performed. In the calculation process of the degree of matching to which the DNS is added, the UV_Sim is calculated based on the sum "z" of squares of inter-UV spectrum distances, the number "a" of data of "x" and the DNS as:

$$UV\_Sim = \sqrt{(z/a)} \times 1.1^{DNS}.$$

This UV_Sim is input to Step S306 in FIG. 81, to finish the process of calculating the degree of matching between UV spectra.

In addition, the process performed in a case where it proceeds from Step S2010 to Step S2009A is the same as that of Step S2009 in FIG. 86.

FIG. 101 is a table illustrating a calculating example of moving averages and moving inclinations.

In FIG. 101, the upper row represents an example of UV data, the intermediate row represents an example of calculation of moving averages, and the lower row represents an example of calculation of moving inclinations. As the example of the UV data, the UV intensity is represented as a1 to a7 instead of specific numeric values. For example, the UV intensity of 220 nm is a1, the UV intensity of 221 nm is a2, and the like. Also in the example of calculation of the moving averages and moving inclinations, UV intensities a1 to a7 are used instead of specific numeric values.

For the example of the interval 1 (w1=3), the moving averages are calculated as m1, m2 . . . as respective values calculated for an interval (a1, a2, a3), an interval (a2, a3, a4) . . . in Step S2012 (see FIG. 100). In addition, for the example of the interval 2 (3), the moving inclinations are calculated as s1 . . . as respective values calculated for an interval (m1, m2, m3), an interval (m2, m3, m4) . . . in Step S2013 (see FIG. 100). For example, a difference m3−m1 between the moving averages is the moving inclination, and (±) thereof are extracted.

In this way, when preparing the FP by means of peak areas, in the assignment process to the reference group FP and the reference FP assigning result integrating process, the degree of matching between UV patterns can be calculated through the process to which the DNS is added. With this calculation, even if a distance (dis) between two corresponding points illustrated in FIG. 66 is larger relative to the FP prepared by means of peak heights, the handing thereof can be easily performed, thereby calculating the degree of matching between UV patterns with high accuracy.

Figure 102:
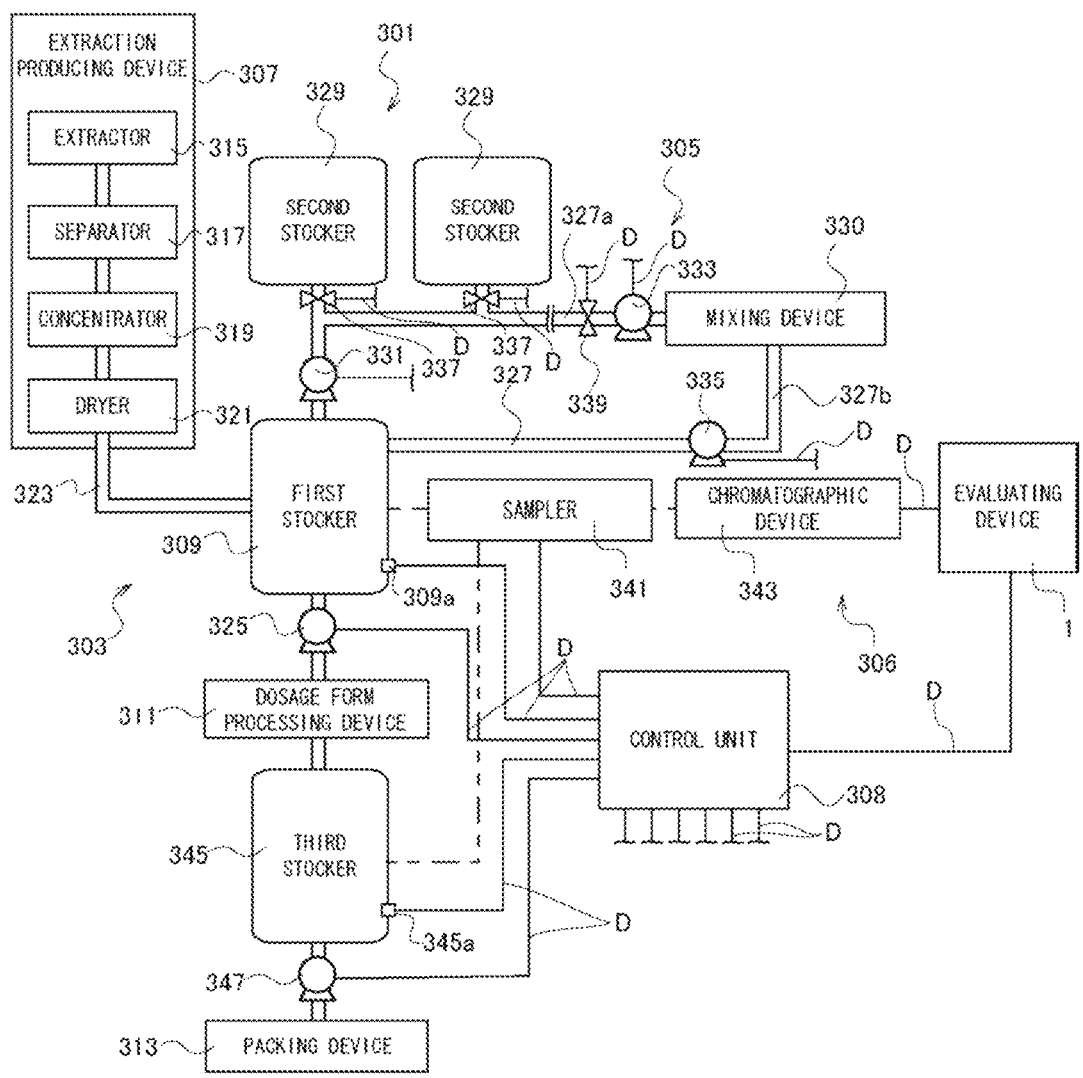
FIG. 102 is a schematic block diagram illustrating a formulating apparatus according to a second embodiment of the present invention.

FIG. 102 is a schematic block diagram illustrating a formulating apparatus according to the second embodiment of the present invention. The second embodiment has the same basic structure as the first embodiment and therefore corresponding parts are represented with the same reference numerals to omit the repetition in the explanation.

The formulating apparatus 301 according to the second embodiment further includes a third stocker 345 and a blower 347 in comparison with the first embodiment of FIG. 1A. The third stocker 45 is arranged or laid downstream of the dosage form processing device 311 on the first pipeline 323. The blower 347 on the first pipeline 323 is arranged downstream of the third stocker 345.

According to the embodiment, the formulating apparatus 301 accommodates in the third stocker 345 granules produced through the dosage form processing at the dosage form processing device 311, evaluates whether the granules meet the criteria for productization at the evaluating device 1, and conveys the granules determined as accepted ones meeting the criteria for productization to the packing device 313 using the blower 347.

The third stocker 345 is a general tank or the like similar to the first stocker 309. The third stocker 345 includes a sensor 345a. The sensor 345a is a load cell or the like similar to the sensor 309a of the first stocker 309.

According to the embodiment, the control unit 308 determines a conveying state of the granules to the third stocker 345 according to the detecting signal from the sensor 345a of the third stocker 345. Then, the control unit 308 controls the sampler 341 according to the conveying state to obtain the sample of the granules stored in the third stocker 345 and feed the obtained sample to the chromatographic device 343.

In response to the feeding, the chromatographic device 343 obtains a 3D chromatogram and outputs the same to the evaluating device 1, and the evaluating device 1 evaluates whether the granules meet the criteria for productization based on the chromatogram and outputs the evaluating result to the control unit 308.

The control unit 308 controls the blower 345 to convey the granules from the third stocker 345 to the packing device 313 in the case where the granules meet the criteria for productization according to the evaluating result.

The second embodiment, therefore, conclusively confirms that the granules meet the criteria after producing the granules and before packing the same. This allows only the granules meeting the criteria to be surely packed.

This embodiment is particularly advantageous for production of the granules from the mixed extract. Namely, the mixed extract of the embodiment is produced to meet the criteria for productization and therefore it is not required to evaluate whether the mixed extract accommodated in the first stocker 309 meets the criteria.

Accordingly, the second embodiment conclusively confirms that the granules stored in the third stocker 345 meet the criteria without confirmation for the mixed extract stored in the first stocker 309, to omit repeated evaluation and improve the efficiency for productization.

In addition, the second embodiment obtains the same effects as the first embodiment.

Figure 103:
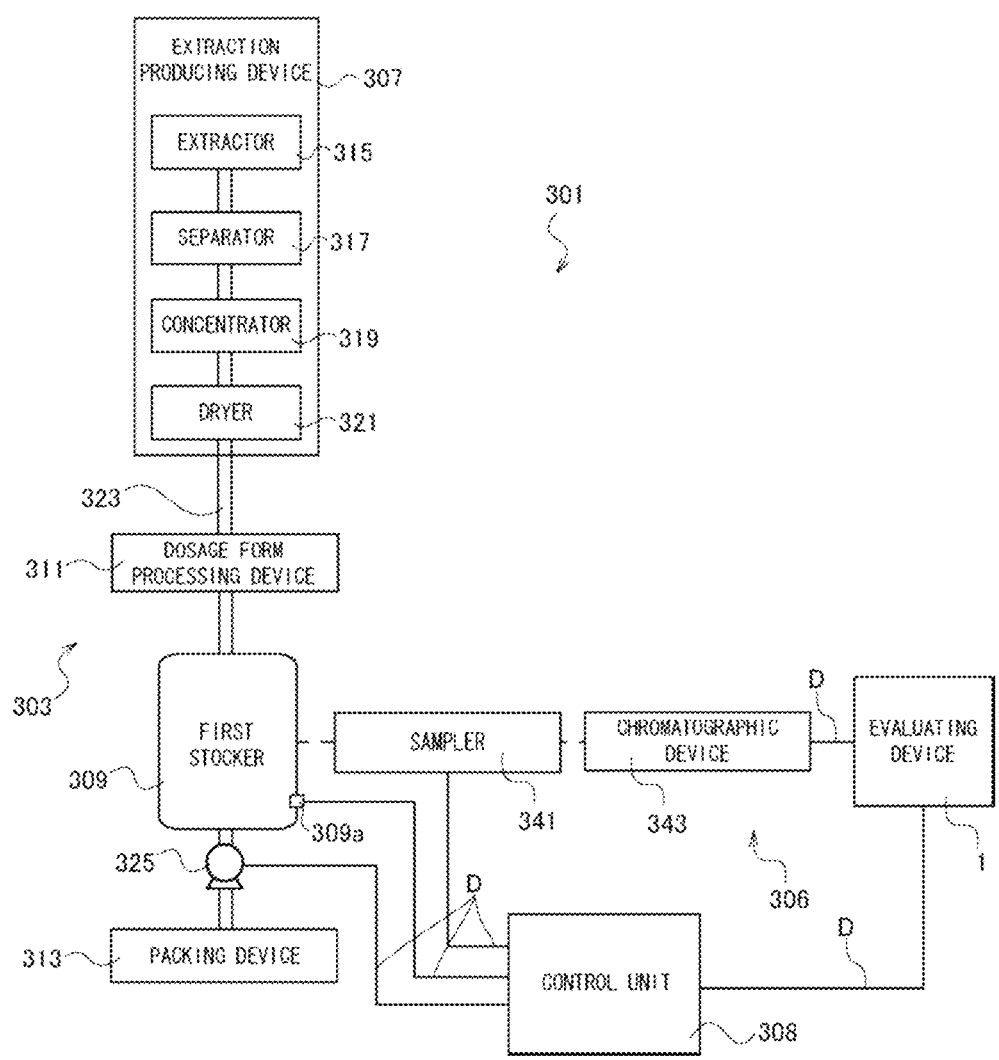
FIG. 103 is a schematic block diagram illustrating a formulating apparatus according to a third embodiment of the present invention.

FIG. 103 is a schematic block diagram illustrating a formulating apparatus according to the third embodiment of the present invention. The third embodiment has the same basic structure as the first embodiment and therefore corresponding parts are represented with the same reference numerals to omit the repetition in the explanation.

The formulating apparatus 301 according to the embodiment conducts evaluation of granules without conducting evaluation of a powder extract.

For this, the dosage form processing device 311 is arranged or laid downstream of the extraction producing device 307 and a powder extraction produced at the extract producing device 307 is conveyed to the dosage form processing device 311 through the first pipeline 323 to produce granules.

On the downstream side of the dosage form processing device 311, the first stocker 309 is arranged to accommodate the granules. To the granules accommodated in the first stocker 309, the evaluating line 306 evaluates whether to meet the criteria for productization.

The evaluating result or determination is input to the control unit 308 and the control unit 308 controls the blower 325 to convey the granules from the first stocker 309 to the packing device 313 in the case where the granules meet the criteria for productization. The packing device 313 subdivides and packs the conveyed granules.

The third embodiment, therefore, packs granules meeting the criteria for productization and does not pack granules not meeting that criteria based on the high-accuracy evaluation at the evaluating device 1, thereby to surely pack the granules for the multicomponent drug meeting that criteria to make the same into a product.

Although this embodiment of the present invention is applied to an evaluation of a kampo medicine as a multicomponent drug, it can be also applied to an evaluation of other multicomponent materials.

An evaluating method for a pattern according to the present invention includes: a pattern acquiring step acquiring a target pattern of an evaluation target whose peaks change in a time series; a peak pattern preparing step preparing individual peak patterns, for each peak, of the target pattern and a reference pattern that corresponds to the target pattern and is evaluation criteria, with use of n+1 peaks that include n peaks being present on at least one of sides located in front and in the rear of each peak in a time axis direction; a peak assigning step comparing the individual peak patterns to specify corresponding peaks; and an evaluating step evaluating the peaks that are specified and assigned in the peak assigning step by comparison with peaks of a plurality of reference patterns that are evaluation criteria. The method is broadly applicable to an evaluation of equivalency between a target pattern and a reference pattern, and the like.

Although all the peaks on the 3D chromatogram are set as targets in the FP of the embodiment, the FP may be prepared with the exclusion of fine data such as peaks each having a peak area corresponding to 5% or less on the 3D chromatogram.

In the above-described embodiment, the FP is prepared based on the peak heights, to acquire evaluations in FIGS. 70 to 74. However, even if the FP is prepared based on peak areas, MD values are acquired by MT method through the same sequence as that of the above-described embodiment that is prepared based on the peak heights, to acquire the evaluations as illustrated in FIGS. 70 to 74 in the same way.

The chromatogram is not limited to the 3D chromatogram, and a FP that is configured by peaks and retention time points, in which UV spectra are not included, may be used. In such a case, the process can be performed similarly to the above-described embodiment with the exception of the degree of matching between UV spectra.

What is claimed is:

1. A method of producing a multicomponent drug in dosage form, comprising the following steps:
   (1) obtaining, with chromatography equipment, a chromatogram from a base of the multicomponent drug, the base being stored in a first stocker;
   (2) evaluating, with a first processor, whether the base meets criteria for productization by evaluating fingerprints based on the obtained chromatogram;
   (3) if the base is evaluated as meeting the criteria for productization, conveying the base, under control of a second processor, from the first stocker to a dosage form processing device, and subjecting the base to productization using a dosage form processing of the base at the dosage form processing device, to produce a multicomponent drug in dosage-form;
   (4) if the base is evaluated as not meeting the criteria for productization, conveying the base, under the control of the second processor, from the first stocker to a respective one of a plurality of second stockers to isolatedly store the base in the second stocker;
   (5) repeating steps (1) through (4) for at least one other base of the multicomponent drug until at least one other base is evaluated as not meeting the criteria for productization and each isolatedly stored in a respective second stocker;
   (6) under the control of the second processor, if the first stocker is empty, conveying, in proportions controlled by the second processor, at least two of the bases each isolatedly stored in the respective second stockers to a mixing device and mixing the at least two of the bases conveyed from the respective second stockers to form a mixed base which meets the criteria for productization; and
   (7) conveying, under the control of the second processor, the mixed base from the mixing device to the first stocker and from the first stocker to the dosage form processing device and subjecting the mixed base to the productization using the dosage form processing at the dosage form processing device to produce a multicomponent drug in dosage form, wherein
   the evaluating, with the first processor, whether the base meets the criteria for productization comprises the following steps:
   (i) preparing a target fingerprint composed of peaks where each peak is defined by a local maximum or an area value in signal strength and a retention time point detected from said obtained chromatogram at a specific wavelength;
   (ii) preparing peak patterns for each assignment target peak of the target fingerprint, each peak pattern for the assignment target peaks configured by n+1 peaks that include an assignment target peak and n peripheral peaks being present on at least one of sides located in front and in the rear of said assignment target peak in a time axis direction;
   (iii) preparing peak patterns for each assignment candidate peak of a reference fingerprint having differences in retention time relative to each assignment target peak within a set range, each peak pattern for the assignment candidate peaks configured by n+1 peaks that includes an assignment candidate peak and n peripheral peaks being present on at least one of sides located in front and in the rear of said assignment candidate peak in the time axis direction, the reference fingerprint being selected from a plurality of reference fingerprints each composed of peaks where a peak is defined by a local maximum or an area value in signal strength and a retention time point detected from a chromatogram of a multicomponent drug that is an evaluation criteria;

(iv) comparing the peak pattern for each assignment target peak and the peak patterns for the assignment candidate peaks within the set range of each assignment target peak in retention time, thereby finding degrees of matching between the peak patterns based on differences in peaks and retention time points and thereby specifying, for each assignment target peak, an assignment candidate peak having a highest one of the degrees of matching as a corresponding peak, thereby specifying corresponding peaks between the target fingerprint and the reference fingerprint to be assigned with each other;

(v) assigning the specified peaks of the target fingerprint to corresponding peaks of a reference group fingerprint, each of the peaks of the reference group fingerprint defined by local maxima or area values in signal strength and retention time points of the peaks of the reference fingerprints;

(vi) evaluating the specified peaks of the target fingerprint by comparison with the corresponding peaks of the reference group fingerprint using a Mahalanobis-Taguchi method to find a Mahalanobis distance; and (vii) determining the base of the multicomponent drug as one that meets the criteria for productization if the Mahalanobis distance is equal to or less than a predetermined threshold value;

wherein the control by the second processor of the proportions of the bases conveyed to and mixed in the mixing device is based on the respective Mahalanobis distance of each of the respective bases in the respective second stockers, the proportions of the bases conveyed to and mixed in the mixing device being controlled by the second controller so that the Mahalanobis distance of each mixed base is equal to or less than the predetermined threshold value; and under the control of the second processor, each mixed base having a Mahalanobis distance equal to or less than the predetermined threshold value is conveyed from the mixing device to the first stocker and from the first stocker to the dosage form processing device and subjected to dosage form processing at the dosage form processing device to produce a multicomponent drug in dosage form.

2. The method according to claim 1, wherein
the respective chromatogram of each of the target fingerprint and the reference fingerprint is a 3D chromatogram,
the target fingerprint and the reference fingerprint include, in addition to detection of the peaks and the retention time points, UV spectra of the detected peaks, and
the specifying of the corresponding peaks is performed based on comparison in peak pattern of the UV spectrum.

3. The method according to claim 2, wherein
the specifying of the corresponding peaks is performed based on a degree of matching of peaks calculated by synthesizing a degree of matching between the peak patterns calculated from all peaks configuring the peak patterns and the retention time points thereof and a degree of matching between the UV spectra.

4. The method according to claim 1, wherein
preparing the target fingerprint comprises composing a plurality of fingerprints that are detected at different detection wavelengths from the chromatogram of the evaluation target to obtain the target fingerprint.

5. The method according to claim 1, wherein
preparing the target fingerprint comprises extracting all the peaks of the chromatogram of the evaluation target to prepare the target fingerprint.

6. The method according to claim 1, wherein
preparing the peak patterns comprises comprehensively preparing peak patterns for both the assignment target peak of the target fingerprint and the assignment candidate peaks of the reference fingerprint by changing peaks configuring the peak patterns.

7. The method according to claim 1, wherein
peak patterns are prepared for all the peaks of the target fingerprint and the reference fingerprint, and
the specifying of the corresponding peaks is performed to all the peaks of the target fingerprint and the reference fingerprint.

8. The method according to claim 1, further comprising:
selecting the reference fingerprint that is an assignment opponent of the target fingerprint from among the plurality of reference fingerprints by comparing peaks in retention time and appearance pattern between the target fingerprint and the plurality of reference fingerprints.

9. An apparatus for producing a multi component drug in dosage form, comprising:
chromatography equipment configured to obtain a chromatogram from a base of a multi component drug;
a multicomponent drug evaluating first program and a second program configured to control stockers, mixing device, conveyors and dosage form processing device, each of the first and second programs being stored in a non-transitory computer readable medium, the first program being configured to be executed by a first processor connected to the chromatography equipment via a data line and the second program being configured to be executed by a second processor connected to the first processor via a data line;
a first stocker configured to receive the base which has been extracted from source materials by an extractor;
a plurality of second stockers;
a conveyor for conveying respective batches of the base supplied form the extractor to the first stocker to respective ones of the plurality of second stockers;
a mixing device configured to mix at least two batches of the base, each batch being received by the mixer from a respective one of the second stockers, to form a mixed base;
a conveyor for conveying the respective batches of the base from the respective second stockers to the mixing device;
a conveyor for conveying the mixed base from the mixing device to the first stocker;
a dosage form processing device configured to subject the base or the mixed base to dosage form processing, to produce the multicomponent drug in dosage form;
a conveyor for conveying the base or the mixed base from the first stocker to the dosage form processing device; and
a sensor configured to detect that all the base supplied to the first stocker by the extractor has been conveyed out of the first stocker, wherein:

the first program is configured to effect the following steps:
(i) preparing a target fingerprint composed of peaks where a peak is defined by a local maximum or an area value in signal strength and a retention time point detected from said obtained chromatogram at a specific wavelength;
(ii) preparing peak patterns for each assignment target peak of the target fingerprint, each peak pattern for the assignment target peaks configured by n+1 peaks that include an assignment target peak and n peripheral peaks being present on at least one of sides located in front and in the rear of said assignment target peak in a time axis direction;
(iii) preparing peak patterns for each assignment candidate peak of a reference fingerprint having differences in retention time relative to each assignment target peak within a set range, each peak pattern for the assignment candidate peaks configured by n+1 peaks that includes an assignment candidate peak and n peripheral peaks being present on at least one of side located in front and in the rear of said assignment candidate peak in the time axis direction, the reference fingerprint being selected from a plurality of reference fingerprints each composed of peaks where a peak is defined by a local maximum or an area value in signal strength and a retention time point detected from a chromatogram of a multicomponent drug that is an evaluation criteria;
(iv) comparing the peak pattern for each assignment target peak and the peak patterns for the relevant assignment candidate peaks within the set range of each assignment target peak in retention time, thereby finding degrees of matching between the peak patterns based on differences in peaks and retention time points and thereby specifying, for each assignment target peak, an assignment candidate peak having a highest one of the degrees of matching as a corresponding peak, thereby specifying corresponding peaks between the target fingerprint and the reference fingerprint to be assigned with each other; and
(v) assigning the specified peaks of the target fingerprint to corresponding peaks of a reference group fingerprint, each of the peaks of the reference group fingerprint defined by local maxima or area values in signal strength and retention time points of the peaks of the reference fingerprints;
(vi) evaluating the specified peaks of the target fingerprint by comparison with the corresponding peaks of the reference group fingerprint using a Mahalanobis-Taguchi method to find a Mahalanobis distance;
(viii) determining the base of the multicomponent drug as an accepted one that meets the criteria for productization if the Mahalanobis distance is equal to or less than a predetermined threshold value; and the second program is configured to effect the following steps:
(i) upon determination that the base supplied to the first stocker from the extractor meets the criteria for productization, conveying of the base from the first stocker to the dosage form processing device and dosage form processing of the base by the dosage form processing device to produce the multicomponent drug in dosage form;
(ii) upon determination that the base supplied to the first stocker does not meet the criteria for productization, conveying of the base from the first stocker to a respective one of the second stockers for individual isolation of each of the bases which do not meet the criteria for productization;
(iii) repeating step (vii) of the first program and steps (i) and (ii) of the second program for at least one other base of the multicomponent drug until at least one other base is evaluated as not meeting the criteria for productization and each isolately stored in a respective second stocker;
(iv) upon detecting by the sensor that all the base supplied to the first stocker from the extractor has emptied from the first stocker, conveying of the bases isolately stored in at least two of the respective second stockers to a mixing device in proportions controlled by the second processor and mixing of the at least two of the bases conveyed from the respective second stockers, to form a mixed base which meets the criteria for productization, wherein the second processor is configured to set the proportions of the bases conveyed to and mixed in the mixing device based on the respective Mahalanobis distance of each of the respective bases in the respective second stockers which are conveyed to and mixed in the mixing device, the proportions of the bases conveyed to and mixed in the mixing device being set so that the Mahalanobis distance of each mixed base is equal to or less than the predetermined threshold value; and
(v) conveying of the mixed base from the mixing device to the first stocker and from the first stocker to the dosage form processing device and subjecting of the mixed base to the productization using the dosage form processing at the dosage form processing device to produce the multicomponent drug in dosage form.

10. The apparatus according to claim 9, wherein
the respective chromatogram of each of the target fingerprint and the reference fingerprint is a 3D chromatogram,
the target fingerprint and the reference fingerprint include, in addition to detection of the peaks and the retention time points, UV spectra of the detected peaks, and
the first program is configured to perform the specifying of the corresponding peaks based on comparison in peak pattern of the UV spectrum.

11. The apparatus according to claim 10, wherein
the first program is configured to perform the specifying of the corresponding peaks based on a degree of matching of peaks calculated by synthesizing a degree of matching between the peak patterns calculated from all peaks configuring the peak patterns and the retention time points thereof and a degree of matching between the UV spectra.

12. The apparatus according to claim 9, wherein
the first program is configured to compose a plurality of fingerprints that are detected at different detection wavelengths from the chromatogram of the evaluation target to obtain the target fingerprint.

13. The apparatus according to claim 9, wherein
the first program is configured to extract all the peaks of the chromatogram of the evaluation target to obtain the target fingerprint.

14. The apparatus according to claim 9, wherein
the first processor is configured to comprehensively prepare peak patterns for both the assignment target peak of the target fingerprint and the assignment candidate peaks of the reference fingerprint by changing peaks configuring the peak patterns.

15. The apparatus according to claim 9, wherein
the first processor is configured to prepare the peak patterns for all the peaks of the target fingerprint and the reference fingerprint, and
the first processor is further configured to perform the specifying of the corresponding peaks to all the peaks of the target fingerprint and the reference fingerprint.

16. The apparatus according to claim 9, further comprising:
the first program being configured to select the reference fingerprint that is an assignment opponent of the target fingerprint from among the plurality of reference fingerprints by comparing peaks in retention time and appearance pattern between the target fingerprint and the plurality of reference fingerprints.

\* \* \* \* \*